US012631623B2

(12) United States Patent
Mendjan et al.

(10) Patent No.: US 12,631,623 B2
(45) Date of Patent: May 19, 2026

(54) HEART TISSUE MODEL

(71) Applicant: IMBA—INSTITUT FÜR MOLEKULARE BIOTECHNOLOGIE GMBH, Vienna (AT)

(72) Inventors: Sasha Mendjan, Vienna (AT); Stefan Jahnel, Vienna (AT); Pablo Hofbauer, Vienna (AT); Nora Papai, Vienna (AT)

(73) Assignee: IMBA—INSTITUT FÜR MOLEKULARE BIOTECHNOLOGIE GMBH, Vienna (AT)

(*) Notice: Subject to any disclaimer, the term of this patent is extended or adjusted under 35 U.S.C. 154(b) by 713 days.

(21) Appl. No.: 17/906,645

(22) PCT Filed: Mar. 19, 2021

(86) PCT No.: PCT/EP2021/057110
§ 371 (c)(1),
(2) Date: Sep. 19, 2022

(87) PCT Pub. No.: WO2021/186044
PCT Pub. Date: Sep. 23, 2021

(65) Prior Publication Data
US 2023/0314413 A1     Oct. 5, 2023

(30) Foreign Application Priority Data
Mar. 20, 2020    (EP) ..................................... 20164637

(51) Int. Cl.
*G01N 33/50* (2006.01)
*C12N 5/071* (2010.01)
*C12N 5/077* (2010.01)

(52) U.S. Cl.
CPC ....... *G01N 33/5082* (2013.01); *C12N 5/0656* (2013.01); *C12N 5/0657* (2013.01);
(Continued)

(58) Field of Classification Search
None
See application file for complete search history.

(56) References Cited

U.S. PATENT DOCUMENTS

| | | | |
|---|---|---|---|
| 2015/0017718 A1* | 1/2015 | Nakatsuji ............. | C07D 277/82 |
| | | | 435/363 |
| 2020/0085880 A1 | 3/2020 | Murry et al. | |
| 2021/0017496 A1 | 1/2021 | Zweigerdt et al. | |

FOREIGN PATENT DOCUMENTS

| | | |
|---|---|---|
| CN | 110268048 A | 9/2019 |
| WO | 2016009196 A1 | 1/2016 |
| WO | WO2019174879 A1 | 9/2019 |

OTHER PUBLICATIONS

Rajala, Kristiina; et al; "Cardiac Differentiation of Pluripotent Stem Cells" Stem Cells International, 383709, 2011 (Year: 2011).*
(Continued)

*Primary Examiner* — David W Berke-Schlessel
(74) *Attorney, Agent, or Firm* — Greer, Burns & Crain, Ltd

(57) ABSTRACT

The present invention provides a heart tissue model of at least 60% cardiac cells, wherein the cardiac cells surround an inner cavity, wherein the cardiac cells are selected from cardiomyocytes, endocardial cells and epicardial cells; method for the generation of such a tissue model and uses thereof.

22 Claims, 108 Drawing Sheets

Specification includes a Sequence Listing.

(52) U.S. Cl.
CPC ......... *C12N 5/0691* (2013.01); *C12N 5/0697* (2013.01); *G01N 33/5023* (2013.01); *C12N 2501/115* (2013.01); *C12N 2501/15* (2013.01); *C12N 2501/155* (2013.01); *C12N 2501/16* (2013.01); *C12N 2501/165* (2013.01); *C12N 2501/415* (2013.01); *C12N 2506/45* (2013.01); *C12N 2513/00* (2013.01); *C12N 2533/52* (2013.01)

(56) References Cited

OTHER PUBLICATIONS

Chen, Vincent C; et al; "Development of a scalable suspension culture for cardiac differentiation from human pluripotent stem cells" Stem Cell Research, 15, 365-375, 2015 (Year: 2015).*

International Search Report and Written Opinion received for PCT/EP2021/057110, mailed May 18, 2021.

International Preliminary Report on Patentability received for PCT/EP2021/057110, completed Jun. 30, 2022.

Bagley, J., et al., "Fused dorsal-ventral cerebral organoids model complex interactions between diverse brain regions," Nat Methods 14(7), 2017, 33 pages.

Chen, G., et al., "Chemically defined conditions for human iPS cell derivation and culture," Nat Methods 8(5), 2011, pp. 424-429.

Cui, Y., et al., "Single-Cell Transcriptome Analysis Maps the Developmental Track of the Human Heart," Cell Reports 26, 2019, pp. 1934-1950.

Deehan, R., "Cardia Bifida and the Development of Pacemaker Function in the Early Chick Heart," Developmental Biology 1, 1959, pp. 586-602.

Doblmann, J., et al., "apQuant: Accurate Label-Free Quantification by Quality Filtering," J. Proteome Res 18, 2019, pp. 535-541.

Guadix, J., et al., "Human Pluripotent Stem Cell Differentiation into Functional Epicardial Progenitor Cells," Stem Cell Reports 9, 2017, pp. 1754-1764.

Hallion, C., et al., "Continuous WNT Control Enables Advanced hPSC Cardiac Processing and Prognostic Surface Marker Identification in Chemically Defined Suspension Culture," Stem Cell Reports, Vo. 13, 2019, pp. 366-379.

Hockemeyer, D., et al., "Highly efficient gene targeting of expressed and silent genes in human ESCs and iPSCs using zinc finger nucleases," Nat Biotechnol. 27(9), 2009,pp. 851-857.

Hoang, P., et al. "Generation of spatial-patterned early-developing cardiac organoids using human pluripotent stem cells," Nature Protocols, vol. 13, No. 14, 2018, pp. 723-737.

Huebsch, N., et al., "Automated Video-Based Analysis of Contractility and Calcium Flux in Human-Induced Pluripotent Stem Cell-Derived Cardiomycytes Cultured over Different Spatial Scales," Tissue Engineering: Part C, vol. 21, No. 5, 2015, pp. 467-479.

Israeli, Y, et al., "Generation of Heart Organoids Modeling Early Human Cardiac Development Under Defined Conditions," bioRxiv, 2020, retrieved from https://www.researchgate.net/profile/Aitor-Aguirre/publication/342488487_Generation_of_Heart_Organoids_ Modeling_Early_Human_Cardiac_Development_Under_Defined_ Conditions/links/5f207de8299bf1720d6b1dfb/Generation-of-Heart-Organoids-Modeling-Early-Human-Cardiac-Development-Under-Defined-Conditions.pdf, 26 pages.

Iyer, D., et al., "Robust derivation of epicardium and its differentiated smooth muscle cell progeny from human pluripotent stem cells," Development 142, 2015, pp. 1528-1541.

Li, S., et al., "Advanced Cardiac Morphogenesis Does Not Require Heart Tube Fusion," Science, vol. 35, 2004, pp. 1619-1622.

Linask, K., "Regulation of Heart Morphology: Current Molecular and Cellular Perspectives on the Coordinated Emergence of Cardiac Form and Function," Birth Defects Research, Part C, vol. 69, 2003, pp. 14-24.

Ma, Z., et al., "Self-organizing human cardiac microchambers mediated by geometric confinement," Nature Communications, 2015, 10 pages.

Mendjan, S., et al., "NANOG and CDX2 Pattern Distinct Subtypes of Human Mesoderm during Exit from Pluripotency," Cell Stem Cell 15, 2014, 38 pages.

Patsch, C., "Generation of vascular endothelial and smooth muscle cells from human pluripotent stem cells," Nat CelL Biol., 2015, vol. 17, No. 8, 2015, pp. 994-1003.

Prandini, M-H., et al., "The human VE-cadherin promoter is subjected to organ-specific regulation and is activated in tumour angiogenesis," Oncogene 24, 2005, pp. 2992-3001.

Ran, F., et al., "Genome engineering using the CRISPR-Cas9 system, Nature Protocols," vol. 8, No. 11, 2013, pp. 2281-2308.

Roberts, B., et al., "Fluorescent Gene Tagging of Transcriptionally Silent Genes in hiPSCs," Stem Cell Reports, vol. 12, 2019, pp. 1145-1158.

Schindelin, J., et al., "Fiji: an open-source platform for biological-image analysis," Nature Methods 9, 2012, pp. 676-682.

Strano, A., et al., "Variable Outcomes in Neural Differentiation of Human PSCs Arise from Intrinsic Differences in Developmental Signaling Pathways," Cell Reports 31, 2020, 34 pages.

Wang, X., et al., "Bulk tissue cell type deconvolution with multi-subject single-cell expression reference," Nature Communications, vol. 10, No. 380, 2019, 9 pages.

Wimmer, R., et al., "Human blood vessel organoids as a model of diabetic vasculopathy," Nature, vol. 563, 2019, pp. 505-510, Supplement and Reporting Summary, 34 pages.

Yan, Y., et al., "Cell population balance of cardiovascular spheroids derived from human induced pluripotent stem cells," Scientific Reports 9 (1295), 2018, 12 pages.

Yap, L., et al., "Laminins in Cellular Differentiation," Trends in Cell Biology, vol. 29, No. 12, 2019, pp. 987-1000.

Supplemental European Search Report received for Application No. 20164637.9, dated Sep. 20, 2022.

Chinese Office Action dated Jul. 19, 2025 for Chinese Application No. 202180022828.5.

Korean Office Action dated Mar. 4, 2026 for Korean Application No. 10-2022-7032606.

Yang, Y., et al., "Endogenous IGF Signaling Directs Heterogeneous Mesoderm Differentiation in Human Embryonic Stem Cells", Cell Reports, Dec. 10, 2019, pp. 3374-3384, vol. 29.

* cited by examiner

E

Normal

Fig 6 (continued)

+Sunitinib

A

B

B.

C.

B

C

G

B

C

- 2D Anterior EC
- 3D Cardioid EC
- 2D HCMEC
- 2D HUVEC

- 2D Patsch et al. EC
- 2D Pluripotency
- 3D Vascular Organoid EC

GO-terms of 3D Cardioid CM

GO-terms of 3D Cardioid EC

GO-Terms of GFP-/Tomato- cells

A  Aligned differentiation and co-culture of Epicardium and Cardioids

Infarct numbers normalized to infarct area
Healthy numbers normalized to healthy area Fold Change of Fibroblasts in Injured Area vs. Fibroblasts in Healthy Area after Cryo-Injury:
• 3.3- to 21.7-fold more fibroblasts in the injured area. Average fold change is 11.9.

Min Fold Change: 1.33
Max Fold Change: 2.13
Fold Change of Mean Intensity (Grey) Value of FN1 of Injured vs. Healthy side: 1.742324296

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: sgRNA

<400> SEQUENCE: 1
gagcattaac agcgcattcg                                          20

<210> SEQ ID NO 2
<211> LENGTH: 20
<212> TYPE: DNA
<213> ORGANISM: Artificial Sequence
<220> FEATURE:
<223> OTHER INFORMATION: sgRNA

<400> SEQUENCE: 2
gacgcacact tggccggtga                                          20

<210> SEQ ID NO 3
<211> LENGTH: 20
<212> TYPE: DNA
<213> ORGANISM: Artificial Sequence
<220> FEATURE:
<223> OTHER INFORMATION: sgRNA

<400> SEQUENCE: 3
acttggccgg tgaaggcgcg                                          20

<210> SEQ ID NO 4
```

-continued

```
<211> LENGTH: 24
<212> TYPE: DNA
<213> ORGANISM: Artificial Sequence
<220> FEATURE:
<223> OTHER INFORMATION: primer

<400> SEQUENCE: 4
caccgagcat taacagcgca ttcg                                                24

<210> SEQ ID NO 5
<211> LENGTH: 25
<212> TYPE: DNA
<213> ORGANISM: Artificial Sequence
<220> FEATURE:
<223> OTHER INFORMATION: primer

<400> SEQUENCE: 5
aaaccgaatg cgctgttaat gctcc                                               25

<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
caccggacgc acacttggcc ggtga                                               25

<210> SEQ ID NO 7
<211> LENGTH: 25
<212> TYPE: DNA
<213> ORGANISM: Artificial Sequence
<220> FEATURE:
<223> OTHER INFORMATION: primer

<400> SEQUENCE: 7
aaactcaccg gccaagtgtg cgtcc                                               25

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
caccgacttg gccggtgaag gcgcg                                               25

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
aaaccgcgcc ttcaccggcc aagt                                                24
```

HEART TISSUE MODEL

REFERENCE TO AN ELECTRONIC SEQUENCE LISTING

The contents of the electronic sequence listing (Sequence Listing.txt; Size: 1,832 bytes) was created on Sep. 19, 2022 is herein incorporated by reference in its entirety.

The present invention relates to the field of heart tissue model generation.

BACKGROUND

The heart is the first functional organ to form in the developing human embryo. The survival of the embryo depends on self-organisation of cardiac progenitors into the four chambered heart and its subsequent maturation. Self-organisation in biology is the ability of cells to self-assemble as they differentiate into organised tissue/organ-like structures either in vivo or in vitro in permissive in vivo-like conditions. This ability of cells to self-organise under the right conditions is crucial for the tissue and organ to function. Missing self-organising and physiological models have a massive impact by hampering progress to understand human cardiac development & regeneration, aetiology of birth defects & cardiovascular disease, and the real physiological and toxicological effect of drugs.

Stem cell-derived self-organising tissue-like structures called organoids are currently revolutionizing biomedical research as they recapitulate key aspects of organ development, physiology and disease. Organoids have been derived from stem cells that mimic aspects of physiological tissues structure formation in small and large intestine, stomach, liver, lung, brain, epidermis, kidney, retina, oesophagus, bladder and placenta. However, there are major challenges to overcome in this field: i) the complexity, structure and shape of organoids is often difficult to control; and ii) the reproducibility of individual organoids is still far from the robustness of in vivo development.

WO 2019/174879 A1 describes an artificial heart tissue organoid that is grown into a multi-layered aggregate that contains large amounts of non-cardiac cells, such as foregut endoderm cells. In this model, only several small inner endodermal cavities develop that do not recapitulate the large cavities that develop into the four large chambers found in a natural heart. In addition, there is no separation and interspace formation (cardiac jelly) between cardiomyocytes and endocardium (cardiac endothelium) found in a vertebrate heart tube. Hence, such an organoid does not recapitulate this key aspect of the in vivo situation of the developing heart, which consists essentially entirely of cardiac cells. Long-term development and maturation of this tissue model will likely not be possible since non-cardiac cell will accumulate and prevent formation of in vivo-like structures with at least one large cavity that will develop into heart chambers.

Mendjan et al., Cell Stem Cell (2014) Vol. 15, p. 310-325 discloses studies of early mesoderm differentiation in 2D cultures. No heart organoid with inner cavities was obtained.

Halloin et al., Stem Cell Reports (2019) Vol. 13, p. 366-379 discloses a cardiac suspension culture of ventricular-like cardiomyocytes with high lineage purity. No inner cavity is described.

Ma et al., Nature Communications (2015) Vol. 6, p. 7413 describe a tissue formed with cardiac microchambers using a PEG-patterned polystyrene microstructure to confine cell growth. These microchambers are thus an artifact of artificial cell growth interference and do not recapitulate natural cavity formation by self-organization in early heart development as occurring in vivo. For example, a separate endocardial layer is missing as is the interspace (cardiac jelly) between cardiomyocytes and endocardium.

There remains a need to provide a tissue model, such as an organoid, that resembles in vivo-like self-organisation and recapitulates early heart development—in particular that of heart chambers. The present invention provides such a tissue model and methods for generating it.

SUMMARY

The present invention relates to a heart tissue model of at least 60% cardiac cells irrespective of optional additional cells of a vascular system of the tissue model, or comprising at least 50% cardiac cells; wherein the cardiac cells surround an inner cavity, wherein the cardiac cells are selected from cardiomyocytes, endocardial cells (or also termed cardiac endothelial cells) and epicardial cells.

The invention further provides a method of generating a heart tissue model comprising the steps of: a) providing pluripotent stem cells, preferably in 2D culture; b1) inducing mesoderm differentiation in the presence of a WNT activator and/or GSK3-beta inhibitor, wherein the WNT activator and/or GSK3-beta inhibitor and/or an optional PI3 kinase inhibitor, and/or any one of FGF2, Activin A, BMP4 or a combination thereof, are in an amount sufficient to differentiate the pluripotent stem cells to exit pluripotency in an amount at least 90% of the pluripotent stem cells within 40 hours of starting induction, thereby producing an aggregate of mesoderm cells, or b2) inducing mesoderm differentiation in the presence of a WNT activator and/or GSK3-beta inhibitor, and further in the presence of a PI3 kinase inhibitor and/or any one of FGF2, Activin A, BMP4 or a combination thereof, in a 3D culture in a low attachment culture, wherein the cells aggregate instead of binding to a culturing vessel, thereby producing an aggregate of mesoderm cells; c) differentiating the mesoderm cells of step b) into cardiac mesoderm cells in a 3D culture in a low attachment culture, wherein the cells bind to each other instead of a culturing vessel to form aggregates of the cells, in the presence of cardiac differentiation factors (preferably BMP4, FGF2, Insulin) and in the absence of a WNT activator and/or in the presence of a WNT antagonist, for at least 3 days for cardiac mesoderm formation and formation of an inner cavity. The indices "b1" and "b2" are referred together as "b".

The invention further provides a heart tissue model obtainable the inventive method.

The present invention further provides screening and testing method of using the inventive tissue model or the methods to observe effects of tested or screened compounds or over- or underexpressed genes.

The invention further provides a kit for performing the inventive method. The kit may comprise i) WNT activator and/or GSK3-beta inhibitor, ii) a PI3 kinase inhibitor, iii) a low-attachment cell culturing vessel.

The invention also provides a vessel plate comprising at least 10 compartments, wherein in each compartment a tissue model according to the invention is present. The tissue models may be at substantially the same stage of development.

All embodiments of the invention are described together in the following detailed description and all preferred embodiments relate to all embodiments, aspects, methods, heart tissue models, organoids, uses and kits alike. E.g. kits or their components can be used in or be suitable for inventive methods. Any component used in the described methods can be part of the kit. Inventive tissue models or organoids are the results of inventive methods or can be used in inventive methods and uses. Preferred and detailed descriptions of the inventive methods read alike on suitability of resulting or used organoids or tissue models of the invention. All embodiments can be combined with each other, except where otherwise stated.

DETAILED DESCRIPTION

The present invention provides a self-organising cardiac tissue or organoid model that can develop one large inner cavity reminiscent of animal and human early left heart, e.g. ventricular, and atrial chambers development. Such a tissue is shown e.g. in FIGS. 1 and 2 and 14. The inventive method of generating the tissue model uses natural growth and signalling factors. This development does not require an exogenous matrix scaffold.

Accordingly, the invention provides a heart tissue model of at least 60%, preferably at least 80%, cardiac cells irrespective of optional additional cells of a vascular system of the tissue model, wherein the cardiac cells surround an inner cavity, wherein the cardiac cells are selected from cardiomyocytes, endocardial cells (or also termed cardiac endothelial cells) and epicardial cells (e.g. FIG. 6, 11G). "Selected from" means that the selected species can be from any one of the members that are grouped as selectable species. The heart tissue model may have at least 60%, preferably at least 80%, cardiac cells, especially when finalising the method step c) of the inventive method. It is possible to add additional cells that then infiltrate the tissue model, especially cells of a vascular system, that should therefore may not be counted when considering the figure of at least 60%, preferably at least 80%, cardiac cells. The inventive features remain the same, irrespective of these infiltrating cells—as long as the infiltrating cells do not replace the cardiac cells to the extent that their function, such as a beating cardiac model, is impaired or abolished. In preferred embodiment, the heart tissue model comprises at least 50%, preferably at least 60%, cardiac cells are selected from cardiomyocytes, endocardial cells and epicardial cells (absolute cell count, also counting any further infiltrating cells).

As used herein, the term "comprising" is open to the presence of any further components, unless otherwise specified. A composition, such as the inventive tissue, which is specified to comprise a component, like cells, in an amount which is defined by a numerical range of values is subject to the proviso excluding the presence of that component in an amount outside of that range.

In particular, the inventive tissue model contains mostly cells of cardiac lineage, such as it comprises at least 60%, preferably at least 70%, especially preferred at least 80%, even more preferred at least 90%, of cells of cardiac lineage. The tissue model can contain also lateral plate mesoderm (HAND1+) cells, which are precursors of all the main three cardiac lineages. For example, the tissue model may comprise at least 0.5% lateral plate mesoderm cells and/or up to 30% lateral plate mesoderm cells, e.g. 1% to 20% lateral plate mesoderm cells. In particular, the tissue model does not contain foregut endoderm cells or at most 5% or less, such as at most 3%, at most 1% or at most 0.1%, foregut endoderm cells. Preferably, the heart tissue model of the invention comprises at most 3% or no foregut endoderm-derived (e.g. expressing SOX17+ and/or EOMES+) cells and/or at most 3% or no hemogenic cells, preferably at most 1% hemogenic cells, and/or at most 3% or no ectodermal-derived cells (SOX2+)(e.g. FIG. 2, 3).

It is another hallmark of the inventive heart tissue model that it has a rhythmic beating activity, e.g. like a naturally grown heart in early development.

The cardiac cells may be selected from several cardiac cell types, such as cardiomyocytes, endocardial cells and epicardial cells. The contents of these cell types may differ based on different treatment option as disclosed herein. According to most options, the heart tissue model comprises at least 40% cardiomyocytes. In particular preferred embodiments, the heart tissue model at least 50%, more preferred at least 60%, or particularly preferred at least 80%, cardiomyocytes. In special embodiments the number may even reach at least 90% cardiomyocytes (e.g. FIG. 4, 6, 10).

In further preferred embodiments of the invention, the heart tissue model comprising at least 2%, preferably at least 5%, even more preferred at least 8%, endocardial cells. Endocardial cells are cardiac endothelial cells that form the endocardium in vivo. They are essentially endothelial cells of the cardiac lineage. The endocardial cells form an inner (facing the inner cavity), or in some cases an outer, compartment/lining of the inventive tissue model. Such cells can be identified by expression markers NPR3, NFATC1, HOX1, HOX2, HOX3, HOX4, HOX5. An important point here is that these endocardial cells (ECs) are most similar to in vivo endocardium (so real ECs of the heart)(e.g. FIG. 4). They express higher levels of NPR3 and NFATC1 compared to control ECs of non-cardiac origin. All cell comparisons herein are under standard conditions for cell cultures for maintaining cells expressing relevant distinctive markers or signature marker expression, in particular so that the markers or marker expression can be determined as a cell-intrinsic property; such conditions usually comprise a medium consisting of all required nutrients for maintenance under ambient pressure and at the cells' physiological temperature. The ECs of the inventive tissue model also express the correct HOX genes typical for the heart (HOX1-5)(e.g. FIG. 4). Another characteristic of these cells is that they show activation of mechanosensing genes (SOX18, KLF2, CDH5, FOS, TEK, FOXO1)(e.g. FIG. 4, FIG. 19). This is considered a difference to ECs in other, non-self-organising organoids where ECs are just mixed with cardiomyocytes. The expression of mechanosensing genes is an important biological hallmark of more functional ECs. Accordingly, the endocardial cells of the invention are more functional than ECs in previous 2D and 3D models.

According to the invention, the amount of endocardial cells can be controlled during growth of the tissue model. The tissue model may have varying amounts of endocardial cells, such as at least 2%, preferably at least 4%, or at least 8%, even more preferred at least 10%, at least 15%, at least 20%, at least 25%, at least 30%, at least 35%, at least 40%, endocardial cells. One option to control endocardial cell formation is using VEGF (Vascular Endothelial Growth Factor) during tissue model generation. If no VEGF is used, usually low amounts of endocardial cells are formed, such as less than 10%, in particular as inner layer. These self-developing ECs express the endothelial markers CD31 and CDH5 (e.g. FIG. 8, FIG. 19).

The inventive tissue model is essentially of a hollow shape, preferably with a continuous layer of endocardial cells surrounding the inner cavity and preferably also facing the inner cavity (e.g. FIG. 2, 8, 11G). The continuous layer preferably has no holes and completely surrounds the inner cavity in all directions as viewed from the center of the inner cavity.

The inventive tissue model has a structured composition and cells of a specific type are usually found in particular compartments. Such compartments are usually layers. Preferably the inventive heart tissue model comprising cardiomyocytes and endocardial cells in different tissue layers. The endocardial cells can be in a separate tissue layer, preferably an inner and/or outer layer (e.g. FIG. 4, 7, 8).

In preferred embodiments of the invention there is an interspace between a compartment, preferably layer, of endothelial cells and a compartment, preferably layer, of cardiomyocytes as is observed in vivo (heart tube cardiac jelly) at this stage of development. (e.g. FIG. 7).

In a further preferred embodiment, the heart tissue model of the invention comprises at least 50%, even more preferred at least at least 60%, at least 70%, at least 80%, at least 85%, at least 90%, or at least 95%, cardiomyocytes (e.g. FIG. 4, 6).

Cardiomyocytes are cardiac muscle cells and are mostly responsible for the beating activity of the tissue model. They are the main component of the inventive tissue model and form a layer in the tissue model surrounding the inner cavity. In early development tissues, they may directly face the inner cavity but in later and more developed tissues the inner layer is formed by endocardial cells (e.g. FIG. 2, 8).

The inventive tissue model is essentially of a hollow shape, preferably with a continuous layer of cardiomyocytes surrounding the inner cavity. The continuous layer preferably has no holes and completely surrounds the inner cavity in all directions as viewed from the center of the inner cavity.

One important aspect of the inventive tissue model is that it develops with high purity of cardiac cells. Non-cardiac cells, such as ectodermal, endodermal cells and hemogenic endothelial cells, should not be present (e.g. FIG. 2, 3), or in very low amounts, such as when they have been added to the tissue model later after the inventive development up to the step of differentiating mesoderm cells into cardiac cells. Accordingly, in preferred embodiments the tissue model of the present invention comprises no endodermal cells or at most 5%, preferably at most 2% or at most 1% endodermal cells. Also, or in combination therewith, in preferred embodiments the tissue model of the present invention comprises no hemogenic endothelial cells or at most 5%, preferably at most 2% or at most 1% hemogenic endothelial cells.

One cell type that is preferably added later to the tissue model are epicardial cells. These cells can form a layer surrounding the inventive tissue model. Epicardial cells preferably express cellular markers WT1 and TCF21 (e.g. FIG. 10). The inventive tissue model may have at least 0.5%, preferably at least 5% or at least 10%, epicardial cells, e.g. 0.5% to 30% epicardial cells (e.g. FIG. 11).

In preferred embodiments of the invention the heart tissue model comprises epicardium-derived smooth muscle cells (also referred to as cardiac smooth muscle cells) and/or epicardium-derived cardiac fibroblasts (also referred to as "endocardial-derived fibroblasts" or just referred to as cardiac fibroblasts). These type of smooth muscle cells (SMCs) and fibroblasts develop from the epicardium and are not of a non-cardiac lineage such. The cardiac lineage of these cell types causes a particular pattern in their distribution in the organoid and different expression marker pattern, such as for smooth muscle cells markers SM22 and/or Calponin and for cardiac fibroblasts markers DDR2 and/or Vimentin. These cells (SMCs and fibroblast both of cardiac lineage) migrate into the cardiomyocyte tissue or layer (e.g. FIG. 10, 11).

In particular embodiments, the heart tissue model comprises at most 3%, preferably at most 1%, or no non-epicardium smooth muscle cells and/or at most 3% preferably at most 1%, or no non-epicardium fibroblasts, i.e. SMCs and fibroblasts not of cardiac lineage/that do not develop from epicardium. Non-cardiac cells may disturb investigations of a heart models' natural behaviour and are therefore preferably not present or in low amounts so that cardiac investigations are not disturbed.

The inventive tissue model is artificial and grown in culture using natural principles of development, but not an in vivo grown heart at any of an in vivo heart's development. Due to the culture process, usually the size is limited. In preferred embodiments of the invention, the heart tissue model having a size in its largest dimension of 0.3 mm to 15 mm, such as 0.5 mm to 1 mm. The tissue model is usually a hollow shape that forms essentially a spherical shape but it may have irregularities. Accordingly, for reference the largest dimension of that shape is used to determine its size (e.g. FIG. 1, 2).

This size applies usually for organoids obtainable by the inventive method after steps a) to c) that develops one cavity. It is possible to fuse the inventive heart tissue models, so structures with more than one inner cavity can be generated that are also larger. The preferred sizes then apply to one chamber of that fused tissue model, i.e. one inner cavity with the surround tissue, not extending to tissue layers that surround another inner cavity.

The inner cavity is quite large (as compared to previous heart tissue models) and takes up a major part of the tissue model's volume (both for the single cavity organoids and the fused organoids). Preferably, the size of the inner cavity at its largest dimension is at least 60% of the size of the heart tissue model at its largest dimension. As above, for fused organoids with more than one inner cavity this applies to only one cavity (and the surround tissue, not extending to tissue layers that surround another inner cavity) (e.g. FIG. 1, 2).

Preferably the tissue model is of mammalian cells, preferably human cells or non-human primate cells, or rodent, mouse, hamster, pig, cat, dog, horse, cow cells.

The invention further provides a method of generating a heart tissue model comprising the steps of a) providing pluripotent stem cells, b) inducing mesoderm differentiation in the presence of a WNT activator and/or GSK3-beta inhibitor, and further in the presence of a PI3 kinase inhibitor, in a 3D culture in a low attachment culture, wherein the cells bind to each other instead of a culturing vessel to form aggregates of the cells, thereby producing an aggregate of mesoderm cells, c) differentiating the mesoderm cells of step b) into cardiac cells in a 3D culture in a low attachment culture, in the presence of cardiac differentiation factors and in the absence of a WNT activator and/or in the presence of a WNT antagonist, for at least 3 days, preferably 3-7 days, for cardiac mesoderm formation and formation of an inner cavity (e.g. FIG. 1).

Step b) can be varied with similar effects, such as b) inducing mesoderm differentiation in the presence of a WNT activator and/or GSK3-beta inhibitor, wherein the WNT activator and/or GSK3-beta inhibitor and/or an optional PI3 kinase inhibitor are in an amount sufficient to differentiate the pluripotent stem cells to exit pluripotency in an amount at least 90% of the pluripotent stem cells within 40 hours of starting induction, thereby producing an aggregate of mesoderm cells, wherein the cells are treated with Activin A, bone morphogenetic protein, fibroblast growth factor and/or albumin. In this case, a PI3 kinase inhibitor is not required, but it is still preferred.

In particular preferred embodiments, the treatment with the WNT activator and/or GSK3-beta inhibitor in step b) is combined with a treatment with a bone morphogenetic protein, especially BMP4, in step c). Preferably, bone morphogenetic protein, especially BMP4, can already be used in the treatment of cells in step b). The use of the bone morphogenetic protein is particular advantageous for robust cavity formation and in consequence beating cardiac model generation.

During in vivo embryonic development, the heart is the first functional organ to form in the developing human embryo. The survival of the embryo depends on self-organisation of cardiac progenitors into the four chambered heart and its subsequent maturation. Self-organisation in biology is the ability of cells to self-assemble as they differentiate into organised tissue/organ-like structures either in vivo or in vitro in permissive in vivo-like conditions. This ability of cells to self-organise under the right conditions is crucial for the tissue and organ to function. The inventive method provides the conditions to allow self-organisation into the organoids of the invention, which includes a self-organized formation of a large central cavity, unassisted by any artificial scaffold. It is a hallmark of the invention that a scaffold, such as a polymeric scaffold is not needed and also not present in the final tissue model of the invention. Such scaffolds that may be avoided according to the invention are for example those as described in Ma et al. (supra, background section) and include for example polymers that would reach through the majority of the tissue model, such as extending through at least 75% of the size of the tissue model in its largest dimension. Also preferably avoided are macromolecular polymeric scaffolds of e.g. polymers with a molecular weight of at least 1 Mio Da.

According to the inventive method self-organisation is driven by growth factor signalling and does not require a polymer scaffold (Ma et al., supra) or exogenous extracellular matrix like Matrigel (WO 2019/174879 A1), although Matrigel can still be used as it is not such a hinderance as a polymer scaffold. The addition of extracellular matrix is still preferably avoided because it increases variability in organoid formation.

The inventive method is based on using pluripotent cells that are differentiated to mesoderm and cardiac cells. Initially, the pluripotent cells can be cultures in a common 2D culture but at least from step c) onwards, the culture should be a 3D culture, such as is possible in low attachment culture vessels. Step b) may be in 2D or is preferably also in 3D (as step c)).

The cells provided in step a) are pluripotent. They are not human totipotent cells.

The pluripotent cells are preferably from a mammal, preferably human cells or non-human primate cells, or rodent, mouse, hamster, pig, cat, dog, horse, cow cells.

The pluripotent cells may be from a cell line or a cell culture. They may be pluripotent stem cells or they may be induced pluripotent cells, i.e. stemming from differentiated cells that were again turned pluripotent, such as by treatment with the Yamanaka factors. Usage of induced pluripotent cells allows investigation of cardiac development of specific individuals, which may or may not have genetic aberrations that may affect heart development. In such embodiments the cells may be induced pluripotent cells that originate from a patient suffering from a heart disease, in particular a genetic heart disease.

In preferred embodiments the pluripotent stem cells are grown in a medium before they are provided for the further steps of the inventive method. This may prime and activate the cells for the further differentiation in the inventive method. The pluripotent cells are preferably passaged and/or they may have been cultured, grown or maintained in a medium comprising albumin and/or a fibroblast growth factor. These components preferably both, have proven to exceptionally prime the cells for the desired development of the invention. Albumin may for example be a serum albumin, e.g. a bovine serum albumin (BSA). The fibroblast growth factor is preferably FGF2, especially human FGF2.

Preferably the pluripotent stem cells have been grown in a medium comprising at least 1.5% (w/v) (at least 1.5 g/l), albumin, preferably BSA, and/or at least 100 ng/ml fibroblast growth factor, preferably FGF2.

Preferably a cell culture medium is used, such as E8 medium. It preferably comprises amino acids required for cell growth and an energy source, such as a carbohydrate, especially preferred glucose. It further shall comprise salts and ions needed for cell growth, such as Ca, Fe, Mg, K, Na, Zn, Cl, $SO_4$, $NO_3$, $PO_4$ ions. Further preferred components of the medium are vitamins, such as vitamin B-12, Biotin, choline, folic acid, inositol, niacinamide, pantothenic acid, pyridoxine, riboflavin, thiamine.

Preferred amino acids include essential amino acids, preferably also any one of the following amino acids alanine, arginine, asparagine, aspartic acid, cysteine, cystine, glutamic acid, glutamine, glycine, histidine, isoleucine, leucine, lysine, methionine, phenylalanine, proline, serine, threonine, tryptophan, tyrosine, valine.

A 2D culture may include growing or maintaining the cells on a surface, such as a tissue culture plate. Such a surface may be coated with suitable culturing substrates, such as vitronectin. The cells may then be dissociated or used as aggregates for use in step b). If one or more passaging steps is used before providing the cells for step b), then the cells may be reseeded.

In preferred embodiments, the cells have been cultured or treated in/with such a medium, especially one comprising albumin and/or a fibroblast growth factor, for at least 1 day, preferably at least 2 days, e.g. 1 to 30 days, such as 2 to 20 days—while maintaining pluripotency of course.

In step b) preferably 100 to 1 million cells (dependent on the culturing vessel) pluripotent cells are provided for culturing in one culturing vessel. The culturing vessel may be for 2D culturing, like for step a), e.g. a culturing plate, or for 3D culturing, e.g. as will be further described below for step c), where 3D culturing is mandatory.

In step b) the cells form aggregates that are no longer split or dissociated but kept whole. The pluripotent cells, either as such or during early differentiation steps, form aggregates by clumping together. The number of cells to do this will have an effect on the future tissue model morphology where tissue models grown from fewer cells are usually more homogenous, accordingly using 100 to 10000, e.g. 200 to 6000, pluripotent cells is preferred. Pluripotency can be controlled by determining the markers SOX2, OCT4 and/or NANOG, for example.

The medium as used in step b) for culturing the cells (which form aggregates, usually one main aggregate that persists to form the final tissue model per culturing vessel) may have the same components as described above for step a), such as it preferably comprises amino acids required for cell growth and an energy source, such as a carbohydrate, especially preferred glucose. The medium in step b) further comprises signalling factors or modulators and optional supporting factors that modulate signalling.

One such signalling modulator is a PI3 kinase inhibitor. An example of a PI3 kinase inhibitor is LY294002 but others work too. The use of the PI3 kinase inhibitor is particularly preferred as it results in the cleanest and most homogenous tissue models. Alternatives to using a PI3 kinase inhibitor exist though, like using a high amount of a WNT activator. A PI3 kinase inhibitor has the effect that many pluripotent cells exit pluripotency and differentiate to mesodermal lineage, which determines the future highly homologous cardiac tissue model (with no or few endoderm, foregut or other non-cardiac cells). LY294002 is preferably used in a concentration of 3 μM to 15 μM.

An important signalling factor for step b) is a WNT activator. A WNT activator for step b) may be a WNT ligand, such as WNT-3a, or CHIR99021. Further WNT activators are for *Homo sapiens*: WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11, WNT16. These are highly conserved and homologous exist in other organisms. A further possible WNT activator is R-spondin 1, which acts synergistically with WNT4. WNT4 may be intrinsic to the cells or may be administered to the cells extrinsically.

The inventive WNT activation drives the cells towards mesodermal differentiation. This works particularly efficient when combined with fibroblast growth factor (FGF), bone morphogenetic protein (BMP, preferably BMP4), Activin A and/or albumin, preferably with all four of them. In such a case it may not even be necessary to use a PI3 kinase inhibitor, especially when high levels of WNT activation are used. Indeed, of these factors, the combination of WNT activation and albumin suffices to produce robust and reproducible tissue models of the invention. As such it is possible in an alternative for step b) to use WNT activation and albumin so that the desired amount of pluripotent stem cells exit pluripotency (and differentiate to mesodermal lineage) within 24-40 hours of cultivation according to step b). This works best with higher than usual amounts of WNT activation. In an alternative (of course also combinable) to (with) albumin FGF is used in combination with BMP and/or activin A.

Preferably, in case the WNT activator is in an amount sufficient to differentiate the pluripotent stem cells to exit pluripotency in an amount at least 90% of the pluripotent stem cells within 40 hours of starting induction then the amount of CHIR99021 as WNT activator is in a concentration of at least 6 μM, preferably at least 9 μM, such as 12 μM.

If a PI3 kinase inhibitor is used then the WNT activation may be in usual low levels, e.g. wherein CHIR99021 as WNT activator is in a concentration of at least, 0.5 μM, preferably 0.5 μM to 12 μM.

Preferably the mesoderm differentiation (step b)) is induced in a medium comprising activin A and/or bone morphogenetic protein, preferably further fibroblast growth factor. A preferred or bone morphogenetic protein (BMP) is BMP4, in particular human BMP4. Preferably the mesoderm differentiation is induced in a medium comprising at least 8 ng/ml bone morphogenetic protein, preferably BMP4. Furthermore, alternatively or in combination, mesoderm differentiation is induced in a medium comprising fibroblast growth factor (FGF) and/or albumin, preferably BSA. Preferred concentrations for FGF are at least 10 ng/ml depending on the batch activity, preferably at least 50 ng/ml, such as 150 ng/ml or more; and for albumin preferred concentrations are 0.2% (w/v) or more, such as 0.4% (w/v) or more, preferably of BSA. Especially albumin, like serum albumin and/or FGF are preferred medium additives because these compounds help to promote uniform and robust differentiation of the forming cell aggregates to a mesoderm (and later cardiac) fate using different pluripotent cell lines.

Activin, e.g. activin A, may be used to specify the tissue model towards a ventricular or atrial fate. Generally, high Activin (e.g. 10 ng/ml or higher) steers the tissue model towards a atrial fate, lower activin (e.g. lower than 10 ng/ml) steers the tissue model towards a ventricular fate. These example concentrations may vary depending on the cell type used.

Culturing of step b) in the specified medium is preferably 18 to 40 hours, preferably 24 to 39 hours, in particular 30 to 38 hours, such as 36 hours. Mesoderm differentiation can be controlled by determining mesoderm cells expressing the markers BRA/T (e.g. FIG. 2), MIXL1, TBX6 and/or GSC. A majority of the cells, such as the desired at least 90% of the cells, should express these markers at the end of step b).

Step b) (optional) and step c) (and optional further steps, like d) and a maturation) contain culturing in 3D culture, which means that the aggregates are not attached to a surface but remain free floating in a suspended condition so that expansion in all 3D directions is uniformly possible. Such culturing is in a low attachment culture so that the aggregates do not attach to culture vessel walls. Preferably, the low attachment culture comprises culturing the cells in a container with a low attachment surface that inhibits adherence of the cells to the surface. Low attachment surfaces are preferably hydrophilic, neutrally charged or non-ionic. They may have a hydrogel layer or coating that repels cell attachment, forcing cells into a suspended state. Such low attachment culture vessels are known in the art, e.g. described in WO 2019/014635 or WO 2019/014636. Preferably the bottom the culturing vessel is round, especially concave. Alternatively, it may be flat or have a V-bottom shape.

Step c), differentiating the mesoderm cells into cardiac cells, comprises differentiating the mesoderm cells of step b) into cardiac cells in a 3D culture in a low attachment culture, wherein the cells bind to each other instead of a culturing vessel to form aggregates of the cells, in the presence of cardiac differentiation factors and in the absence of a WNT activator and/or in the presence of a WNT antagonist, for at least 2 days, preferably for 3-7, e.g. up to 5, days, for cardiac mesoderm formation and formation of an inner cavity. A WNT antagonist is preferably not used for the entire duration of step c). Preferably a WNT antagonist is used for 12 hours to 72 hours, preferably 24 to 60 hours. Step c) is preferably performed until at least 80% of the cells of the tissue culture have left a pluripotent and a non-cardiac mesoderm stage. A "non-cardiac mesoderm stage" is a multipotent stage and precursor to a cardiac differentiation stage where the cells are not yet differentiated to cardiac lineage. Such a treatment according to step is preferably for at least 2, 3, 4, 5 days and preferably up to 7 or 5 days.

Cardiac mesoderm formation and cardiac progenitor differentiation can be controlled by determining cardiac cells expressing the markers NKX2-5, HAND1, HAND2, TBX5, MYH6, MYH7, MYL7, Troponin T, Troponin I and/or a-Actinin (e.g. FIG. 2, 4, 5, 6, 7).

Preferably step c) comprises culturing in a medium with fibroblast growth factor, bone morphogenetic protein, or a combination thereof. These compounds further differentiate the mesoderm cells obtained from step b) into cardiac cells, i.e. they act as cardiac differentiation factors. The medium preferably further comprises insulin, which helps cell growth, proliferation and survival, especially when the medium contains glucose as energy source.

In preferments of all embodiments of the invention, the cells are treated with Activin A, bone morphogenetic protein (BMP, preferably BMP4) and/or fibroblast growth factor (FGF, preferably FGF2) in step c), especially preferred all of these compounds. These compounds and factors increase robustness and cavity formation of the inventive tissue model. Preferably and/or albumin is used in also used, optionally in combination with Activin A, BMP and/or FGF. Albumin protects cells from toxicity of small molecules such as the WNT activators/inhibitors and is therefore highly recommendable in step c), but also or alternatively in step b).

WNT antagonists are known in the art. They are also referred to as WNT inhibitor and inhibit WNT pathway activity. WNT antagonist is preferably selected from Wnt-059, IWR-1, XAV939, IWP-2, IWP-4, DKK1 or a combination thereof (e.g. FIG. 9). Particular preferred WNT antagonists are IWP2 and XAV, such as at a concentration of at least 1 µM, preferably at least 5 µM. The WNT antagonist may not be used for the entire duration of step c) (at least 3 days) but may e.g. but used for only 12 h to 48 h, preferably 18 h to 36 h, especially at the start of step c) or its treatment beginning within 12 h form the start of step c). Preferably the WNT antagonist is used at least 3 days or throughout the entire step c). The medium as used in step c) may be similar as in step b), preferably comprising comprises amino acids required for cell growth and an energy source, such as a carbohydrate, especially preferred glucose. Vitamins and/or salts are further preferred as described above.

The medium preferably comprises fibroblast growth factor, preferably FGF2, at a preferred concentration of at least 6 ng/ml. The medium preferably comprises bone morphogenetic protein, preferably BMP4, at a preferred concentration of at least 8 ng/ml.

After step c) the cells, that form aggregates with cavities at this point are further left to differentiate in an appropriate medium. This is done in an optional step d). Accordingly, the inventive method comprises step d), further differentiating the aggregate with cardiac mesoderm into a tissue with a cardiomyocyte layer with cardiac differentiation factors for a further one day or more, such as 1 to 3 days, preferably 2 days. Medium, culturing vessels and differentiation factors may be the same as for step c). WNT inhibition is not used at this point anymore. The medium for step d) preferably comprises fibroblast growth factor, preferably FGF2, at a preferred concentration of at least 6 ng/ml. The medium preferably comprises bone morphogenetic protein, preferably BMP4, at a preferred concentration of at least 8 ng/ml. Preferably also insulin is used. Retinoic acid may be further used during this step, which drives differentiation further for complete differentiation.

Preferably the media in each step a), b) and or c) and/or d) is changes every day or every 2 days or any interval in between these values.

The inventive method may further comprise maturation of the cells in a medium with nutrients, preferably at least until an inner layer of cardiac endothelial cells is formed lining the inner cavity. Further induction of differentiation is not needed for such a maturation step. After steps c) or d), the tissue models are stable and can be maintained. During such maintenance the cells may mature further, while keeping the inventive hallmark, the large inner cavity. Maturation may lead to the formation of an inner layer of cardiac endothelial cells, e.g. that resembles the endocardial lining in vivo (e.g. FIG. 8).

Cardiac endothelial cell differentiation may be prevented by using a VEGF signalling (vascular endothelial growth factor) inhibitor. According to one option of the invention, a VEGF inhibitor is applied at steps b) and/or c), and/or optional step d), to prevent differentiation of cardiac endothelial cells. An example VEGF inhibitor is the VEGFR inhibitor Sunitinib or an anti-VEGF antibody (e.g. FIG. 5, 6).

On the other hand, it is possible to culture the cells with VEGF to increase the formation of cardiac endothelial cells. An example VEGF is VEGF-A. This will lead to tissue models with larger endothelial cell contents as described above, e.g. 40% or more cardiac endothelial cells. VEGF is preferably applied in step b), preferably optionally also in step c) or not in step c)(e.g. FIG. 4, 7).

When VEGF is used, it was surprisingly found that WNT activation (in step b) can be used to control the location of endothelial cell formation, i.e. inside (facing the inner cavity) or on the outside of the tissue model. Such a method may comprise adding WNT activator, preferably CHIR99021, in an amount sufficient to induce formation of cardiac endothelial cells on the outside of the heart tissue model, preferably 1 uM-10 µM CHIR99021, during step b). Lower WNT amounts may lead to the formation of an inner endothelial cell layer, such as no CHIR to 5 µM CHIR99021 depending on the cell line (e.g. FIG. 4, 7, 8). Addition of VEGF helps to develop tissue models with three separate layers, such as in the following orientation, from the inside to the outside: cavity—cardiomyocytes, endocardial-derived fibroblasts and cardiac endothelial cells (FIGS. 18 F, F', F" and 19A). The inventive tissue model may have this orientation. It is also possible to stimulate development of an inner endothelial lining without VEGF, e.g. in conditions with low activin, e.g. low activin A, such as 5 ng/ml or less. These numbers may vary depending on the cell types used. The tissue model may have an inner endothelial lining.

The inventive method may optional further comprise the step of adding epicardial cells to the tissue model (e.g. FIG. 11). This step may be done directly after steps c), d) or anytime during maturation. The addition of epicardial cells leads to the formation of an epicardial layer on the outside on the tissue model. After even further maturation, this epicardial layer may give rise to cardiac SMCs and/or fibroblast as noted above. The epicardial cells may be simply added to the culture of the heart tissue models and may attach to the models and extend/migrate thereon to provide the outer layer.

The inventive heart tissue may be used to recapitulate specific normal or abnormal conditions of the heart, such as diseases, illnesses or injuries, as well as a recovery from such conditions. The inventive heart tissue model may comprise an injury or a healed injury. The inventive method may comprise causing an injury to the tissue model and optionally further a recovery from such an injury. Agents, like test compounds, can be tested to cause such a condition or to test the compound's effects during an injury as well as for or during recovery and/or healing processes.

The injury or healed injury of the tissue model may comprise elevated amounts of fibroblasts and/or collagen and fibronectin as compared to non-injured parts of the heart tissue model. E.g. the elevated amounts of fibroblasts in the injury or healed injury are at least 2-fold, preferably at least 3-fold, especially preferred 3-fold to 25-fold, such as 3.3-fold to 21.7-fold, as compared to the non-injured parts of the heart tissue model. The elevated amounts of collagen and/or fibronectin in the injury or healed injury may be at least 1.1-fold, preferably at least 1.25-fold, especially preferred 1.3-fold to 3-fold, such as 1.33-fold to 2.13-fold, as compared to the non-injured parts of the heart tissue model.

The injury or healed injury can be from freezing, e.g. a cryo-injury. A cryo-injury is a reproducible injury model and is preferably used for standardised studies, such as of test compounds mentioned above.

The injury or healed injury part of the heart tissue model is preferably 1% to 30%, preferably 4% to 20%, of the volume of the heart tissue model. Since cells, e.g. fibroblast migrate from healthy tissue to the injured tissue, it is preferred that enough healthy tissue remains. In other embodiments, fibroblasts may also migrate from adjacent tissues and their migration is not dependent on the healthy volumes. AS such also injured or healed injured parts of larger sizes are possible, e.g. 1% to 80% of the volume of the tissue model, preferably 10% to 60% of the volume of tissue model.

The injury or healed injury may comprise increased collagen amounts as compared to a non-injured part of the tissue model or a collagen deposit. Such an increase may e.g. be at least 1.5-fold, or at least 2-fold.

The invention further provides a heart tissue model obtainable by any method of the invention. The obtained heart tissue model may have any of the structural elements as described above.

The present invention further comprises a kit for performing a method of the invention. Such a kit may comprise a i) WNT activator and/or GSK3-beta inhibitor, ii) a PI3 kinase inhibitor, iii) a low-attachment cell culturing vessel. All of these, in particular preferred examples thereof, are described above. The kit may comprise any further component used in the media as described above. For example, it may further comprise a WNT inhibitor, BMP, FGF, Insulin, albumin etc. In particular preferred is a combination with BMP, or any other further or alternative compound for the reasons provided above. The kit may be used in a method of using the inventive methods as described above.

The kit may further comprise instructions for performing the inventive method. Such instructions may be in printed form or in a computer-readable format on a suitable data carrier.

The present invention further provides a vessel plate comprising at least 10 compartments. The inventive method provides homogenous and reproducible results so that in each compartment a tissue model according to the invention is present, preferably at substantially the same stage of development. The high reproducibility and robustness of the method is an advantage especially when performing parallel comparative tests, such as genetic screenings or compound testing (e.g. FIG. 9, 12).

The inventive method can be used for screening or testing a candidate compound on its effects on heart development and function (e.g. FIG. 9). Such a method may comprise generating a heart tissue model according to the invention while treating the cells (at any stage during development, e.g. step a), b) and/or c) and/or d), with the candidate compound. Also, the final tissue model may be used to test the candidate compound. The method may comprise comparing development or functionality of the heart tissue model with development or functionality of a heart tissue model that was not treated with the candidate compound. For comparison all treatment steps should be the same except of course the treatment with the candidate compound. An example function is e.g. any heart function, like the beating behaviour (e.g. intensity and/or rhythm, e.g. arrhythmias) or metabolic turnover or genetic expression of genes of interest that may be influenced by the candidate compound. Development of function may be a toxic development or function that may be caused by the candidate compound. As such, the inventive method or tissue model can be used for toxicity testing or screening.

Similarly, to candidate compounds, a genetic alteration may be tested. E.g. The invention provides a method of observing the effects of mutated (e.g. disease-related), suppressed or overexpressed genes during heart development comprising generating a heart tissue model according to the invention wherein the cells have a suppressed candidate gene or overexpress a candidate gene and comparing development of the heart tissue model with development of a heart tissue model that was not generated with a suppressed or overexpressed gene (e.g. FIG. 12). Mutation, overexpression or suppression of expression can be done with any known method in the art, such as suppression by gene knock out, siRNA inhibition or CRISPR/Cas-based inactivation. Overexpression can be done by introduction of a transgene or applying a gene activator that leads to upregulation of expression of a gene. Such mutated tissues or method using mutation in the cells and generating inventive cardiac tissues with these cells can also be used for screening or testing a candidate compound as discussed above. As such, the invention provides using the inventive cardiac tissues or the methods as disease models, e.g. heart disease models, in particular to study heart functionalities. Accordingly, the method of screening or testing a candidate compound can also be combined with observing the effects of sup-pressed or overexpressed genes. In the combined method, the comparisons can be made between the variants of the tissue or method with ("drugged") or without ("not-drugged") candidate treatment, both with the mutation or between the mutated and non-mutated variants, both in drugged configuration, or a comparison between all four states (mutated+drugged, mutated+not-drugged, non-mutated+drugged, non-mutated+not-drugged).

Provided is the following experimental outline, which highlights some preferred elements that can be selected according to the invention. Therein, even more preferred elements are given in brackets:

A first pluripotent media for growing pluripotent stem cells that can be provided in step a) is preferably based on E8 media. This medium is modified by including BSA (2.5 μg/ml) and by increasing the dose of human FGF2 to 200 ng/ml. The cells are passaged in 12-well plates either by TrypLE as single cells or by EDTA as small clumps, but this does not affect organoid generation. When pluripotent cells are grown in standard commercial conditions without the above combinations, the protocol did not work as well. The pluripotency stage is characterized by expression of SOX2, OCT4 and NANOG as the main cell markers.

The next stage in the protocol is mesoderm induction in differentiation (Step b)). Base differentiation media CDM (Johansson & Wiles Molecular and Cellular Biology, 1995, p. 141-151) is used. It contains BSA as noteworthy addition. The CDM differentiation media contains the signaling ligands FGF2 (200 ng/ml), Activin A (50 ng/ml), BMP4 (10 ng/ml) and CHIR99021 (activator of WNT signaling) at varying concentrations. As unique aspect PI3-kinase inhibitor LY294002 (at 5-10 μM) is used. The purpose is to ensure all cells exit pluripotency within 24 h, so that the differentiation is more homogenous later on. However, Activin, FGF2 and BMP4 addition are not essential as it is possible to get mesoderm induction only with CHIR99021 (also abbreviated "CHIR") in CDM, but in this case results might be more variable. The CHIR dosage is optimized for different lines and it varies from 1 μM to about 10 μM. Typical mesoderm markers expressed at this stage are: BRA, EOMES, MIXL1, TBX6, GSC.

One point about the mesoderm induction is the timing when the differentiation is induced. Three options have been tested and work: pluripotent cells from a 2D 12-well plate are split and seeded into a 96-well ULA (ultra-low attachment) plate, left for another 18-36 h in E8 pluripotency media and then mesoderm is induced. The second possibility is to seed the pluripotent cells and start the mesoderm induction in CDM immediately, and the third option is to start mesoderm induction in 2D culture and after the first 36 h step, split the cells into the 96-well low-attachment plate for 3D cultivation. The second and the third option tend to give cleaner and more homogenous differentiations with higher number of cells (e.g. >2000 cells/aggregate, however the first option works as homogenous with <2500 cells).

The next stage is cardiac mesoderm differentiation (Step c)), which is continued in the 96-well ULA plates, it lasts for 4 days and this is the time when inner cavities appear. It is performed in CDM media with FGF2, Insulin, BMP4 and WNT inhibition by the IWR-1, XAV939 or IWP-2 inhibitors (also others work). It was found that external WNT inhibition alone is sufficient to induce the cavities in CDM medium. However, the endogenous activity of other pathways like BMP that is downstream of WNT is also beneficial. This stage is where the cardiac-specific program gets activated including some structural markers that will continue to rise until day 7 of the protocol. The structural markers seen are: MYH6, 7, MYL7, Troponin T, a-Actinin; transcription factors that drive this program upstream are: NKX2-5, HAND1, TBX5, ISL1, GATA4/6.

A final maturation stage with further differentiation uses FGF2 and BMP4 for 2 days and this drives robustly the final differentiation into beating cardiomyocytes as in vivo. This stage again is not essential because leaving cells only in CDM plus insulin can be sufficient, but will be variable. The cells at this stage continue to express the structural and transcription factor markers mentioned for the cardiac mesoderm stage. When the final stage is maturation in CDM+ insulin only, then the cardiomyocyte organoids tend to mature further after about a month as seen by the upregulation of the MYL2 ventricular marker. In general, these cardiomyocytes in 3D organoids have higher levels of cardiac gene expression compared to cardiomyocytes in 2D. With this protocol cardiac endothelial cell (ECs, CD31+, CDH5+) show up over time—they are detectable already around day 4-5, but increase in number after a month and form a nice lining of the cavity inside. However, the vast majority of cells in this basic protocol are still cardiomyocytes (about 80-90%), while cardiac endothelial cells are essentially the rest. Other cell types were not detected—no endoderm or ectoderm derivatives.

If organoids with more cardiomyocytes (over 95%) should be produced without even any endothelial cells then a VEGF inhibitor, like Sunitinib (100 nM, a VEGF pathway inhibitor) can be used in the first 10 days of differentiation or longer (e.g. FIG. 6). Advantageously, both protocols (without and with VEGF) allow maintenance of these structures for months, which is again very important for applications and screening tests.

It is possible to control cell ratios. For example, it is possible to modify the cardiac mesoderm stage by adding VEGF (200 ng/ml) to induce also endothelial cell fate. With 200 ng/ml VEGF the cardiomyocyte to endothelial cells ratio is typically around 53% endothelial cells and 41% cardiomyocyte with around 5% variation (other ratios are possible by changing the VEGF concentration)(e.g. FIG. 4). The endothelial cells form a compartment/lining around the cardiomyocytes in conditions with high WNT activity (5-8

µM CHIR) during mesoderm induction vs inside lining facing the cavity in organoids induced using lower WNT activity (1-4 µM CHIR). So, it is possible to control the cell ratios but also whether the endothelial lining is inside or outside. This control is an important aspect because different applications may depend on it. Moreover, there is a space between the endothelial and cardiomyocyte compartments as observed in vivo during the heart tube stage. We can observe expression of fibronectin on the cardiomyocytes facing that space which is consistent with the in vivo situation. This is a major component for the cardiac jelly that forms between endothelial cells and cardiomyocytes.

An important point here is also that these endothelial cells are most similar to endocardium (so they are real cardiac endothelial cells of the heart) as they express higher levels of NPR3 and NFATC1 compared to control non-cardiac endothelial cells (e.g. FIG. 4E). They also express the correct HOX genes typical for the heart (HOX1-5 range).

Another important point is that activation of mechano-sensing genes (SOX18, KLF2, CDH5, FOS, TEK, FOXO1) in endothelial cells from organoids is observed as opposed when endothelial cells are just cultured in 2D. This is a very important biological hallmark of more functional true cardiac endothelial cells (e.g. FIG. 4).

A third lineage that is preferably added is the epicardium (WT1+, TCF21+, TBX18+) for which additional steps are applied. Again, CDM is preferably used in 3D culture (e.g. FIG. 10, 11). Epicardial cells are added to the cardiac organoids which produces an epicardium that engulfs the organoids from the outside within days (as in vivo, and then later the epicardium cells differentiate into smooth muscle cells (SM22+, Calponin+) and cardiac fibroblasts (DDR2+, Vimentin+) that migrate into the cardiomyocyte tissue (e.g. FIG. 11). This is what is happening also in vivo. Smooth muscle cells and fibroblasts are not simply added but develop naturally, which is important for their proper function. The natural development of the system is important for the functionality of the end product.

Overall, there are several possible end-products. Preferred tissue models or organoids are with: a) over 95% cardiomyocyte pure organoids, b) 90% cardiomyocytes and 10% endothelial cells with inner lining; c) 45% cardiomyocytes and 55% endothelial cells (or some other ratio that can be manipulated by VEGF), d) cardiomyocytes and epicardium alone, f) all three main lineages together (e.g. FIG. 11G), g) and finally if the epicardium differentiates into cardiac smooth muscle cells and cardiac fibroblasts, there will be five cell types in there, all essential for heart function and all are cardiac cell types as in vivo (e.g. FIG. 11). No cell types are detectable that do not belong in the heart (like endoderm, hemogenic endothelium, non-cardiac smooth muscle cells and non-cardiac fibroblasts that are not derived from epicardium, etc.). In preferments, the tissue model comprises endocardial-derived fibroblasts, such as 0.1% to 40%, preferably 1% to 35%, especially preferred 10% to 30%, endocardial-derived fibroblasts. Preferably the tissue model comprises at least 1%, preferably at least 5%, endocardial-derived fibroblasts.

A hallmark of the invention is the architecture—so cardiomyocytes or endothelial cells facing one inner cavity, epicardial cells around the structure and migrating cardiac smooth muscle cells and cardiac fibroblasts migrate into the myocardium. This is how cardiac cavities/chambers are formed also in vivo and this specific architecture with all its variations is very important for functionality and applicability to model and test in vivo like development and physiological behaviour.

The present invention is further described by the following numbered embodiments:

1. A heart tissue model of at least 60% cardiac cells irrespective of optional additional cells of a vascular system of the tissue model, or comprising at least 50% cardiac cells; wherein the cardiac cells surround an inner cavity, wherein the cardiac cells are selected from cardiomyocytes, endocardial cells and epicardial cells.

2. The heart tissue model of 1 comprising at least 30% cardiomyocytes.

3. The heart tissue model of 2 further comprising at least 2% endocardial cells.

4. The heart tissue model of any one of 1 to 3 comprising cardiomyocytes and endocardial cells in different tissue layers.

5. The heart tissue model of any one of 1 to 4 comprising epicardial cells in a separate tissue, preferably an outer layer.

6. The heart tissue model of any one of 1 to 4 comprising at least 40%, preferably at least 60%, more preferred at least 80%, cardiomyocytes.

7. The heart tissue model of any one of 1 to 6 comprising at most 5%, preferably at most 3%, or no foregut endodermal cells and/or at most 3% or no hemogenic cells.

8. The heart tissue model of any one of 1 to 7 comprising epicardium smooth muscle cells and/or epicardium cardiac fibroblasts.

9. The heart tissue model of any one of 1 to 8 comprising at most 3% or no non-epicardium-derived smooth muscle cells and/or at most 3% or no non-epicardium-derived or endocardium-derived fibroblasts.

10. The heart tissue model of any one of 1 to 9 having a size in its largest dimension of 0.3 mm to 15 mm.

11. The heart tissue model of any one of 1 to 10 wherein the size of the inner cavity at its largest dimension is at least 20% of the size of the heart tissue model at its largest dimension.

12. The heart tissue model of any one of 1 to 11 wherein cardiomyocytes or endocardial cells directly face the inner cavity.

13. The heart tissue model of any one of 1 to 12 comprising an injury or a healed injury.

14. The heart tissue model of 13, wherein the injury or healed injury comprises elevated amounts of fibroblasts, collagen and/or fibronectin as compared to non-injured parts of the heart tissue model.

15. The heart tissue model of 14, wherein the elevated amounts of fibroblasts in the injury or healed injury are at least 2-fold, preferably at least 3-fold, especially preferred 3-fold to 25-fold, such as 3.3-fold to 21.7-fold, as compared to the non-injured parts of the heart tissue model.

16. The heart tissue model of 14 or 15, wherein the elevated amounts of fibronectin and/or collagen in the injury or healed injury are at least 1.1-fold, preferably at least 1.25-fold, especially preferred 1.3-fold to 3-fold, such as 1.33-fold to 2.13-fold, as compared to the non-injured parts of the heart tissue model.

17. The heart tissue model of any one of 13 to 16 wherein the injury or healed injury is from freezing, e.g. a cryo-injury.

18. The heart tissue model of any one of 13 to 17 wherein the injury or healed injury part of the heart tissue model is at 1% to 30%, preferably 4% to 20%, of the volume of the heart tissue model.

19. A method of generating a heart tissue model comprising the steps of
  a) providing pluripotent stem cells,
  b) inducing mesoderm differentiation in the presence of a WNT activator and/or GSK3-beta inhibitor, and further in the presence of a PI3 kinase inhibitor, in a 3D culture in a low attachment culture, wherein the cells bind to each other instead of a culturing vessel to form aggregates of the cells, thereby producing an aggregate of mesoderm cells,
  c) differentiating the mesoderm cells of step b) into cardiac cells in a 3D culture in a low attachment culture, wherein the cells aggregate with each other instead of binding to a culturing vessel to form aggregates of the cells, in the presence of cardiac differentiation factors and in the absence of a WNT activator and/or in the presence of a WNT antagonist, for at least 3 days, preferably for 3-7 days, for cardiac mesoderm formation and formation of an inner cavity.

The method may further comprise separating endothelial and cardiomyocyte compartment by a space, e.g. as in vivo.

20. A method of generating a heart tissue model comprising the steps of
  a) providing pluripotent stem cells,
  b) inducing mesoderm differentiation in the presence of a WNT activator and/or GSK3-beta inhibitor, wherein the WNT activator and/or GSK3-beta inhibitor and/or an optional PI3 kinase inhibitor are in an amount sufficient to differentiate the pluripotent stem cells to exit pluripotency in an amount at least 90% of the pluripotent stem cells within 40 hours of starting induction, thereby producing an aggregate of mesoderm cells, wherein the cells are treated with fibroblast growth factor and/or albumin,
  c) differentiating the mesoderm cells of step b) into cardiac cells in a 3D culture in a low attachment culture, in the presence of cardiac differentiation factors and in the absence of a WNT activator and/or in the presence of a WNT antagonist, for at least 3 days, preferably 3-7 days, for cardiac mesoderm formation and formation of an inner cavity.

The method may further comprise separating endothelial and cardiomyocyte compartment by a space, e.g. as in vivo 21. The method of 19 or 20, wherein the WNT activator in step b) is a WNT ligand, such as WNT-3a, or CHIR99021.

22. The method of 20, wherein in case the WNT activator is in an amount sufficient to differentiate the pluripotent stem cells to exit pluripotency in an amount at least 90% of the pluripotent stem cells within 40 hours of starting induction then the amount of CHIR99021 as WNT activator is in a concentration of at least 1 μM, preferably at least 6 μM, or 12 μM in case the PI3 kinase inhibitor is present then CHIR99021 as WNT activator is in a concentration of at least, 0.5 μM, preferably 0.5 μM to 12 μM μM.

23. The method of any one of 19 to 22, wherein the pluripotent stem cells are induced pluripotent stem cells or cells from a cell line and/or wherein the provided pluripotent stem cells of step a) have been passaged, preferably in a medium comprising albumin and/or a fibroblast growth factor, more preferred further comprising BMP and/or Insulin.

24. The method of any one of 19 to 23, wherein provided pluripotent stem cells of step a) have been grown in a medium comprising at least 1.5% (w/v), albumin, preferably BSA, and/or at least 100 ng/ml fibroblast growth factor, preferably FGF2, more preferred further comprising BMP and/or Insulin.

25. The method of any one of 19 to 24 wherein the PI3 kinase inhibitor is LY294002 or any other PI3 kinase inhibitor.

26. The method of any one of 19 to 25, wherein mesoderm differentiation is induced in a medium comprising activin A and/or bone morphogenetic protein, preferably further fibroblast growth factor.

27. The method of 26, wherein mesoderm differentiation is induced in a medium comprising at least 1 ng/ml bone morphogenetic protein, preferably BMP4.

28. The method of any one of 19 to 27, wherein mesoderm differentiation is induced in a medium comprising fibroblast growth factor and/or albumin, preferably BSA.

29. The method of any one of 19 to 28, wherein the low attachment culture comprises culturing the cells in a container with a low attachment surface that inhibits adherence of the cells to the surface.

30. The method of any one of 19 to 28, wherein differentiating the mesoderm cells into cardiac cells comprises culturing in a medium with fibroblast growth factor, insulin, bone morphogenetic protein, or a combination thereof.

31. The method of any one of 19 to 30, wherein the WNT antagonist is selected from Wnt-059, IWR-1, XAV939, IWP-2, IWP-4 DKK1.

32. The method of any one of 19 to 31, further comprising d) further differentiating the aggregate with cardiac mesoderm into a tissue with a cardiomyocyte layer with cardiac differentiation factors for a further one day or more.

33. The method of any one of 19 to 32 further comprising maturation of the cells in a medium with nutrients, preferably at least until an inner or outer layer of cardiac endothelial cells is formed, preferably lining the inner cavity or surrounding a cardiomyocyte layer, optionally separated by a space.

34. The method of any one of 19 to 33 further comprising applying a VEGF inhibitor at steps b) and/or c), and/or optional step d) of 32, to prevent formation of an inner layer of cardiac endothelial cells.

35. The method of any one of 19 to 33 further comprising culturing the cells with VEGF to increase the formation of cardiac endothelial cells and/or cardiac fibroblasts.

36. The method of 35, comprising adding WNT activator, preferably CHIR99021, in an amount sufficient to induce formation of cardiac endothelial cells on the outside of the heart tissue model, preferably 1-12 µM CHIR99021, during step b).

37. The method of any one of 19 to 36, further comprising the step of adding epicardial cells to the tissue model.

38. The method of any one of 19 to 37, wherein the cells are treated with albumin in step b).

39. The method of any one of 19 to 38, wherein step a) is in 2D culture, preferably wherein step b) is also in 2D culture.

40. The method of any one of 19 to 39, comprising the step of causing an injury, preferably a cryo-injury, of a part of the tissue model, preferably in a part of 1% to 30%, preferably 4% to 20%, of the volume of the heart tissue model.

41. A kit for performing a method of any one of 19 to 40 comprising i) WNT activator and/or GSK3-beta inhibitor, ii) a PI3 kinase inhibitor, iii) a low-attachment cell culturing vessel.

42. The kit of 41 further comprising a WNT inhibitor.

43. A heart tissue model obtainable by a method of any one of 19 to 40, preferably as further defined as in any one of 1 to 18.

44. A vessel plate comprising at least 10 compartments, wherein in each compartment a tissue model according to any one of 1 to 18 and 43 is present at substantially the same stage of development.

45. The method of any one of 19 to 40 for screening or testing a candidate compound on its effects on heart development and/or functionality comprising generating a heart tissue model according to any one of 19 to 40 while treating the cells with the candidate compound and comparing development of the heart tissue model with development and/or or functionality of a heart tissue model that was not treated with the candidate compound.

46. The method of observing the effects of suppressed or overexpressed genes during on heart development comprising generating a heart tissue model according to any one of 19 to 40 wherein the cells have a suppressed candidate gene or overexpress a candidate gene and comparing development of the heart tissue model with development of a heart tissue model that was not generated with a suppressed or overexpressed gene.

47. The method of screening or testing a candidate compound on its effects on heart development and/or functionality according to 45 in combination with observing the effects of suppressed or overexpressed genes during on heart development according to 46.

The present invention is further illustrated by the following figures and examples, without being limited to these embodiments of the invention.

H9, WTC. (E) Chamber-like structures and 2D CMs display calcium transients that are similar. Calcium transients were analyzed by loading the cells with Fluo-4-AM and analyzing the fluorescence intensity over time. F/F0: Fluorescence intensity over background. ISI: inter-spike-interval. (F) Analysis of beating parameters using a published algorithm (Huebsch et al., 2015, Tissue Engineering Part C: Methods 21, 467-479). (G) Representative average action potential trace of ventricular cardioid (d10), with listed APD30, APD50, and APD90. The organoids contracted with a mean frequency (dT) of 7.33 seconds. Average was taken over 14 action potentials from one organoid using the FluoVolt system. Used cell line in all experiments of this figure: WTC (if not stated otherwise).

Figure 2:
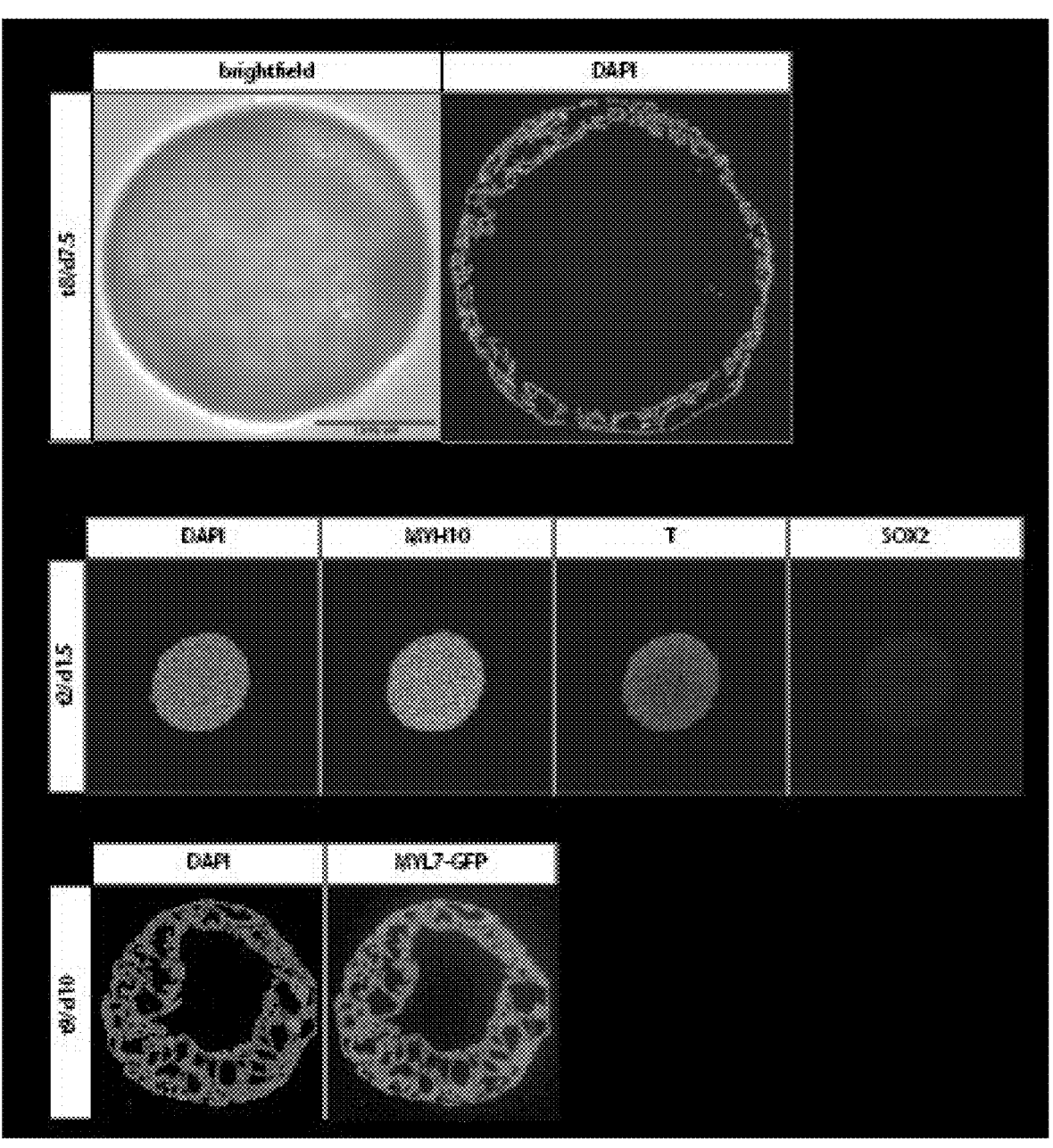
FIG. 2: A Cardiac organoid at d7.5 derived from hPSCs (WTC MYL7-GFP) using a concentration of 8 uM CHIR99021 during induction. Left: whole mount brightfield image showing the size of the organoid. Right: Cryosection of stained with DAPI showing the relation of organoid to cavity size. B Aggregate of mesodermal cells derived from 1000 hPSCs (WTC MYH10-GFP) showing that hPSCs efficiently exited pluripotency after 40 h of mesoderm induction (using 8 uM CHIR99021) by upregulation of the primitive streak marker T and downregulation of the pluripotency marker SOX2. C Cardiac organoid (WTC MYL7-GFP after 10 days in culture showing expression of the endogenous expression of the cardiomyocyte-specific marker MYL7.
Figure 23:
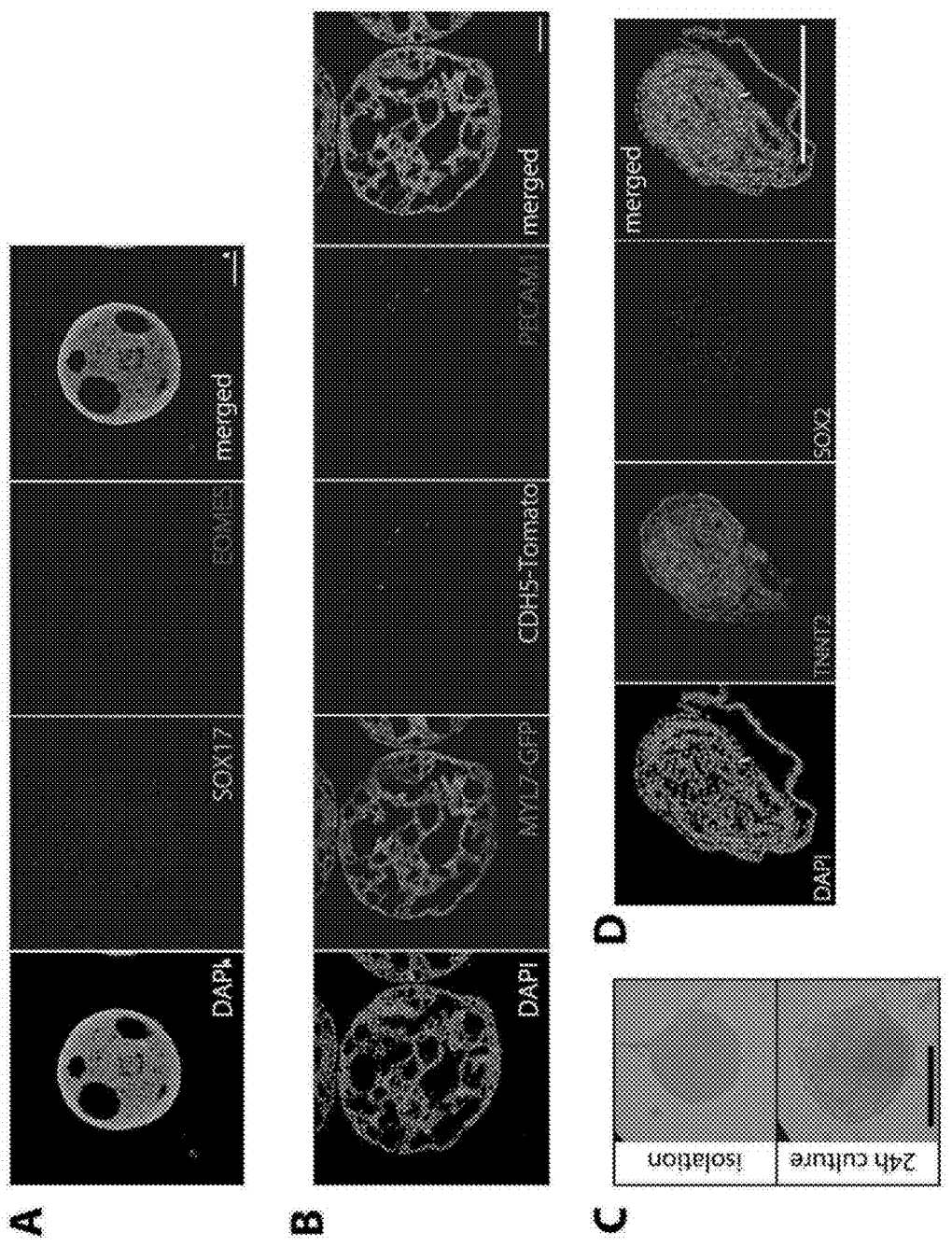

FIG. 23: Characterization of Cardioids and Chick Cardiac Mesoderm Explants. Related to FIG. 2. (A) Self-organizing cardiac mesoderm at d2.5 showing absence of SOX17$^+$ and EOMES$^+$ endoderm. Scalebar: 200 μm. (B) Cavity formation in cardioids (d7.5) happens in the absence of endothelial cells (PECAM1$^+$) upon treatment with Sunitinib (100 nM). Scalebar: 200 μm. (C) Chick cardiac mesoderm explants form a spherical structure with cavities in vitro upon culture in cardiac mesoderm media. Scalebar: 200 μm. (D) Control chick cardiac mesoderm explants section (same structure as shown in FIG. 2B) shows near absence of the foregut marker SOX2. Scalebar: 200 μm. Used cell line in all experiments of this figure: WTC (if not stated otherwise).

Figure 24:
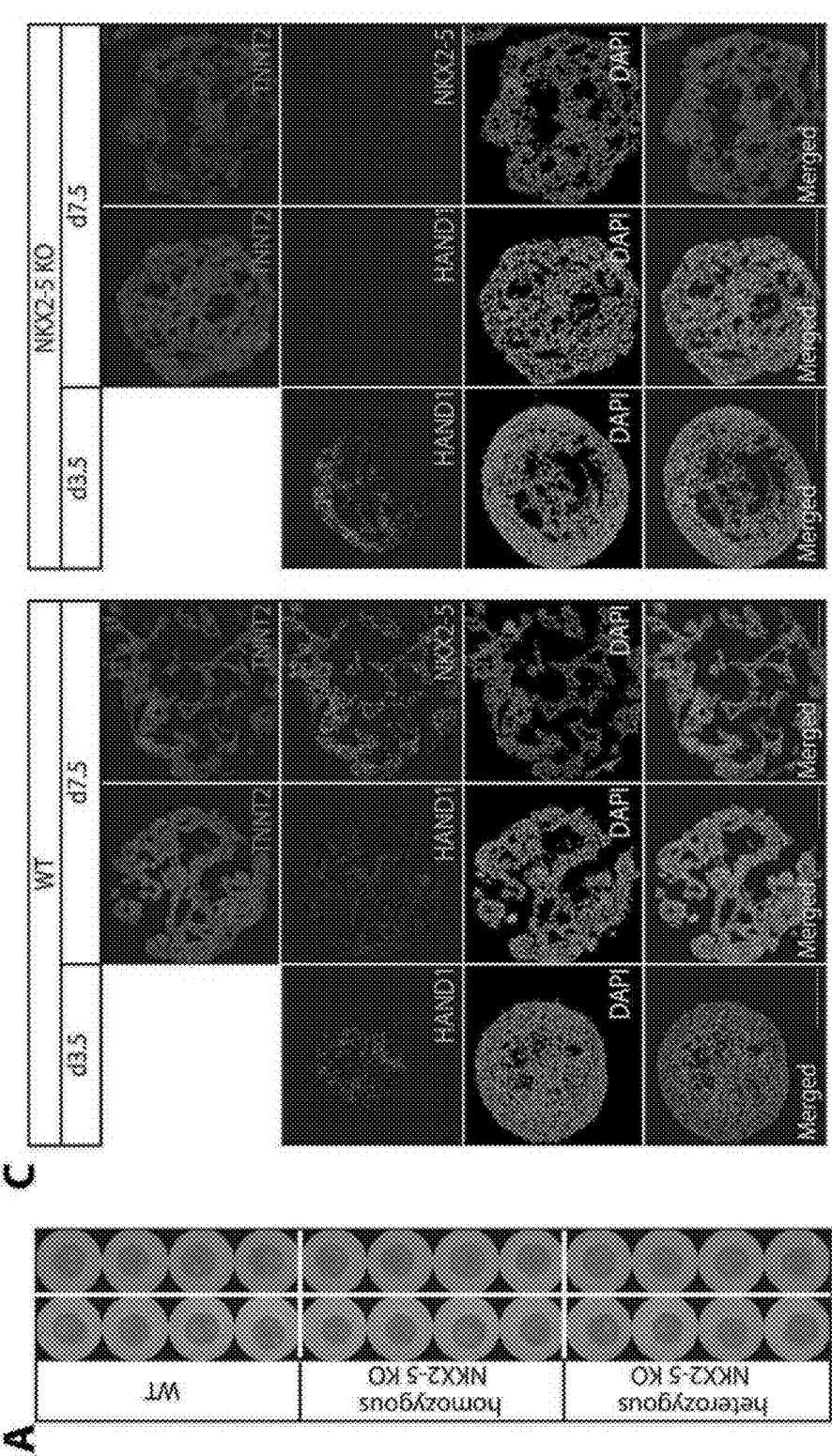
Figure 24:
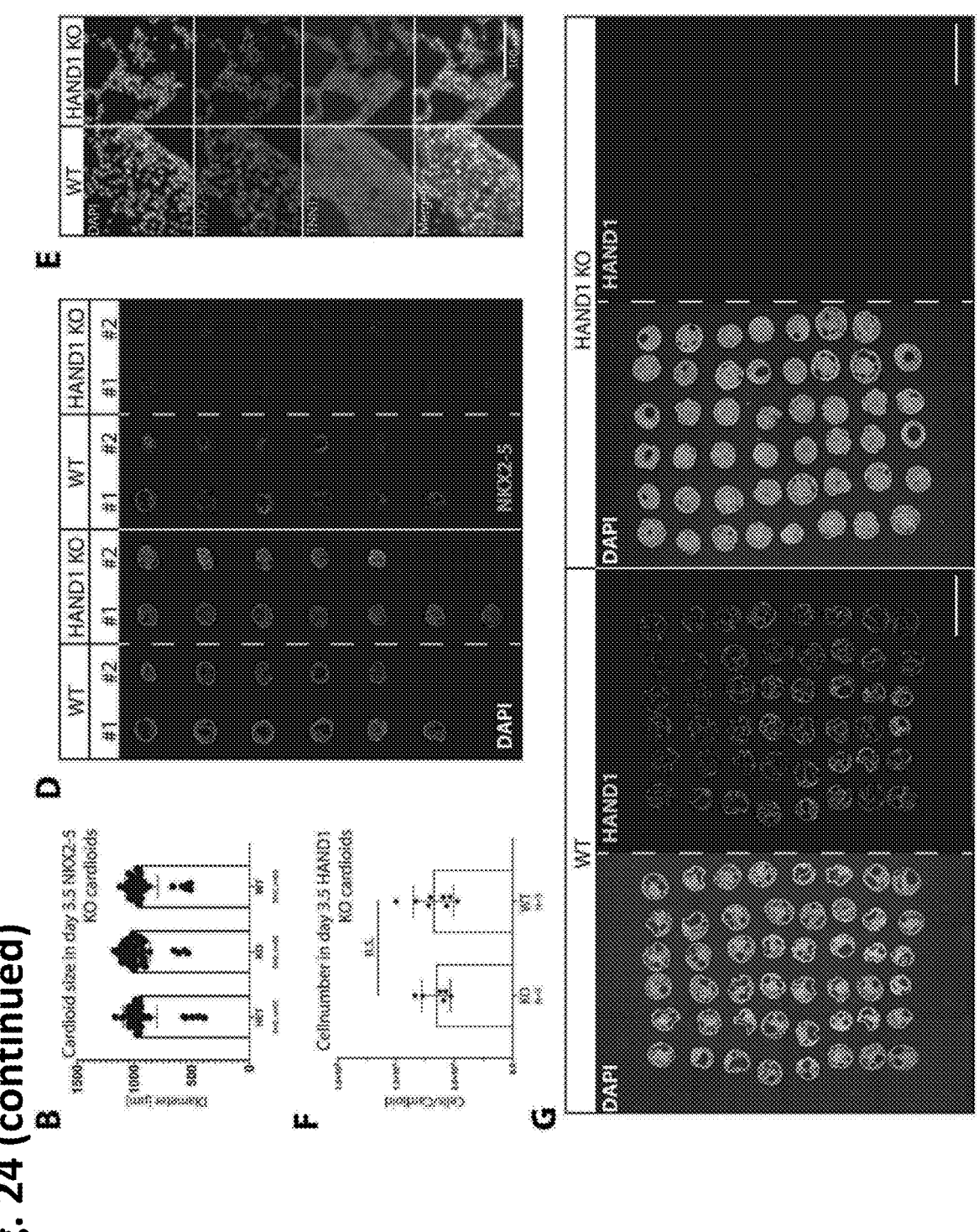

FIG. 24: NKX2-5 and HAND1 KO hPSC and Cardioid Characterization. Related to FIG. 4. (A) NKX2-5 KO cardioids do not show impaired cavity expansion. Scalebar: 200 μm. (B) Quantification of cardioid diameter confirms no reduction of NKX2-5 KO cardioids at day 3.5. (C) Immunostaining of HAND1, NKX2-5 and TNNT2 in WT and NKX2-5 KO cardioids at d3.5 and d7.5. (D) Immunostaining of NKX2-5 in WT and HAND1 KO organoids at d3.5. (E) Closeup of immunostaining of d7.5 cardioids showing the presence of CMs (NKX2-5$^+$/TNNT2$^+$) in HAND1 KO cardioids. (F) Quantification of cell number/cardioid showing no significant change between WT (N=3) and HAND1 KO (N=3). (G) Immunostaining of sections (48 WT/47 HAND1 KO) of cardioids (d3.5) showing a cavity formation defect as well as the lack of HAND1 protein expression in HAND1 KO cardioids. Scalebars: 2000 μm. Used cell line in all experiments of this figure: HAND1 KO (H9), WT (H9), NKX2-5 KO (H9).

Figure 25:
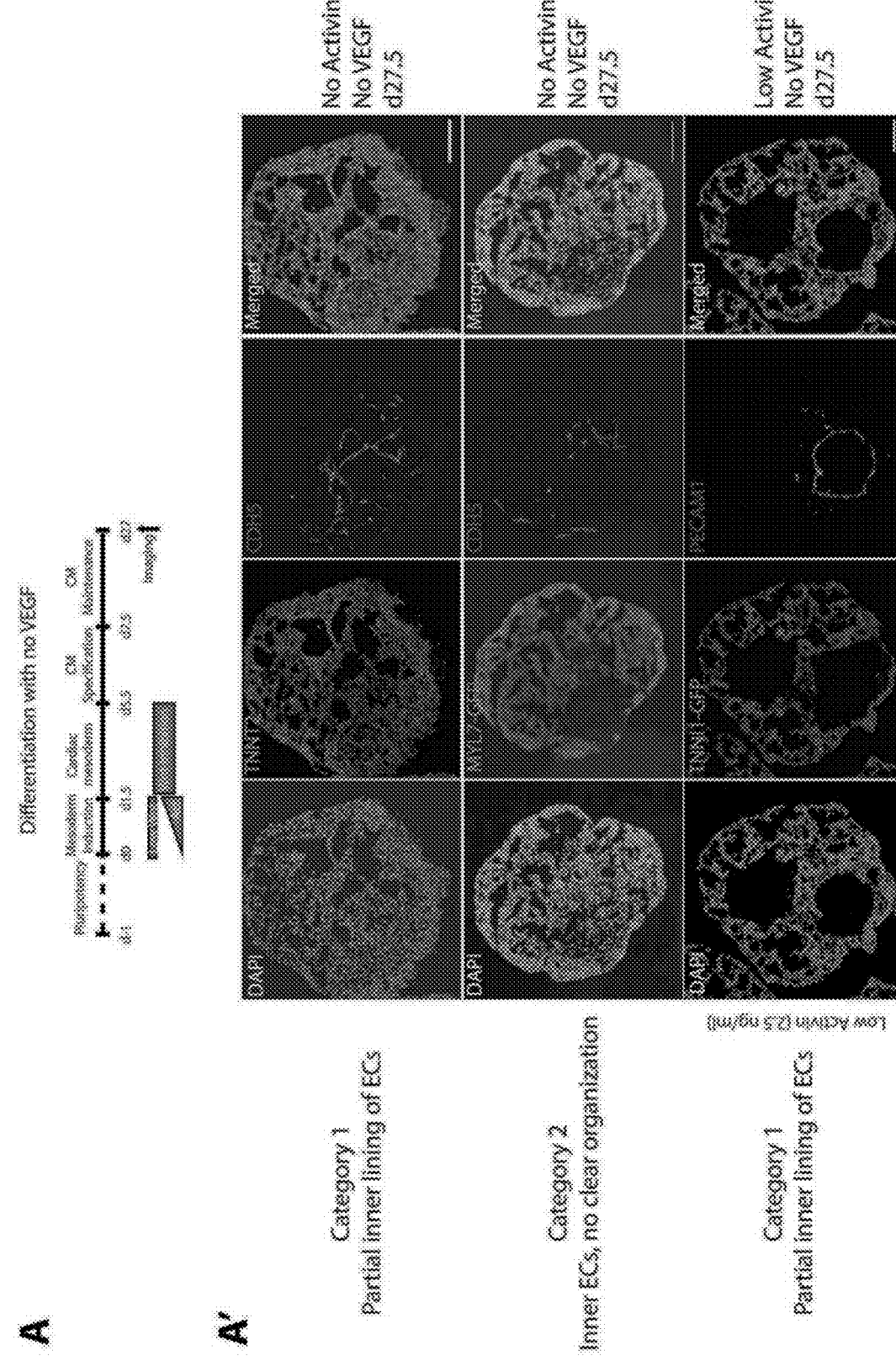
Figure 25:
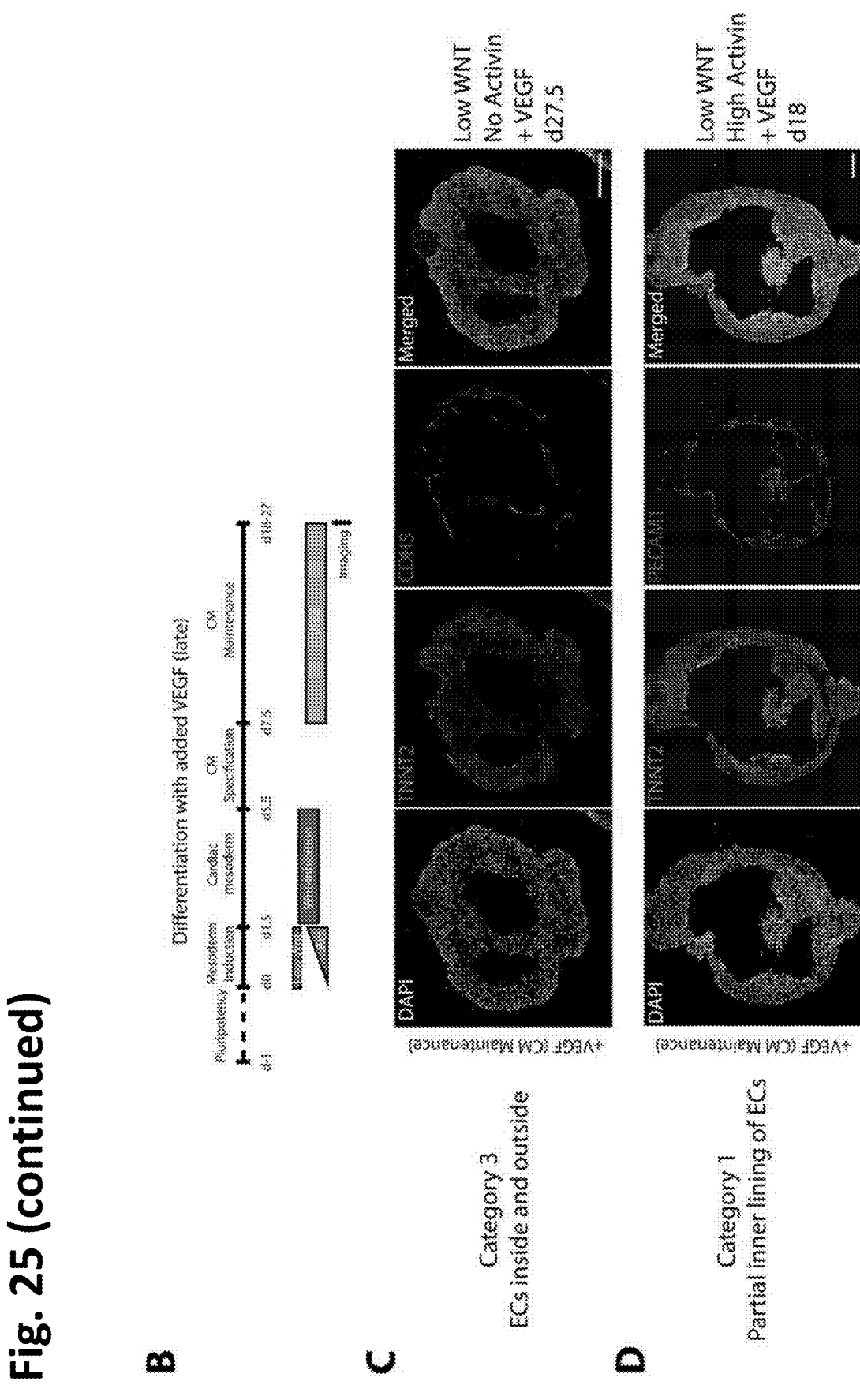

FIG. 25. Further Examples of Range of EC Self-Organization. (A) Timeline of differentiations performed with no VEGF addition and low WNT and no Activin or low Activin conditions. (A') Example images of Categories 1 and 2 in low WNT/low Activin conditions. Scalebars: 200 μm. (B) Timeline of differentiations performed with VEGF added after CM specification in low WNT and High/No Activin conditions. (C) and (D) Addition of VEGF after CM specification occasionally led to partial EC lining of cavities but often also to ECs forming a partial outside layer. Scalebars: 200 μm. Used cell line in (D): H9. Used cell line in all experiments of this figure: WTC (if not stated otherwise).

Figure 26:
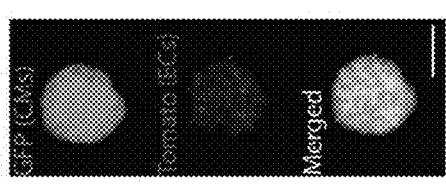
Figure 26:
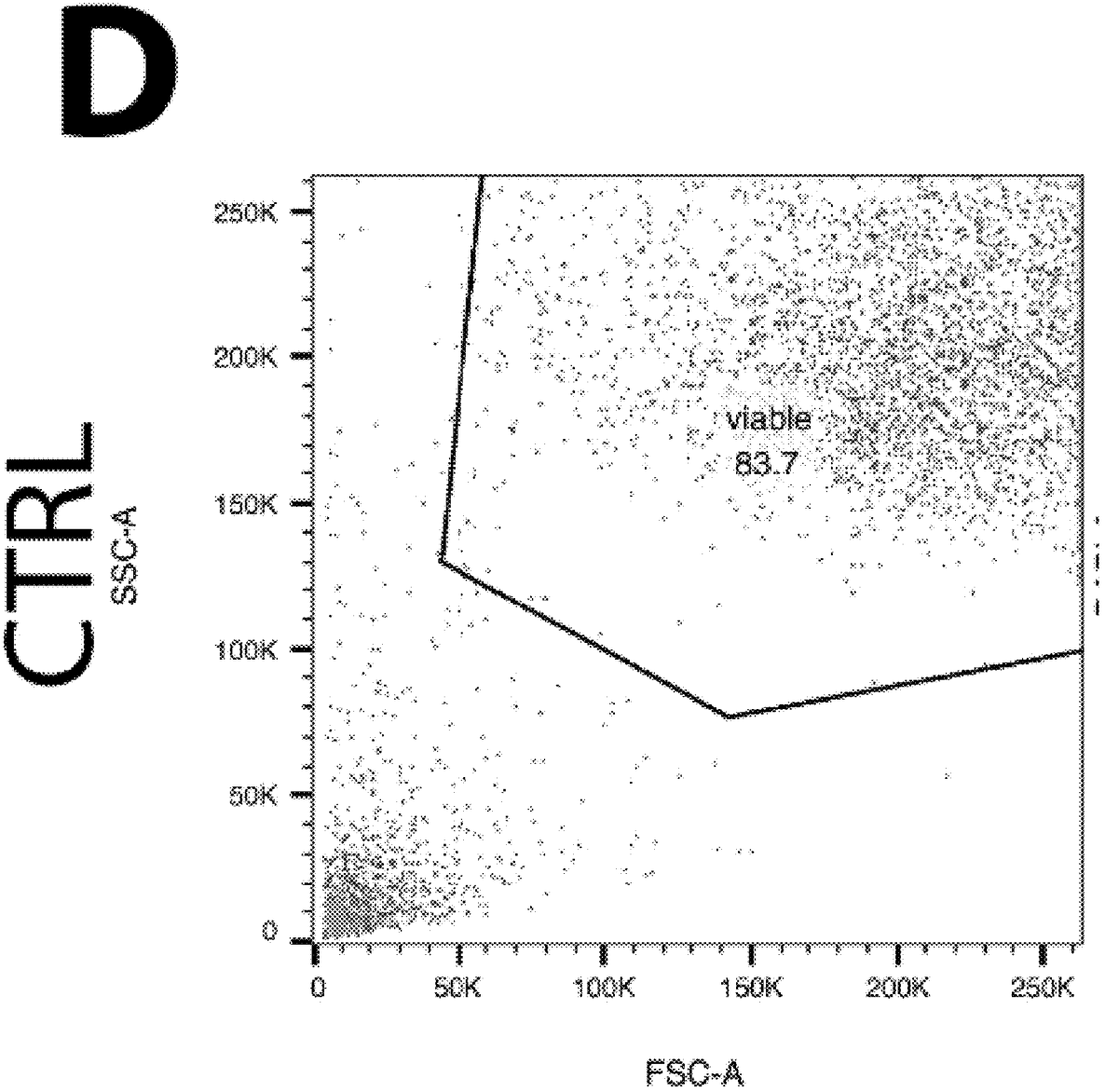
Figure 26:
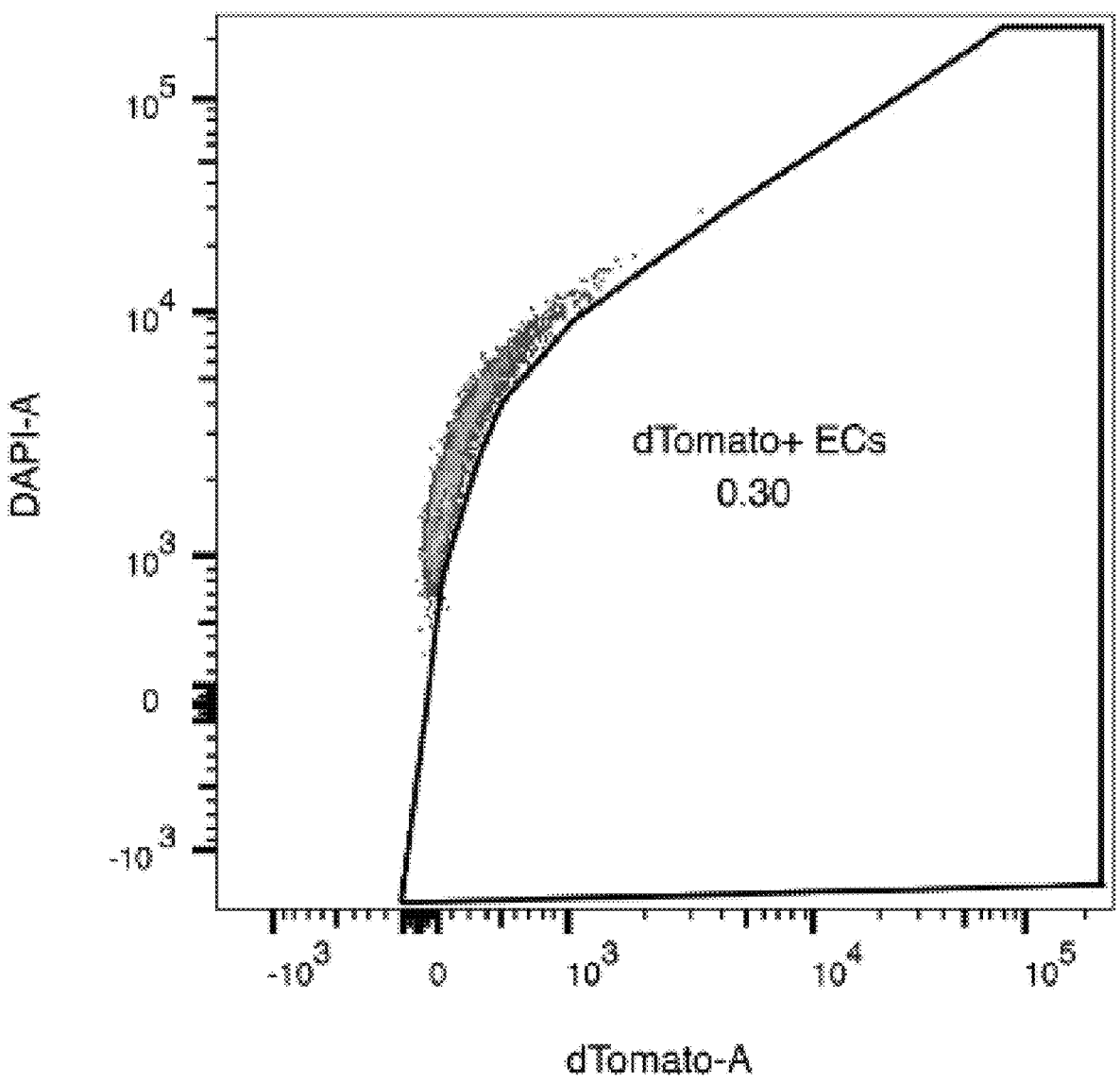
Figure 26:
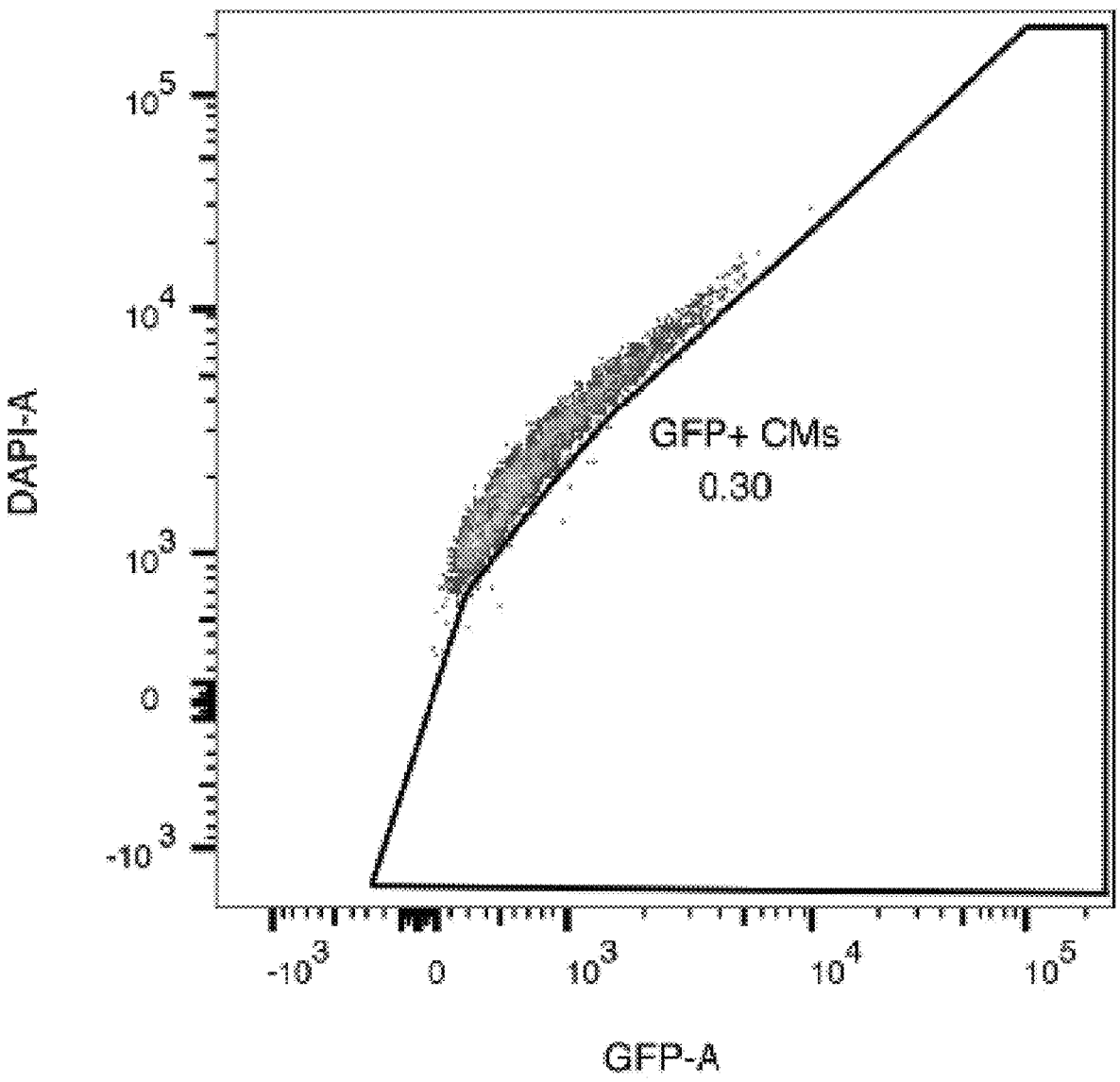
Figure 26:
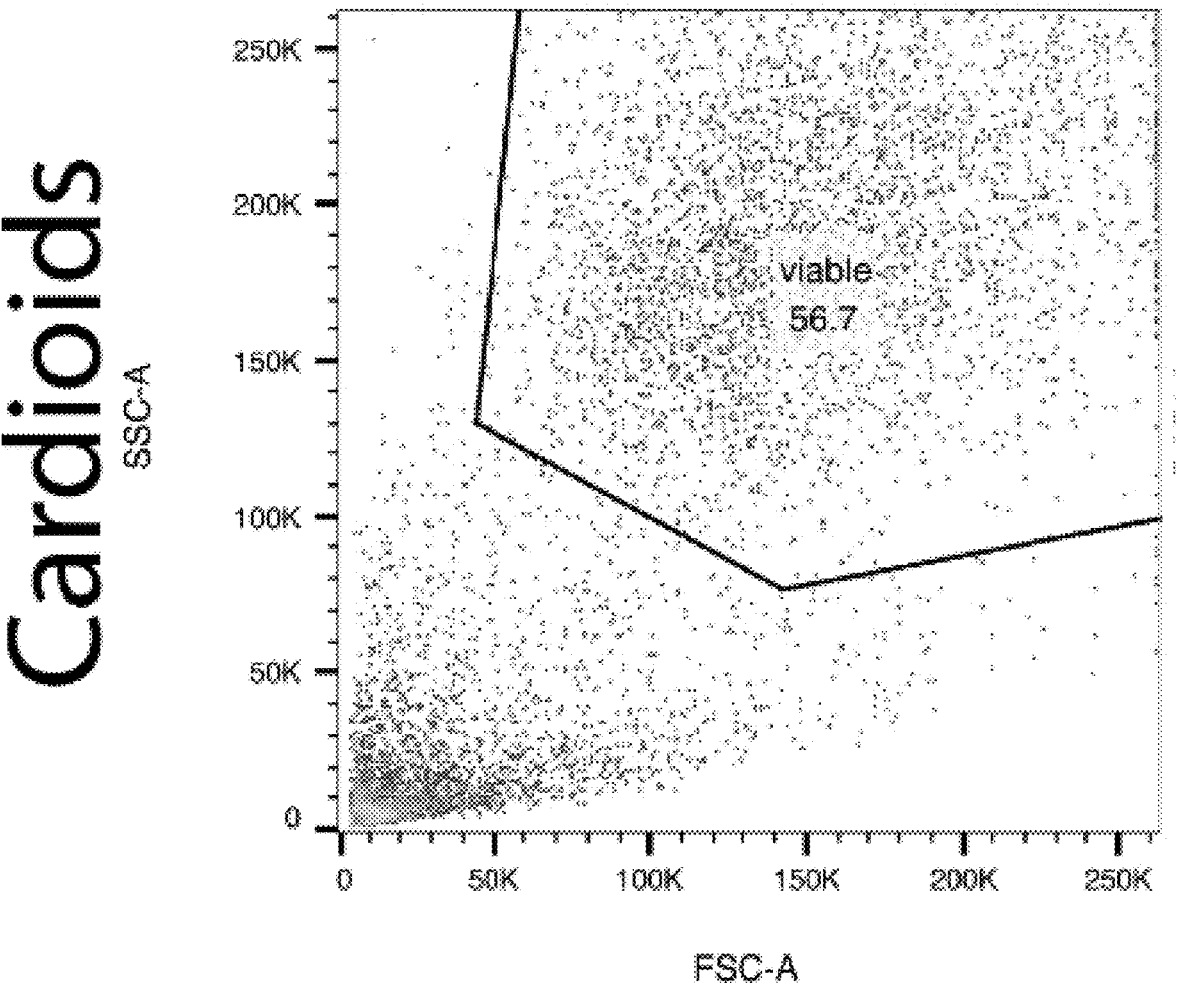
Figure 26:
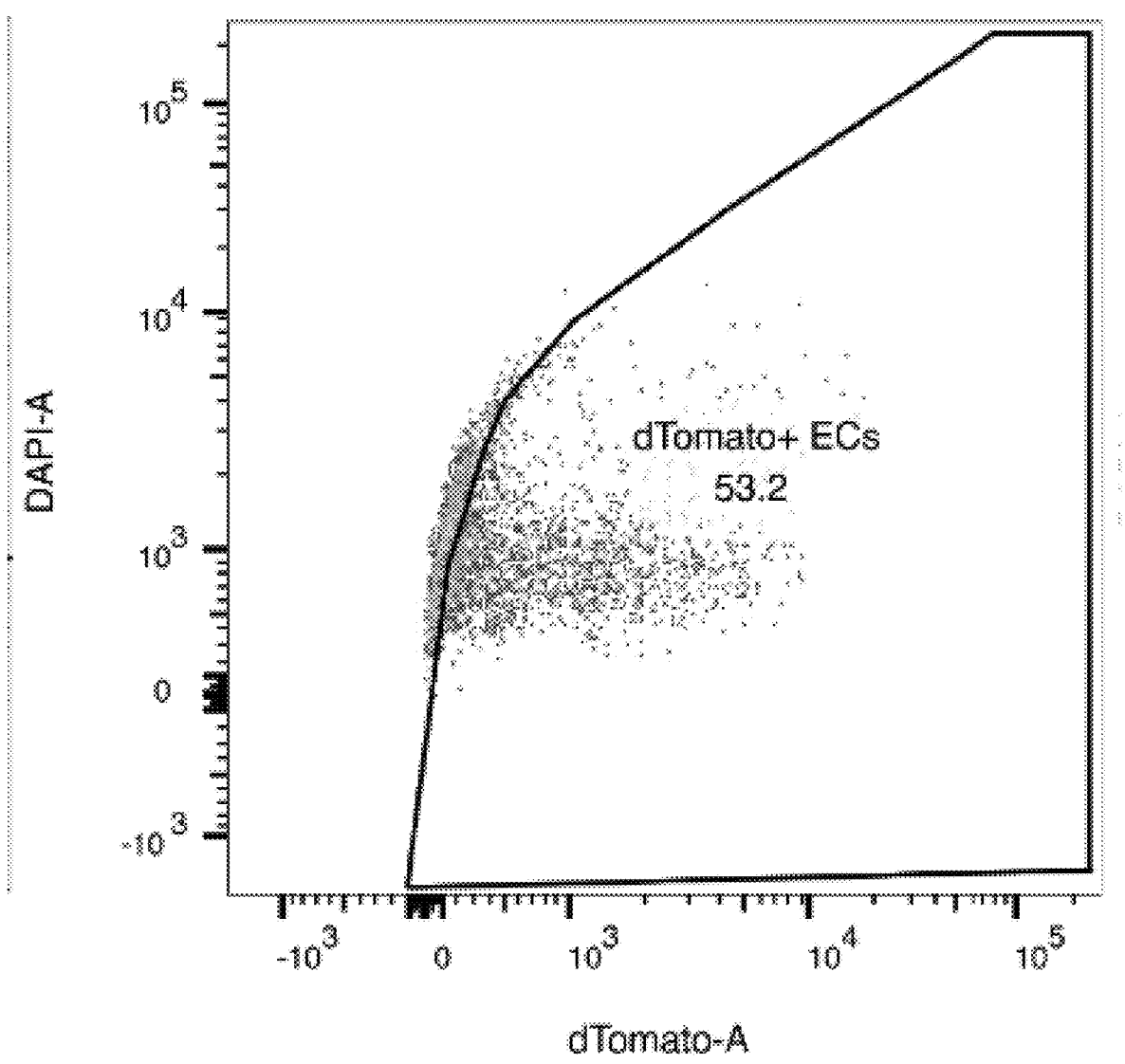
Figure 26:
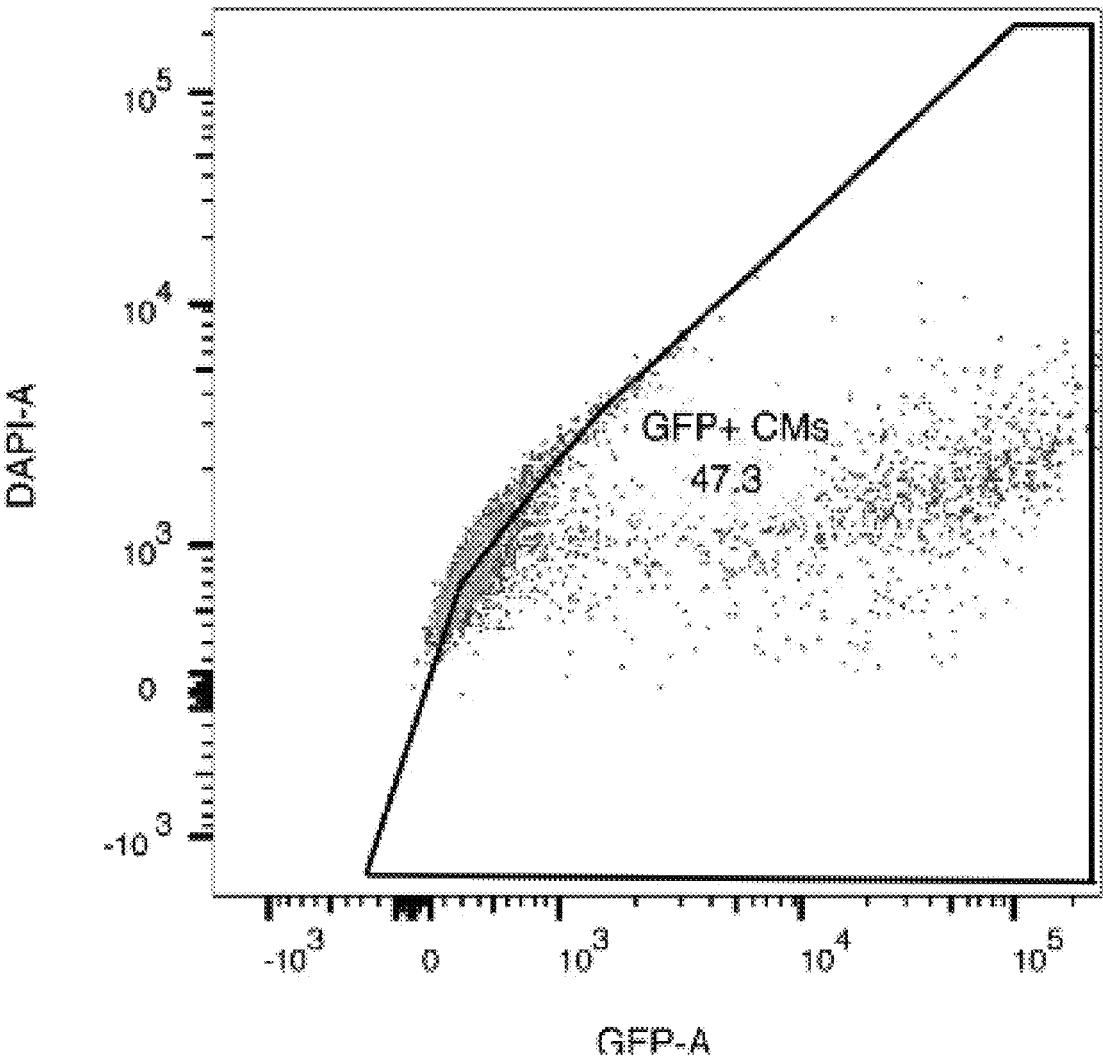
Figure 26:
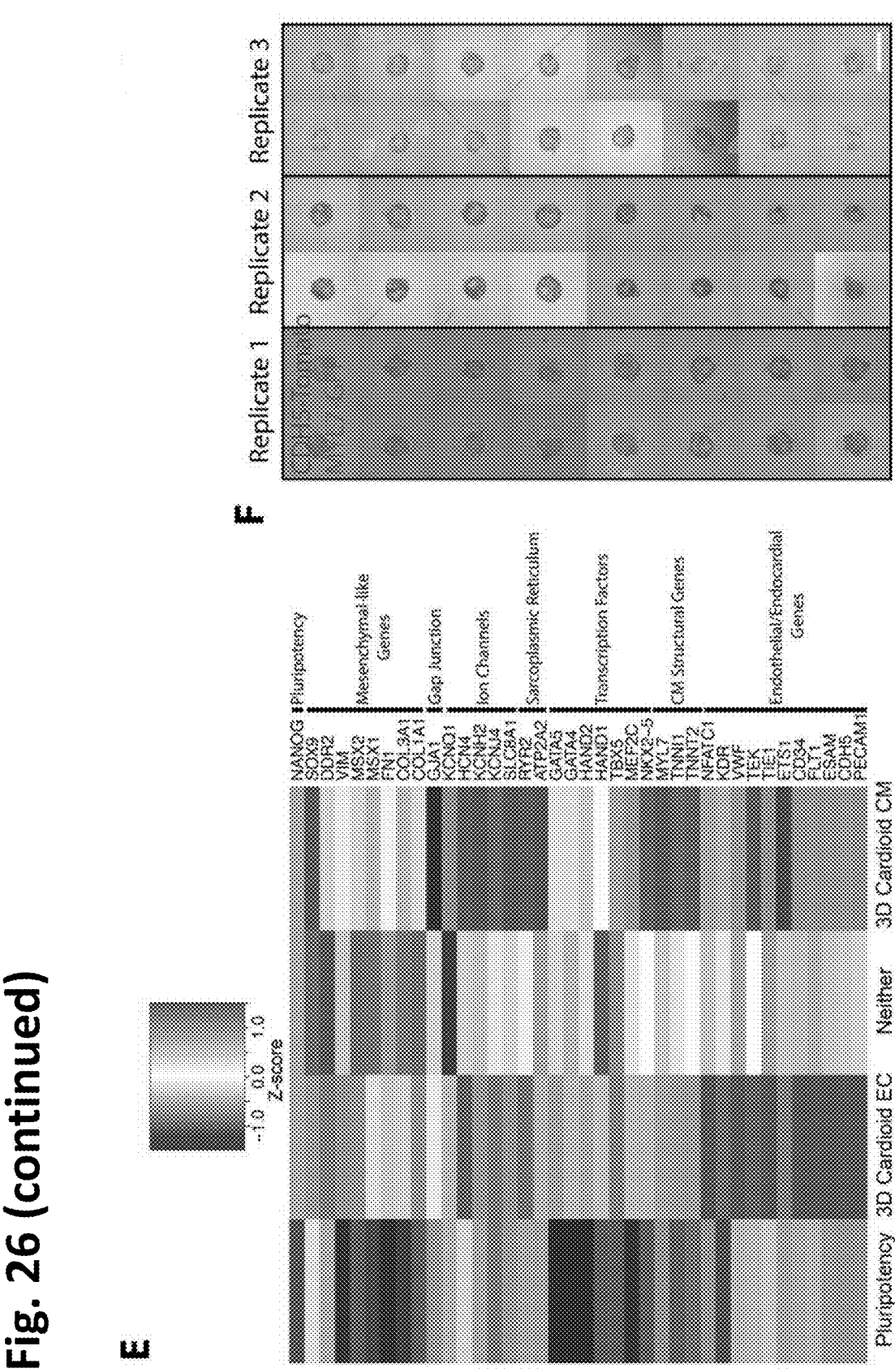

FIG. 26. Characterization of Cardioids with Endothelial and Fibroblast-like Cell Layers. (A) Three biological replicates showing reproducible generation of cardioids with separate CM and EC layers using an intermediate WNT dosage (CHIR99021, 6 μM). Scalebar: 2000 μm. (B) ECs in aggregated CM microtissues build a rudimentary network within the cardiomyocytes, not a separate layer. Scalebar: 400 μm. Used cell line: H9. (C) ECs build a network layer surrounding the cardioid. Max. Int. Projections. Cryo-sections show that FN1 is expressed by all three cell types, while VIM is expressed primarily by ECs and fibroblast-like cells. Scalebars: 200 μm. (D) Example FACS plots showing the distribution of cardiomyocytes (CM) and (EC) in co-differentiated cardioids at day 7.5 using the MYL7– GFP/CDH5-Tomato iPSC (WTC) line. CTRL: WT WTC line. (E) Heatmap of Smart-Seq2 data of sorted hPSC, CM, EC, and Non-EC/Non-CM (fibroblast-like) cells showing expression of the respective key genes. Fibroblast-like (Neither) cells express genes related to putative EC-derived fibroblast-like cells and confirm stainings from (C). (F) Three biological replicates showing the reproducibility of cardioid formation without CM contribution (MYL7–, CDH5+). Scalebar: 500 μm. Used cell line in all experiments of this figure: WTC (if not stated otherwise).

Figure 27:
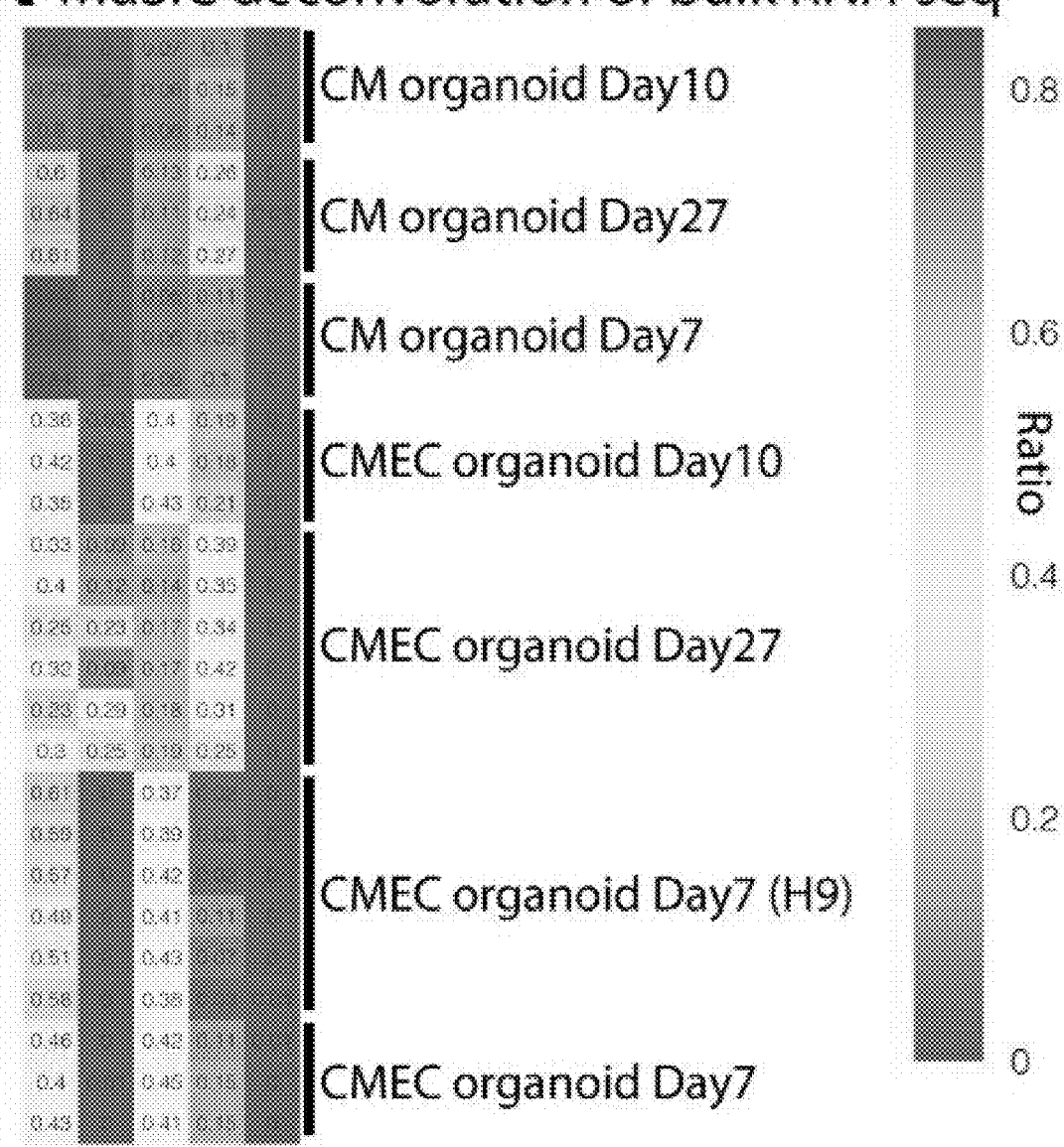
Figure 27:
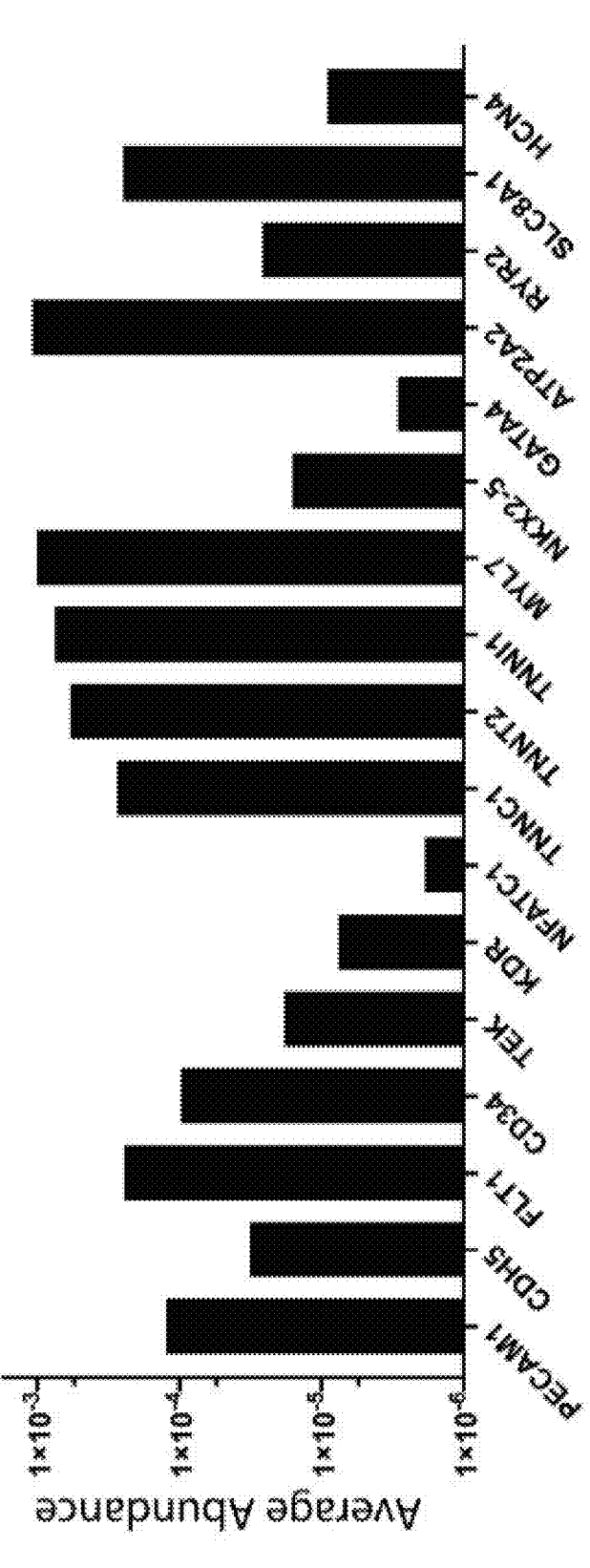
Figure 27:
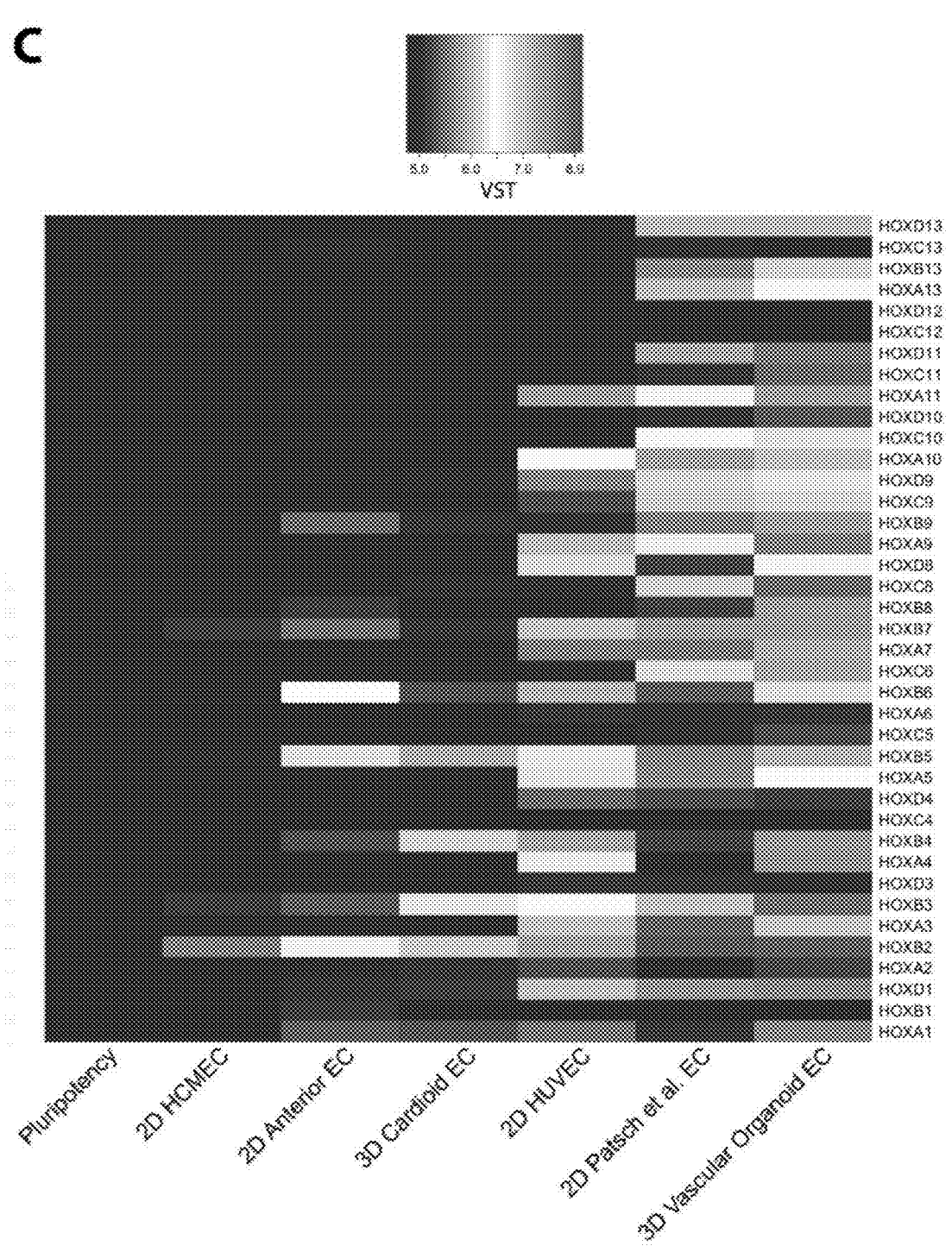
Figure 27:
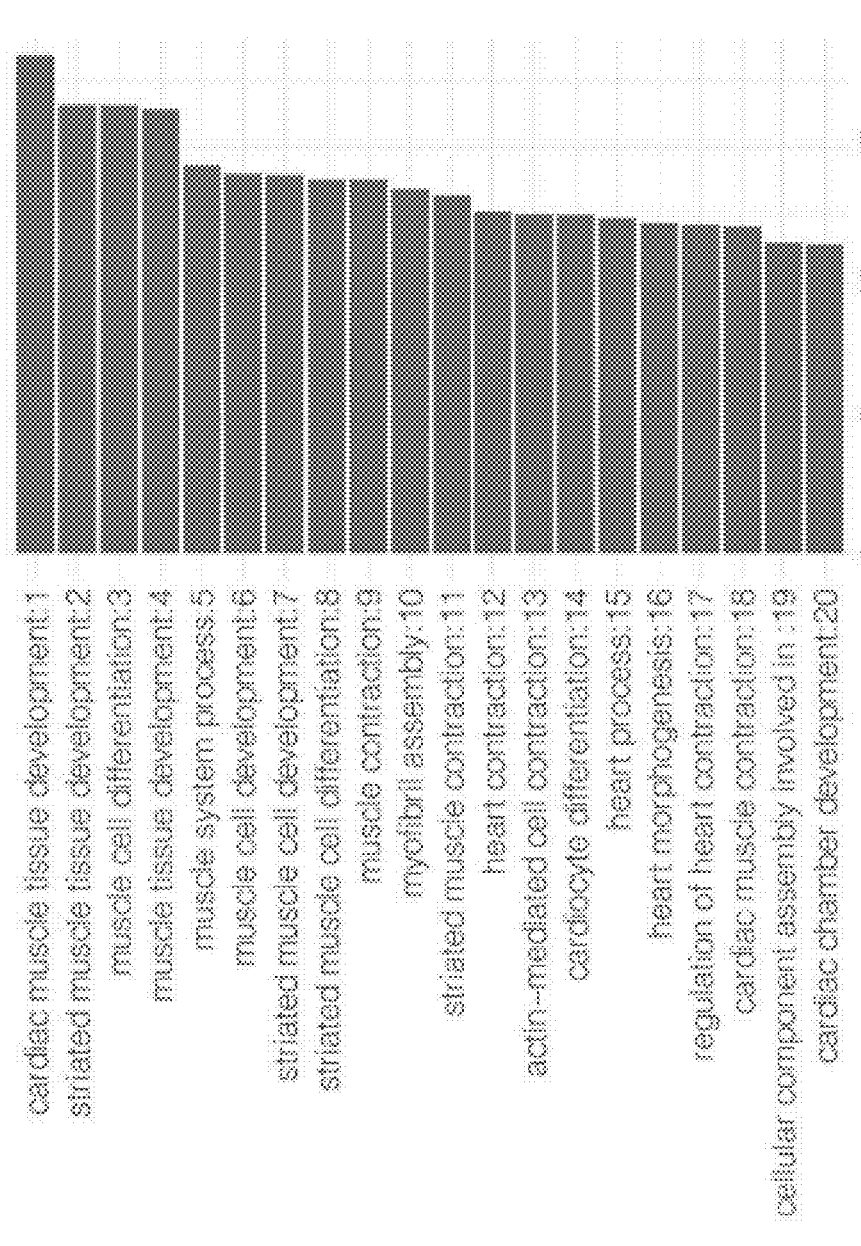
Figure 27:
Figure 27:
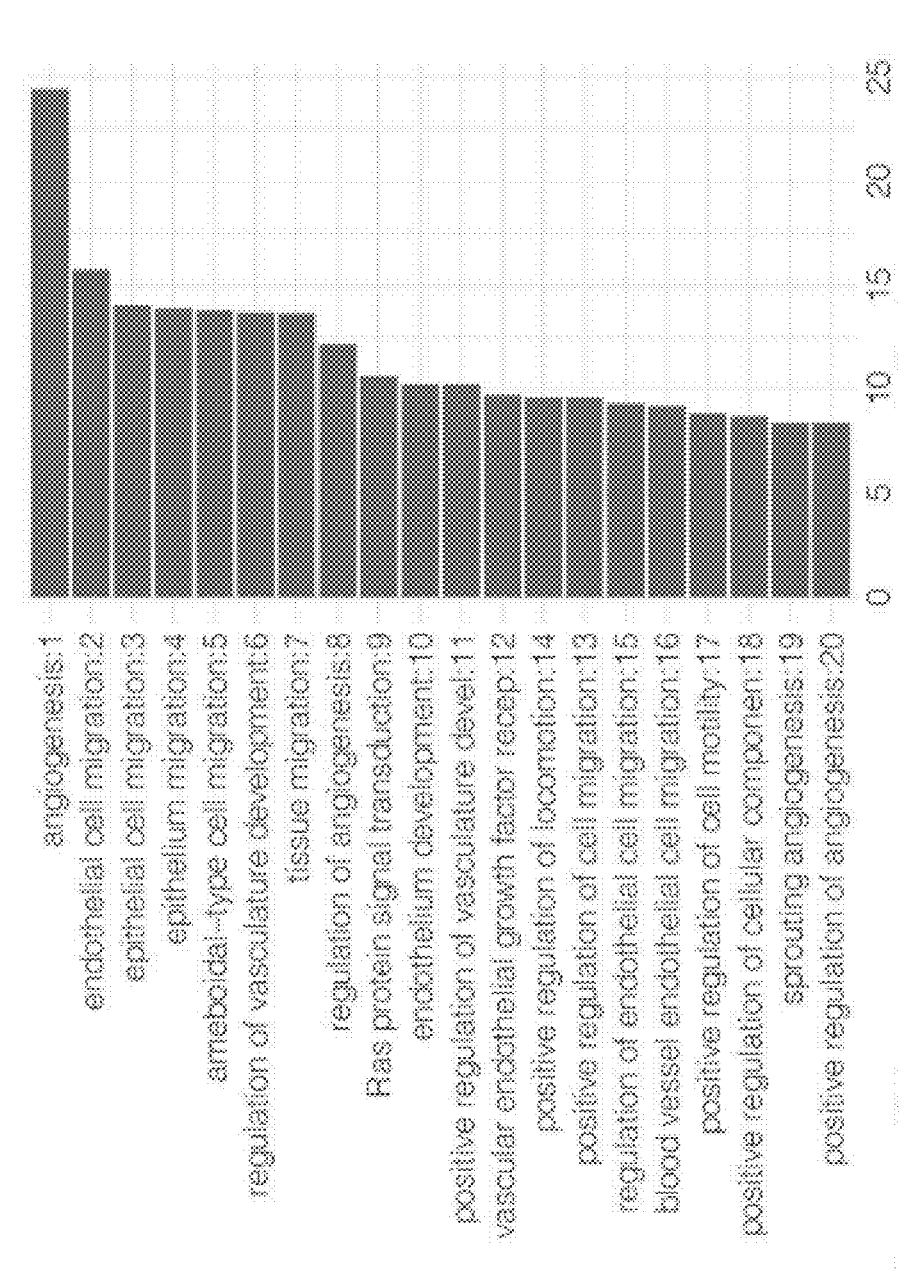
Figure 27:
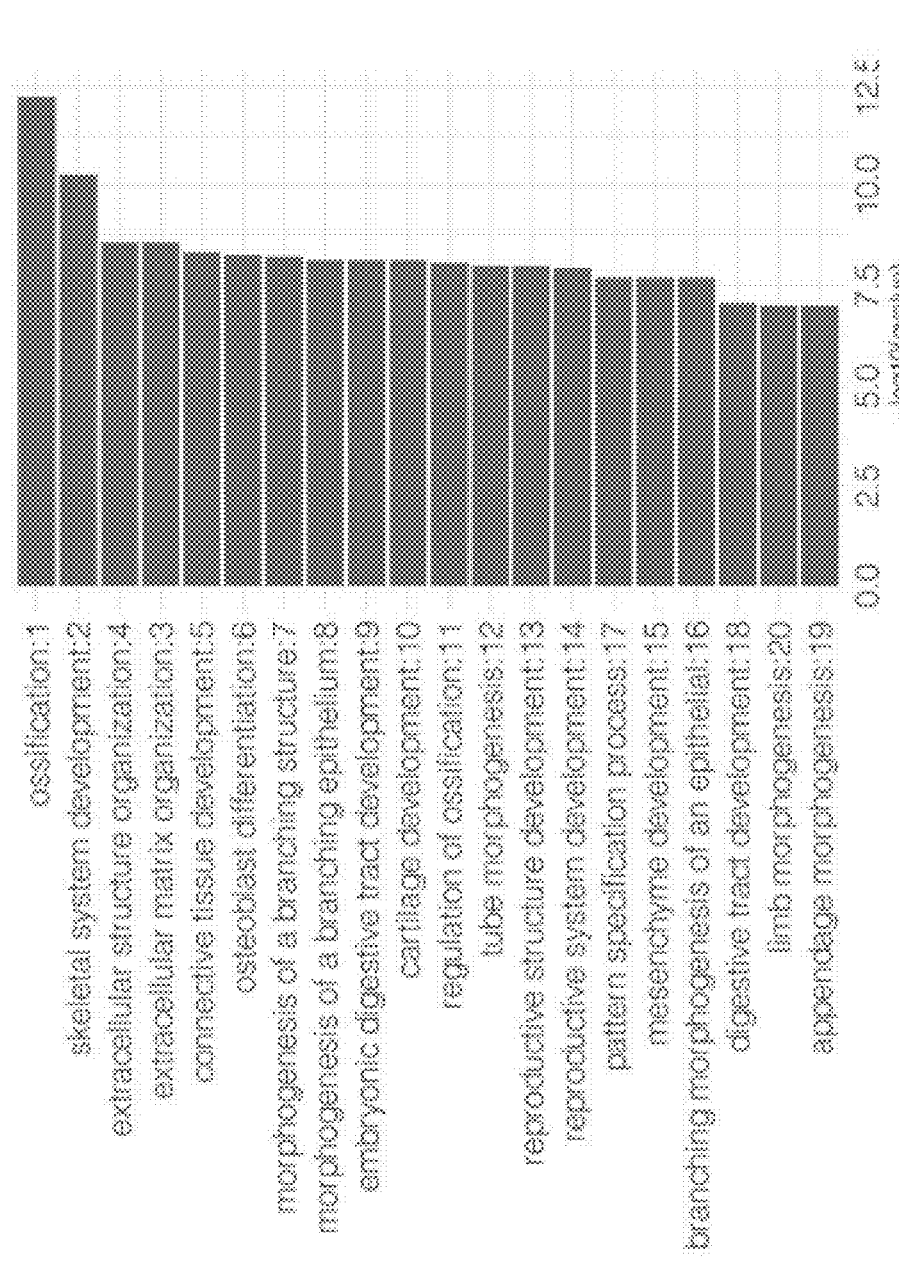

FIG. 27. Further Characterization of Cardioid Cell Identity. (A) MuSiC deconvolution (Wang et al., 2019, Nature Communications 10, 380-389) of bulk RNA-seq data of cardiac organoids showing CM/EC contributions similar to the FACS quantification and lack of ECs in CM-only cardioids. Reference dataset: single cell RNA-seq of the developmental trajectory of the human heart (Cui et al., 2019, Cell Rep 26, 1934-1950.e1935). Used cell lines: H9, WTC. (B) Proteomic analysis of cardioids shows key markers of CMs and ECs are detected on a protein level. (C) HOX-gene expression analysis of cardioid ECs, HCMECs and Anterior ECs shows expression of anterior HOX genes, while all other ECs show expression of posterior HOX genes as well. VST: variance-stabilized transformed counts. Anterior ECs: H9 line, Vascular Organoid ECs as indicated by Wimmer et al., 2019, Nature 565, 505-510. (D) GO-terms of genes upregulated in CMs show terms related to cardiac muscle development. (E) GO-terms of genes upregulated in cardiac ECs. (F) GO-terms of genes upregulated in fibroblast-like cells (GFP–/Tomato–) shows terms related to connective tissue development and ECM organization. Used cell line in all experiments of this figure: WTC (if not stated otherwise).

Figure 7:
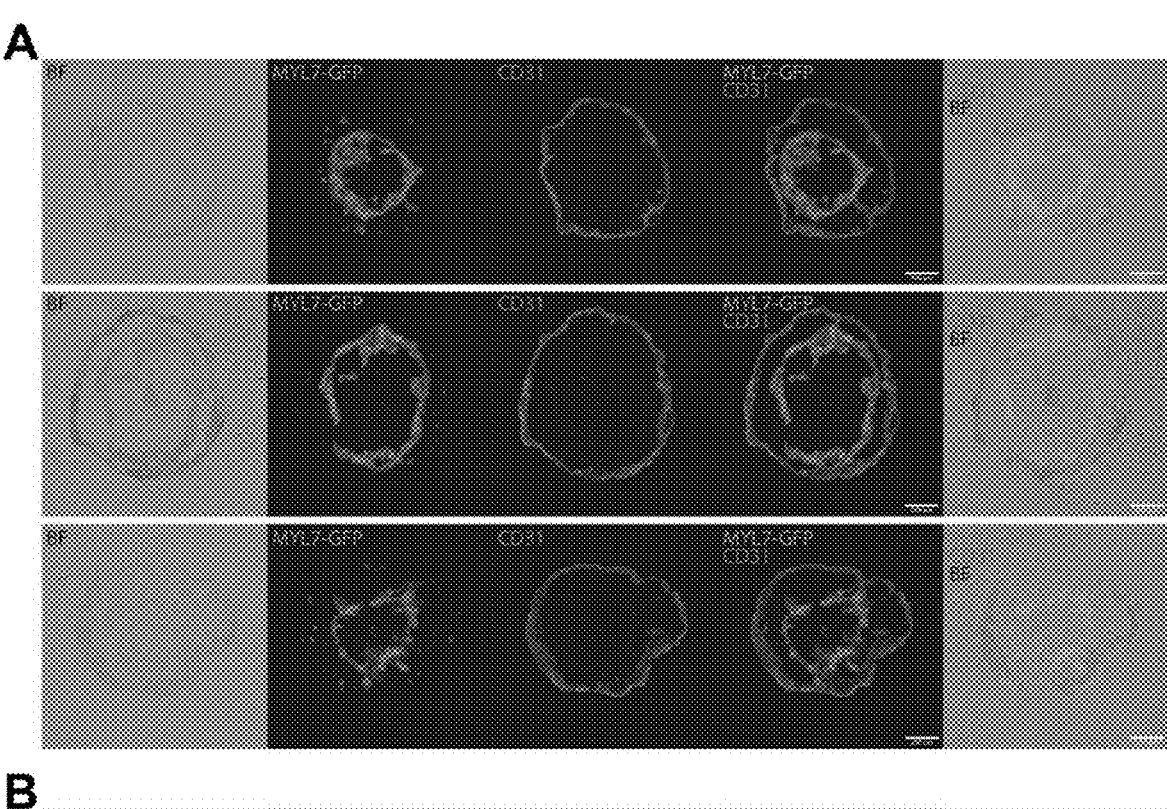
FIG. 7: A: Representative images of sections of organoids containing cardiomyocytes (CM) and endothelial cells (EC) in separate layers. A brightfield image (BF) shows the cellular organization and images for MYL7-GFP (CM) and CD31 (EC) show an inner cavity surrounded by a CM layer that is in turn separated from the EC layer by another cavity. B: Representative images of sections of organoids containing cardiomyocytes (CM) and endothelial cells (EC) in separate layers. A BF image shows the cellular organization and a staining for the CM marker TN NT2 shows its overlap with the other CM marker MYL7. Scalebars=200 μm.
Figure 7:
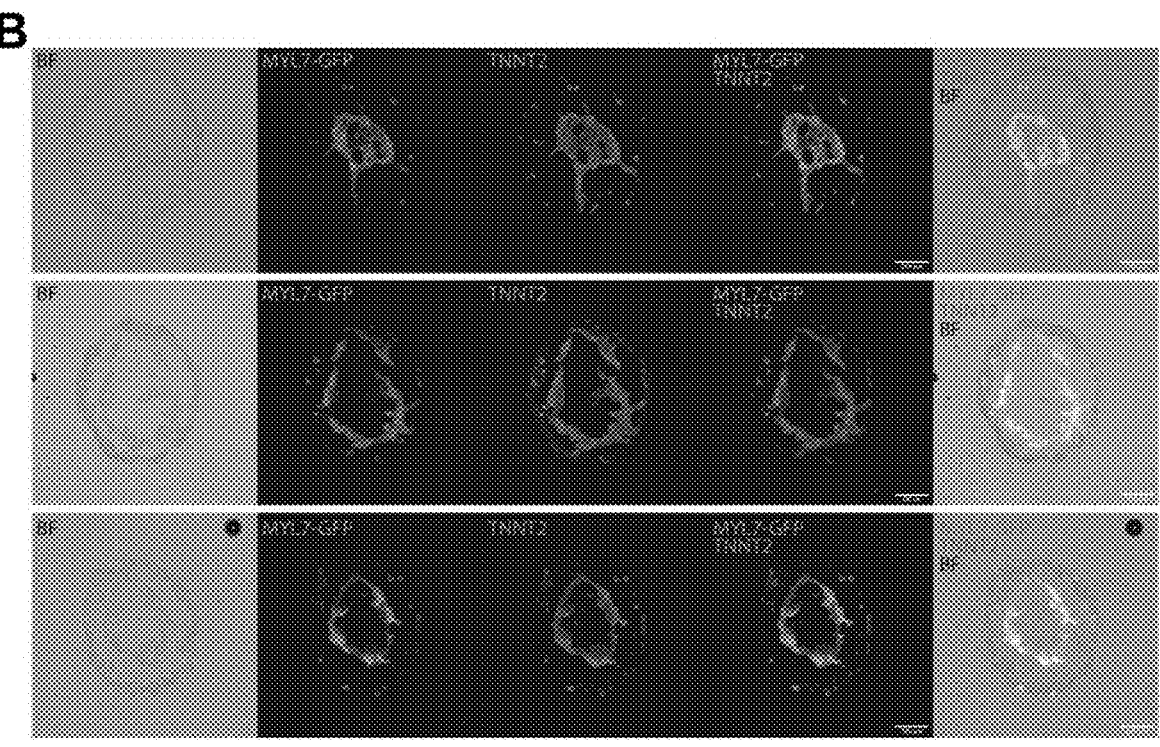
Figure 28:
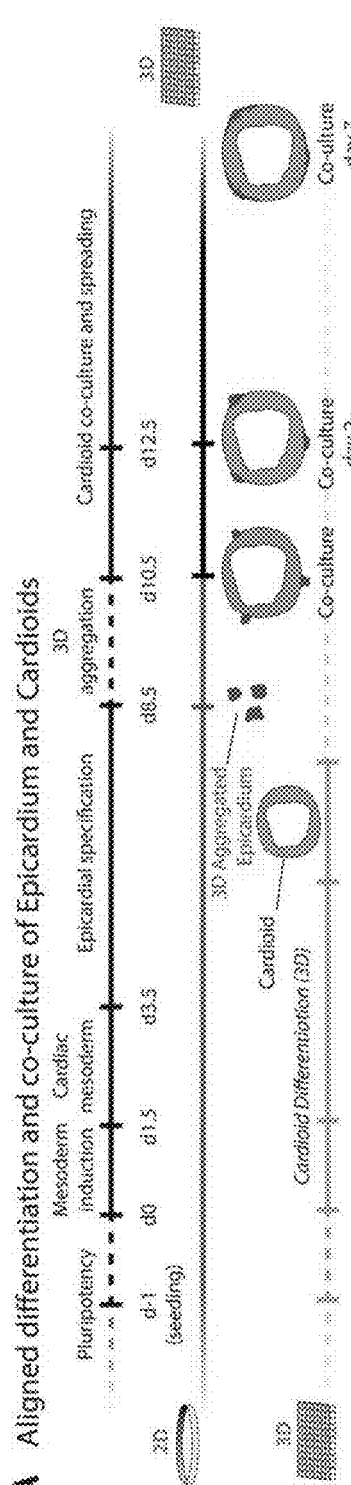
Figure 28:
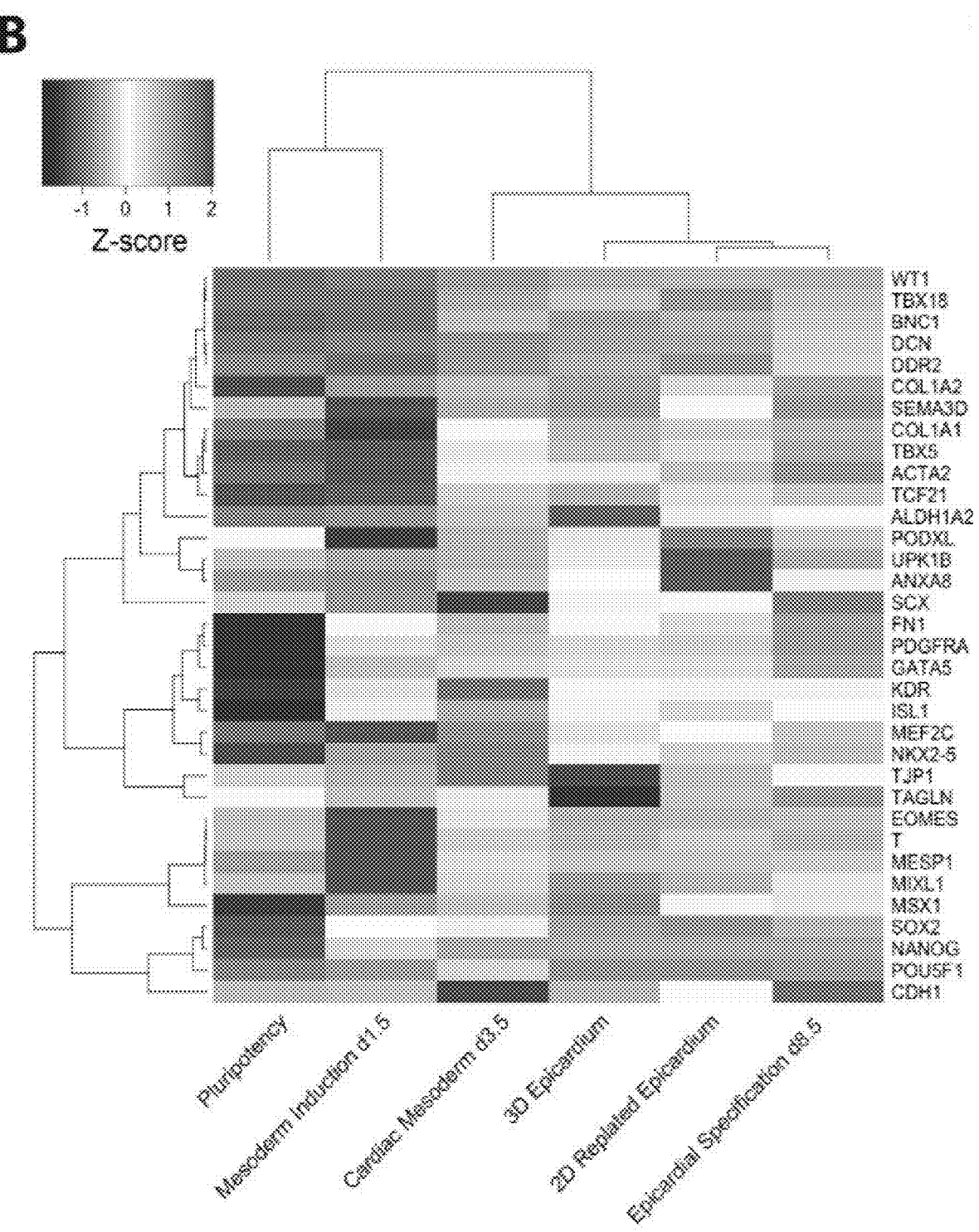
Figure 28:
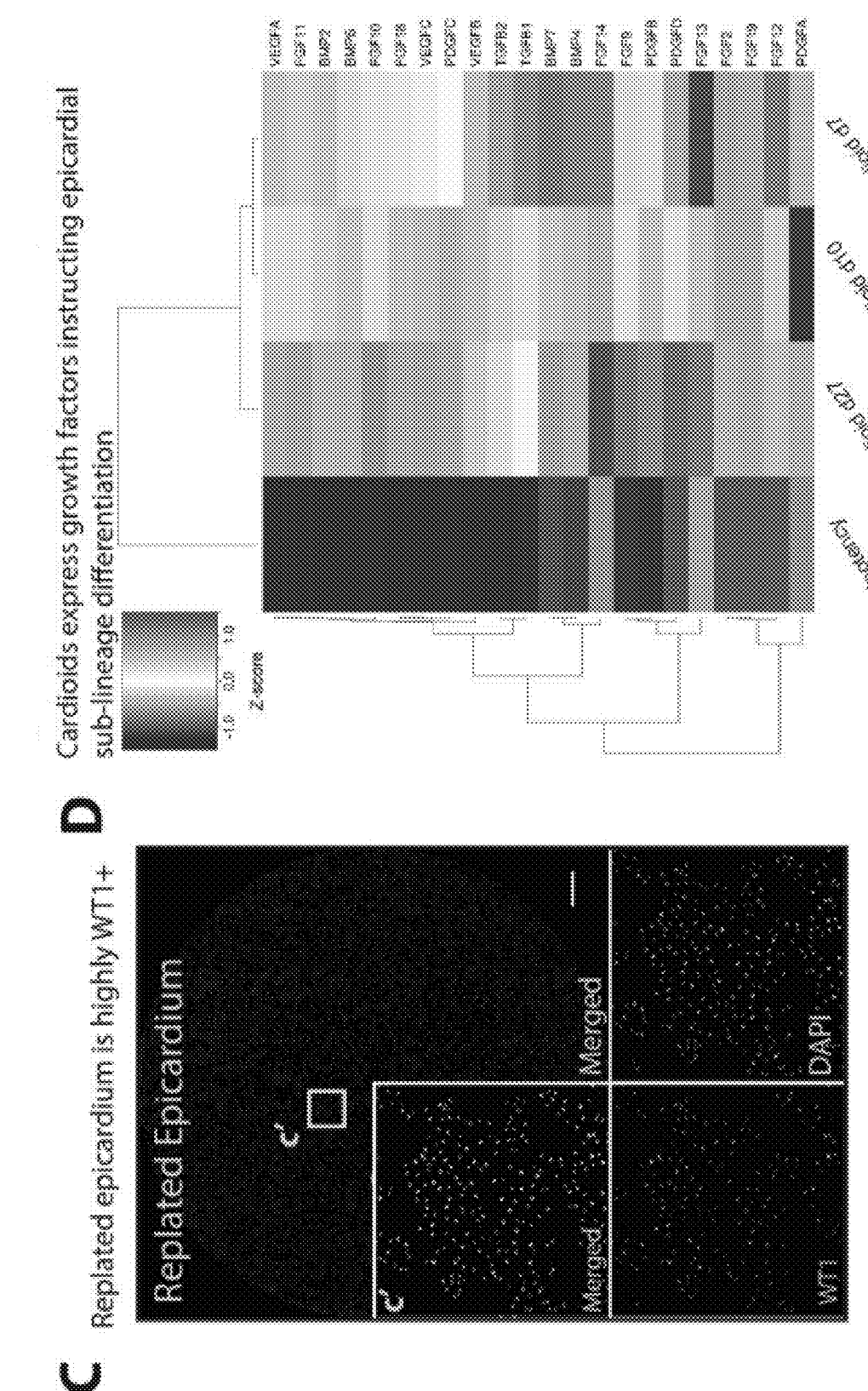
Figure 28:
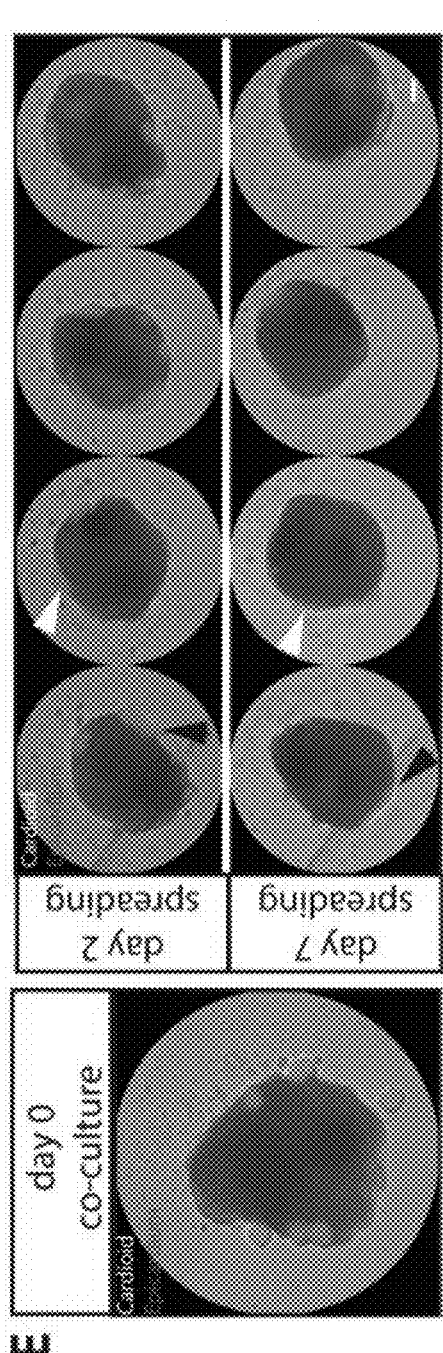
Figure 28:
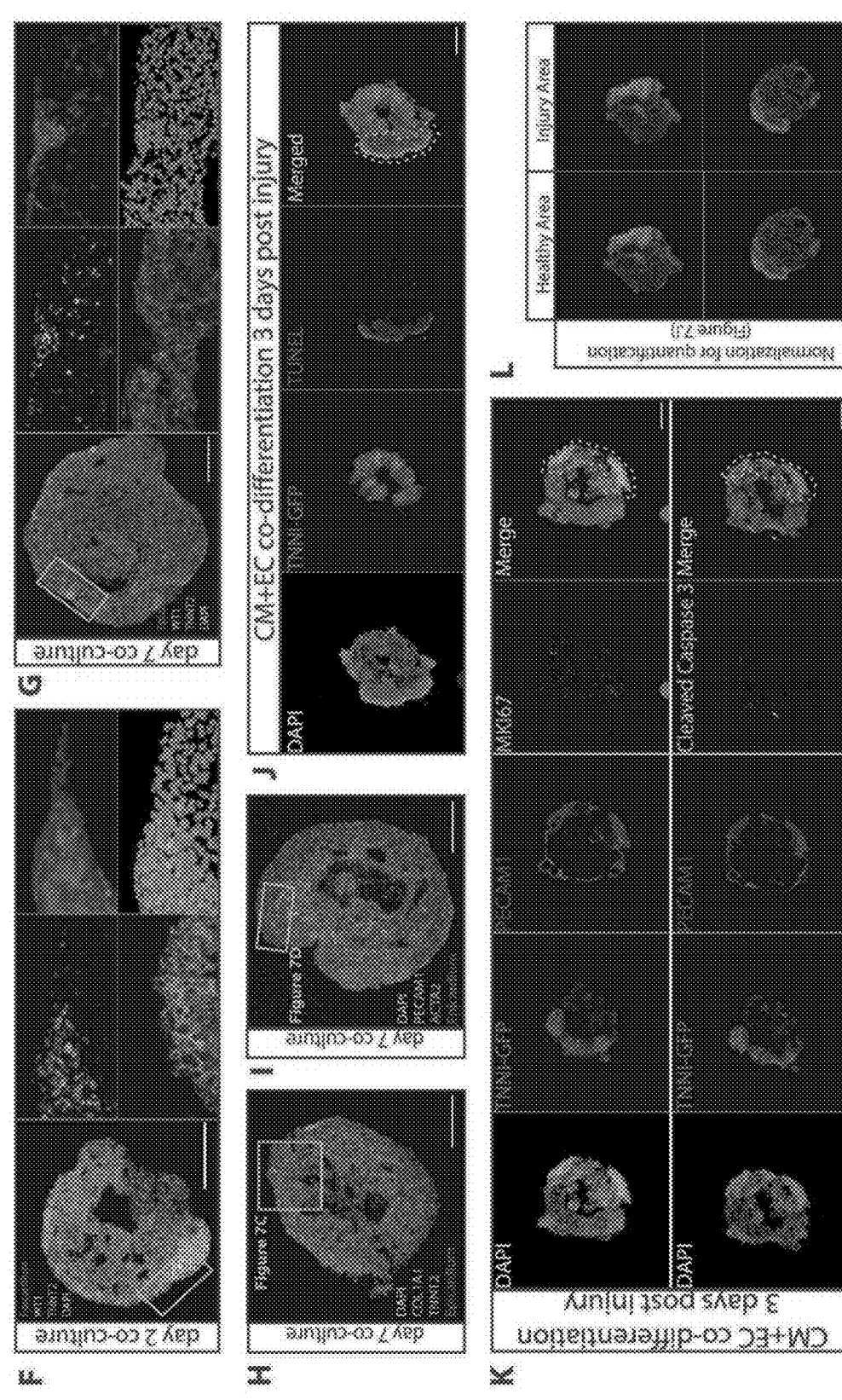

FIG. 28. Epicardium Interacts with Cardioids and the Epicardial- or Endocardial-derived Fibroblasts React to Cryoinjury. (A) Developmentally aligned protocol schematic. (B) Differential expression of pluripotency, mesoderm specification, cardiac mesoderm and epicardium specific genes, comparing day 8.5 (end of differentiation), 2D re-plated and 3D aggregated epicardium. Used cell line: H9. (C) Whole well WT1 immunostaining of 2D re-plated epicardium. Scalebar: 1 mm. c' is a 1×1 mm detail of C. Used cell line: H9 (D) Differential expression of growth factors involved in epicardial sub-lineage specification in pluripotency and 7/10/27-day cardioids without co-culture. Used cell line: WTC. (E) Fluorescently labelled 3D aggregates of 2D epicardial differentiations co-cultured with time matched cardioids. Arrows indicate morphology changes and spreading over time. Scalebar: 200 μm. (F-G) Confocal images of TNNT2 (CMs) and WT1 (epicardium) of 2- and 7-day co-cultures of epicardium and cardioids. Scalebars: 200 μm. (H-I) Whole cardioid images of details from FIG. 7C-D, Scalebars: 200 μm. (J-K) Confocal images of CM+EC+Fibroblast co-differentiated cardioids marking cell death (TUNEL, Cleaved Caspase 3) and lack of cell proliferation (MKI67) 3 days upon cryoinjury. Scalebar: 200 μm. (L) Examples of areas used for Healthy vs. Injury normalization for the quantification shown in FIG. 71. Dashed lines indicate the injury areas in figures. Used cell lines for epicardial figures: H9, experiments repeated with WTC as well. Used cell line for CM+EC+Fibroblast co-differentiation: WTC.

Figure 29:
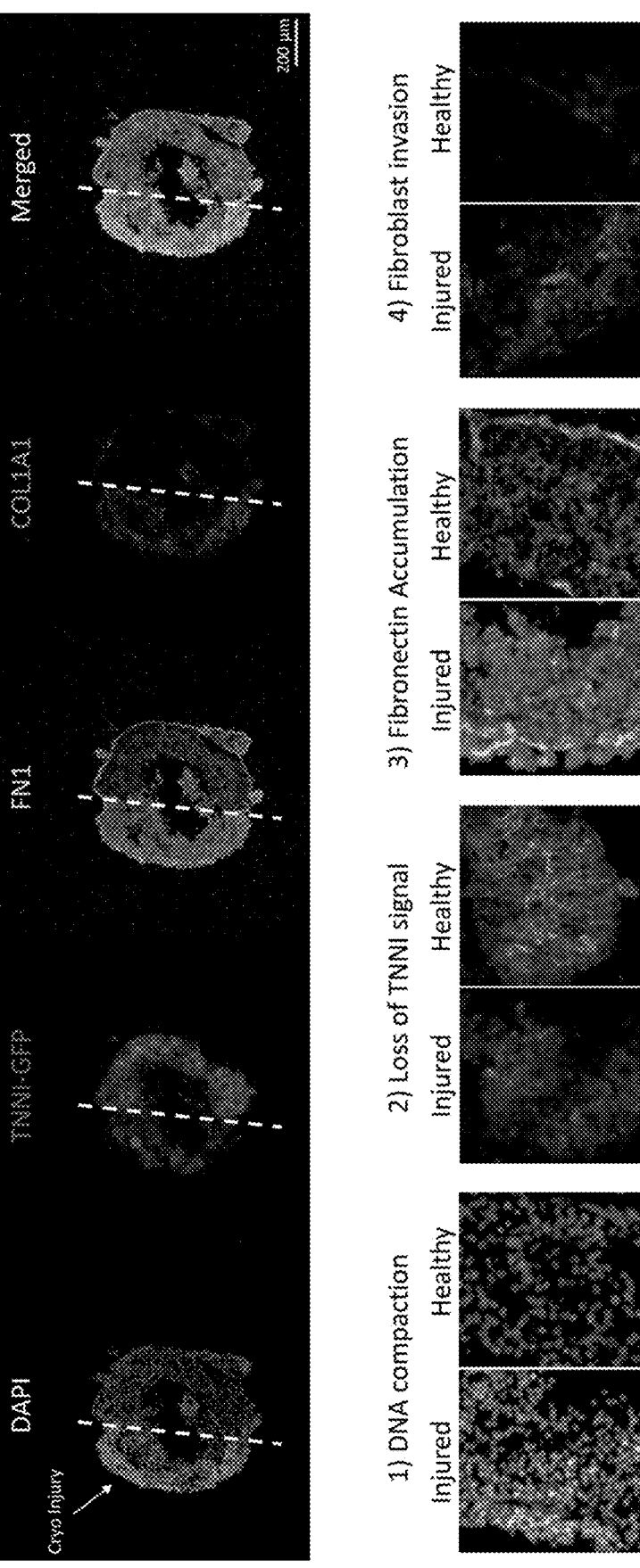

FIG. 29: Cryo-injured cardioids recapitulate aspects of injury response.

28

Figure 30:
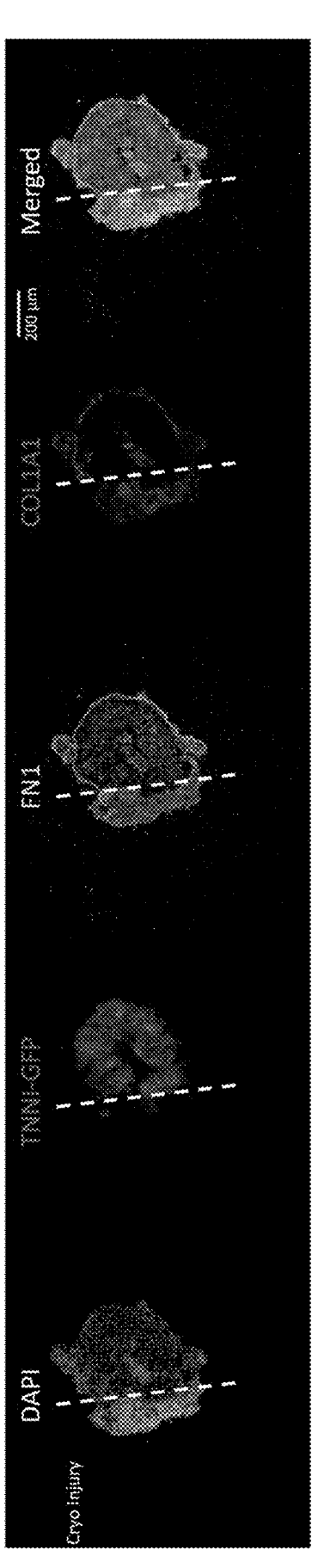
Figure 30:
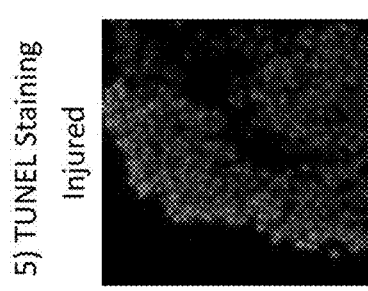
Figure 30:
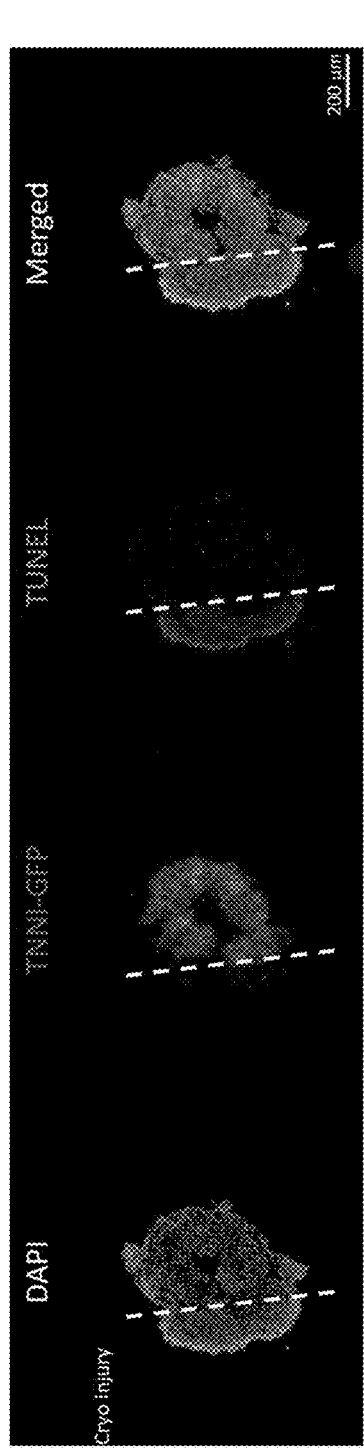

FIG. 30: Necrosis in cryo-injured cardioids as shown by TUNEL staining recapitulates aspects of injury response.

Figure 31:
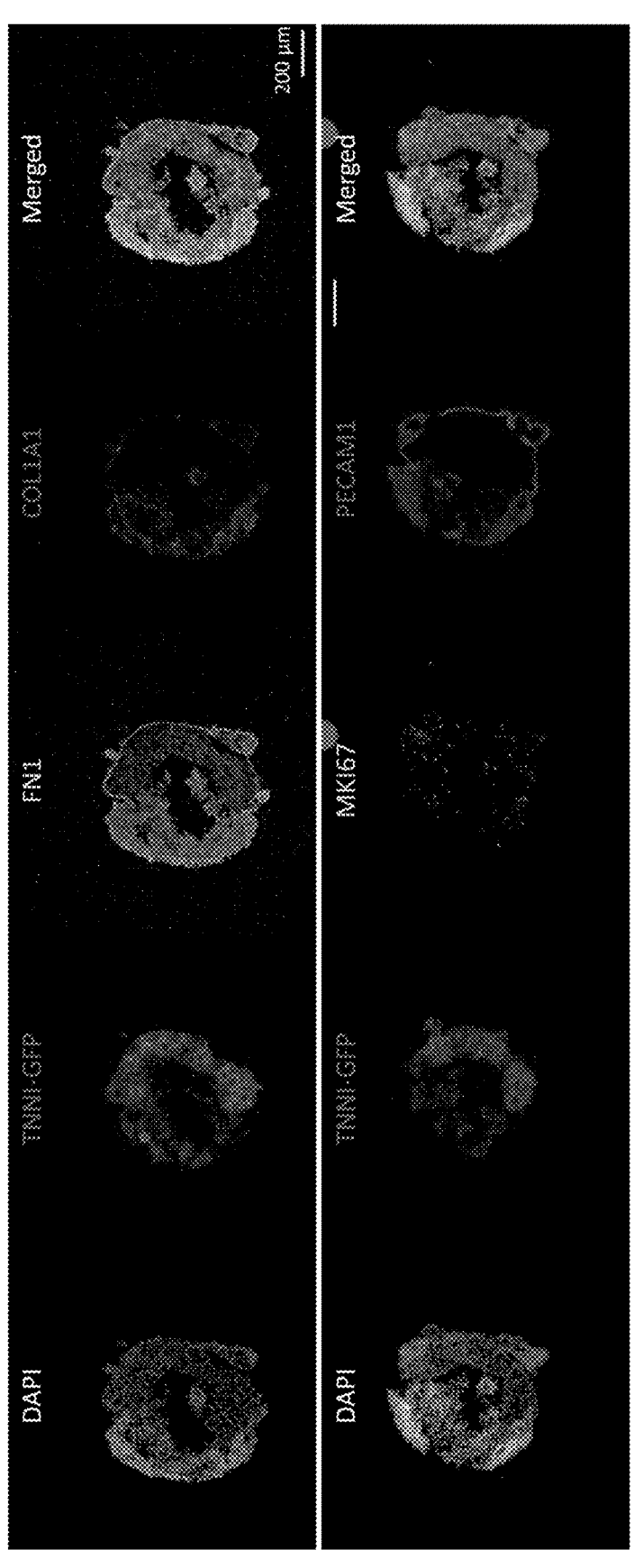

FIG. 31: No increased proliferation at injury site—Endothelial cells outside/part of injured area.

Figure 32:
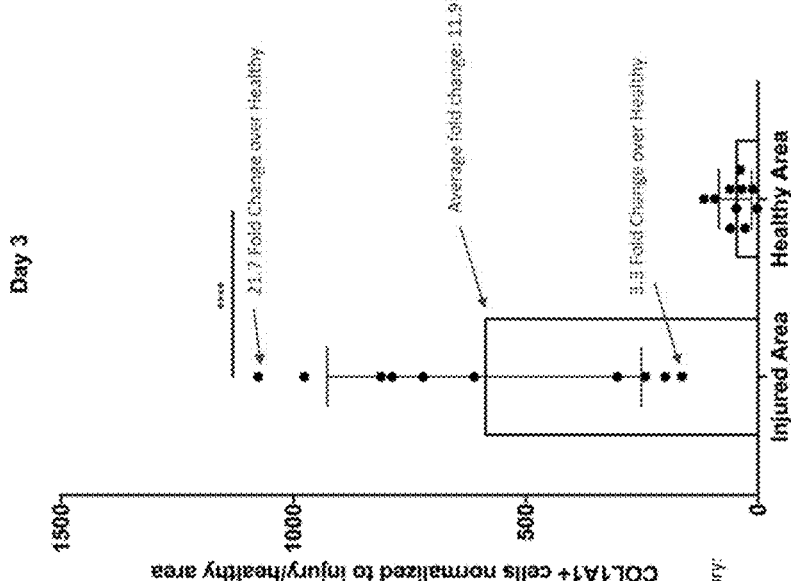

FIG. 32: Increased Numbers of Fibroblasts in Injured Area

Figure 33:
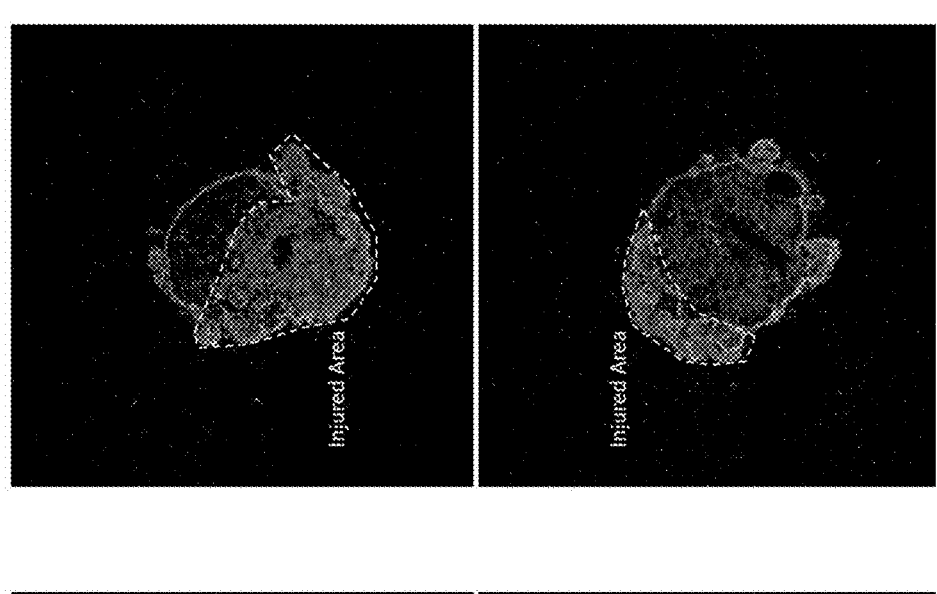
Figure 33:
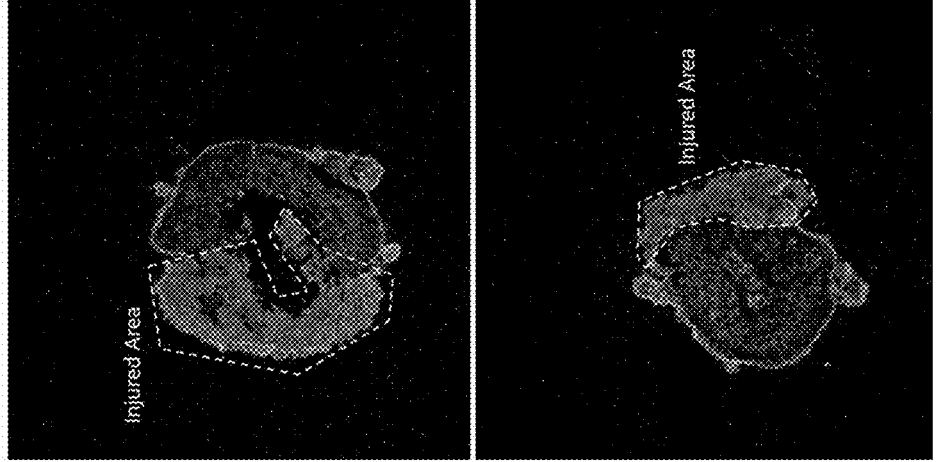

FIG. 33: FN1 accumulation in injured area.

Figure 34:
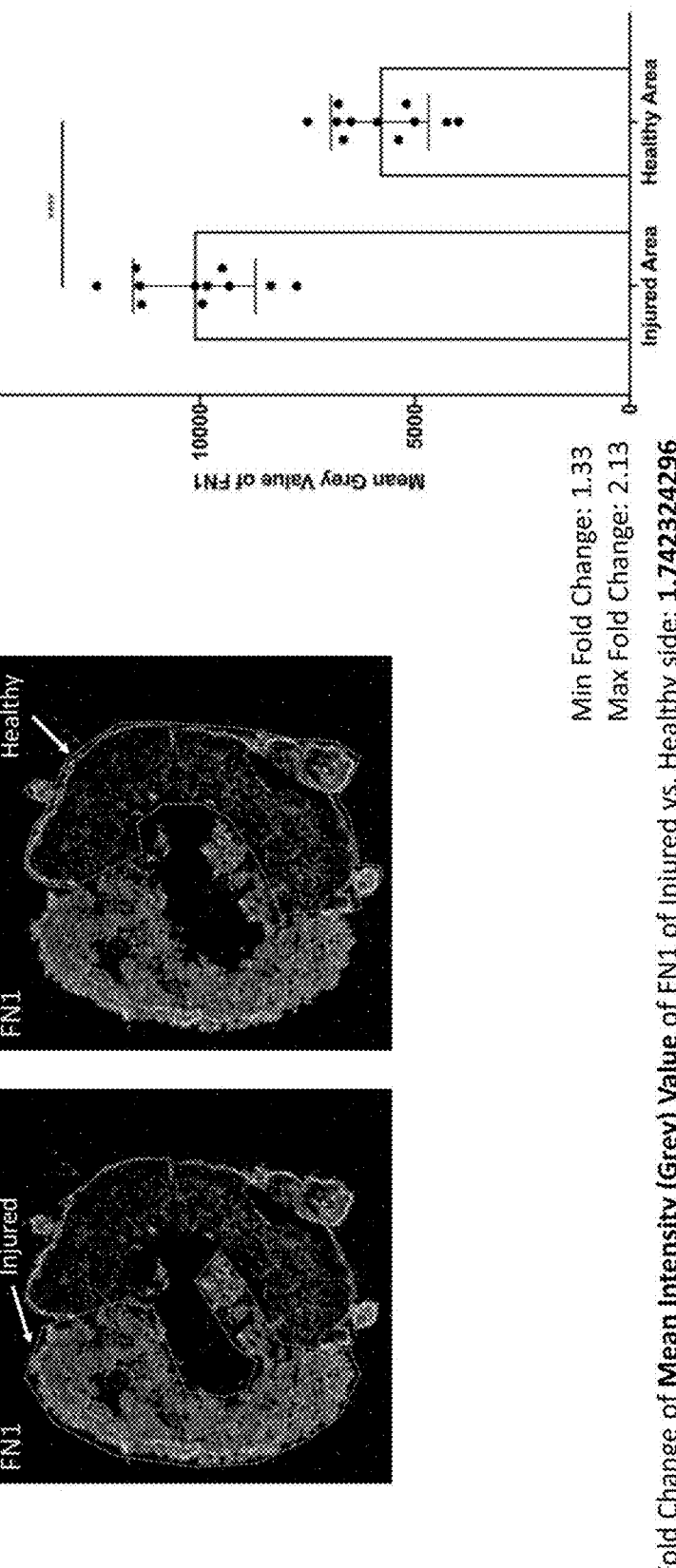

FIG. 34: Fibronectin mean intensity value quantification.

EXAMPLES

Example 1: Materials & Methods

General human pluripotent stem cell culture—Human pluripotent stem cell lines (H9, WiCell; WT and modified WTC, Allen Institute for Cell Science) were cultured in a modified in-house medium based on the E8 culture system. The E8 recipe was supplemented with 0.5% BSA (Europa Biosciences) and in-house produced FGF2. Cells were grown on either Corning or Eppendorf tissue culture-treated plates coated with Vitronectin (Stem Cell Technologies) and passaged using either TrypLE Express Enzyme (Gibco) or PBS-EDTA every 3-4 days.

hPSCs differentiation into cardiomyocytes in 2D and 3D aggregates—hPSCs were seeded at 160-175,000 cells/24 well plate in E8+ROCKi (Y-27632, Tocris) for 24 h. Cells were then induced for 36 h-40 h with CDM medium (Mendjan et al. Cell Stem Cell (2014) Vol. 15, p. 310-325) containing FGF2 (30 ng/ml, Cambridge University), LY294002 (5 μM, Tocris), Activin A (50 ng/ml, Cambridge University), BMP4 (10 ng/ml, R&D Systems), CHIR99021 (1-1.5 μM for H9, 3-4 μM for WTC, Tocris). 1 μg/ml of Insulin (Roche) was optionally added to increase cell viability during this stage. This medium was termed FLyABCH (Ins). Following 36 h-40 h, cells were induced with CDM medium containing BMP4 (10 ng/ml), FGF2 (8 ng/ml), Insulin (10 μg/ml), IWP2 (5 μM, Tocris) and Retinoic Acid (0.5 μM, Sigma Aldrich) for 4 days with medium change every day. This medium was termed BFIIWPRa. Subsequently, the medium was changed to CDM medium containing BMP4 (10 ng/ml), FGF2 (8 ng/ml) and Insulin (10 μg/ml) for 2 days with medium change every day. This medium was termed BFI. For maintenance of the obtained cardiomyocytes, medium was changed to CDM medium containing Insulin (10 μg/ml) and half the medium exchanged every day. This medium was termed CDM-I. For the generation of assembled/aggregated cardiomyocytes, cardiomyocytes maintained until Day 21 were dissociated using the StemDiff cardiomyocyte dissociation kit (Stem Cell Technologies) and reseeded as aggregates in AggreWell400 plates (Stem Cell Technologies) at 1000 cells/well in CDM-I and 5% FBS (PAA). After 2 days, formed aggregates were transferred to ultra-low cluster 96-well plates (Corning) in CDM-I and put on a shaker at 58 rpm, 37 C and 5% CO2. After 4 days, with a medium change after 2 days, the aggregates were used for analysis.

Generation of cardiac organoids—hPSCs were harvested at around 70% confluency. 5000 cells/well were subsequently seeded into ultra-low attachment 96-well plates (Corning) containing E8+ROCKi (Y-27632, Tocris) and collected by spinning for 5 minutes at 200G. After 24 h formed aggregates were induced with FLyAB(Ins) containing 4-8 μM CHIR99021. Cardiac differentiation was proceeded as described for 2D cultures. For maintenance of the obtained cardiac organoids, medium was changed to CDM medium containing Insulin (10 μg/ml) and exchanged every second day.

Generation of cardiac organoids with endothelial lining—Pluripotency maintenance medium was refreshed 6 h prior to seeding cells. Then, 2500-3000 hPSC were seeded into ultra-low cluster 96-well plates (Corning) in FLyAB(Ins) medium with CHIR (5-6 µM) and ROCKi (5 µM) for 36 h-40 h. Next, medium was exchanged to BFIIWPRa with the addition of VEGF-A (200 ng/ml, Peprotech) for 4 days with medium exchanged every day. Subsequently, medium was exchanged to BFI+VEGF-A (100 ng/ml) for 2 days with a medium changed after 1 day. For maintenance, CDM medium with 100 ng/ml of VEGF-A was used and exchanged every second day.

Epicardial engulfment of cardiac organoids—For epicardial differentiation, ~70% confluent hPSCs were seeded at 55,000 cells/24 well plate in E8+ROCKi (Y-27632, Tocris) 24 h prior differentiation. Cells were induced with CDM medium (Mendjan et al. 2014, supra) containing FGF2 (30 ng/ml, Cambridge University), LY294002 (7.5 µM, Tocris), BMP4 (10 ng/ml, R&D Systems) and CHIR99021 (1.5 µM, Tocris). Following 36 h-40 h, differentiation medium was exchanged to CDM medium containing BMP4 (10 ng/ml), FGF2 (8 ng/ml), Insulin (10 µg/ml), IWR-1 (1 µM, Tocris) and Retinoic Acid (1 µM, Sigma Aldrich) for 2 days with medium change every day. Subsequently, the medium was changed to CDM medium containing BMP4 (10 ng/ml), Insulin (10 µg/ml) and Retinoic Acid (1 µM) for 5 days with one medium change in-between. For maintenance of the obtained epicardium, cells were seeded at the end of differentiation onto Bovine Fibronectin (2 µg/ml, Sigma) coated plates in CDM medium containing Insulin (10 µg/ml) and SB431542 (10 µM, Tocris) supplemented with ROCKi for the first day of seeding. This medium was termed CDM-SBI. The replated epicardium was routinely passaged at 80-90% confluency every 3-5 days at 1:3 ratio; or subsequently differentiated to Cardiac Fibroblast (CF) or Smooth Muscle (SMC) Cells for 12 days, using CDM medium containing FGF2 (30 ng/ml, Cambridge University), TGFb2 (2 ng/ml, R&D Systems), L-ascorbic acid (100 µg/ml, Sigma), Insulin (10 µg/ml) or CDM medium containing PDGF-BB (10 ng/ml, R&D Systems), L-ascorbic acid (100 µg/ml, Sigma), Insulin (10 µg/ml) supplemented with TGFb2 (2 ng/ml, R&D Systems) for the first 2 days of differentiation, respectively.

For the generation of aggregated epicardium used in the engulfment assay, day 8.5 epicardial cells were dissociated using TrypLE Express Enzyme (Gibco) and re-seeded as aggregates in AggreWell400 plates (Stem Cell Technologies) at 1000 cells/well in CDM-SBI and 5% FBS (PAA). After 2 days, on average 8-12 formed aggregates/well were transferred to ultra-low cluster 96-well plates (Corning) containing differentiated cardiac organoids in CDM-I, put on a shaker at 58 rpm, 37 C and 5% $CO_2$, and co-cultured together for 1 week with CDM-I medium refreshed every second day.

Example 2: Cardiac Mesoderm with Cavities Formed In Vitro

The central morphological hallmark of the heart is a cavity surrounded by cardiomyocytes (CM), with the potential to become beating CMs, and with an endothelial (endocardial) lining. In vivo, this cavity forms through a complex process of migration of cardiac mesoderm and fusion of endocardial tubes that are assisted by foregut endoderm constriction. The resulting heart tube goes on to develop into a multi-chambered heart. However, heart tubes and chambers can form in vivo in the absence of endocardium and foregut endoderm constriction.

Figure 1:
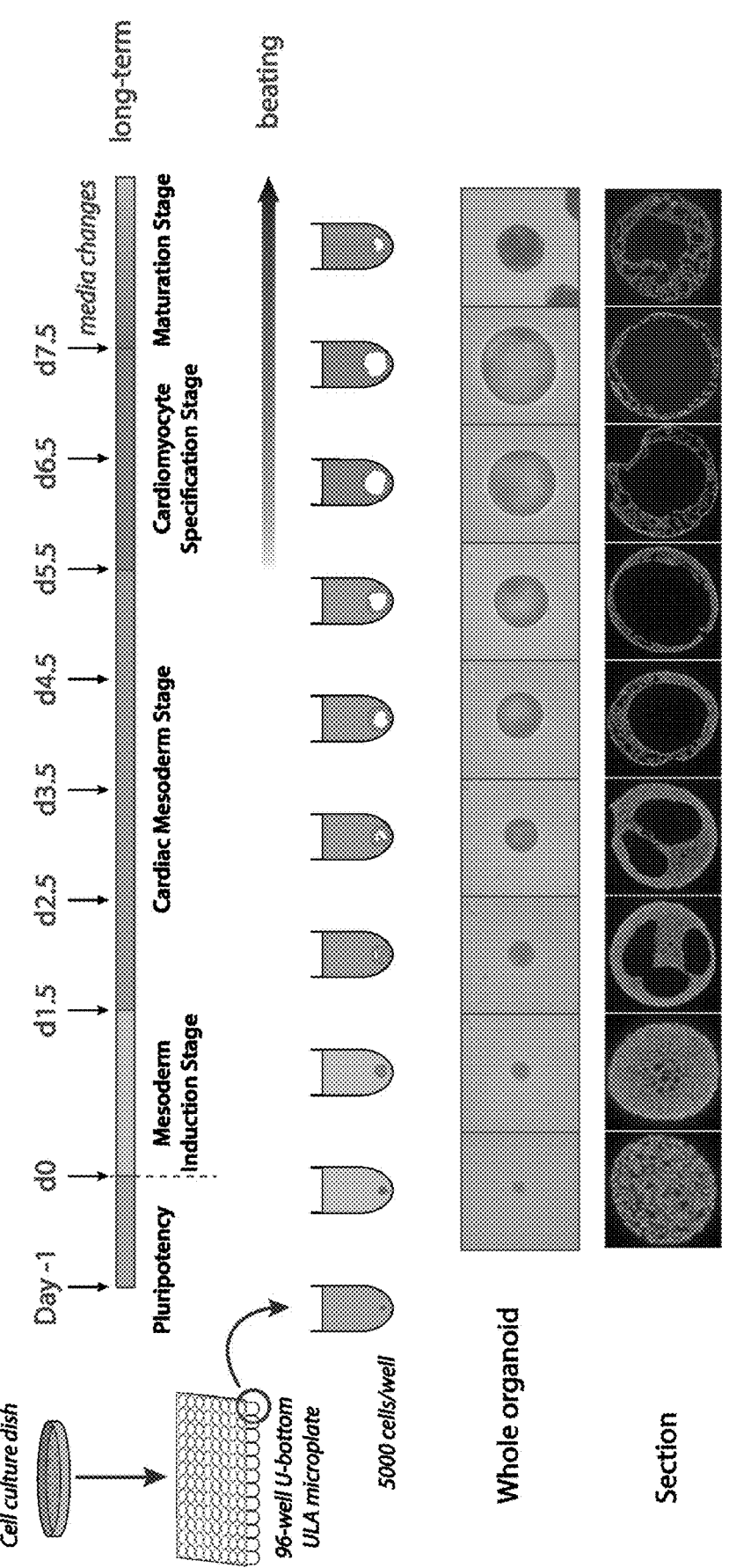
FIG. 1: Overview of the basic cardiac organoid protocol starting from pluripotent stem cells, aggregation in 96-well plate, formation of cardiac cavity until the beating cardiomyocyte stage. An actual time course with section is shown below.

We tested whether cardiac mesoderm might be sufficient to form a cavity under permissive conditions in vitro. To this end, we applied a high-throughput differentiation approach in adherent 96-well plates based on temporal control of cardiogenic signalling pathways while testing Activin, BMP, FGF, retinoic acid and WNT to their effects on differentiation while differentiating hPSCs into mesoderm, cardiac mesoderm and (beating) cardiomyocyte progenitors (FIG. 1). To screen for factors that could mediate cavity formation in vitro, we supplemented the media with selected extracellular matrix (ECM) proteins that are involved in early cardiogenesis. For instance, addition of Laminins 521/511 before mesoderm induction resulted in rapid, dose-dependent self-aggregation at different stages of specification, from a 2D layer into 3D spherical structures that were beating by day 7 of differentiation (FIG. 1). Strikingly, these structures were hollow, as confirmed by the presence of a cavity in confocal and histological section (FIG. 1,2). Analysis of a MYL7-GFP reporter and staining for CM markers TROPO-T/MYL7 confirmed that the structures were built mostly from cardiomyocytes.

We next tested whether exogenous ECM was necessary for self-aggregation of mesoderm or directly involved in cavity formation. When we performed cardiac differentiation in 3D non-adherent 96-well plates, we found that exogenous ECM was not required for rapid self-aggregation, robust self-organisation and differentiation into beating TROPO-T+/MYL7+ structures containing a cavity (FIG. 2), HT imaging, live imaging & sections). This high-throughput approach therefore allowed us to rapidly optimise timing, cell number and media conditions towards a highly reproducible self-organising cardiac model in vitro.

Figure 3:
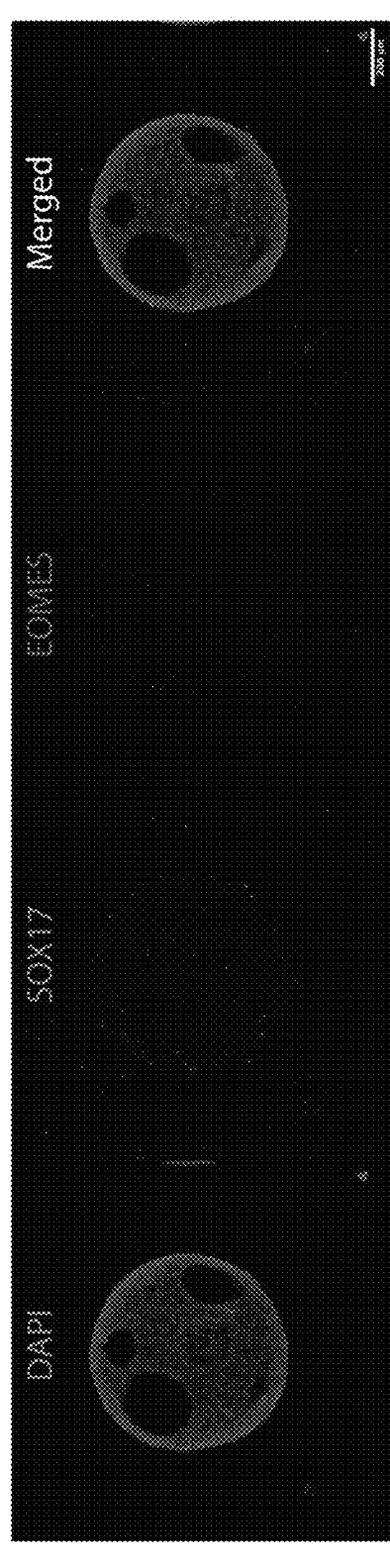
FIG. 3: A: Section of an organoid at day 3.5 showing absence of endodermal markers SOX17 and EOMES. Scalebar 200 µm.
Figure 5:
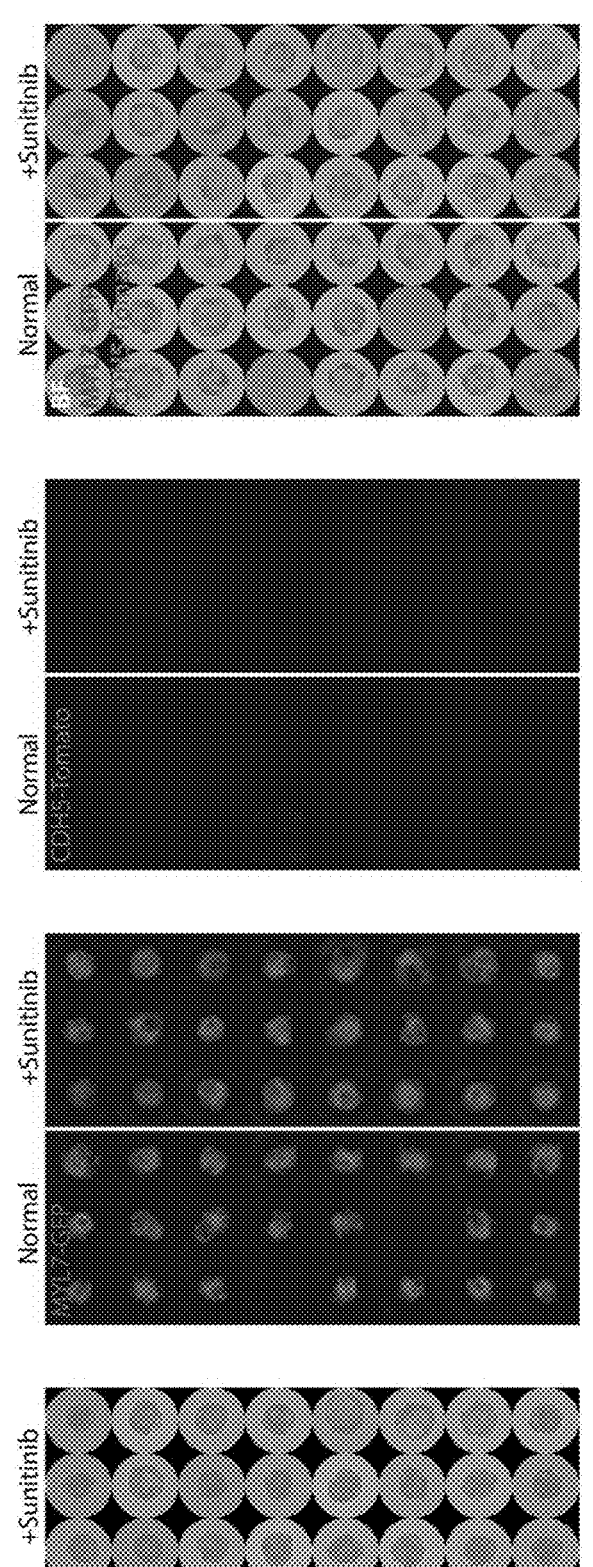
FIG. 5: A: Brightfield (BF), MYL7-GFP, CDH5-Tomato and merged images of organoids treated with Sunitinib (100 nM) designated as "+Sunitinib" or differentiated with the standard protocol ("Normal"). Images show a more homogenous MYL7-GFP expression in the "+Sunitinib" condition and an absence of CDH5-Tomato expression in both conditions. Each organoid image is 2500×2500 μm
Figure 6:
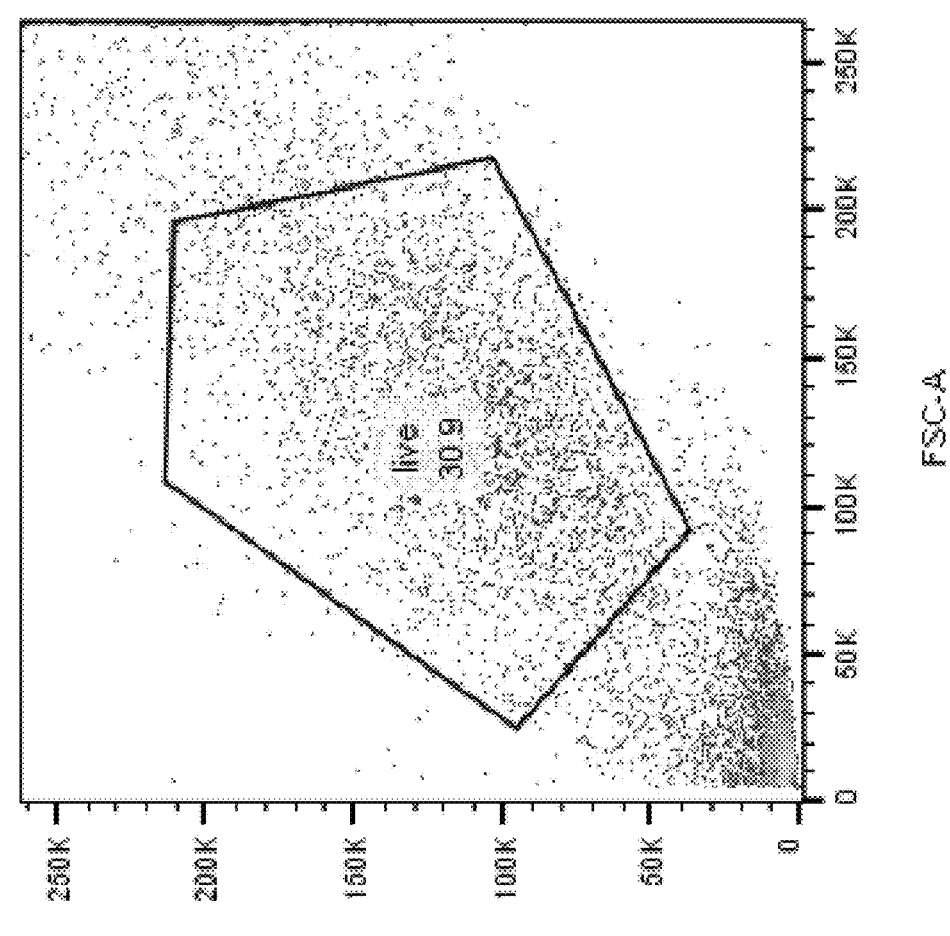
FIG. 6: A: Representative images of the quantification strategy performed on flow cytometry data at the end of the differentiation (day 7.5). "WT CTRL" designates wild-type cells from organoids not expressing any fluorophore, "Normal" designates the standard differentiation protocol, and "+Sunitinib" designates organoids that were treated with Sunitinib (100 μM). B: Quantification of the flow cytometry data shows about 60% MYL7-GFP expressing cardiomyocytes in the standard protocol that can be boosted to 96% upon Sunitinib treatment. Quantification also shows approximately 2% of cells expressing the endothelial marker CDH5-Tomato in the standard protocol and a similarly low 3% in the "+Sunitinib" condition.
Figure 6:
Figure 6:
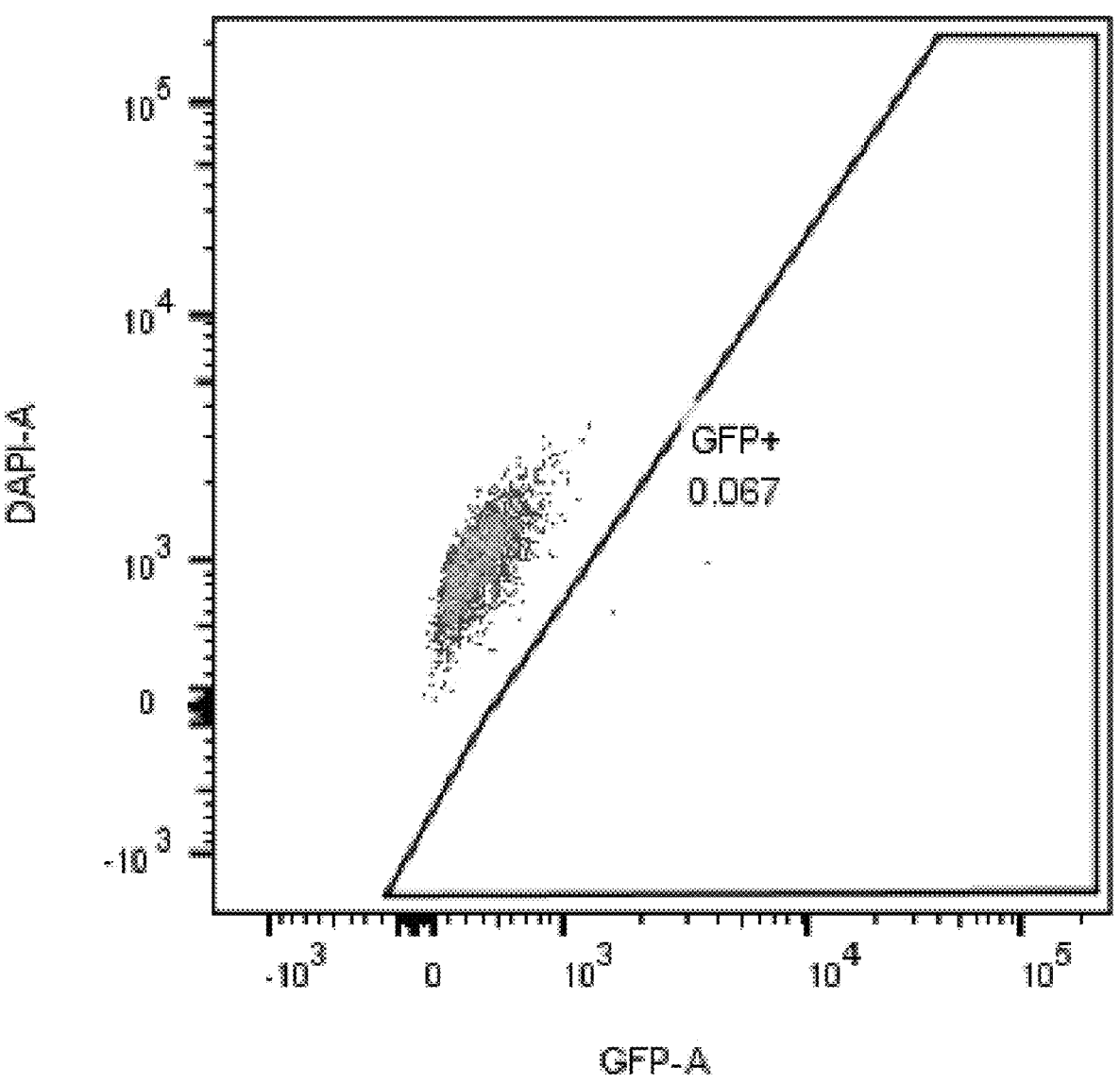
Figure 6:
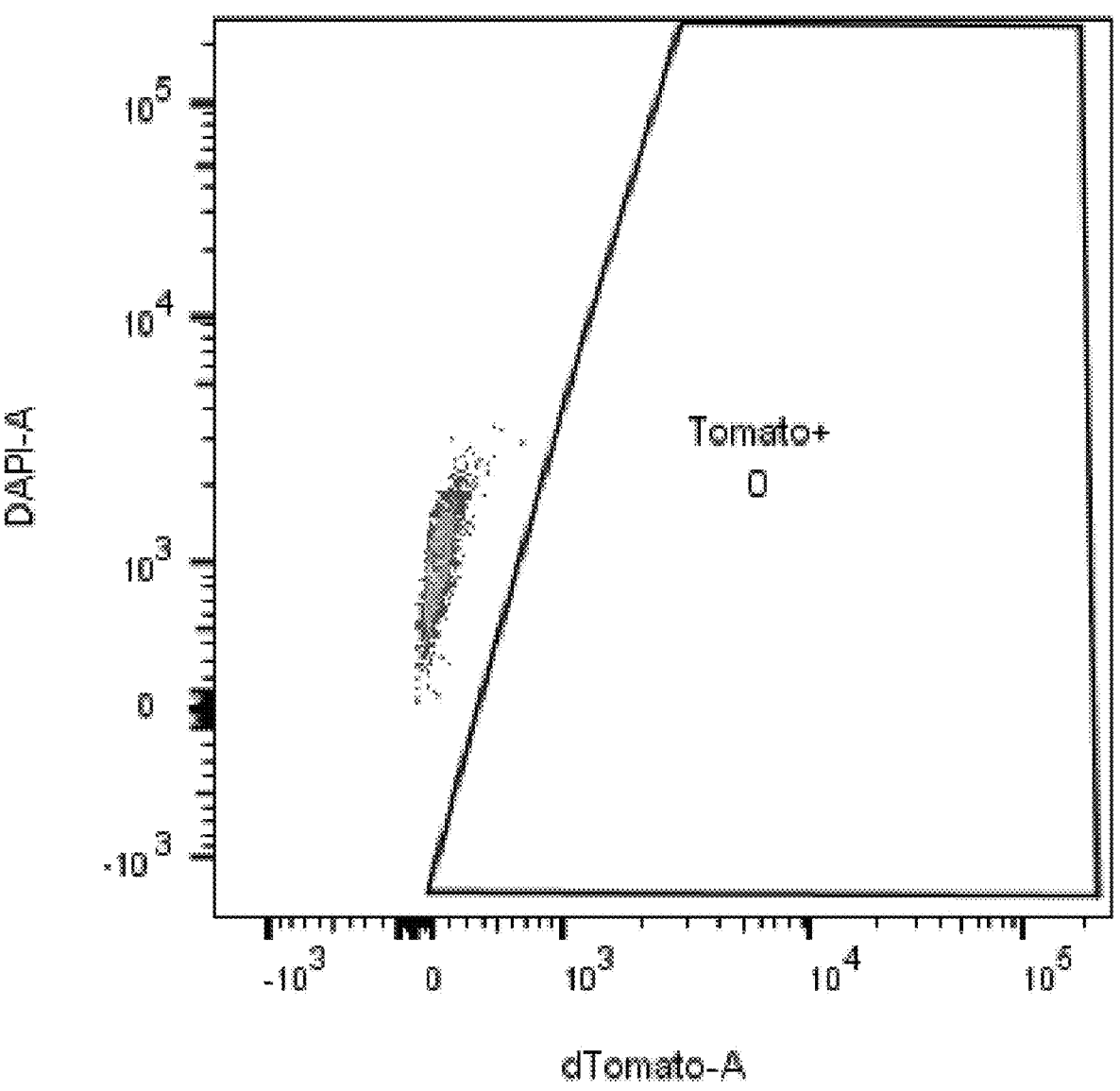
Figure 6:
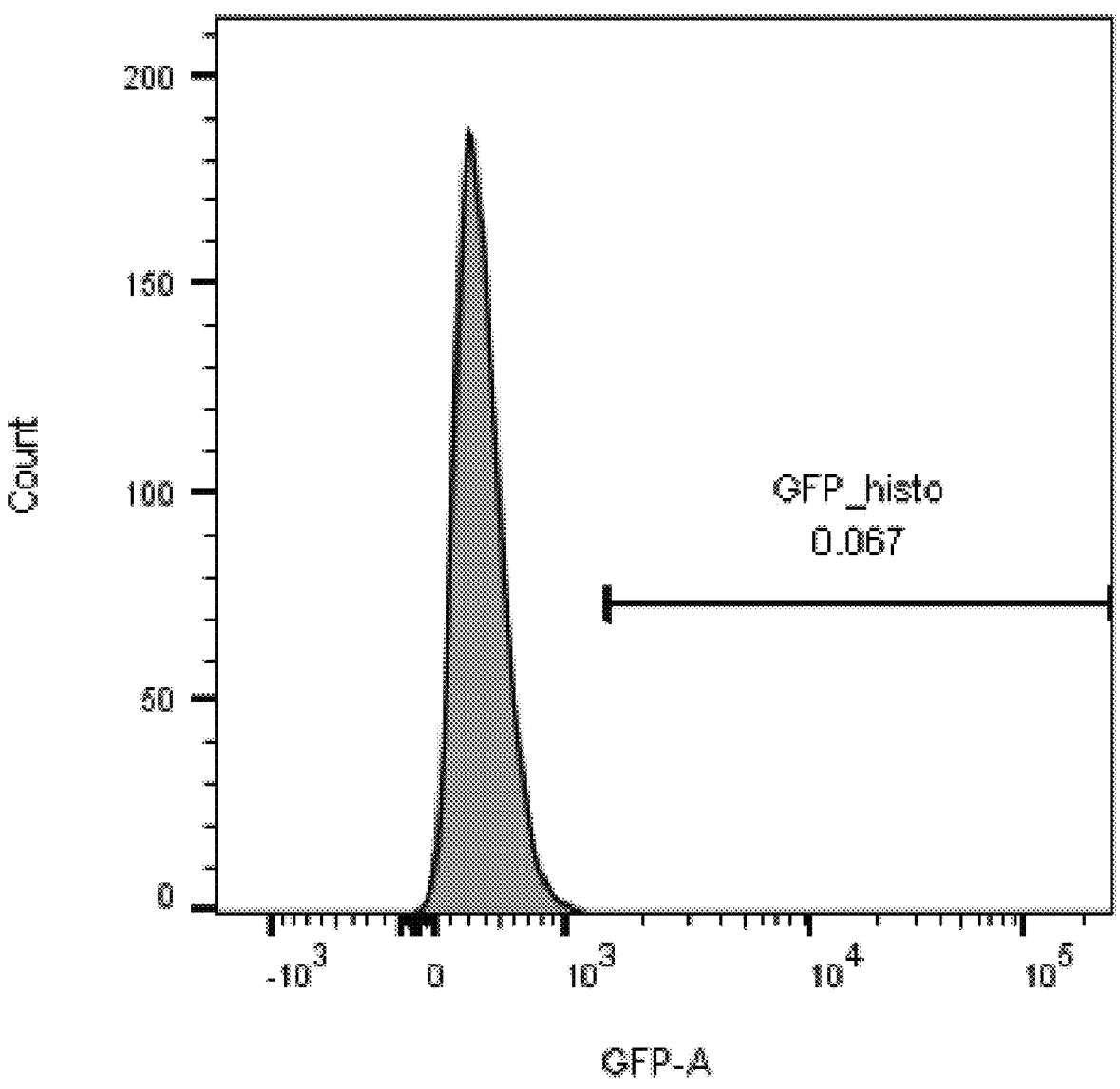
Figure 6:
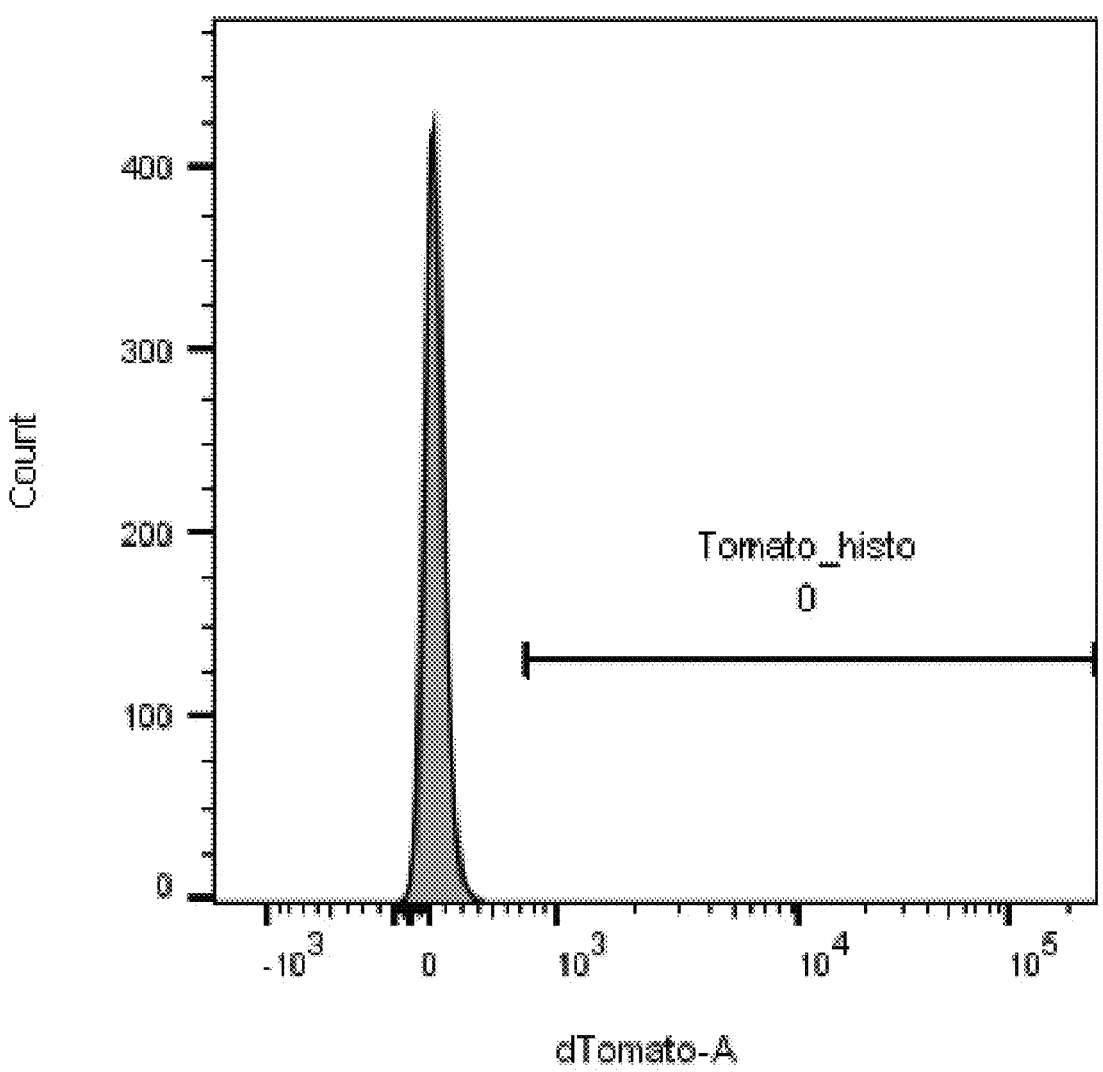
Figure 6:
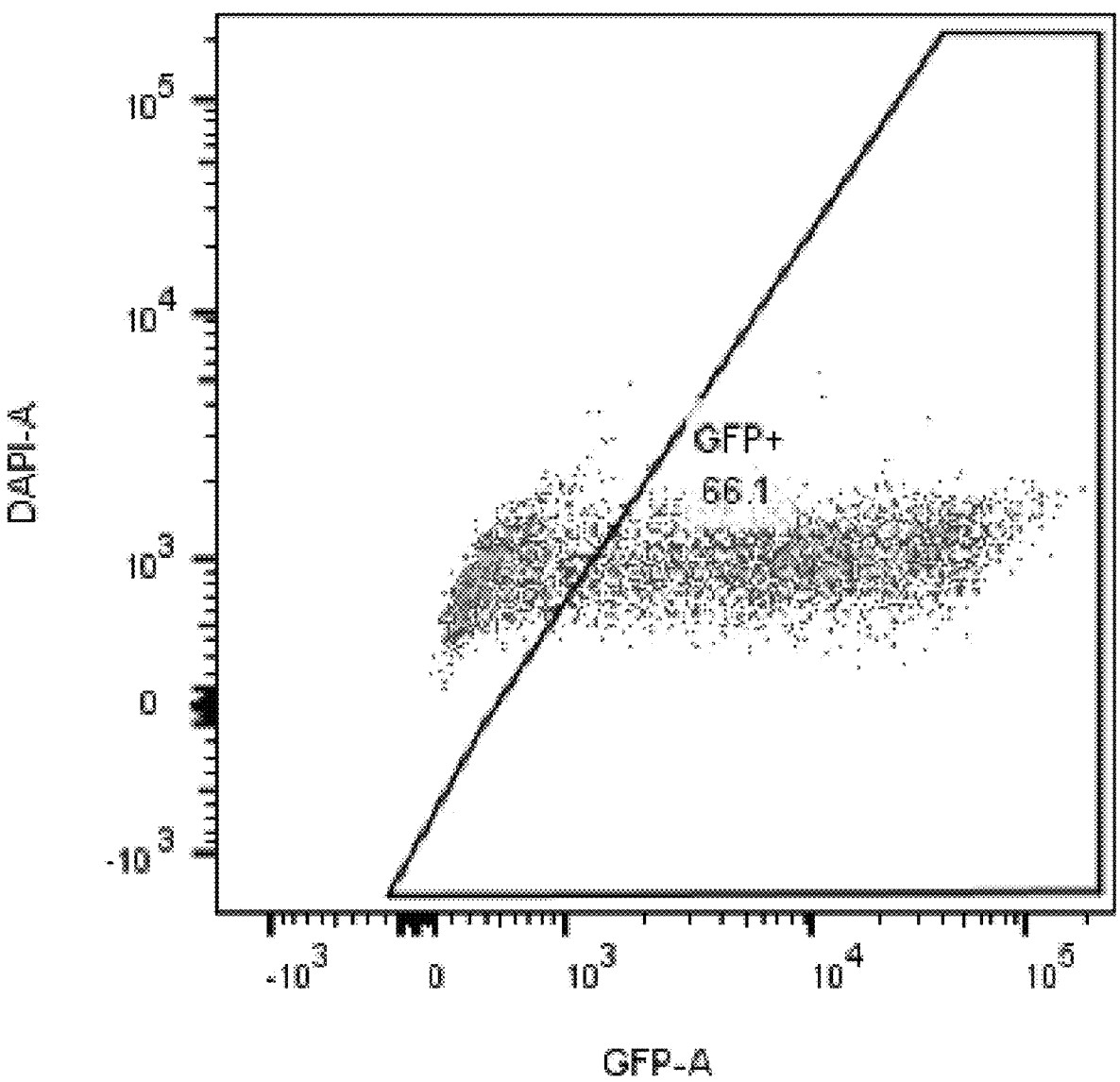
Figure 6:
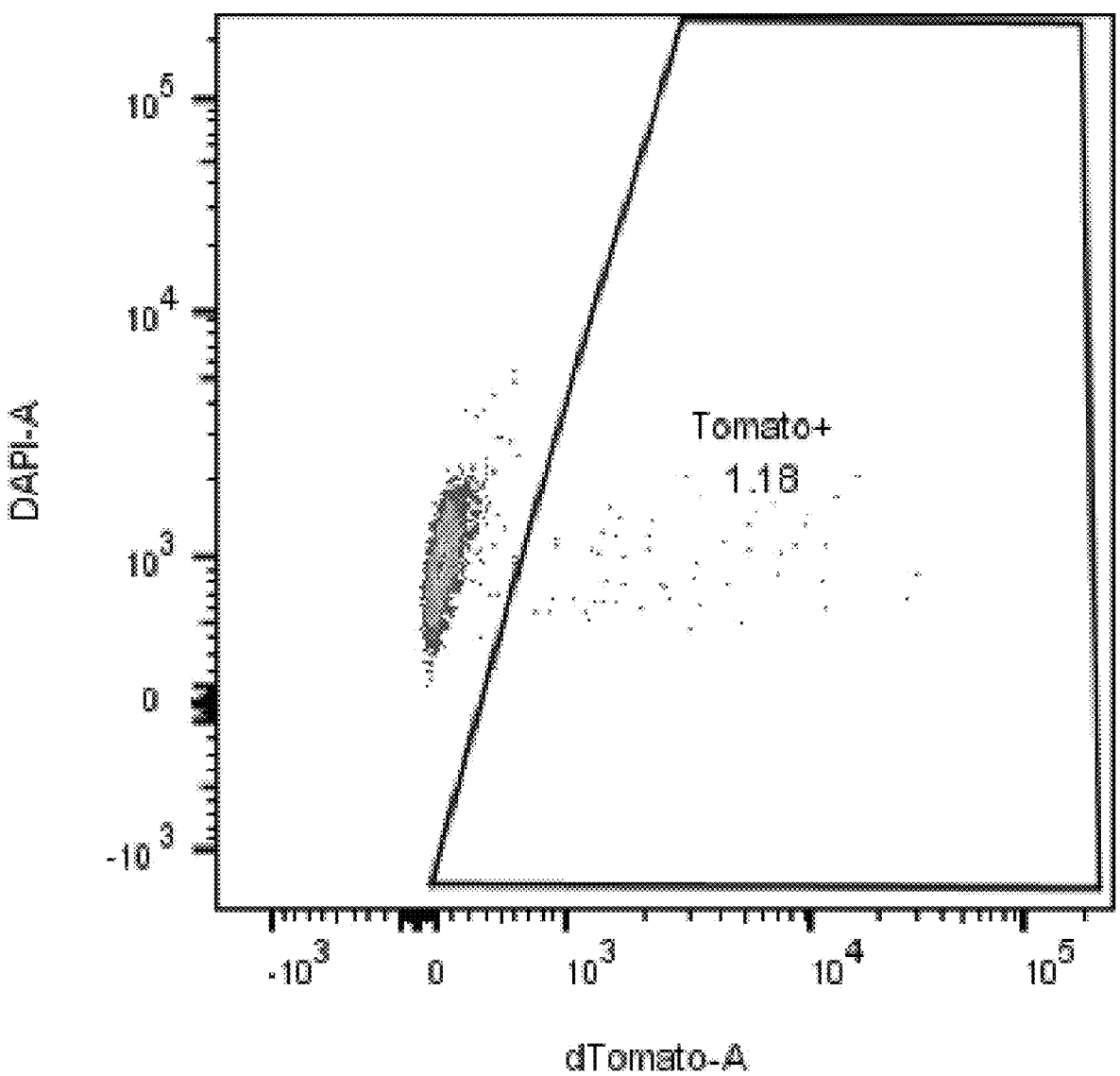
Figure 6:
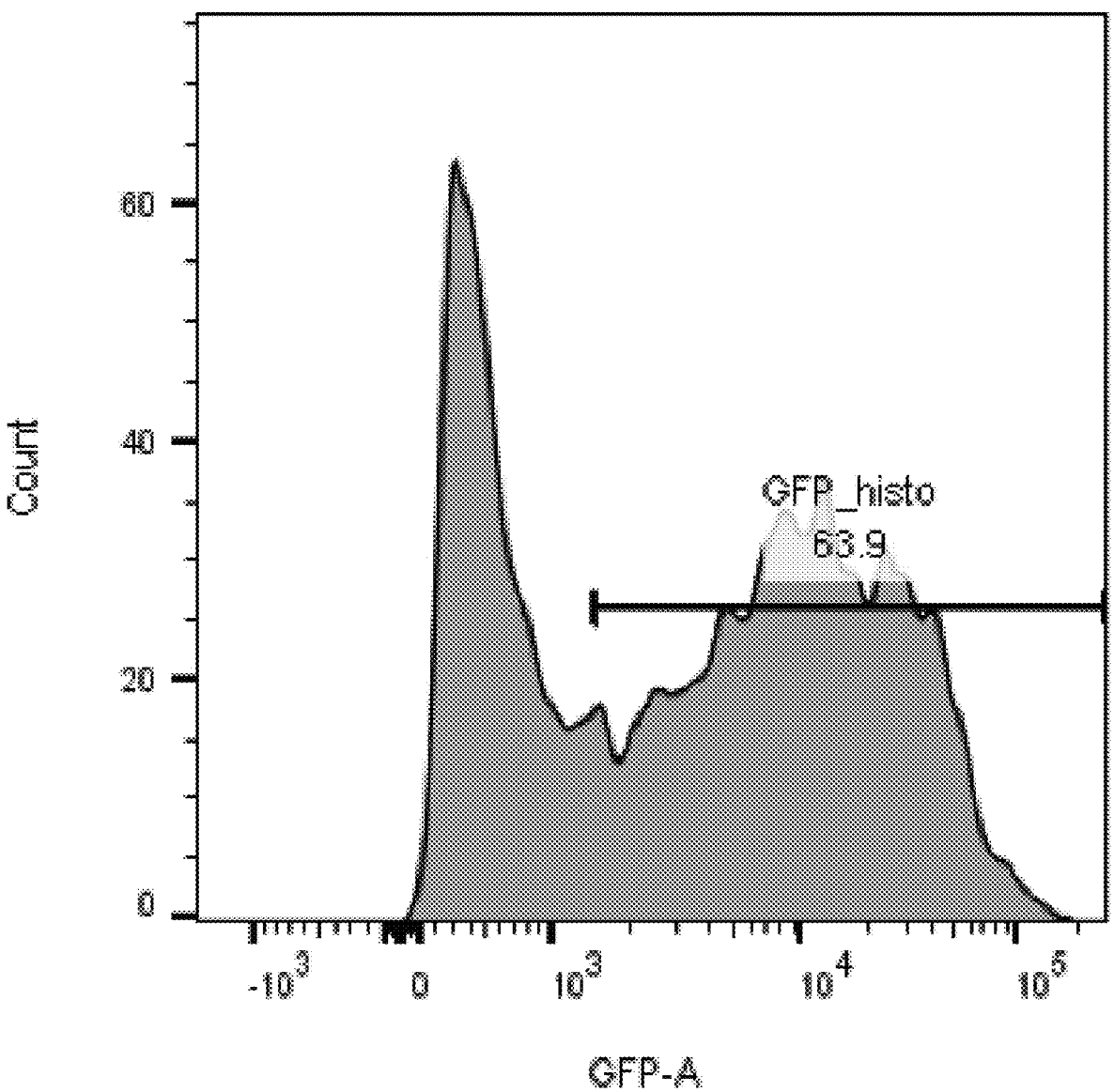
Figure 6:
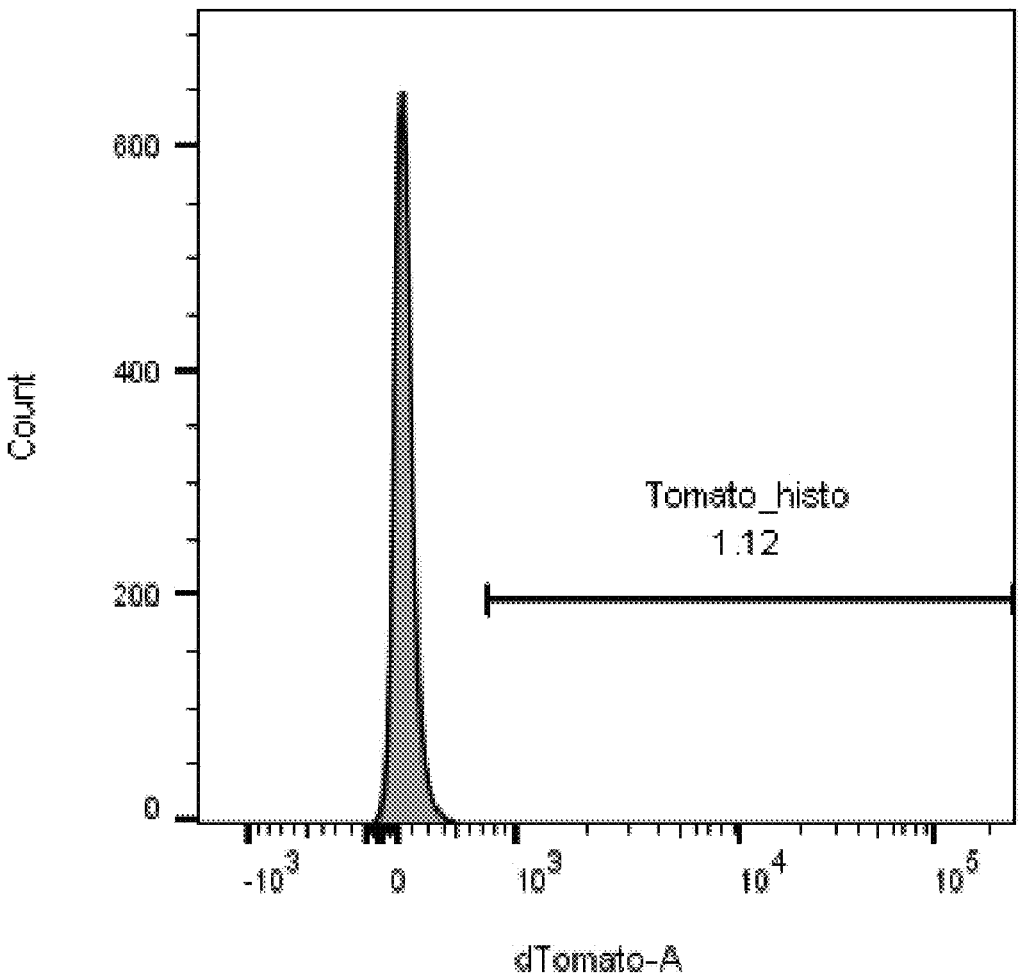
Figure 6:
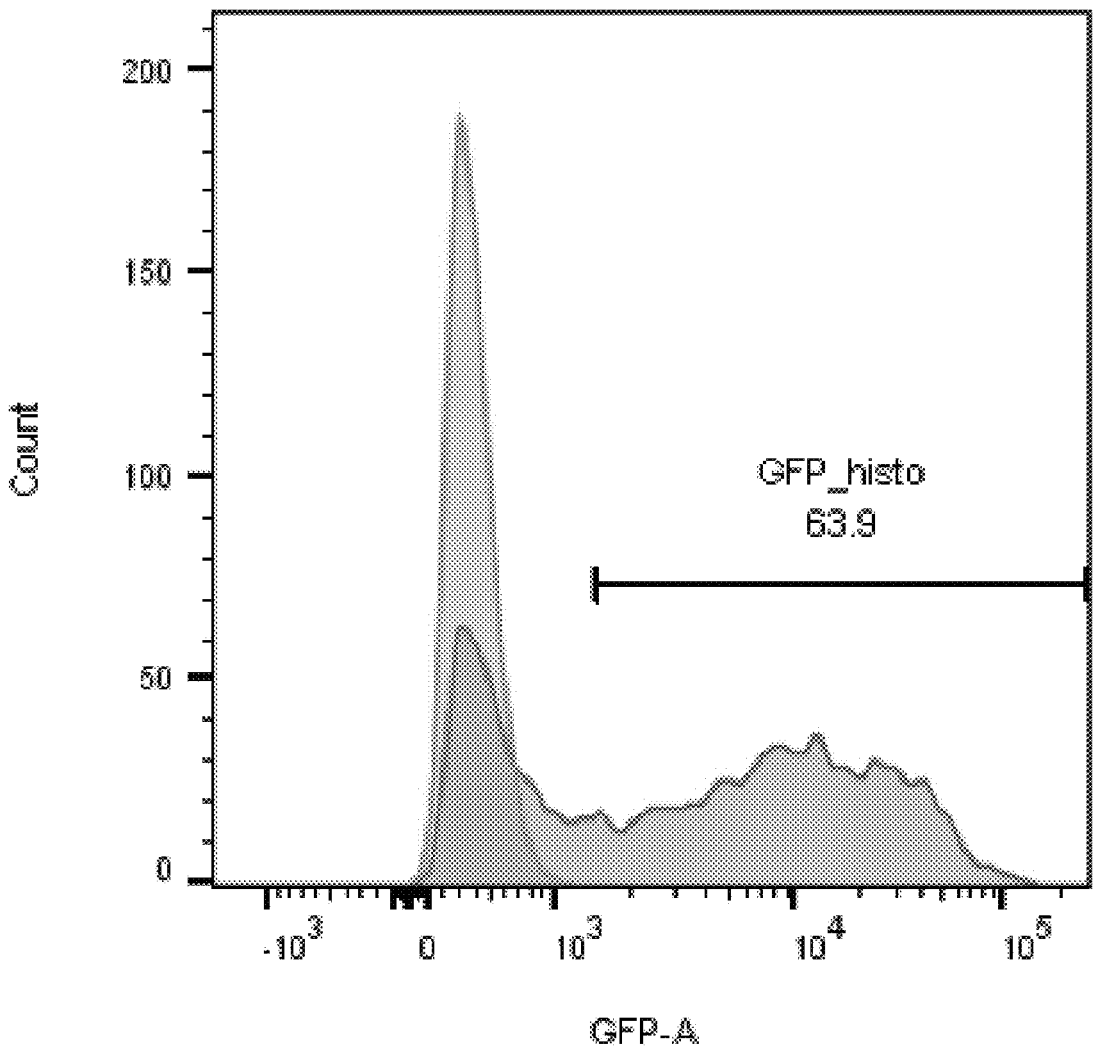
Figure 6:
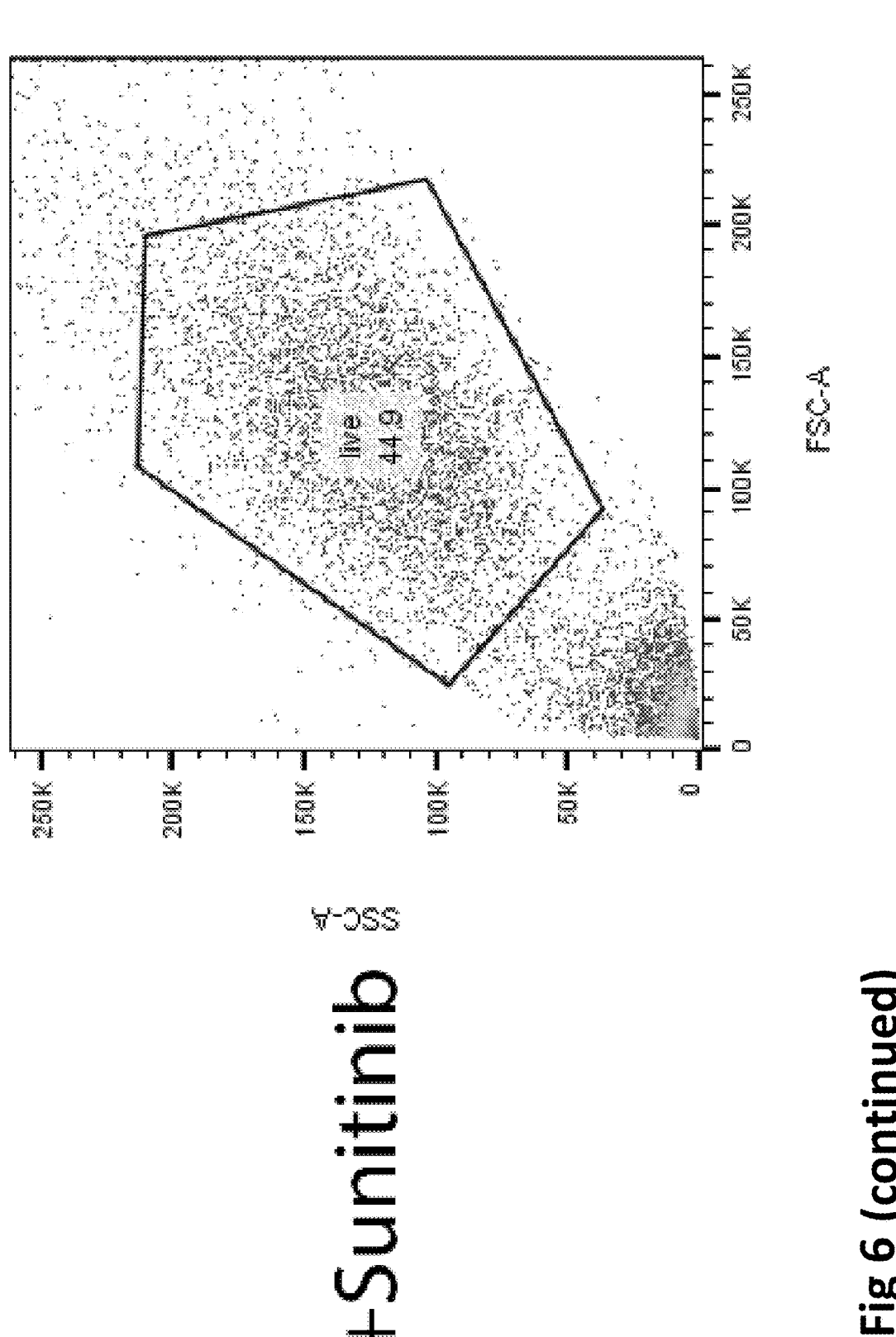
Figure 6:
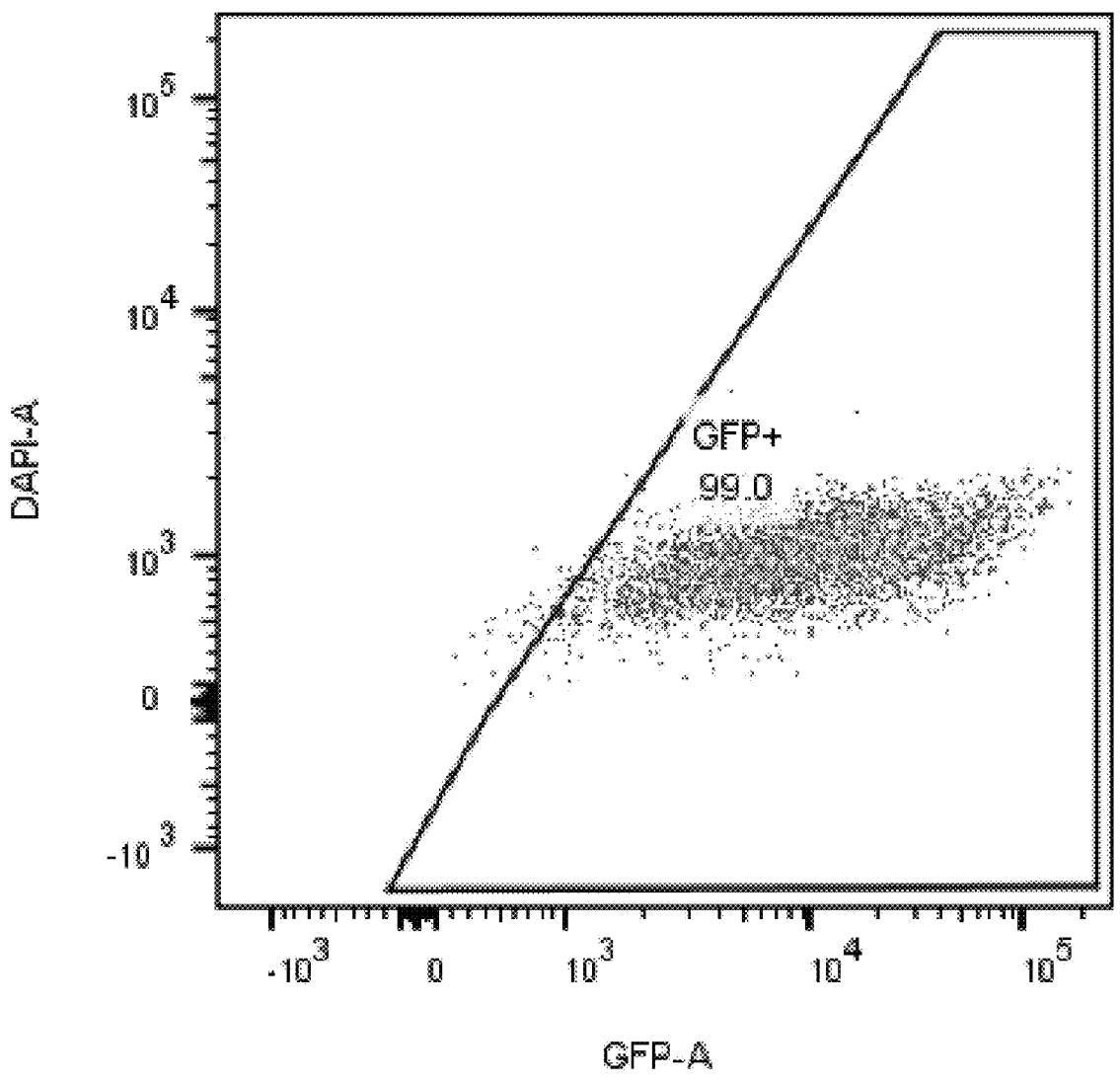
Figure 6:
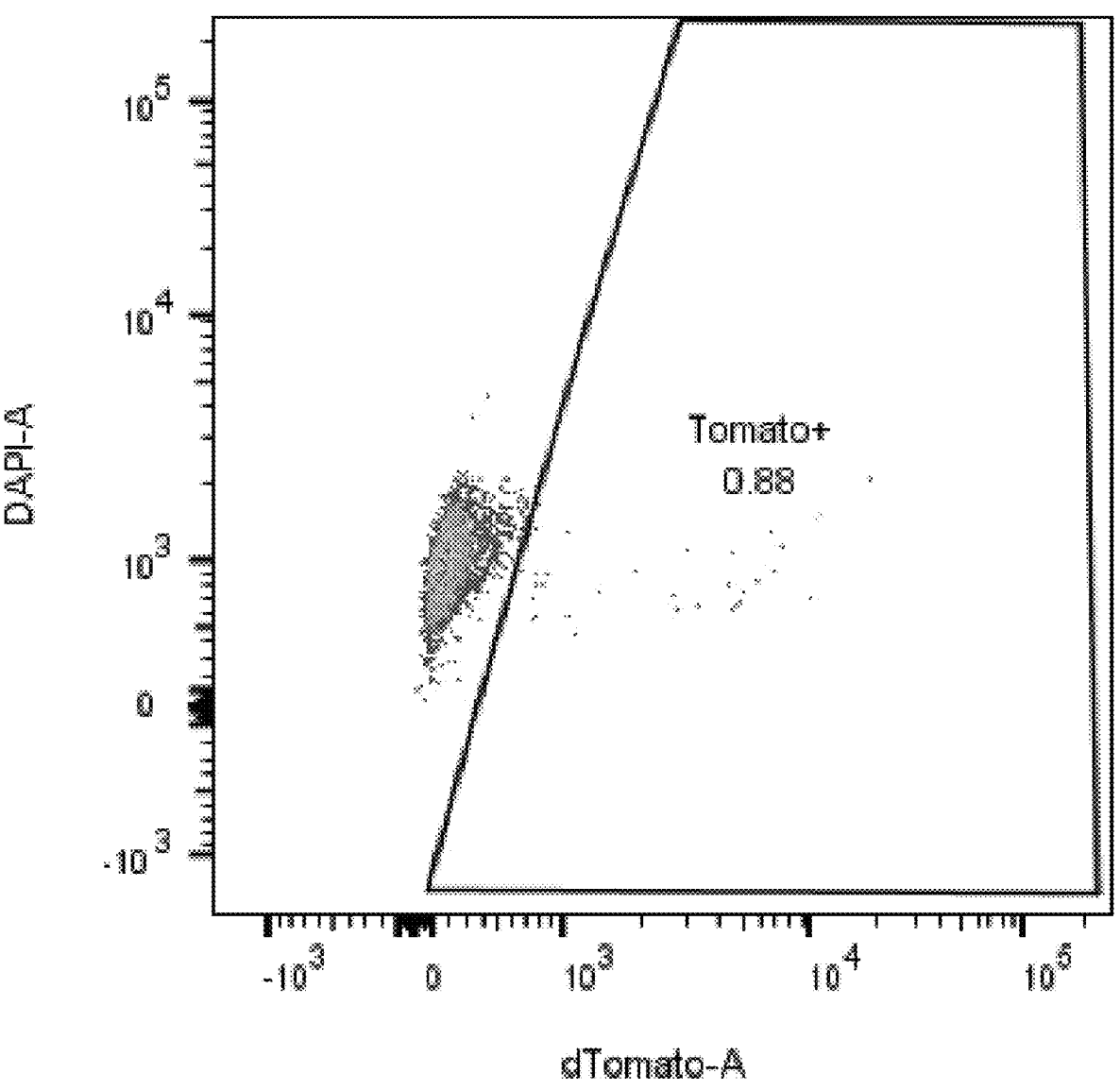
Figure 6:
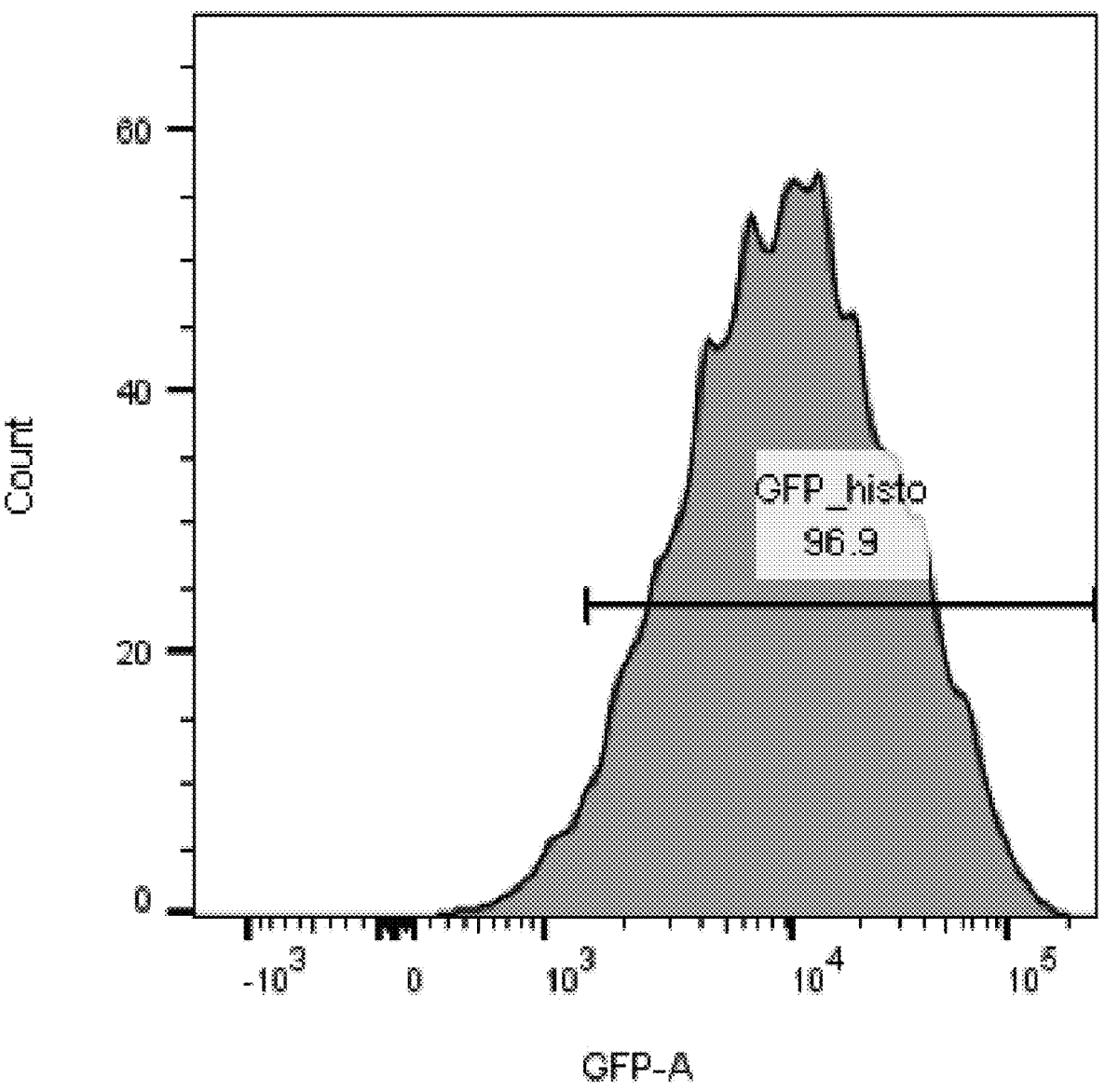
Figure 6:
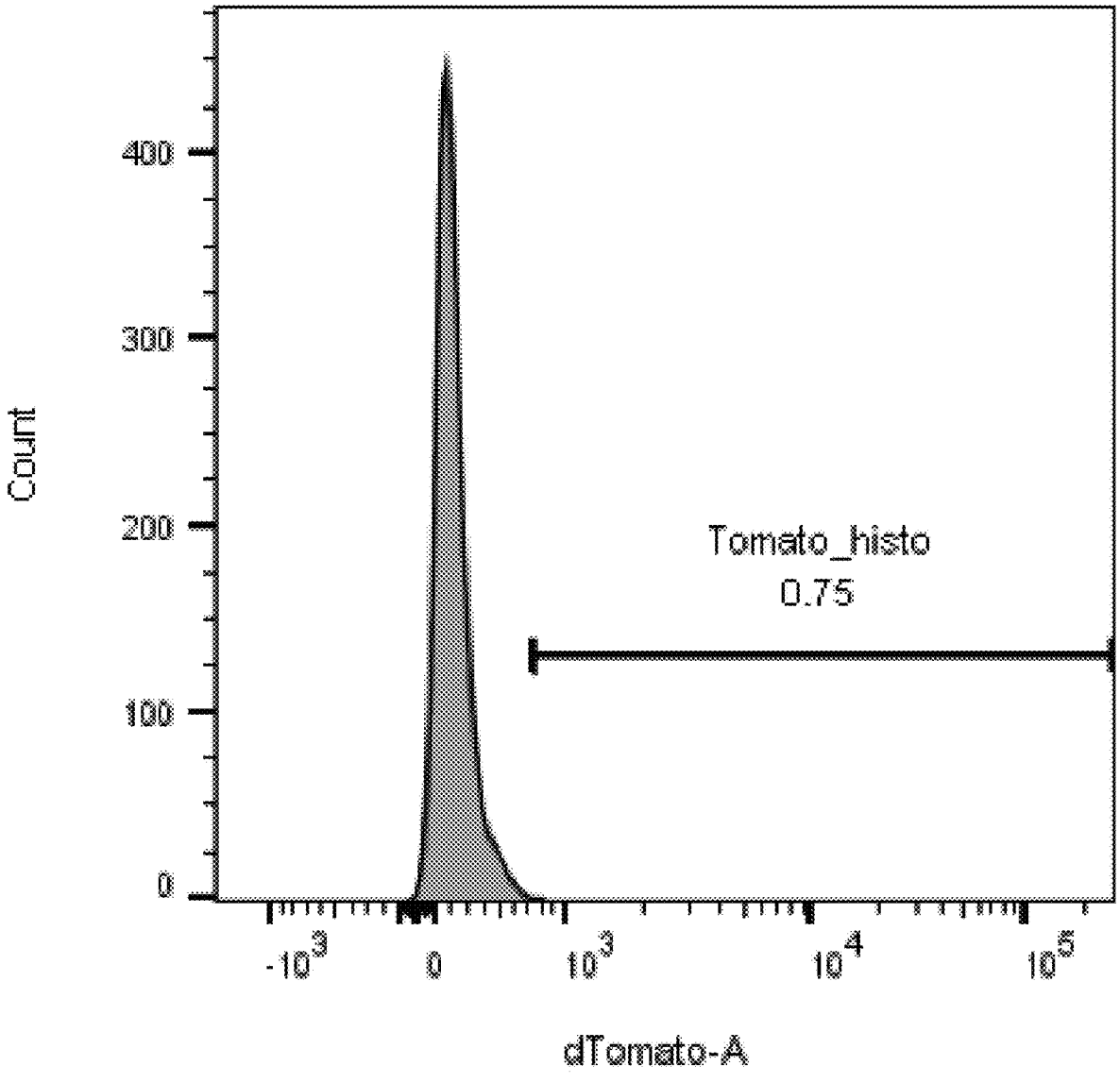
Figure 6:
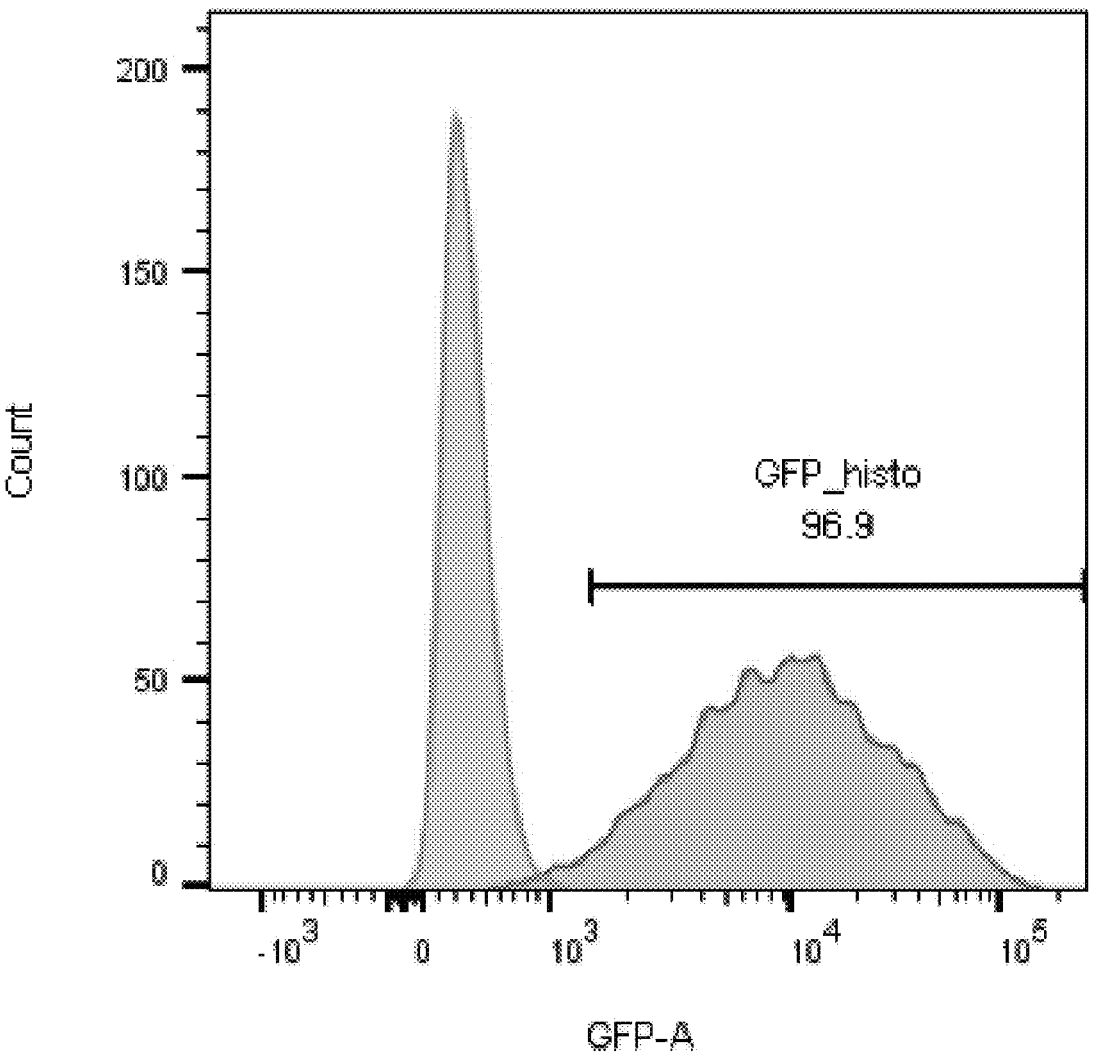
Figure 6:
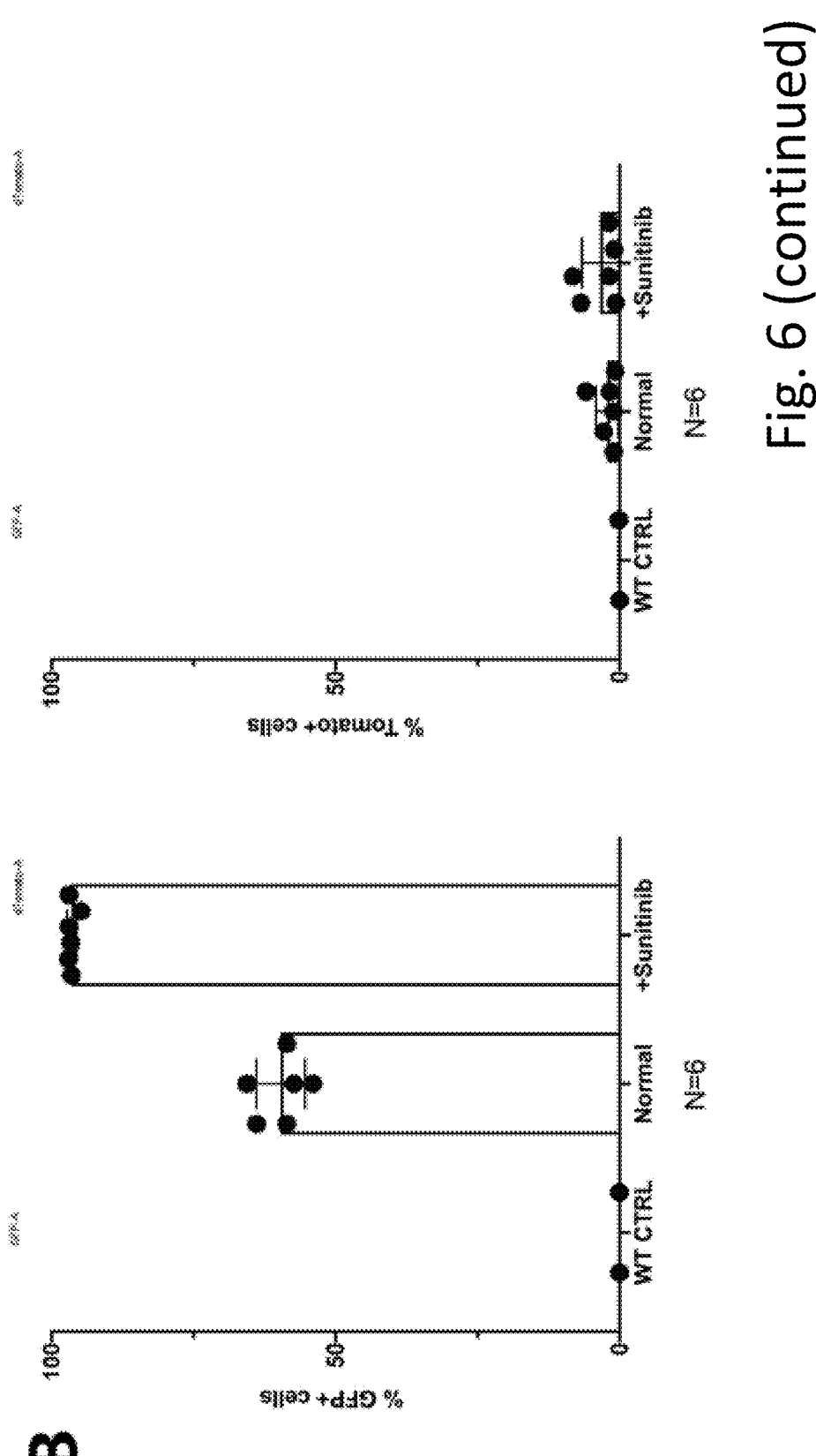

To determine the timing of cardiac cavity formation, we performed live imaging and cryosection time-course analysis revealing that cavities appear during the cardiac mesoderm stage before expression of key cardiac structural markers (FIG. 1,2). These cavities then typically coalesced into one major cavity. Lumen formation was not mediated by ECs, as cardiac cavity formation occurred in the absence of VEGF signalling and without detectable endothelial markers CD31 and VE-Cad (FIG. 1, ICC sections (FIG. 5). Importantly, SOX17+ and EOMES+ endoderm was also absent during differentiation, which indicates that these cardiac mesoderm cavities were not generated by foregut endoderm constriction (FIG. 3). In contract, cardiac mesoderm showed strong expression of the cardiac mesoderm marker HAND1 and upregulation of specific structural markers (MYL7, TROPO-T). By day 7.5, these structures were >90% positive for MYL7 when VEGF signalling was inhibited (FIG. 6). In conclusion, a combination of signalling and high-throughput differentiation in 3D reveals that cardiac mesoderm can specify and self-organise into a CM-made cavity, a key feature of the heart.

The current state of the art for CM differentiation includes either 2D or 3D approaches. We therefore sought to compare the 3D cavity-containing structures to CMs differentiated in 2D. Typically, at day 7 of differentiation, the structures started beating at a similar rate and frequency of $Ca^{2+}$ transients compared to CMs differentiated in 2D. The structures could be maintained beating for months in culture without appearance of non-cardiac contaminating cell types. A comparison at the molecular level using RNAseq time-course analysis revealed an expression signature most similar to the first heart field sub-lineage of cardiac mesoderm (HAND1+, TBX5+, NKX2–5+, TBX1–, HOXB1–), which in vivo gives rise to the heart tube and then later the left chamber and a portion of both atria. Overall, we observed a higher expression of cardiac genes in cavity-forming structures and 3D aggregates compared to CMs in 2D (PCA & heatmap). Genes encoding ion channels, structural proteins, cardiac transcription factors and sarcoplasmic reticulum proteins showed significantly higher expression levels ( ). This effect was also visible at the protein level as seen by whole proteome analysis. Thus, hPSC-derived cardiac mesoderm is sufficient to robustly form cavity-containing CM structures that are functional, reproducible and that can be maintained in long-term culture.

Example 3: Endothelial Cells Line the Cavity of Cardiac Organoids

Figure 4:
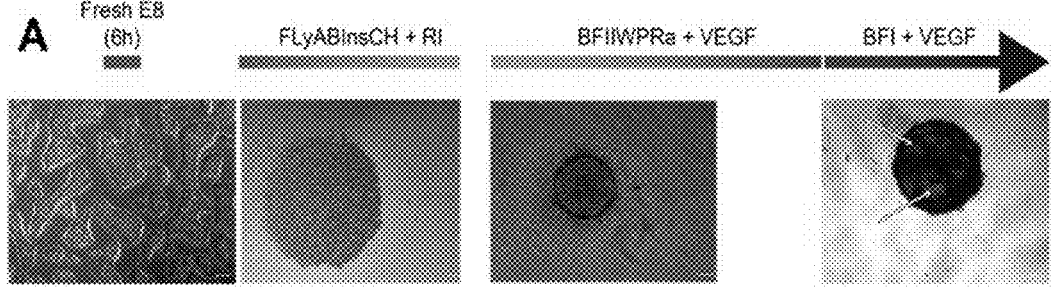
FIG. 4: A: Schematic and brightfield images of the protocol to generate cardiac organoids containing cardiomyocytes (CM) and endothelial cells (EC) in separate layers. Arrows indicated the formed cavity. B: Multiple cardiac organoids showing expression of MYL7-GFP (green) and CDH5-Tomato (red) in separate layers. C: Quantification of flow-cytometry results showing the composition of the organoids to be 53% EC and 41% CM on average. D: Section through an organoid showing the presence of an inner cavity surrounded by a ring of CM expressing MYL7-GFP and HAND1, which are in turn surrounded by a layer of EC expressing CD31. E: Heatmap of vst-counts (variance stabilized transformation) of different EC and pluripotent stem cells showing HOX-gene expression. The analyzed EC are: 2D human cardiac microvascular endothelial cells (HC-MEC), 2D EC differentiated with the anterior differentiation protocol, 3D CDH5-Tomato positive EC from cardiac organoids, 2D human umbilical vein endothelial cells (HU-VEC), 2D EC differentiated with the Patsch et al. protocol (example 3), 3D EC from vascular organoids (Wimmer et al., see example 3). The HOX gene expression of EC from cardiac organoids shows a very similar signature compared to HCMEC. F: Sections of 6 μM and 4 μM CHIR99021 (CHIR) showing an inner ring of EC expressing CD31 in the lower (4 μM) CHIR condition. Cleaved caspase 3 staining indicated low levels of apoptosis in 6 μM CHIR condition, but increased levels inside the EC ring (CD31+) in the 4 μM CHIR condition. VST=variance stabilized transformation.
Figure 4:
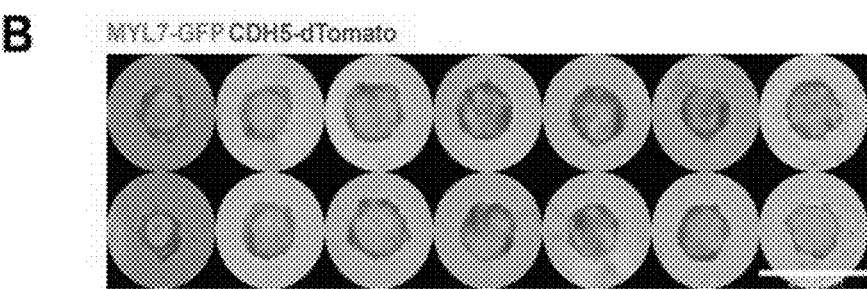
Figure 4:
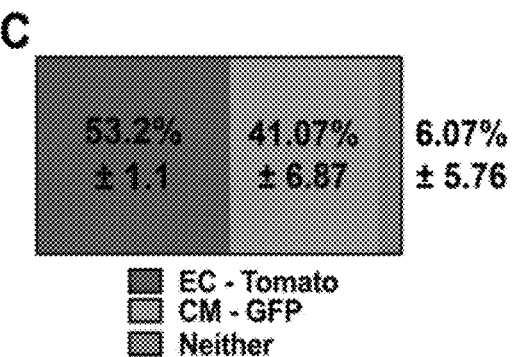
Figure 4:
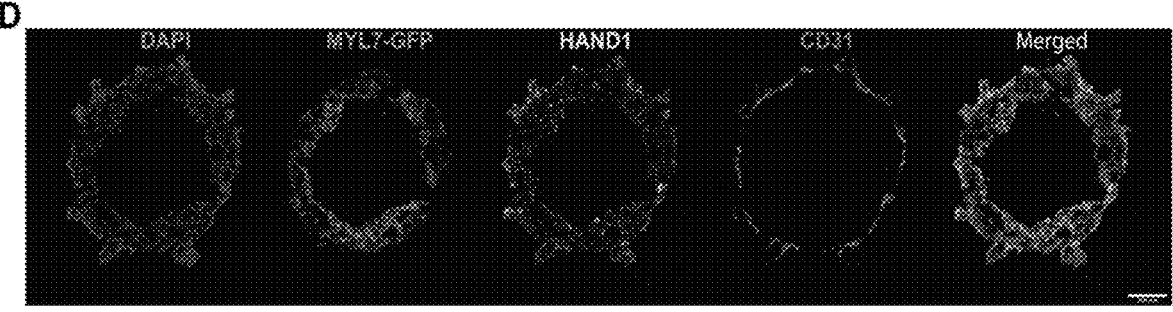
Figure 4:
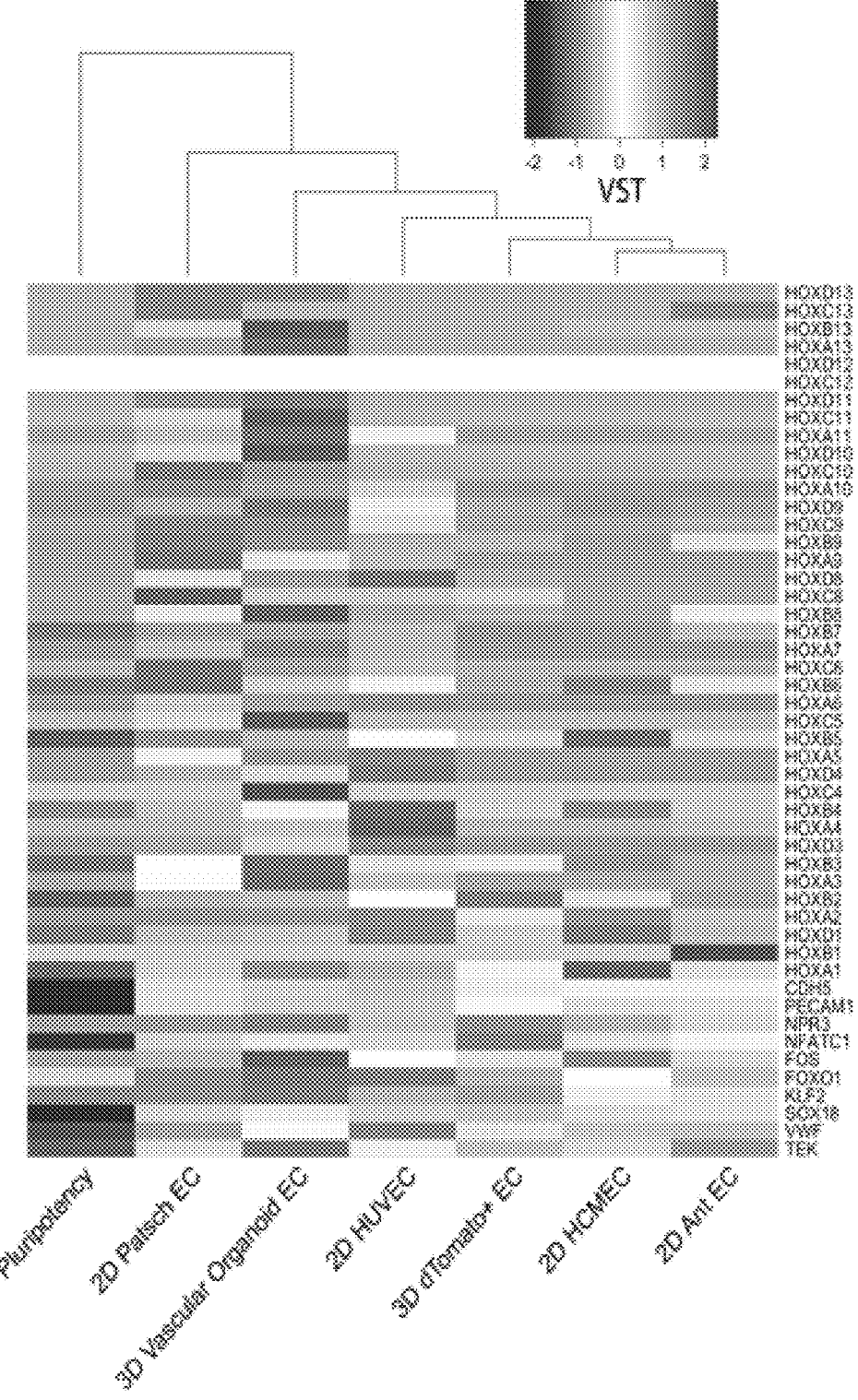
Figure 4:
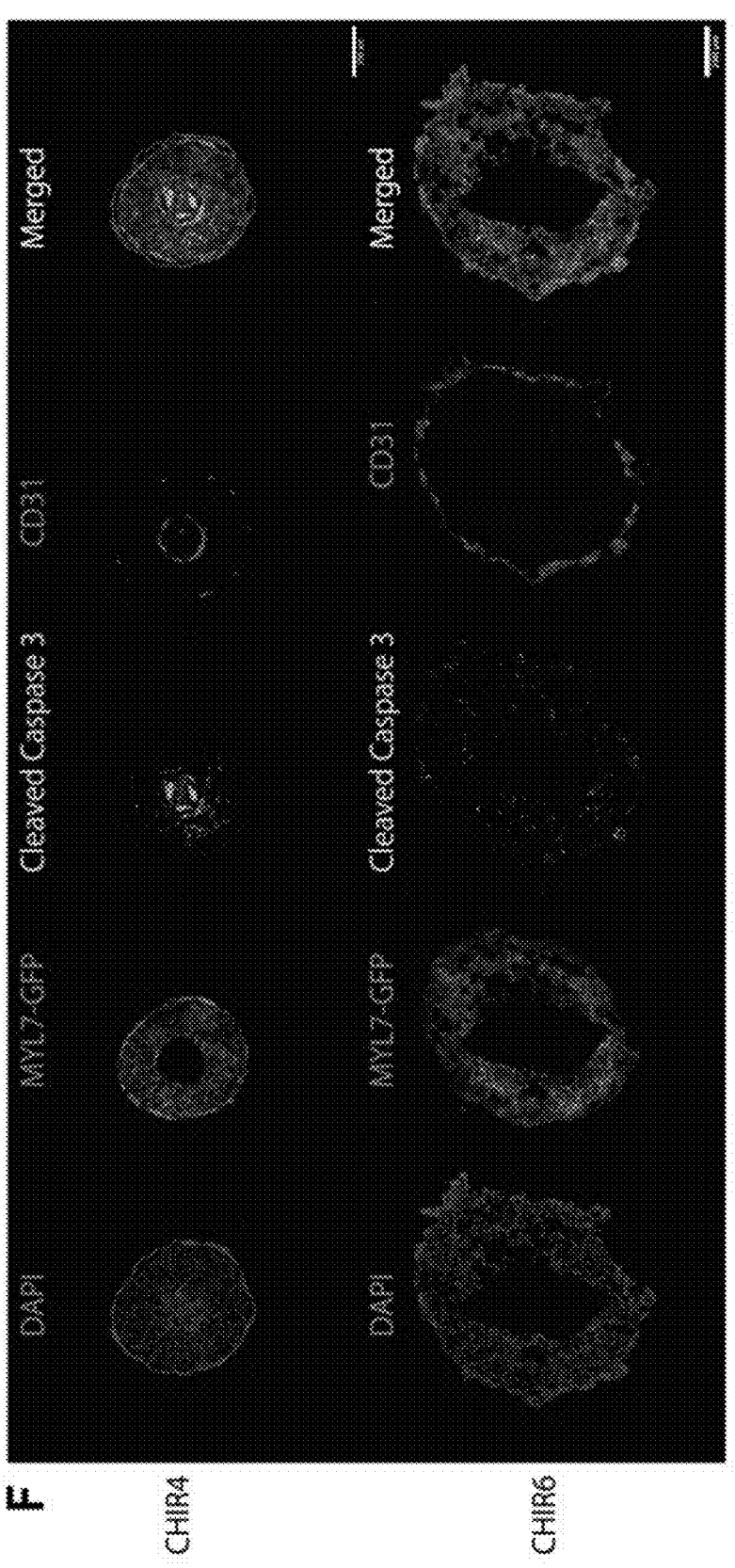
Figure 8:
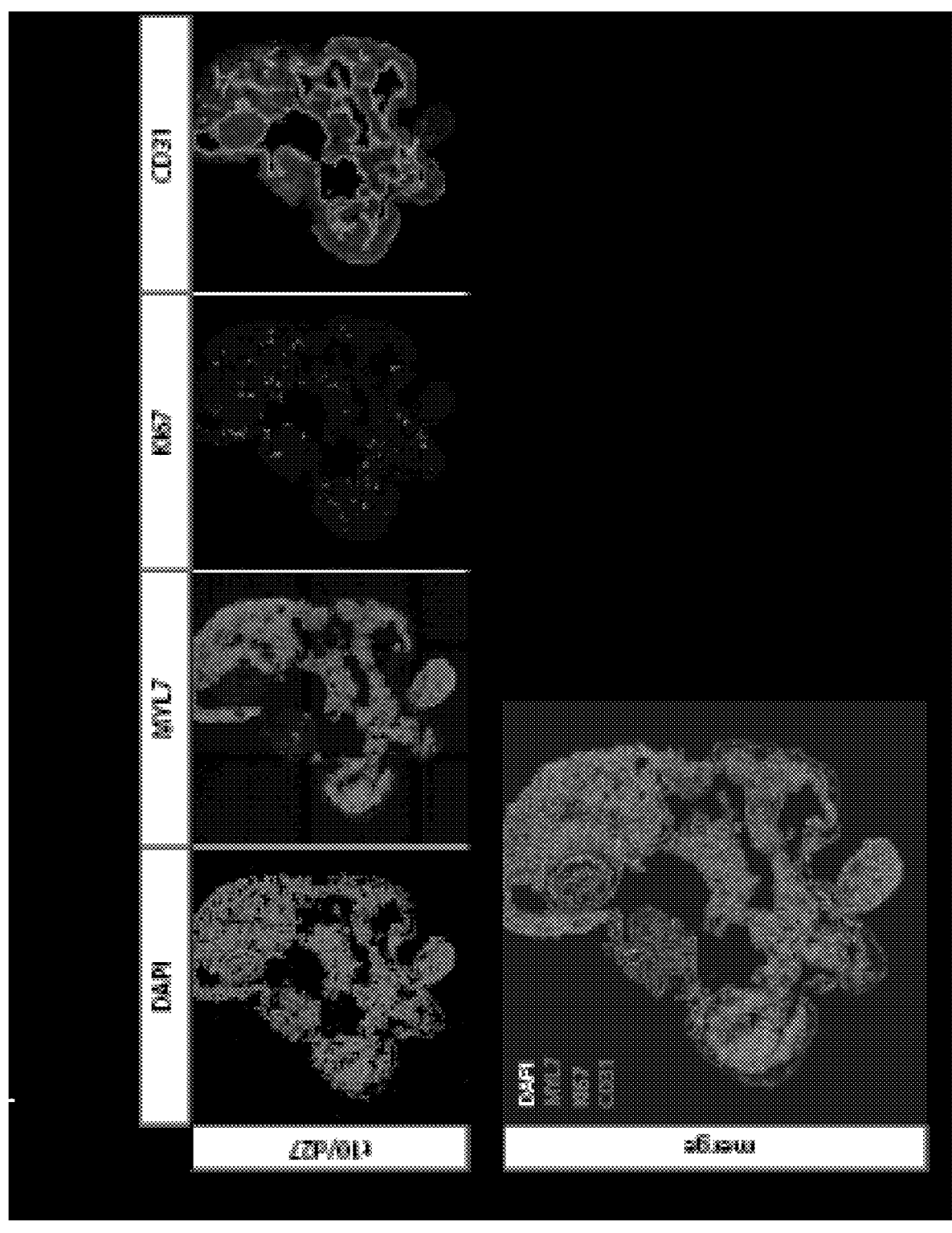
FIG. 8: Cardiac organoid at d27 derived from hPSCs (WTC MYL7-GFP) using a concentration of 4 uM CHIR99021 during induction showing the lining of internal cavities by endothelial (CD31+) cells.
Figure 9:
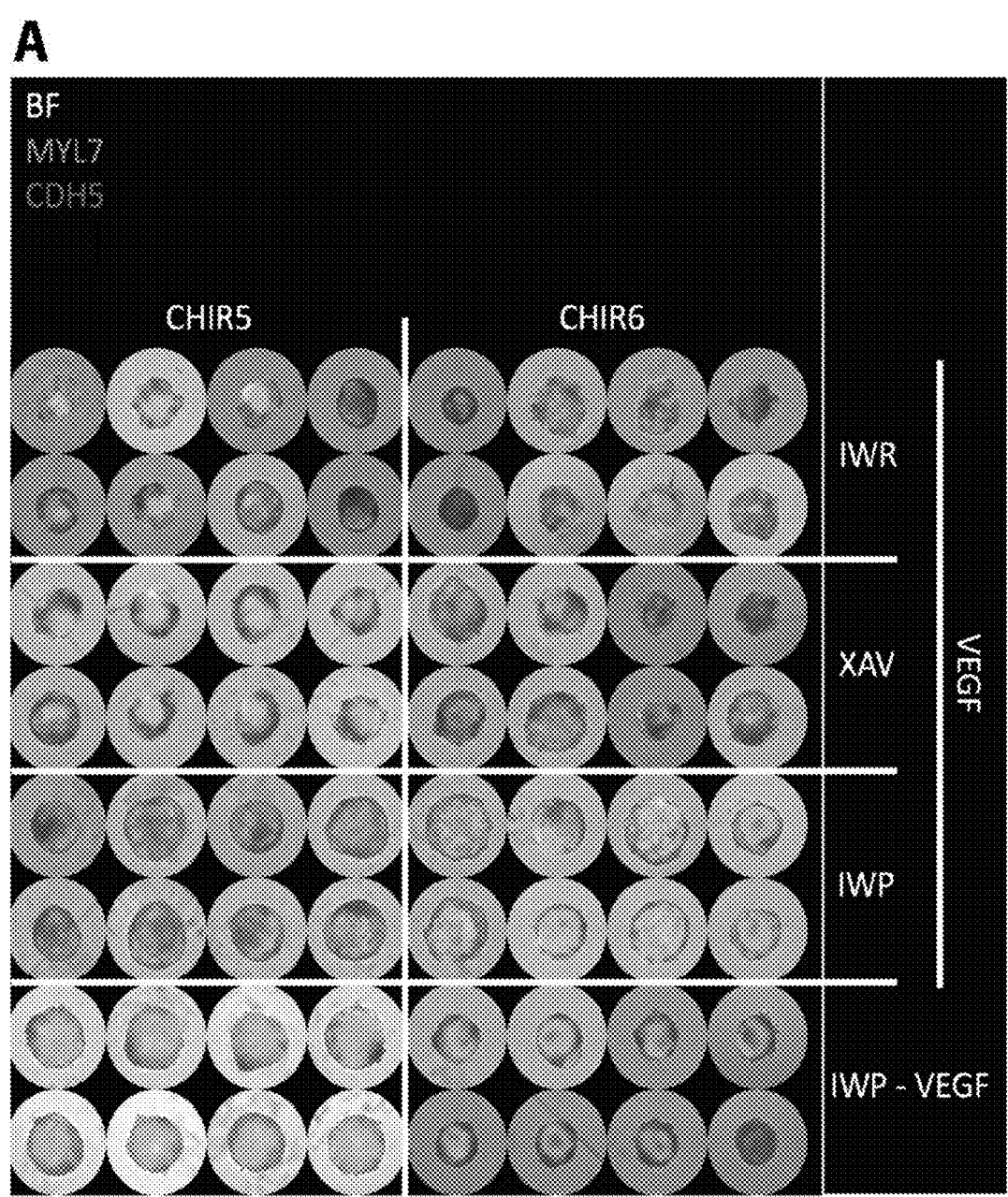
FIG. 9: A: Merged image of brightfield (BF), MYL7-GFP and CDH5-Tomato images showing the two-layered organization of cardiomyocytes (MYL7-GFP) and endothelial cells (EC, CDH5-Tomato) when using different Wnt-inhibitors (IWR-1 (IWR), XAV939 (XAV) and IWP2 (IWP)) during differentiation with two CHIR99021 concentrations (5 μM (CHIR5) and 6 μM (CHIR6)). Also included is a "IWP-VEGF" condition showing the absence of EC. Each organoid image is 2000×2000 μm.

In vivo, before heart tube assembly, cardiac mesoderm co-develops with endocardial progenitors that form the bilateral endocardial tubes, a separate compartment with a lumen. We tested whether this compartmentalisation can be reconstituted in vitro by co-differentiation of cardiac mesoderm into both endocardial-like ECs and CMs (FIG. 4). To promote co-differentiation, we included VEGF-A, the embryonic inducer of endothelial cell identity, at the cardiac mesoderm stage and screened for optimal conditions using a double reporter hPSC line for a CM marker (MYL7-GFP+) and an endothelial cell (EC) marker (FIG. 4). Strikingly, when CMs and ECs co-differentiate from cardiac mesoderm into cavity-containing structures in the presence of VEGF, they separate into a CM and an EC layer with a space between them reminiscent of the in vivo situation (FIG. 4). We could control whether the EC layer surrounded the CMs or faced the cavity depending on the dosage of WNT signalling activation during mesoderm induction (FIG. 2,7,8). The ratio of CMs to ECs was remarkably stable at 41% (MYL7+) to 53% (CHD5+). Without exogenous VEGF, cardiac organoids contained a lower proportion of ECs and over time (day 10 to day 27) formed an endothelial lining that faced exclusively the cardiac cavity (FIG. 8), as occurs in vivo.

ECs within the layer had the potential to form rapidly extended CD31+ networks within their compartment, which also extended into the CM layer (FIG. 4,7). To address whether early co-differentiation is necessary for compartmentalisation, we developed control 3D cardiac microtissues in which CMs and ECs were first differentiated separately from cardiac mesoderm and then aggregated in 3D. In these cardiac microtissues, ECs only formed networks and did not compartmentalise to form a separate layer. In conclusion, as in vivo, only CMs and ECs that co-differentiate in 3D from cardiac mesoderm self-organise to form distinct layers containing a cavity, endothelial lining and extended endothelial networks. We termed these structures cardiac organoids as they emerge from a homogenous hPSC population and self-organise into a cavity, compartments and EC lining while giving rise to the first two cardiac cell types.

In general, ECs are characterised by expression of markers such as CD31 and CDH5, but early cardiac ECs (endocardium) have additional specific signatures. To compare these molecular features of cardiac organoid ECs, we performed SMART-seq2 analysis on sorted CDH5+ cells (FIG. 4). Compared to those generated using a well-established 2D hPSC EC differentiation protocol (Patsch et al. Nature Cell Biology 17, 994-1003 (2015)), ECs from 3D vascular organoids, human umbilical vein endothelial cells (HUVECs) and human cardiac microvascular endothelial cells (HCMECs), CHD5+ cardiac organoid-derived ECs were most similar to those from 3D vascular organoids (Wimmer et al., Nature 565, 505-510 (2019)(FIG. 4E). Importantly, ECs from cardiac organoids upregulated cardiac transcription factors such as GATA4/5 and genes associated with endocardium (NFATC1, NPR3). Their anterior HOX gene expression profile, which matches HCMECs (FIG. 4E) is consistent with ECs derived from cardiac mesoderm in 2D but not with other EC subtypes. On the other hand, SMART-seq2 analysis of sorted MYL7+ CMs from cardiac organoids showed that sorted cells that were neither MYL7+ nor CDH5+ upregulated genes associated with lateral plate mesoderm and ECM genes. Thus, the molecular signature of ECs derived from cardiac organoids is consistent with an endocardial-like identity.

The ability of the endothelium to sense fluid flow, pressure and mechanical stretch plays crucial developmental and physiological roles. As would be predicted for a bona fide model of cardiac development, RNAseq analysis of bulk cardiac organoids revealed an upregulation of key mechanosensitive genes (SOX18, KLF2, CHD5) compared to cardiac microtissues in 3D, and CMs and ECs in 2D (FIG. 4E). This was corroborated by a SMART-seq2 analysis of sorted ECs from cardiac organoids showing induction of mechanosensitive stress genes (KLF2, FOXO1, TEK, FOS) and immunofluorescent staining of cardiac organoids for CDH5, SOX18 and KLF2 (FIG. 4E). Overall, these results suggest that co-differentiation, self-organisation and compartmentalisation of CMs and ECs is crucial to achieve activation of key cardiac identity and mechanosensing genes, both essential aspects of cardiac physiology.

Example 4: Epicardium Engulfs Cardiac Organoids

Figure 10:
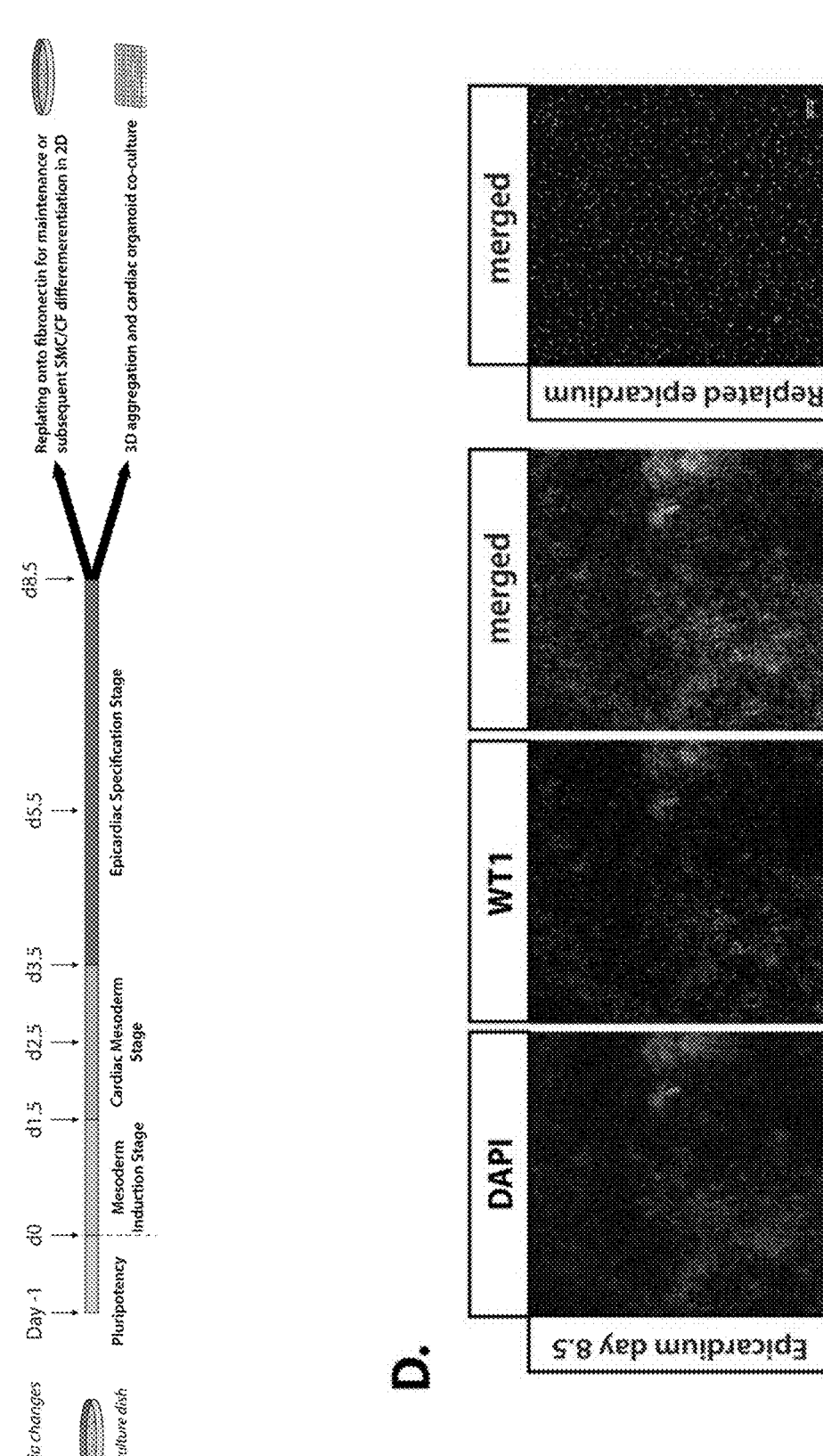
FIG. 10: A. Schematic representation of epicardiac differentiation. B. Heatmap of vst-counts (variance stabilized transformation) of different stages of epicardial differentiation. Pluripotency markers get downregulated after mesoderm induction, while over time cardiac mesoderm specific marker expression is upregulated. During epicardiac specification and maintenance epicardium specific marker expression can be seen. C. Expression of the epicardiac markers TCF21 and TBX18 of epicardium and fibronectin replated epicardium compared to pluripotency seen by qPCR. D. Epicardiac cells at the end of differentiation (day 8.5) and after relating are highly positive for the epicardiac marker WT1 (Wilms' tumor protein) as seen by antibody staining. Scalebar: 100 μM E. After 12 days of SMC (smooth muscle cell) differentiation of the replated epicardium in the presence of TGF-beta, Insulin, L-Ascorbic-Acid and PDGF-BB, the obtained cells are highly positive for SMC-markers a-SMA (alpha smooth muscle actin) and calponin. Scalebar: 1 mm, merged and zoomed image is 1 mm×1 mm. F. After 12 days of CF (cardiac fibroblast-like cell) differentiation of the replated epicardium in the presence of TGF-beta, Insulin, L-Ascorbic-Acid and FGF, the obtained cells are highly positive for CF-markers DDR2 (Discoidin Domain Receptor Tyrosine Kinase 2) and vimentin. Scalebar: 1 mm, merged and zoomed image is 1 mm×1 mm.
Figure 10:
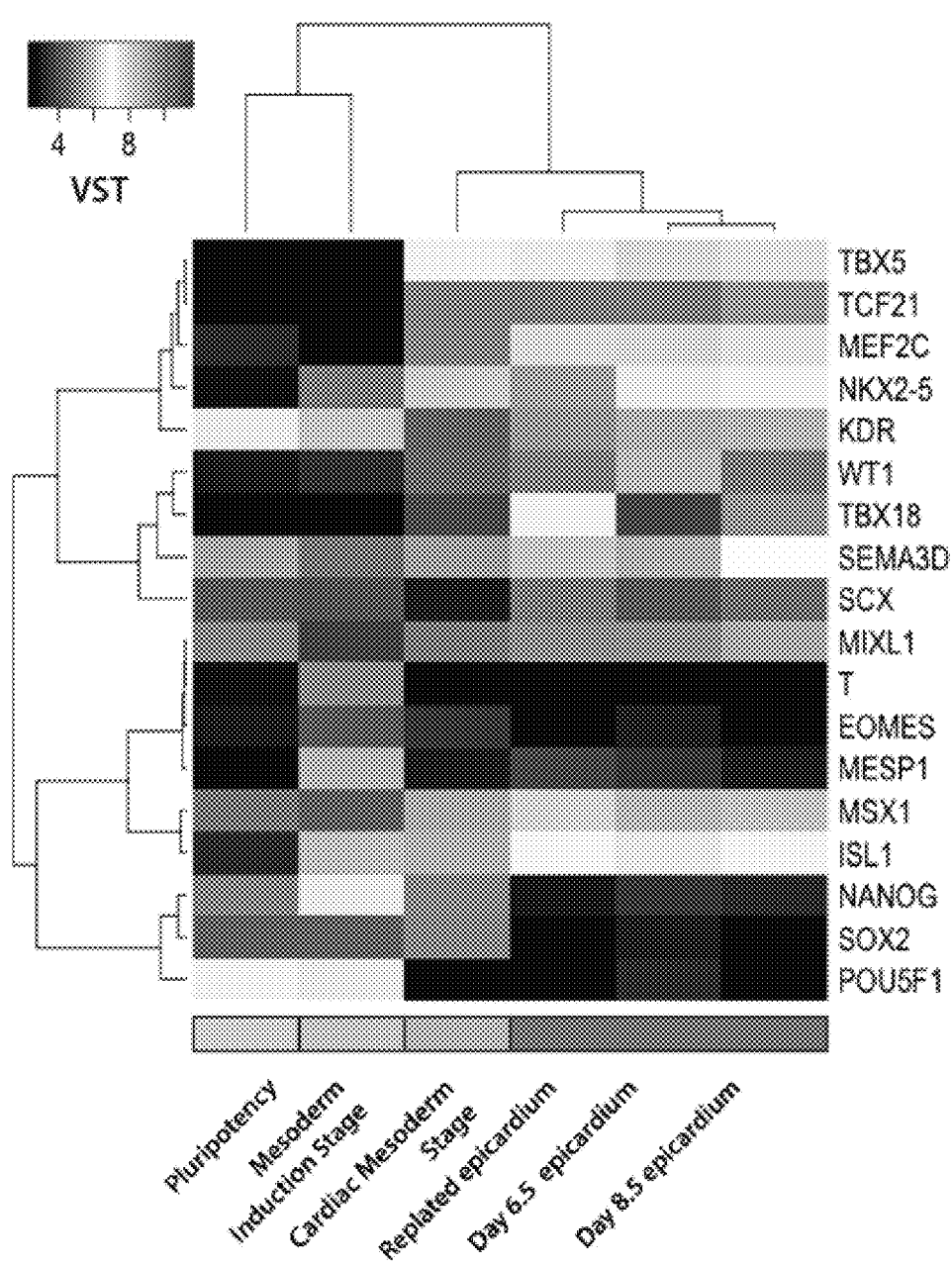
Figure 10:
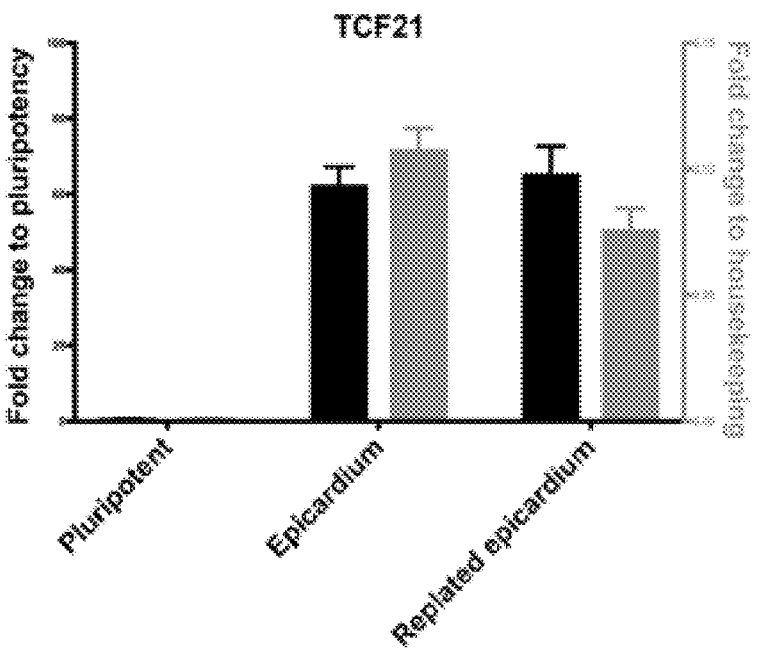
Figure 10:
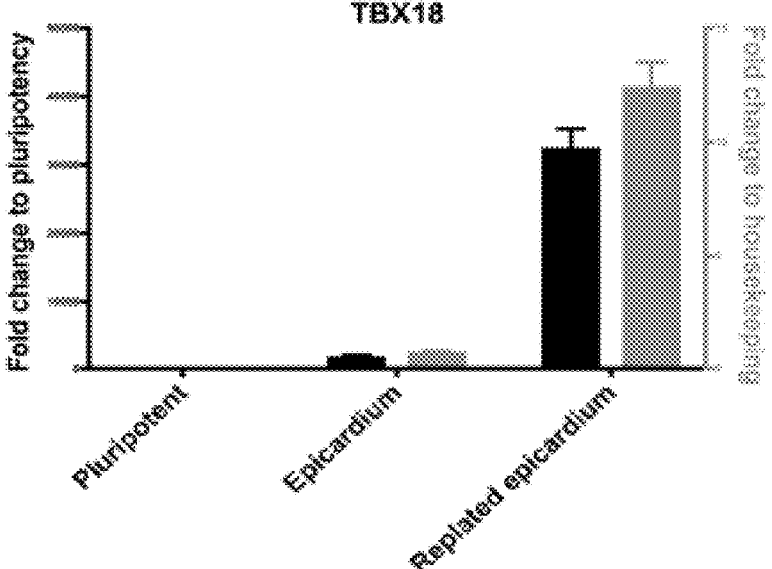
Figure 10:
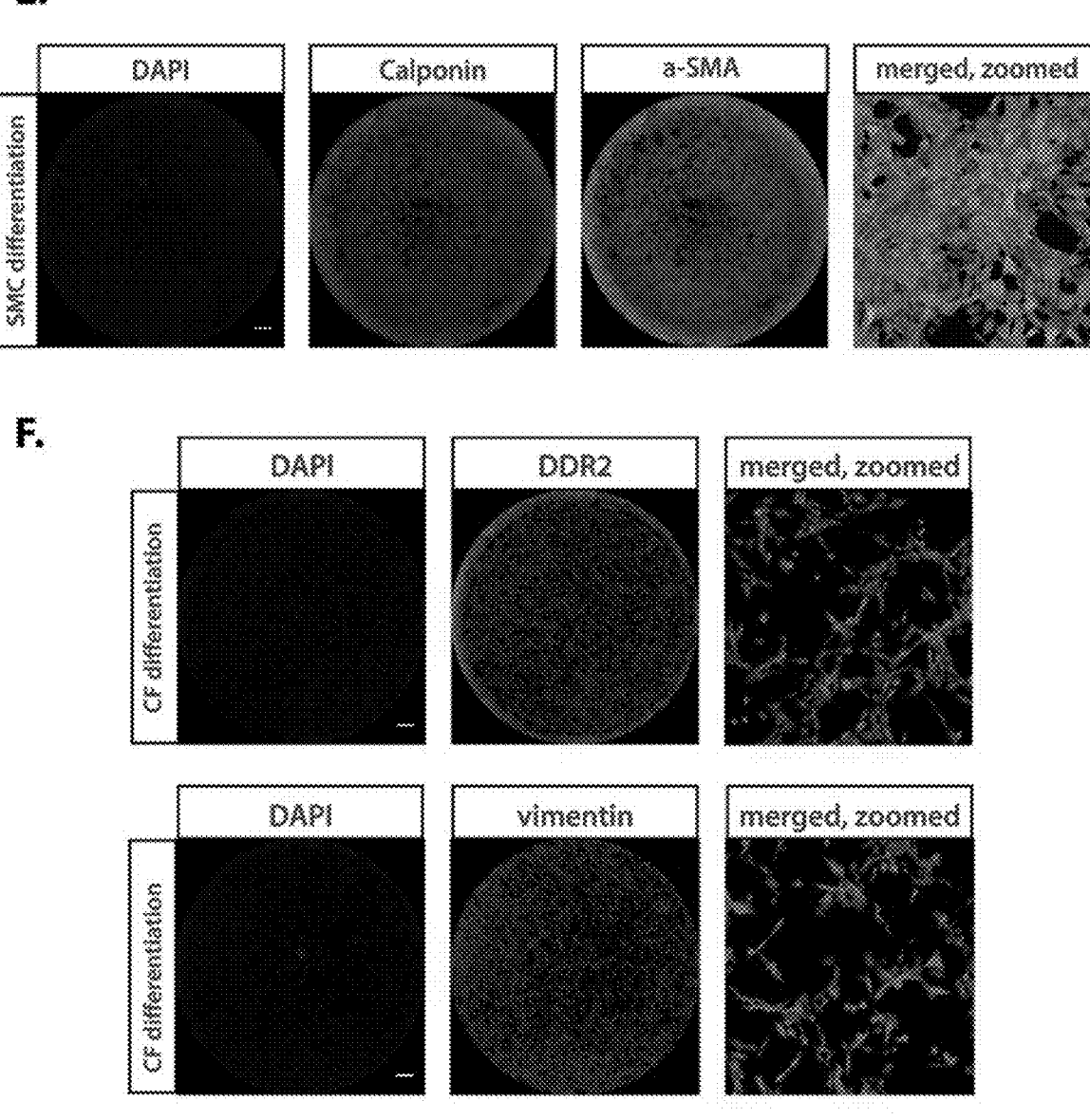

After cavity formation and establishment of an endothelial layer and lining, epicardial engulfment of early myocardial chambers is the third major cardiac self-organising event. In vivo, the epicardium engulfs the myocardium starting from a small clump of cells called the pro-epicardial organ. After engulfment, signals from the CMs drive epicardial cell differentiation into smooth muscle cells (SMCs) and cardiac fibroblasts (CFs), which are crucial cell types for later development and maturation of the heart. To mimic this critical feature of early cardiogenesis, we developed an epicardial differentiation protocol in 2D and 3D that corresponds to the estimated timing of human epicardial developmental stages and signalling known to specify the pro-epicardial organ in vertebrates. Importantly, this protocol was compatible with the cardiac organoid approach in terms of basic media conditions (FIG. 10, overview). Timecourse RNAseq and flow cytometry analysis confirmed efficient epicardial differentiation as seen by widespread expression of the markers WT1, TCF21 and TBX18(%) (FIG. 10). As in vivo, depending on activation of TGF-b, FGF and PDGF signalling, epicardial cells had the potential to differentiate in 2D into SMCs expressing Calponin, a-SMA and SM22, and CFs expressing DDR2 and Vimentin (FIG. 10).

Figure 11:
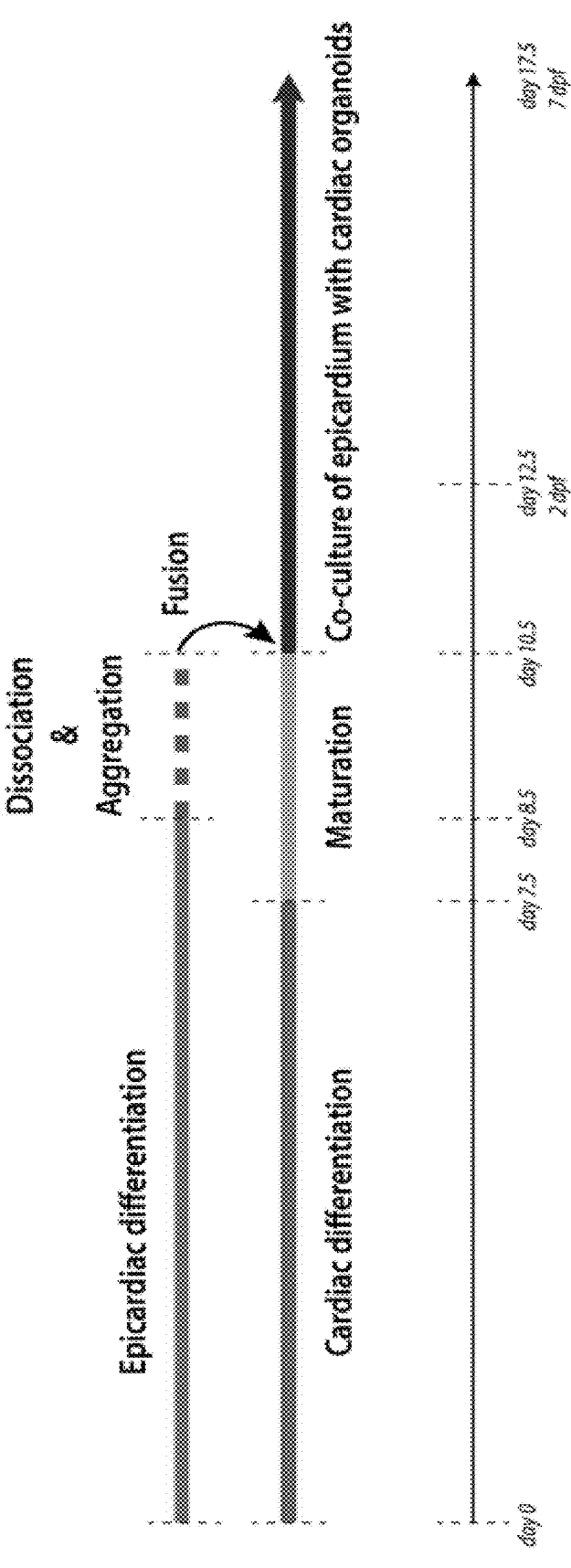
FIG. 11: A. Schematic representation of epicardiac co-culture system with cardiac organoid differentiation. (dpf: days post fusion) B. Cardiac organoid co-cultured together with epicardium, 2 days post fusion. The epicardium is still expressing the epicardial marker WT1 (Wilms' tumor protein), while the cardiac organoid is highly positive for cTNT (Cardiac Troponin-T). Scalebar: 100 uM (b') and 50 uM (b"). C. Epicardial cells (marked by TdTomato expression) migrate into the cardiomyocyte layer (marked by arrows), and undergo subsequent differentiation marked by SM22 (Taglin) and VIM (vimentin). Speciment fixed 24 dpf. Scalebar: 20 uM. D. Epicardial cells form the outside layer of cardiac organoids and also migrate into the cardiac layer (epicardium is marked by TdTomato expression). Cells are positive for the fibroblast specific Col1A2. Speciment fixed 8 dpf. Scalebar: 50 μM. E. Epicardial cells migrate into the cardiac layer (epicardium is marked by TdTomato expression). Cells are positive for the fibroblast specific DDR2 (Discoidin Domain Receptor Tyrosine Kinase 2). Speciment fixed 7 dpf. Scalebar: 20 μM. F. Epicardial cells form the outside layer of cardiac organoids and also migrate into the cardiac layer (epicardium is marked by TdTomato expression). Cells are positive for the fibroblast specific decorin. Speciment fixed 16 dpf. Scalebar: 50 μM. G: A schematic of the trilineage cardiac model with outer epicardial cells, middle cardiomyocyte layer and inner endocardial (cardiac endothelial cells) layer.
Figure 11:
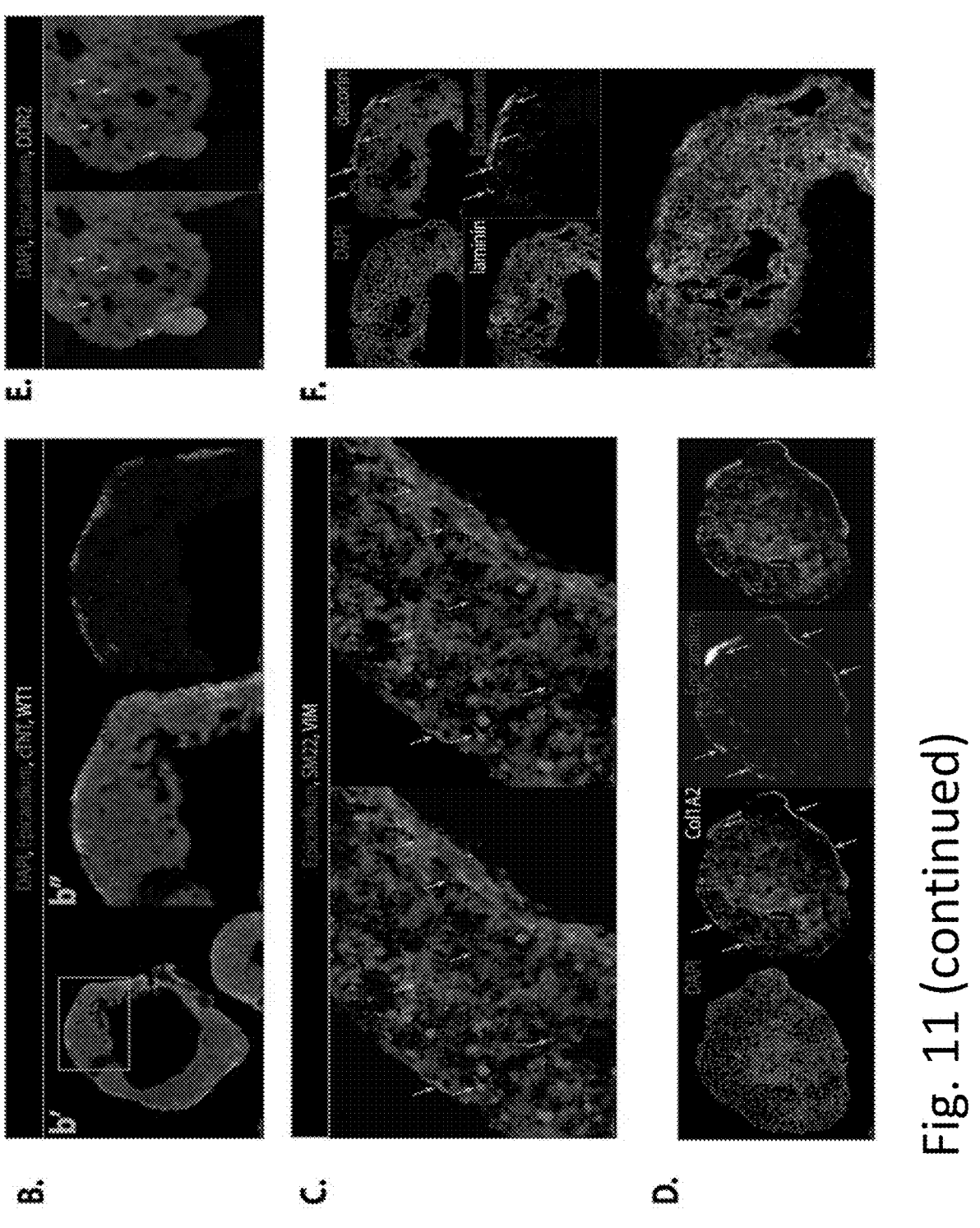
Figure 11G:
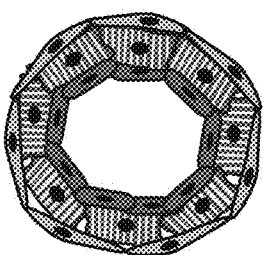

To mimic the process of epicardial engulfment, we co-cultured cardiac organoids with epicardial aggregates in basic media conditions without additional growth factors (FIG. 11). We observed efficient spreading of epicardial cells on top of cardiac organoids within 4 days (FIG. 11). Importantly, when we further incubated these structures under the same conditions without additional growth factors, we observed migration of epicardial cells into the cardiomyocyte compartment and differentiation into SMCs (Calponin+, SM22+) and CFs (DDR2, Vimentin, Decorin) (FIG. 11). We conclude that epicardial engulfment of cardiac organoids and co-culture without external signalling manipulation is sufficient to stimulate engulfment of cardiac organoids by the epicardium, migration of the epicardium into the CM compartment and differentiation into SMCs and CFs. Overall, our high-throughput 3D differentiation approach can be used to establish a self-organising, lineage-controlled cardiac organoid platform that mimics key aspects of human cardiogenesis.

Example 5: Mechanisms of Cardiac Cavity Formation

Although reductionist molecular and cellular in vitro models cannot recapitulate the full complexity of in vivo models, they have proven to be complementary and useful in addressing mechanistic questions. Our organoid platform allowed us to develop semi-automated image-analysis pipelines to quantify phenotypes with high statistical power. We employed this platform to tackle how signalling pathways control cardiac cavity formation, which includes several possibilities: i) signalling during the mesoderm stage could affect lumen formation during the cardiac mesoderm stage, ii) cardiac mesoderm signalling could be decisive, or iii) it could be a combination of both. Since the high-throughput cardiac organoid platform is stage-/lineage-controlled, we systematically tested the effects of key mesoderm and cardiac mesoderm signalling pathway dosages (e.g. WNT, BMP) on cardiac cavity formation. Surprisingly, we found that the dosage of canonical WNT signalling activation (by e.g. CHIR99021) during mesoderm induction had striking effects on lumen expansion during the cardiac mesoderm stage (FIG. 4F). This dramatic effect was not dependent on cell proliferation. There was an optimal intermediate WNT activation dosage that promoted both cavity formation and CM differentiation. We observed WNT-dependent cavity formation both in organoids differentiated in the presence of VEGF containing an EC lining and in organoids without ECs (FIG. 4,5). The optimal WNT activation level varied depending on the hPSC line, which can be easily determined with the cell culture system described herein, e.g. using parallel approaches on a well-plate.

Figure 12:
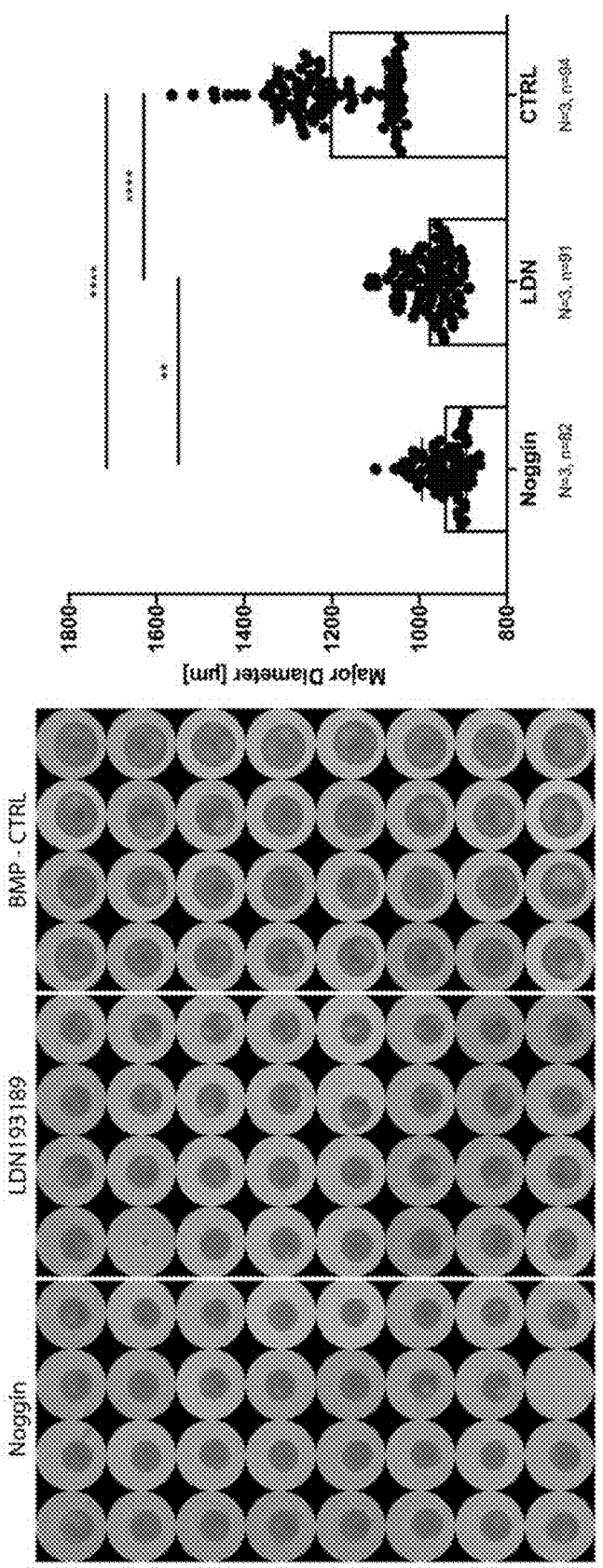
FIG. 12: A: Organoids (WTC iPS cells) at day 3.5 treated with the BMP inhibitors Noggin and LDN193189 followed by diameter quantification showing a significantly decreased diameter upon inhibitor treatments. B: Organoids (H9 embryonic stem cells) at day 3.5 of wild-type (WT) control cells compared to HAND1 knock-out (KO) cells. Quantification shows a significantly reduced diameter size in KO organoids.
Figure 12:
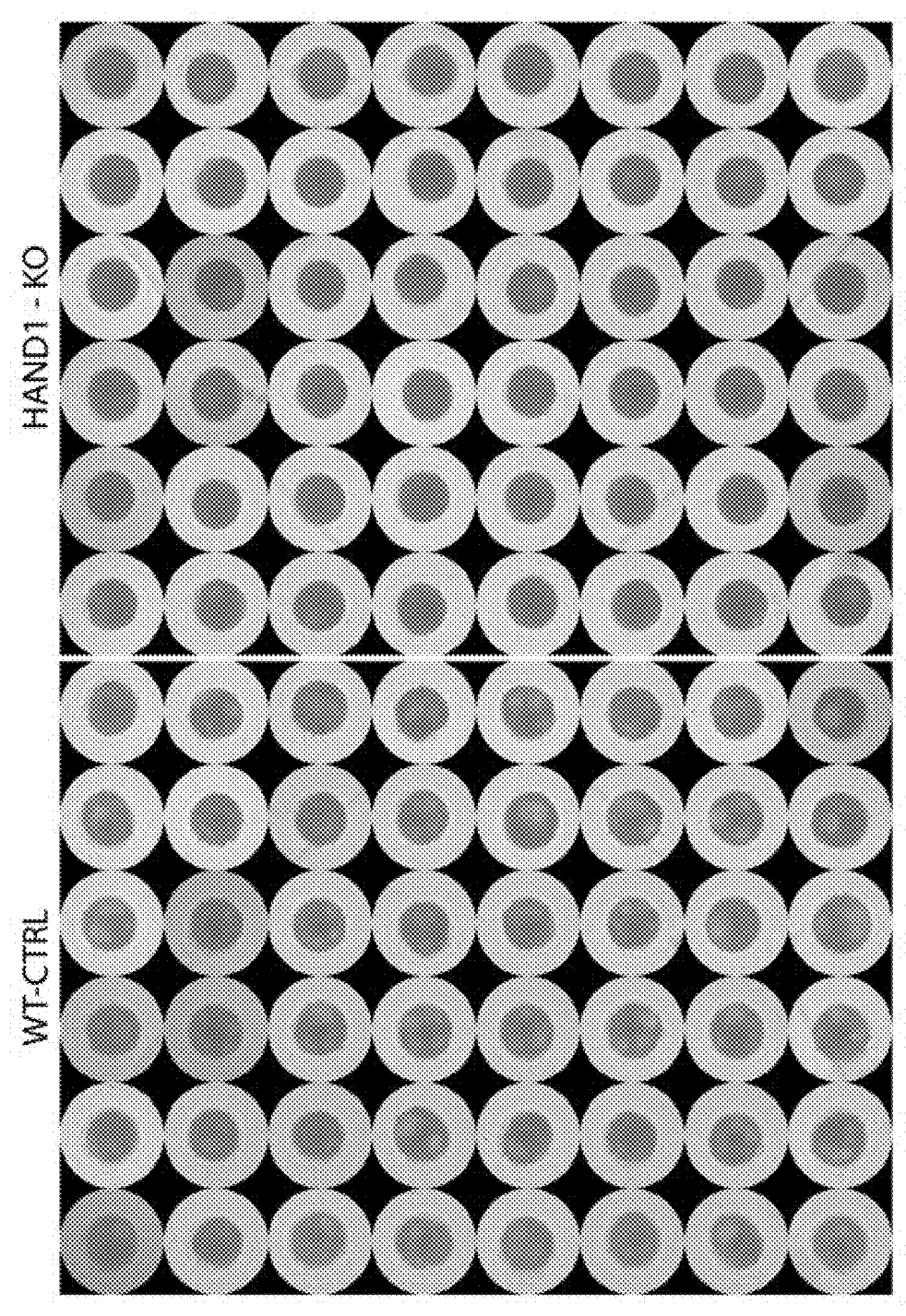
Figure 12:
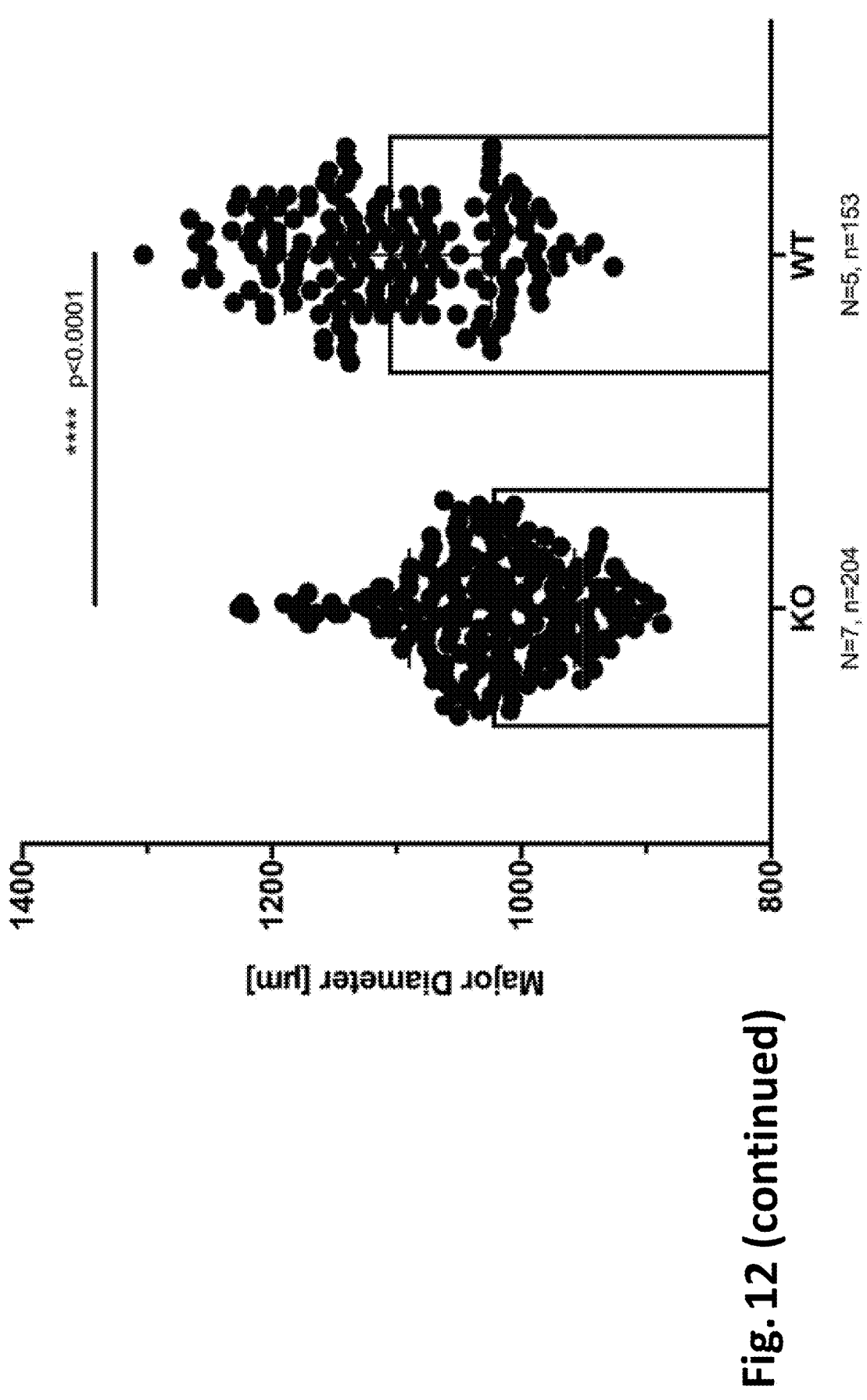
Figure 13:
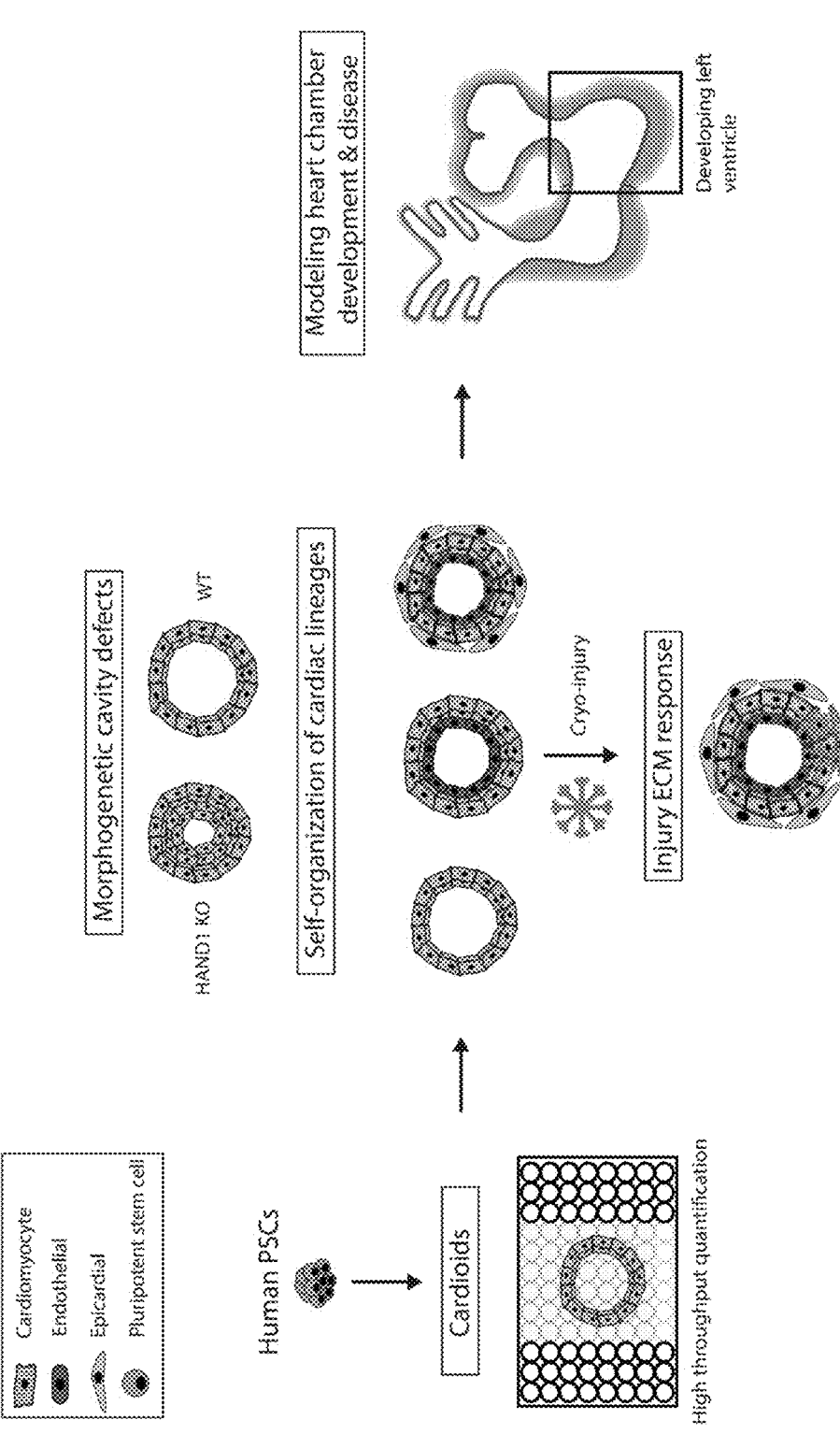
FIG. 13: Illustration of cardiac organoids ("cardioids") and some uses thereof. Left: product of cardioids and use in high throughput methods. Middle: different cardioids at different stages, with either cardiomyocyte or epicardium inner lining, with and without epicardial cells on the outside. Use as injury model, e.g. through cryo-injury is illustrated at the bottom with fibroblasts infiltrating the injured area. Right: modelling of a heart chamber FIG. 14. Formation of Cardiac Chamber-like Structures in vitro. (A) Cardiac differentiation protocol. WNT signaling activation (by CHIR99021), WNT signaling inhibition (by IWP-2/IWR-1/XAV-939), PI3K signaling inhibition (by LY294002). (B) Representative whole mount image (day 5.5) of a high-throughput differentiation approach showing robust generation of cavity-containing, beating structures in three biological replicates (iPSC WTC line). (C) Cryosection of a cardioid at d7.5 showing the cavity and expression of the CM-specific marker TNNT2. Scalebar: 200 μm. (D) Quantification of TNNI1-GFP+ cells in cardioids at d7.5 via flow cytometry. (E) Heatmap showing transcriptional change of key cardiac genes, including cardiac mesoderm markers between d1.5 and d5.5, during CM specification and CM maintenance. VST: variance-stabilized transformed counts. (F) RT-qPCR results from day 14 organoids with varying Activin and CHIR99021 concentrations at induction stage and varying retinoid acid concentration at the cardiac mesoderm stage with either the presence or absence of SB 43154. Scale bar shows the fold change from housekeeping gene, PBGD, and pluripotent stem cells normalized with min-max normalisation. (G) Immunostaining for ventricular (IRX4) and atrial (NR2F2) CMs of a cardioid (d10) showing the optimized left ventricular conditions (A4CH4 RA50) versus the non-optimized condition (A50CH4 RA500). A, Activin; CHIR, CHIR99021, RA, Retinoic acid; SB, SB 43154. Scale bar: 100 μm. (H) scRNA-seq analysis of percentage of CMs in intermediate WNT(CHIR6)/High Activin (A50)/RA500 (N=2, n=1717) vs. Low WNT(CH4)/ Low Activin(A4)/RA50 (N=2, n=5097) conditions expressing more atrial vs. more ventricular markers. TNNT2 is expressed in all CM. Used cell lines in this figure: WTC.

To identify downstream mediators of WNT that control cardiac cavity formation, we performed an RNA-seq analysis and compared gene expression profiles of mesoderm induced by a higher (large cavity) or lower (small cavity) WNT signalling dosage. Among differentially expressed genes at the onset of the cardiac mesoderm stage, we found multiple components of BMP signalling (BMP4, BMP2, BMPR) and of its targets. BMP is a well-known driver of cardiac specification at multiple stages, but a direct role in cardiac cavity formation has not been demonstrated. We therefore tested whether different levels of BMP signalling at the cardiac mesoderm stage drive cardiac cavity formation. Inhibition of BMP signalling using its natural inhibitor Noggin during the initial two days of the cardiac mesoderm stage heavily impaired cavity expansion (FIG. 12). We observed a clear BMP signalling dosage effect in which higher levels of BMP4 drove cavity expansion (FIG. 12). In conclusion, our data show that a WNT-BMP signalling axis controls cavity expansion in cardiac organoids.

In vivo, there are several well-known cell-biological mechanisms of embryological lumen formation downstream of signalling control. However, since the driving forces of cardiac cavity expansion are less clear, especially in mammals and humans, we used the cardiac organoid platform to probe for underlying mechanisms of lumen formation. Cavity expansion under optimal WNT and BMP activation dosages was not driven by either apoptosis or regional proliferation differences, as seen by Caspase 3 and Ki67 staining (FIG. 2). We instead observed compaction at the periphery of the cardiac mesoderm layer characterised by higher density/localisation of N-Cadherin/Actin/MYH10/DAPI and an absence of E-Cadherin, while the inner layer where cavities first appeared mesenchymal (FIG. 2). Importantly, outer layer compaction was visible only in high WNT and BMP promoting cavity conditions, and not with low WNT and BMP activation without a cavity. These observations are consistent with the pattern of N-cadherin localisation in the compacted regions of cardiac and splanchnic mesoderm of vertebrate embryos, while the region facing endocardial tubes is mesenchymal. In support of a compacted epithelial-like barrier, the cardiac mesoderm cavity structures were not permeable to low-molecular-weight (4 KDa) dextrans. Since lumen expansion across epithelia typically depends on an osmotic gradient driven by ion pumps, we next tested the involvement of chloride ion and sodium/potassium pumping in cardiac organoids. We conclude that a WNT-BMP-driven process of differential cardiac mesoderm compaction accompanies cavity formation in vitro.

Example 6: Modelling of Cardiac Defects

Mutations in transcriptions factors (TFs) are the best-known underlying causes of cardiac cavity defects that affect heart tube and chamber development and cause severe human birth defects. For instance, disruption of NKX2-5 and HAND1 downstream of BMP leads to severe cardiac cavity defects in vertebrates, including the most severe cardiac malformation in humans. However, since these factors are present throughout cardiogenesis and in multiple cell types, it is difficult to discern the underlying mechanism. We hypothesised that downstream of the WNT-BMP axis one or more of these TFs are critical for cavity formation in cardiac organoids. We therefore generated hPSC lines with heterozygous and homozygous deletions of the HAND1 and NKX2-5 genes. Surprisingly, there were no detectable cavity formation defects at the cardiac mesoderm stage in NKX2-5 mutant lines. In contrast, HAND1 homozygous KO lines showed a clear defect in cardiac cavity formation at cardiac mesoderm and CM stages (FIG. 12B). N-Cadherin localisation in these KO organoids was also affected. Importantly, increased dosage of WNT signalling during mesoderm induction could partially rescue this effect, confirming its role in cavity expansion. Consistent with this observation, HAND1 expression levels were higher in WNT signalling dosage conditions that promoted cavity formation. Taken together, our high-throughput and lineage-controlled cardiac organoid platform can be employed to quantitatively decipher mechanisms of cardiac formation and genetic defects.

Example 7: Extended Materials & Methods

General human pluripotent stem cell culture—Human pluripotent stem cell lines (WT H9, WiCell and constitutively fluorescent H9 clones (Wimmer et al., 2019, Nature 29, 40) WT and modified WTC, Allen Institute for Cell Science) were cultured in a modified in-house medium based on the E8 culture system (Chen et al., 2011, Nature Methods 8, 424-429). The original E8 recipe was supplemented with 0.5% BSA (Europa Biosciences, #EQBAH70), in-house produced FGF2 and 1.8 ng/ml TGβ1 (R&D RD-240-B-010). Cells were grown on either Corning or Eppendorf tissue culture-treated plates coated with Vitronectin XF (Stem Cell Technologies #7180) and passaged using either TrypLE Express Enzyme (Gibco, #12605010) or PBS-EDTA (Biological Industries, 01-862-1B) every 2-4 days at ~70% confluency. Cells were routinely tested for Mycoplasma.

hPSC differentiation into cardiomyocytes in 2D and 3D aggregates—hPSCs were seeded at 160-175,000 cells/24 well plate in E8+ROCKi (Y-27632, Tocris #1254) for 24 h. Cells were then induced for 36 h-40 h with CDM medium (Mendjan et al., 2014, Cell Stem Cell 15, 310-325) containing FGF2 (30 ng/ml, Cambridge University), LY294002 (5 μM, Tocris, #1130), Activin A (50 ng/ml, Cambridge University), BMP4 (10 ng/ml, R&D Systems RD-314-BP-050), and CHIR99021 (R&D Systems RD-4423/50). 1 μg/ml of insulin (Roche, #11376497001) was optionally added to increase cell viability during this stage. This medium was termed FLyABCH(Ins). After 36 h-40 h, cells were induced with CDM medium containing BMP4 (10 ng/ml), FGF2 (8 ng/ml), insulin (10 μg/ml), IWP2 (5 μM, Tocris, #3533) (can optionally also be done with IWR-1 (1 μM, Tocris, #3532/10) or XAV-939 (5 μM, SelleckChem, #S1180) and Retinoic Acid (0.5 μM, Sigma Aldrich, #R2625) for 4 days with medium change every day. This medium was termed BFIIWPRa. Subsequently, the medium was changed to CDM medium containing BMP4 (10 ng/ml), FGF2 (8 ng/ml) and insulin (10 μg/ml) for 2 days with medium change every day. This medium was termed BFI. For maintenance of the obtained cardiomyocytes, medium was changed to CDM medium containing insulin (10 μg/ml) and half the medium exchanged every day. This medium was termed CDM-I. For the generation of assembled/aggregated cardiomyocytes, cardiomyocytes maintained until Day 21 were dissociated using the STEMdiff cardiomyocyte dissociation kit (Stem Cell Technologies, #05025) and re-seeded as aggregates in AggreWell400 plates (Stem Cell Technologies, #34425) at 1000 cells/well in CDM-I and 5% FBS (PAA, #A15-108). After 2 days, formed aggregates were transferred to ultra-low-attachment 96-well plates (Corning, #7007) in CDM-I and put on a shaker at 58 rpm, 37° C. and 5% CO2. After 4 days, with a medium change after 2 days, the aggregates were used for analysis.

ECM molecules used—Vitronectin (10 μg/ml), Laminin-511 E8 fragment (Takara Bio, #T303, 0.05-2 μg/ml) and Laminin-521 (Biolaminin, #LN521-02, 0.1-5 μg/ml) were either used to pre-coat wells or added to the cell suspension prior to seeding. Further cardiomyocyte differentiation was performed as described above.

Generation of cardioids—hPSCs were harvested at around 70% confluency. Cardioids were generated by seeding 7500 cells/well for the KO and BMP inhibition experiments and 5000 cells/well for the rest of the experiments. Cells were seeded in a volume of 200 μl into ultra-low-attachment 96-well plates (Corning) containing E8+ROCKi and collected by centrifugation for 5 minutes at 200 g. After 24 h, formed aggregates were induced with FLyAB(Ins) containing the WNT activator CHIR99021 (see below for cell-line-dependent concentration). Cardiac differentiation was performed as described for 2D cultures. For maintenance of the obtained cardioids, medium was changed to CDM-I and exchanged every second day. In order to stop endothelial cell differentiation, 100 nM sunitinib malate (Biovision, #1611) was added from the cardiac mesoderm stage (BFIIWPRa) onward. For the BMP inhibition experiments, 100 ng/ml Noggin (R&D System, #RD-6057-NG-025) or 0.2 μM LDN-193189 (Stemgent, #04-0074) were used. For the optimized generation of cardioids (more ventricular/inner EC lining), hPSCs were induced using F, Ly, B, lower Activin (4 ng/ml), Ins, and CHIR99021 (see below for cell-line-specific concentration) in 2D. Subsequently, 15 k cells were seeded in in a volume of 200 μl into ultra-low-attachment 96-well plates (Corning) and the above CM-differentiation protocol was followed.

Generation of cardioids containing CMs, ECs and fibroblast-like cells in defined layers—Pluripotency maintenance medium was refreshed 6 h prior to seeding cells. Then, 2500 hPSCs were seeded directly into ultra-low-attachment 96-well plates (Corning) in FLyAB(Ins) medium with CHIR99021 (see below for cell-line-specific CHIR99021 concentration) and ROCKi (5 μM) for 36 h-40 h. Next, medium was exchanged to BFIIWPRa with the addition of VEGF-A (200 ng/ml, Peprotech, #AF-100-20) for 4 days with medium changed every day. Subsequently, medium was changed to BFI+VEGF-A (100 ng/ml) for 2 days with a medium change after 1 day. For maintenance, CDM medium with 100 ng/ml of VEGF-A was used and exchanged every second day. In order to generate cardioids that contained only EC and fibroblast-like cells, the above protocol was followed with the exception of the lack of IWP2 addition and low WNT (CHIR99021: 4 μM)/low Activin (4 ng/ml) during mesoderm induction. For Smart-Seq2 analysis, day 7.5 cardioids containing cardiomyocytes and endothelial cells were dissociated using the STEMdiff cardiomyocyte dissociation kit (STEMCELL Technologies, #05025), and GFP+ CMs and Tomato+ ECs as well as GFP−/Tomato− cells were FACS-sorted into home-made lysis buffer.

Cryo-injury of cardioids—Cardioids were temporarily transferred onto a 10 cm dish without medium and observed under an EVOS microscope (Thermo Fisher) positioned within the laminar flow hood. They were then touched with a liquid N2-cooled steel rod until the wavefront of freezing tissue/medium was clearly within the cardioid. Cardioids were then transferred back into maintenance medium containing wells for further culture.

Cell-line-dependent CHIR99021 concentration—We noticed that for optimal differentiations, the different hPSC lines react at different concentrations of CHIR99021 (Wnt-activation). This is consistent with previous reports (Strano et al., 2020, Cell Reports 31, 107732) and meant that we empirically determined the best "high" (large cavity) and "low" (small cavity) CHIR99021 concentrations for the different hPSC lines. In 2D differentiations, H9 cells were induced with 1-2 μM of CHIR99021, whereas WTC lines were induced with 3-4 μM of CHIR99021. In 3D cardioid differentiations, CM-only cardioids were generated according to the protocol described in the "Generation of cardioids" section with "high" and "low" CHIR99021 concentrations being 8 μM and 4 μM for WTC cells. 1.5-3 μM CHIR99021 were used for H9 cells. In CM/EC/Fibroblast-like cell co-differentiations according to the "Generation of cardioids containing CMs, ECs and fibroblast-like cells in defined layers" section, CHIR99021 of 4 μM was used as a "low" concentration, 5-6 μM were optimal for CM/EC differentiation and cavity expansion ("intermediate"), and 9 μM was used as a "high" concentration of CHIR99021.

Epicardial co-culture with cardioids—hPSCs were seeded at 55,000 cells/24 well plate in E8+ROCKi (5-10 μM) 24 h prior to differentiation. Cells were induced with CDM (Mendjan et al., 2014, Cell Stem Cell 15, 310-325) medium containing FGF2 (30 ng/ml, Cambridge University), LY294002 (7.5 μM), BMP4 (10 ng/ml) and CHIR99021 (1.5 μM) (Iyer et al., 2015, Development 142, 1528-1541). After 36 h-40 h, differentiation medium was changed to CDM medium containing BMP4 (10 ng/ml), FGF2 (8 ng/ml), insulin (10 μg/ml), IWR-1 (1 μM) and Retinoic Acid (1 μM) for 2 days with medium change every day. Subsequently, the medium was changed to CDM medium containing BMP4 (10 ng/ml), insulin (10 μg/ml) and retinoic acid (1 μM) for 5 days with one medium change in-between (Guadix et al., 2017, Stem Cell Reports 9, 1754-1764). For maintenance of the obtained epicardium, cells were seeded at the end of differentiation onto Bovine Fibronectin (2 μg/ml, Sigma, #F1141) coated plates in CDM medium containing insulin (10 μg/ml) and SB431542 (10 μM, Tocris, #1614) supplemented with ROCKi for the first day of seeding. The replated epicardium was routinely passaged at 80-90% confluency every 3-5 days at 1:3 ratio.

For the generation of aggregated epicardium used in the engulfment assay, day 8.5 epicardial cells were dissociated using TrypLE Express Enzyme and re-seeded as aggregates in AggreWell400 plates at 1000 cells/well in CDM-SBI and 5% FBS. After 2 days, on average 8-12 formed aggregates/ well were transferred to ultra-low-attachment 96-well plates (Corning) containing differentiated cardioids in CDM-I, put on a shaker at 58 rpm, 37 C and 5% CO2, and co-cultured together with CDM-I medium refreshed every second day. Control (epicardial only) aggregates were kept in CDM-SBI medium in the ultra-low-attachment 96-well plates (Corning).

2D Anterior endothelial cell differentiation—Pluripotent stem cells were seeded at 100,000 cells/24 well coated with vitronectin in E8 medium supplemented with 10 μM ROCK-inhibitor. On the following day, cells were induced with FLyABCH (Ins), 1-3 μM (for H9), 3-6 μm (for WTC) CHIR99021, and incubated for 36-40 hours. For the following two days, medium was exchanged to BFIIWPRa. Subsequently, differentiation medium comprising CDM with 200 ng/ml VEGF and 2 μM Forskolin (Sigma-Aldrich, #F3917) was provided for 2 days followed by 1 day of culture in CDM+100 ng/ml VEGF. ECs were maintained in CDM supplemented with 100 ng/ml VEGF.

Culture of Human Cardiac Microvascular Endothelial Cells—Human cardiac microvascular endothelial cells (HC-MEC) were obtained from PromoCell (PC-C-12285 HCMEC-c) and cultured according to manufacturer's instructions using Endothelial Cell Growth Medium MV (PromoCell, #PC-C-22020). For Smart-Seq2 analysis, HCMEC were dissociated with TrypLE Express Enzyme and FACS-sorted into home-made lysis buffer.

Chick cardiac mesoderm explant culture—Explants from the cardiogenic region of developing chicken (Gallus gallus) embryos were isolated at Hamburger and Hamilton stage 7-8 and cultured for 24 h at 37° C. in cardiac mesoderm (BFIIWPRa) media. Subsequently explants were embedded, cryosectioned and immunostained for further analyses as described below.

Cryosectioning—Cryosectioning was done based on {Bagley:2017ga}. Briefly, 4% PFA-fixed tissues were cryo-protected with 30% sucrose in PBS overnight at 4° C. and embedded the next day using O.C.T. cryoembedding medium (Scigen, #4586K1). Embedded tissues were frozen using a metal surface submerged in liquid nitrogen and tissues were stored in a −80° C. freezer until sectioning on a Leica cryostat. Sections were collected on Ultra Plus slides and kept at −20° C. or −80° C. until immunostaining. O.C.T. was removed by washing with PBS before continuing with the immunostaining protocol.

Immunostaining—Following fixation with 4% PFA (Sigma-Aldrich, #16005) specimens were washed twice in 1×PBS and the 3D constructs additionally once in PBS/ Tween20 (0.1%, Sigma-Aldrich, #P1379) for at least 15 min each. Tissues were incubated in blocking solution consisting of PBS (Gibco, #14190094) with 4% goat (Bio-Rad Laboratories, #C07SA) or donkey serum (Bio-Rad Laboratories, #C06SB) and 0.2% Triton X-100 (Sigma-Aldrich, #T8787) for at least 15 minutes. The primary antibody was subsequently applied in above blocking buffer for 1-3 hours at room temperature or overnight at 4° C. in the case of the 2D samples and 2 days at 4° C. on a shaker for 3D samples. Following washing twice with PBS/Tween20, 3D tissues were incubated with the secondary antibody solution at 4° C. on a shaker for 2 more days while 2D samples were incubated up to 2 hours at room temperature. Following these washing steps and an additional PBS wash, tissues were ready for analysis or storage at 4° C. in PBS, while slides were mounted using fluorescence mounting medium (Dako Agilent Pathology Solutions, #S3023). 3D tissues were cleared with FocusClear (CellExplorer Labs, #FC-101) prior to imaging.

Trichrome staining—Masson Trichrome staining (Bio Optica, #04-010802) was performed on 20 μM cryosections according to the manufacturer's recommendations.

Electron microscopy—Samples were fixed using a mixture of 2% glutaraldehyde (EM grade; Agar Scientific, Essex, UK) and 2% paraformaldehyde (EM grade; Electron Microscopy Services, Hatfield, US) in 0.1 mol/L sodium cacodylate buffer, pH 7.2 over night at 4° C. Organoids were then rinsed with the same buffer and post-fixed in 1% osmium tetroxide (Electron Microscopy Services, Hatfield, US) in buffer on ice for 40 min. After 3 rinsing steps, the samples were dehydrated in a graded series of acetone on ice and embedded in Agar 100 resin (Agar Scientific, Essex, UK). 70-nm sections were picked up with 100 mesh Cu/Pd grids (Agar Scientific, Essex, UK), previously coated with a formvar support film and were post-stained with 2% uranyl acetate (Merck) and Reynolds lead citrate.

Dextran and Fluo-4 incorporation assays—A 4.4 kDa Dextran conjugated with TAMRA (Sigma Aldrich, T1037) was added to the cardioid culture between 64 h and 90 h. Cardioids were live imaged as cavities started to form. To image and analyze calcium-transients, 3D cardioids and 2D CM were loaded with Fluo-4 AM (Thermo Fisher Scientific, #F14217). After a 15-min incubation, cardioids were incubated for another 15 min in Tyrode's salt solution (Sigma Aldrich, #T2397). Subsequently, cardioids were imaged live and videos were analyzed with FIJI software (Schindelin et al., 2012, Nature Methods 9, 676-682) to acquire the signal intensity (F) of regions of interest and background (F0).

Contraction characteristics measurements—2D CM and 3D cardioids were live-imaged and videos were analyzed with a published algorithm (Huebsch et al., 2015, Tissue Engineering Part C: Methods 21, 467-479) to determine contraction velocity and beating rate.

Optical action potentials—Cardioids were incubated at 37° C., 5% $CO_2$ in CDM medium. Before the experiments, organoids were transiently loaded with the voltage-sensitive dye (VSD) FluoVolt (×0.5, for 30 min at room temperature). Afterwards, the medium containing VSD was replaced by fresh serum-free medium (DMEM, Sigma-Aldrich). The multi-well plate was placed in an environmentally controlled stage incubator (37° C., 5% CO2, water-saturated air atmosphere, Okolab Inc, Burlingame, CA, USA). The FluoVolt fluorescence signal was recorded from a 0.2×0.2 mm area of the organoid. Excitation wavelength was 470±10 nm using a light-emitting diode (LED), and emitted light was collected by a photomultiplier (PMT, Cairn Research Ltd. Kent, UK). Fluorescence signals were digitized at 10 kHz. 120 s recordings were subsequently analyzed offline using the pClamp software package v. 10.0 (Molecular Devices, Inc., Sunnyvale, CA, USA). APDs were measured at 30%, 50% and 90% repolarization.

Image acquisition and analysis—Fixed whole mounts and sections were imaged with point scanning (upright Zeiss LSM800 Axio Imager with an Apochromat 20× objective lens at 1× magnification) and spinning disk confocal microscopes (Olympus spinning disk system based on a IX3 Series (IX83) inverted microscope, equipped with a Yokogawa W1 spinning disc), or a widefield microscope (Zeiss Axio Imager 2, Axio Vert A1, Panoramic FLASH 250 II System). Live imaging experiments were performed using a Zeiss Celldiscoverer 7 or above-mentioned spinning disk microscope. For high-throughput imaging and analysis, images were taken with a Celigo Imaging Cytometer microscope (Nexcelom Biosciences, LLC) and analyzed with custom-made scripts written for the FIJI software. Sections for transmission electron microscopy were examined with aFEI Morgagni 268D TEM (FEI, Eindhoven, The Netherlands) operated at 80 kV. Images were acquired using an 11 megapixel Morada CCD camera (Olympus-SIS).

Statistics—Data is presented as Mean+/−SD. To calculate significant differences, data was analyzed for normality and lognormality using the D'Agostino & Pearson and the Shapiro-Wilk test in Prism 8 software (GraphPad Software Inc.). If normally distributed, a parametric test (two-tailed t-test, one-way ANOVA) was performed to determine significant differences. If not normally distributed, a nonparametric test (two-tailed Mann-Whitney, Kruskal-Wallis) was performed using Prism 8 software. Corrections for multiple comparisons using statistical hypothesis testing (Tukey test for parametric and Dunn's test for non-parametric) was performed using Prism 8 software. The p-values for significant differences are visualized as: *: p<0.05, : p<0.01, *: p<0.001, ****: p<0.0001.

Flow cytometry—Cells were dissociated using the CM dissociation kit (Stem Cell Technologies, #05025). After centrifugation for 3 min at 130 g, cells were resuspended in 300 µl PBS supplemented with 0.5 mM EDTA (Biological Industries, #01-862-1B) and 10% FBS (PAA Laboratories, #A15-108). Cells were acquired with a FACS LSR Fortessa II (BD) and analysed with FlowJo V10 (FlowJo, LLC) software. FACS sorting was performed using a Sony SH800 Cell Sorter (Sony Biotechnology).

RNA isolation and RNA-seq/Smart-Seq2/single-cell (sc) RNA-seq preparation—RNA was isolated with the RNeasy Mini Kit (Qiagen, #74104). Generation of the bulk RNA-seq libraries was performed according to the manufacturer's instructions with QuantSeq 3' mRNA-Seq Library Prep Kit FWD (Lexogen GmbH, #015). After the preparation of the libraries, samples were checked for an adequate size distribution with a fragment analyzer (Advanced Analytical Technologies, Inc) and were submitted to the Vienna Biocenter Core Facilities (VBCF) Next-Generation-Sequencing (NGS) facility for sequencing. For Smart-Seq2 analysis, 400 cells were sorted into lysis buffer and stored at −80° C. until further processing. Samples were QC'd/libraries prepared and sequenced by the VBCF NGS facility using a homemade Smart-Seq2 kit. For scRNA-seq, cardioids (two biological replicates, 3 cardioids each) at day 7.5 of differentiation were dissociated and cells submitted to the VBCF NGS facility for library preparation using the 10× Genomics Chromium platform (10× Genomics, CA, USA).

Bioinformatic analysis—Trimming was performed for Smart-Seq2 experiments using trim-galore v0.5.0 and for QuantSeq 3' mRNA-Seq experiments using BBDuk v38.06 (ref=polyA.fa.gz,truseq.fa.gz k=13 ktrim=r useshortkmers=t mink=5 qtrim=r trimq=10 minlength=20). Reads mapping to abundant sequences included in the iGenomes UCSC hg38 reference (human rDNA, human mitochondrial chromosome, phiX174 genome, adapter) were removed using bowtie2 v2.3.4.1 alignment. Remaining reads were analyzed using genome and UCSC gene annotation provided in the iGenomes UCSC hg38 bundle (support.illumina.com/sequencing/sequencingsoftware/igenome.html). Reads were aligned to the hg38 genome using star v2.6.0c and reads in genes were counted with featureCounts (subread v1.6.2) using strand-specific read counting for QuantSeq experiments (−s 1). Differential gene expression analysis on raw counts, and principal component analysis on variance-stabilized, transformed count data were performed using DESeq2 v1.18.1. Functional annotation enrichment analysis of differentially expressed genes was conducted using clusterprofiler v3.6.0 in R v3.4.1.

Bulk tissue cell type deconvolution was performed using MuSiC v0.1.1 (Wang et al., 2019, Nature Communications 10, 1-9). We used cell type-specific marker genes and a cell-type specific single-cell expression reference for the human developing heart (Cui et al., 2019, CellReports 26, 1934-1950.e5). Bulk cardioid RNA-seq samples were processed with the previously described pipeline using the hg19 UCSC iGenomes reference to match the published data. The proportion of cell types from developing heart in bulk cardioid RNA-seq samples was estimated and MuSiC estimated proportions were visualized in a heatmap. Single cell RNA-seq reads were processed with cellranger count v4.0.0 using the prebuild 10×GRCh38 reference refdata-gex-GRCh38-2020-A. Count data were further analyzed using Seurat v3.2.2. Cells with more than 500 detected genes, and less than 15% mitochondrial content were retained. Doublets detected by scDblFinder v1.4.0 were removed. That led to the further analysis of 9632 cells for the cell type analysis in cardioids. In order to compare the CMs with the optimized ventricular-like CMs, 1717 CMs from the standard condition (Intermediate CHIR/High Activin) were analyzed next to 5097 CMs from the optimized low CHIR/low Activin condition. Log-normalized expression values were derived using the LogNormalize method with the default scale factor of 10000. Replicates were integrated using FindIntegrationAnchors and IntegrateData functions using 15 dimensions and default settings. singleR v1.4.0 was used to annotate single-cells using the Cui et al. reference (supra). 2-dimensional representations were generated using uniform manifold approximation and projection using uwot v0.1.9.

Proteomics—Cells were lysed in 8M urea 100 mM 4-(2-hydroxyethyl)-1-piperazineethanesulfonic acid buffer (HEPES), reduced with 10 mM 1,4-dithioerythritol with 1 U Benzonase (Merck KGaA, #1.01654.0001) and alkylated with 20 mM 2-iodoacetamide. Digests were carried out in 4M urea 100 mM HEPES with LysC (Wako, #121-05063, 1/100 (w/w) protease/substrates) for 3 h at 37 C and subsequent trypsin digest (Promega, #V5280, 1/100 (w/w) protease/substrates) overnight at 37 C. Peptides were desalted using reverse-phase solid phase extraction cartridges (Sep-Pak C-18, Waters, #186000308), dried under vacuum, reconstituted in HEPES to a neutral pH and labeled with TMT10-plex (Thermo Fisher Scientific, #90110) according to manufacturer's instructions. TMT labeled peptides were pooled in equal amounts and fractionated by high pH reversed phase chromatography (UPLC Peptide CSH C18 column, 130 Å, 1.7 µm, 1 mm×150 mm, ACQUITY) to obtain 10 final fractions.

The samples were separated by reversed phase chromatography (75 um×250 mm PepMap C18, particle size 5 um, Thermo Fisher Scientific), developing a linear gradient from 2% to 80% acetonitrile in 0.1% formic acid within 60 minutes (RSLC nano, Dionex—Thermo Fisher Scientific) and analyzed by MS/MS, using electrospray ionization tandem mass spectrometry (Orbitrap QExactive HFX, Thermo Fisher Scientific). The instrument was operated with the following parameters: MS1 resolution 120,000; MS1 AGC target 3e6; MS1 maximum inject time 50 ms; MS1 scan range 380 to 1650 m/z; MS2 resolution 45,000; MS2 AGC target 1e5; Maximum inject time 250; TopN 10; Isolation window 0.7 m/z; Fixed first mass 110 m/z; Normalized collision energy 35; Minimum AGC target 1e4; Peptide match preferred; Exclude isotope on; Dynamic exclusion 30 s.

All MS/MS data were processed and analysed using Proteome Discoverer 2.3 (PD 2.3.0.484, Thermo Scientific), searched using MSAmanda v2.0.0.14114 against the *Homo sapiens* database (SwissProt TaxID=9606) (v2017-10-25). Maximal missed cleavages: 2, with iodoacetamide derivative on cysteine and peptide N-terminal ten-plex tandem mass tag (fixed mod.); oxidation on methionine, ten-plex tandem mass tag on lysine (variable mod.). Peptide mass tolerance: ±5 ppm; fragment mass tolerance: ±15 ppm. Filtered to 1% FDR on protein and peptide level using Percolator; reporter ions were quantified using IMP Hyperplex (Doblmann et al., 2019, Journal of Proteome Research 18, 535-541) (ms.ip.ac.at/index.php?action=hyperplex).

Generation of MYL7-GFP/CDH5-Tomato double reporter line—The endogenously tagged WTC MYL7-GFP hPSC line was obtained from the Allen Institute for Cell Science (Cell Line ID: AICS-0052). A gBlock of the CDH5 promoter sequence (−1135 to −5 relative to TSS) (Prandini et al., 2005) was ordered from Integrated DNA Technologies, Inc. and cloned according to Bagley et al., into a modified backbone of a vector that integrates into the AAVS1 locus with TALEN technology (Hockemeyer et al., 2009, Nature Biotechnology 27, 851-857). The modified backbone contained flanking tandem repeats of the core chicken HS4 insulator (2×CHS4). Thus, the following reporter expression cassette was inserted in the AAVS1 locus: 2×CHS4-CDH5promoter-dTomato-WPRE-SV40-2× CHS4. Nucleofection and clone picking/validation was done as in (Bagley et al., 2017, Nature Methods 14, 743-751).

Generation of HAND1 and NKX2-5 Knock Out Cell Lines—HAND1 and NKX2.5 were knocked out in H9 cells using CRISPR/Cas9. sgRNAs for target sites were identified using the Sanger Institute Genome Editing (WGE) website, as well as the Benchling sgRNA designing tool. (HAND1_sgRNA1: GAGCATTAACAGCGCATTCG (SEQ ID NO: 1); NKX2.5_sgRNA1: GACGCACACTTGGCCGGTGA (SEQ ID NO: 2); NKX2.5_sgRNA2: ACTTGGCCGGTGAAGGCGCG (SEQ ID NO: 3)). sgRNAs were cloned into pSpCas9(BB)-2A-Puro (PX459) V2.0 (Feng Zhang Lab; Addgene plasmid #62988; n2t.net/addgene:62988; RRID:Addgene 62988) according to the Zhang Lab General Cloning Protocol (Ran et al., 2013, Nature Protocols 8, 2281-2308). Cells were transfected using the P3 Primary Cell 4D-Nucleofector™ X Kit S (Lonza-BioResearch, Cat #: V4XP-3032) and Amaxa™ 4D-Nucleofector™ (Lonza-BioResearch). Post nucleofection, cells were incubated in E8 supplemented with 10 μM Y-27632 (Cat #72302) for 24 h. After that period, cells were selected with puromycin (concentration 0.2 ng/μL; (Sigma-Aldrich, Cat #P8833) for 48 h. Following this treatment, the cell culture media was changed back to E8 supplemented with 10 μM Y-27632 (Cat #72302) to promote re-growth. Once the cells formed colonies, they were picked and transferred into a 96w-plate (Corning, Cat #CLS3370). Successful editing was first assessed on a pool level. Subsequently, single colonies were genotyped two times independently in order to be confirmed a successful knock out. Genome editing on a pool and clonal level was assessed by Synthego's online tool ICE (ice.synthego.com/#/)

Primers:

```
HAND1_G1_forward
                              (SEQ ID NO: 4)
5'-CACCGAGCATTAACAGCGCATTCG-3'

HAND1_G1_reverse
                              (SEQ ID NO: 5)
5'-AAACCGAATGCGCTGTTAATGCTCC-3'

NKX2.5_G1_forward
                              (SEQ ID NO: 6)
5'-CACCGGACGCACACTTGGCCGGTGA-3'

NKX2.5_G1_reverse
                              (SEQ ID NO: 7)
5'-AAACTCACCGGCCAAGTGTGCGTCC-3'

NKX2.5_G2_forward
                              (SEQ ID NO: 8)
5'-CACCGACTTGGCCGGTGAAGGCGCG-3'

NKX2.5_G2_reverse
                              (SEQ ID NO: 9)
5'-AAACCGCGCCTTCACCGGCCAAGT-3'
```

Example 8: Formation of Cardiac Chamber-Like Structures In Vitro

Figure 14:
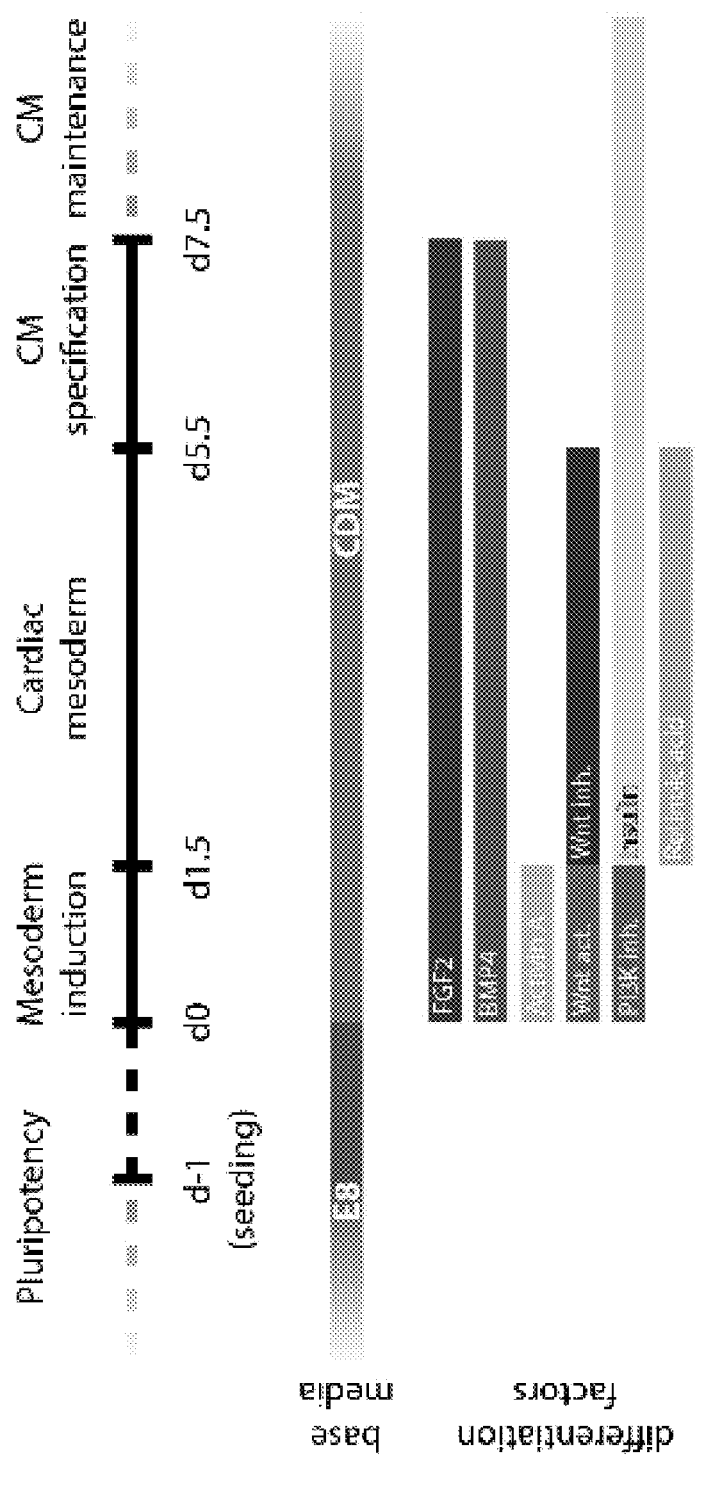
Figure 14:
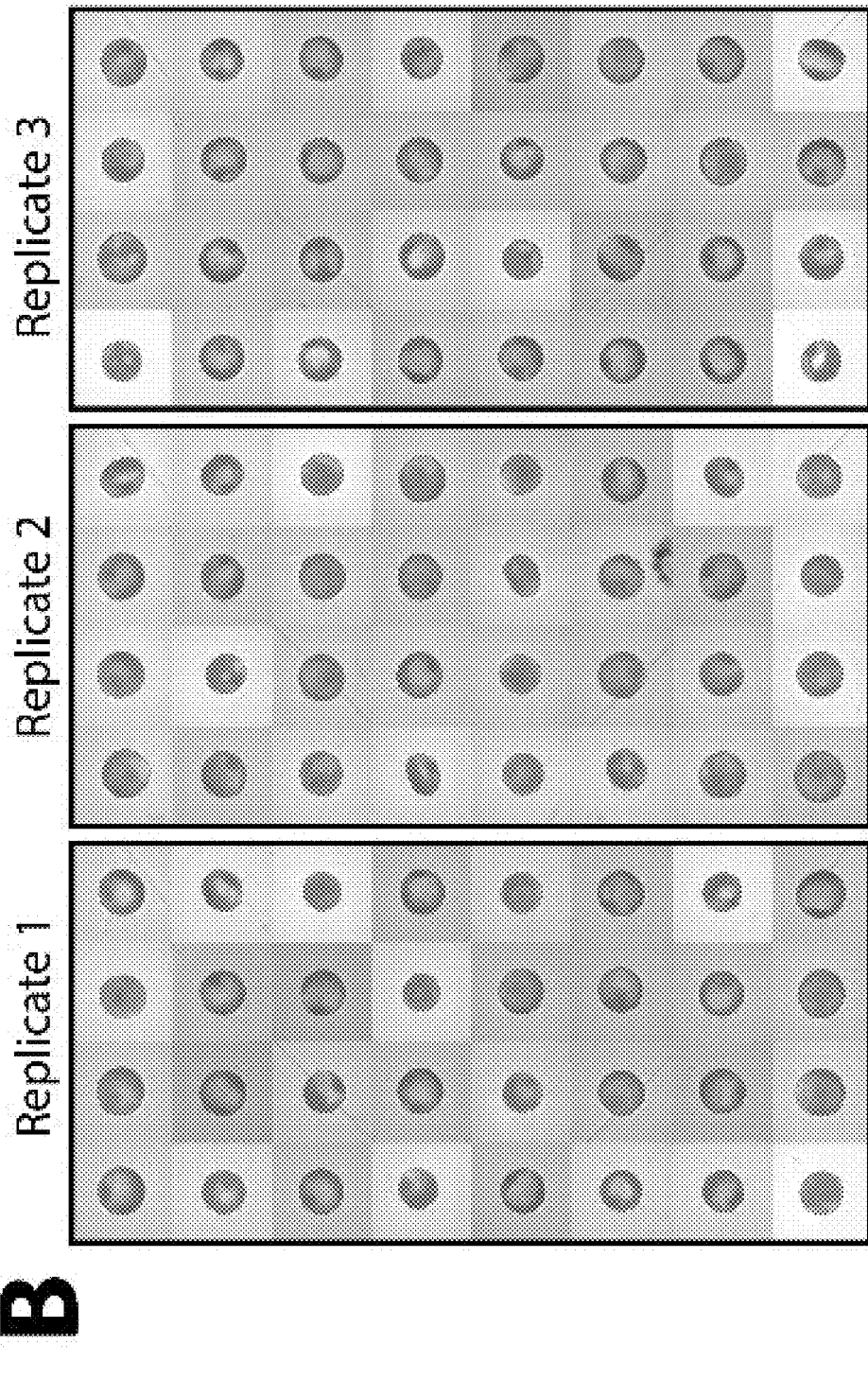
Figure 14:
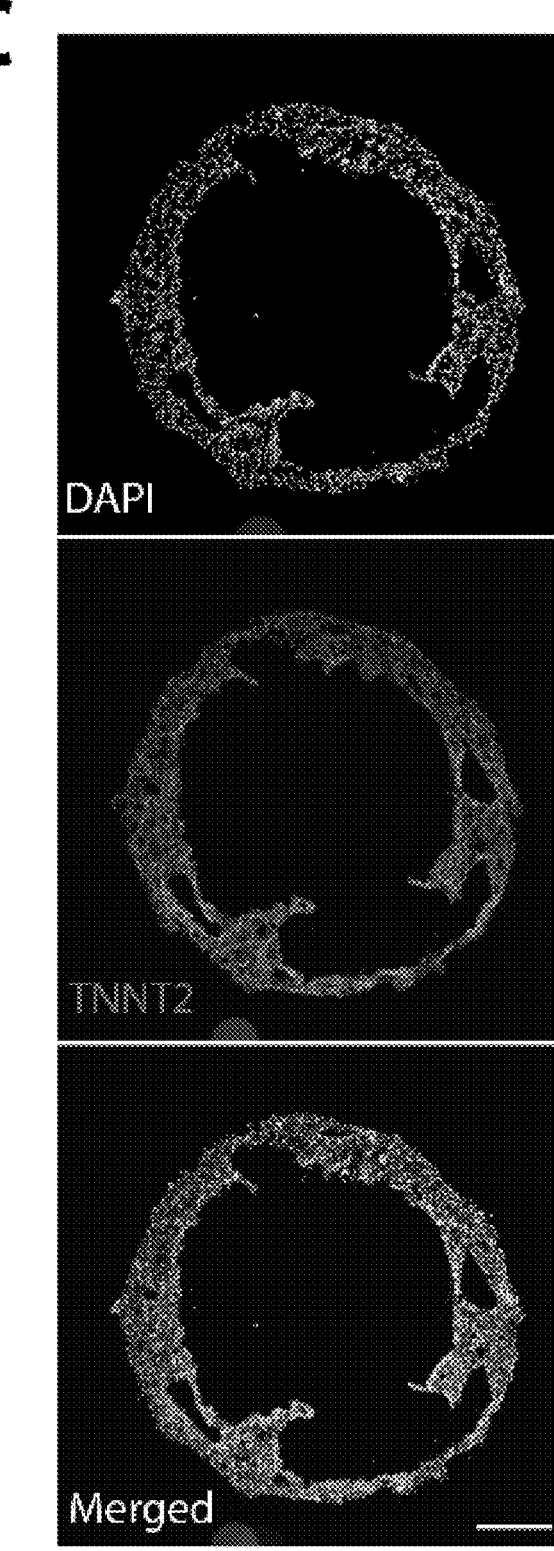
Figure 14:
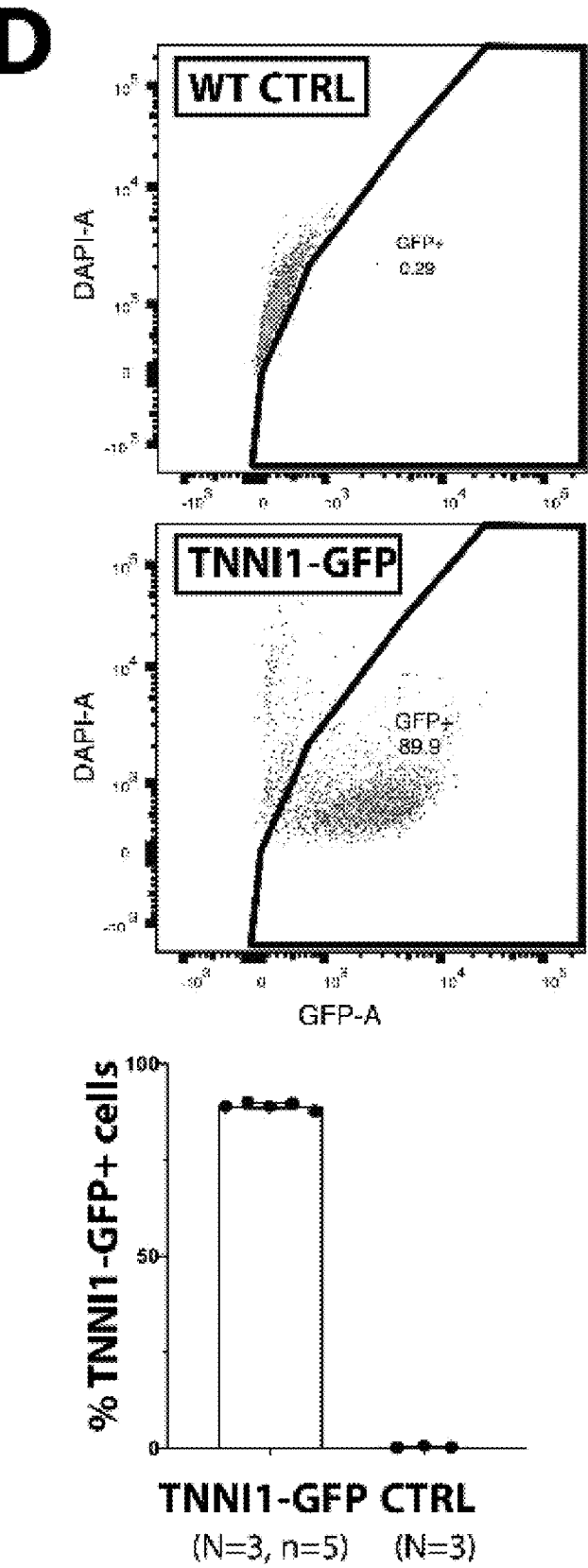
Figure 14:
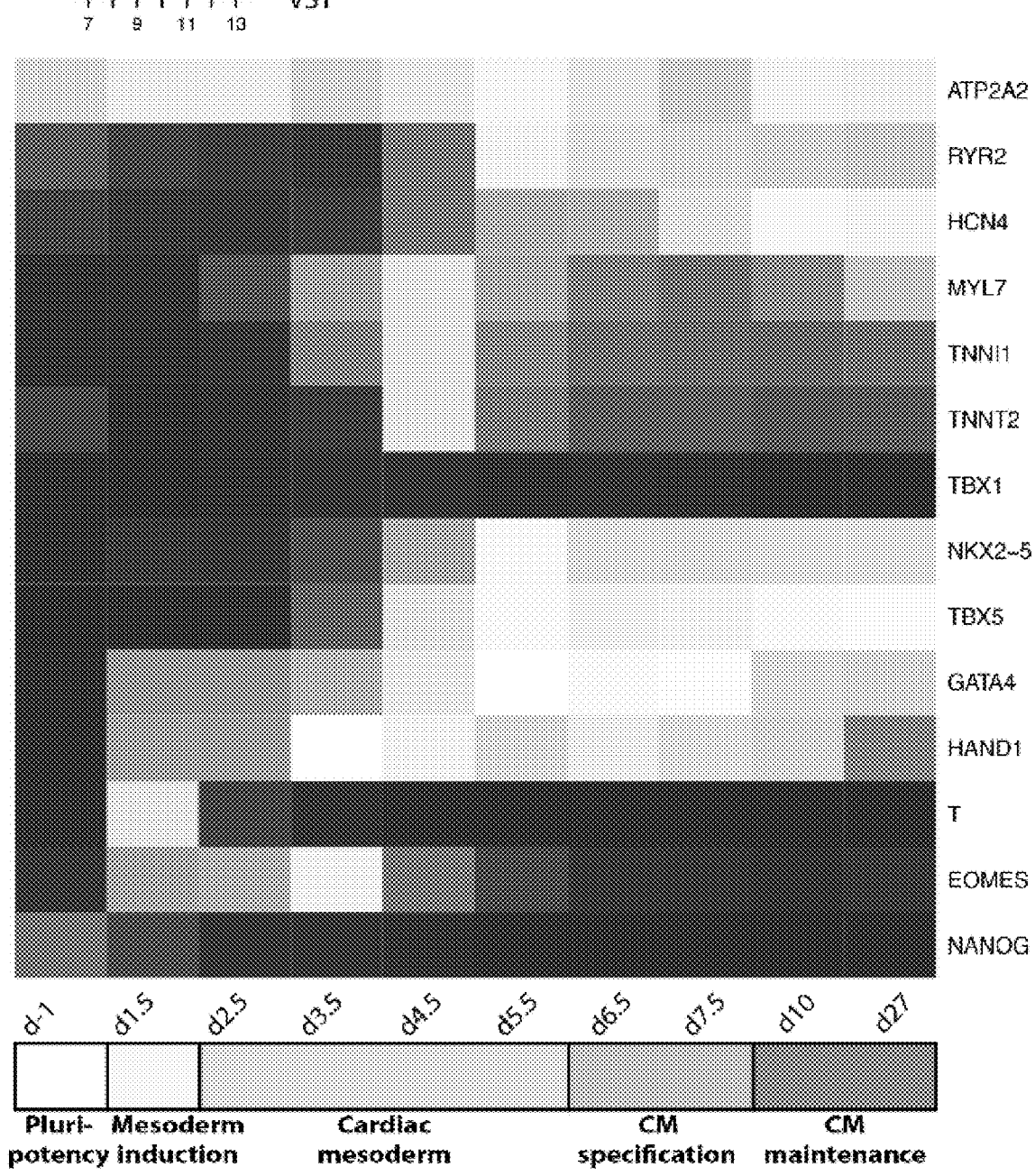
Figure 14:
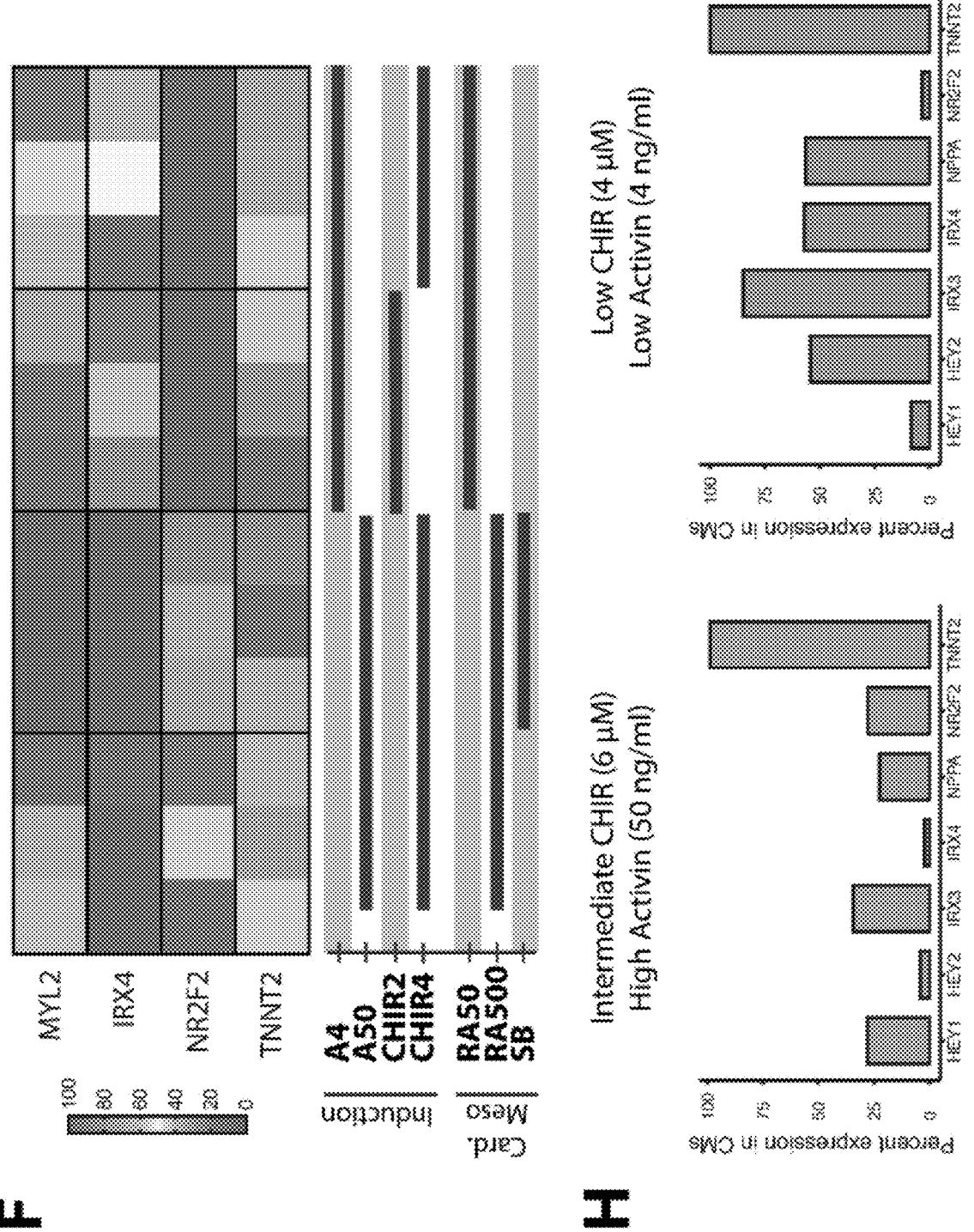
Figure 14:
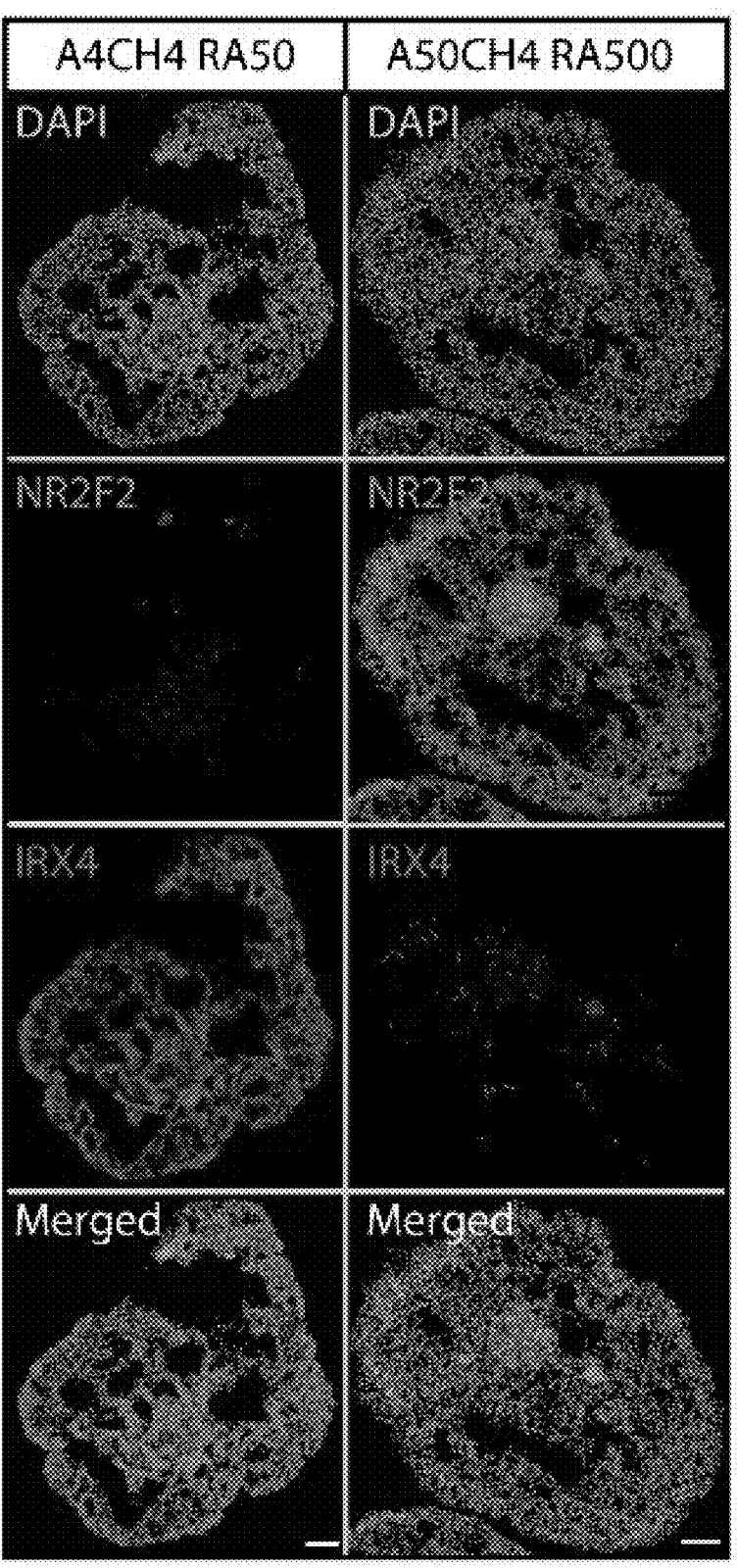
Figure 21:
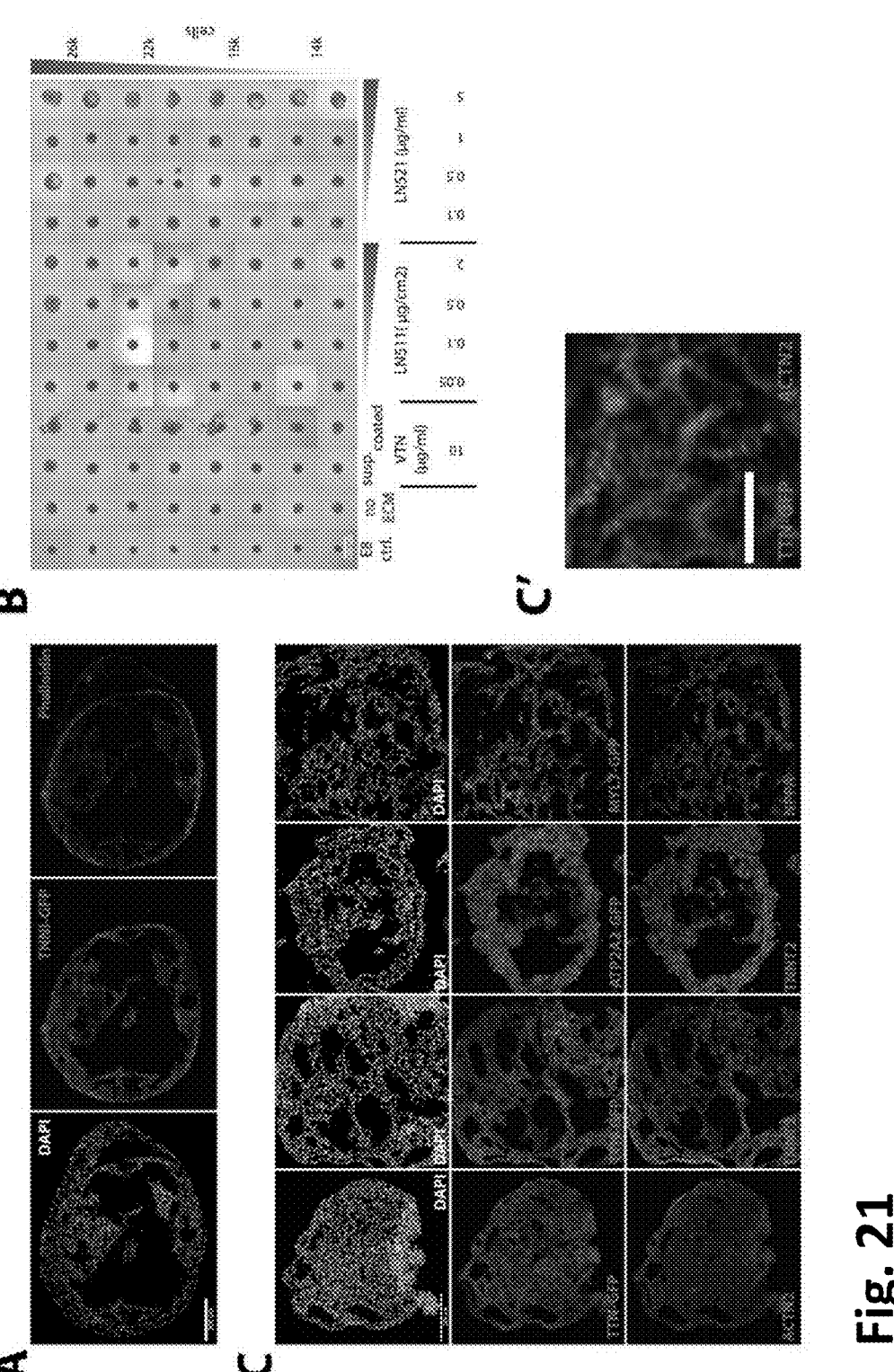
FIG. 21: Generation and Functional Characterization of Cardiac Chamber-like Structures. Related to FIG. 1. (A) Example of a beating chamber-like structure (day 8.5) containing a large cavity derived by adding laminin LN511 (0.1 μg/ml) to the cell suspension during seeding prior to differentiation in a 2D flat bottom well. Scalebar: 100 μm. (B) CM differentiation in ultra-low attachment plates results in the formation of beating 3D structures containing cavities even in the absence of extrinsic ECM molecules ('no ECM' column). Timepoint: day 8.5. Scalebar: 500 μm. (C) Expression of several CM-specific markers in cardioids (d7.5). Scalebar: 200 μm. (C') Detail of (C) (TTN-GFP/ACTN2) showing the sarcomeric organization within cardioid CMs. Scalebar: 6 μm (D) Electron micrograph of a d7.5 cardioid. S, sarcomere; ID, intercalated disc; Z, Z-line; D, desmosome. Scalebar: 1 μm. (E) Immunostaining with CM-markers showing robust generation of cardioids using various hPSC-lines (hESC H7) (hiPSC 176/177/178). Scalebar: 200 μm. (E') Whole mount brightfield images of several technical replicates of cardioids shown in (E). Scalebar: 200 μm (F) Quantification of overlap between DAPI and TNNI1+-area in optical sections capturing 500 μm of organoids. N=3, n=8. Used cell line in all experiments of this figure: WTC (if not stated otherwise).

To investigate whether an in vitro 3D chamber-like structure can be created intrinsically, we developed a differentiation approach based on temporal control of the key cardiogenic signaling pathways—Activin, BMP, FGF, retinoic acid and WNT. By recapitulating in vivo developmental staging, we sequentially specified hPSCs into mesoderm, cardiac mesoderm and beating cardiomyocyte progenitors at above 90% efficiency in 2D culture (Mendjan et al., 2014, Cell Stem Cell 15, 310-325) (FIG. 14A). To screen for factors that are sufficient to stimulate intrinsic 3D cardiac structure formation in 2D culture, we supplemented the media with selected ECM proteins that are involved in mesoderm development (Yap et al., 2019, Trends in Cell Biology 29, 987-1000). Addition of Laminins 521/511 before mesoderm induction resulted in intrinsic self-assembly of cells and the striking formation of hollow, beating 3D structures expressing the CM marker TNNT2 after 7 days of differentiation (FIG. 21A). When we performed cardiac differentiation entirely in 3D non-adherent high-throughput culture, we found that exogenous ECM was not required for rapid and reproducible self-assembly into beating cavity-containing structures positive for CM markers ACTN2, TNNT2, TNNI1, MYL7, TTN, LAPPA and ATP2A2 (FIGS. 14B, 14C, 21B, 21C). On an ultrastructural level these CMs contained organized sarcomeres and are interconnected via intercalated discs (FIGS. 21C', 21D). The self-assembly was robust in the WTC hiPSC line, including its vast live fluorescent reporter resource collection (Roberts et al., 2019, Stem Cell Reports 12, 1145-1158), the widely used hESC lines H9 and H7, as well as in three hiPSC lines routinely used to generate cerebral organoids (FIGS. 21E, 21E'). The CM differentiation efficiency measured by flow cytometry (N=3, n=5) and 3D Z-stack image analysis (N=3, n=8)

averaged approximately at 90% (FIG. 14D, 21F). We here-after refer to these cavity-containing cardiac structures as cardioids.

Figure 22:
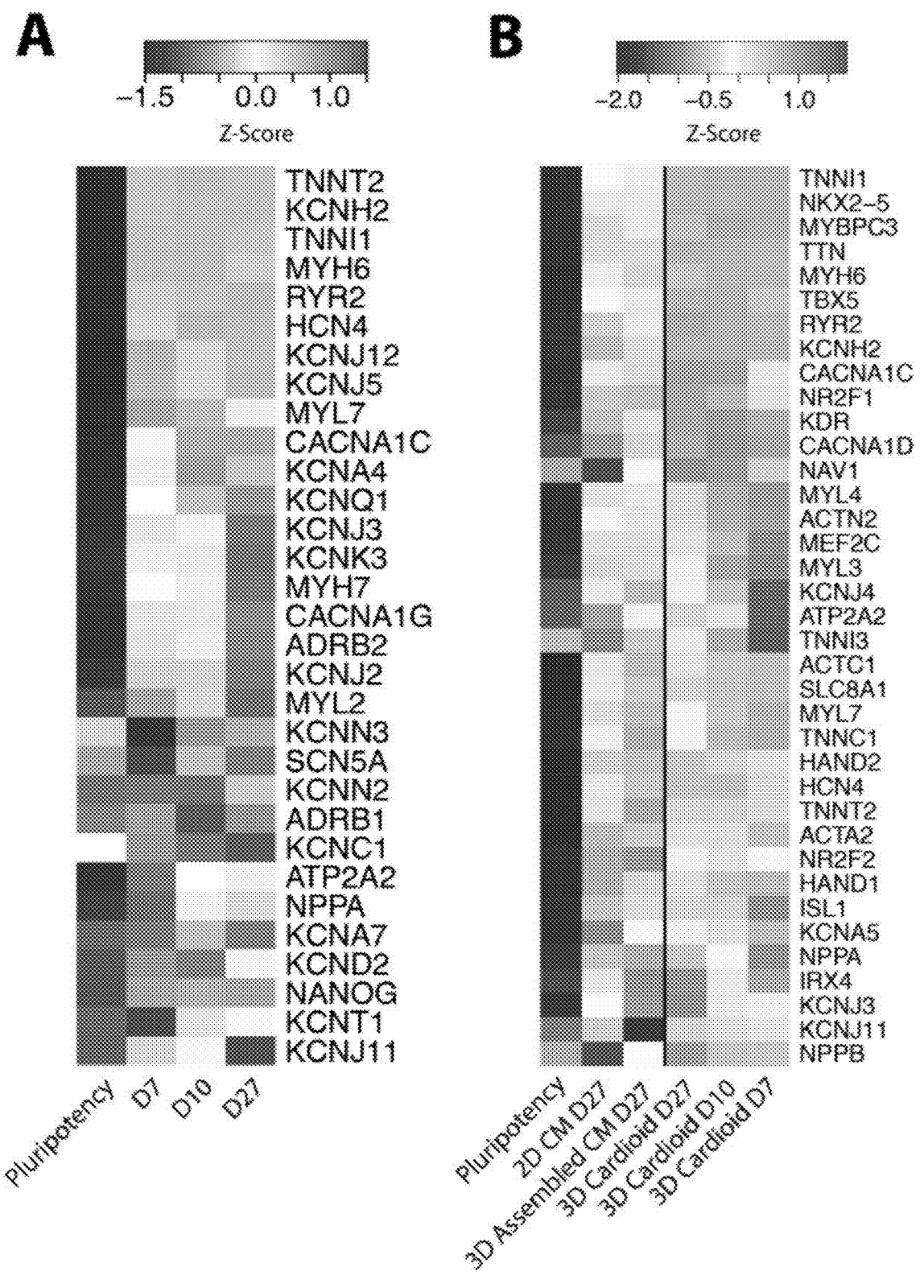
FIG. 22: Generation and Functional Characterization of Cardiac Chamber-like Structures. Related to FIG. 1. (A) Heatmap showing gene expression of cardiac structural genes/ion channel in d7/d10/d27 cardioids. (B) Comparison of gene expression signatures between cardioids, 3D assembled CMs, 2D CMs and hPSCs at different timepoints. Used cell lines: H9, WTC. (C) GO terms upregulated in day 7 cardioids compared to day 7 CMs in 2D. Used cell lines: H9, WTC. (D) GO terms upregulated between day 7 in cardioids and day 27 3D aggregated CMs. Used cell lines.
Figure 22:
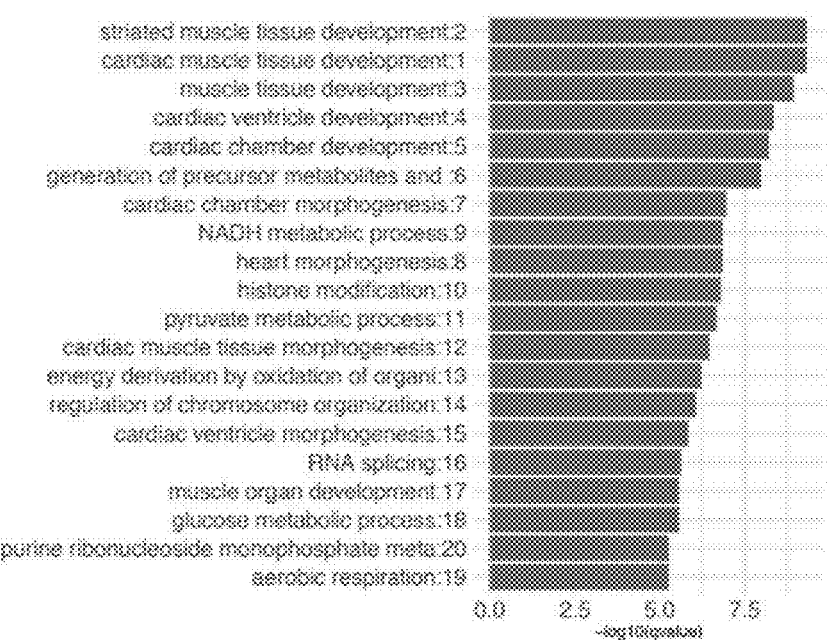
Figure 22:
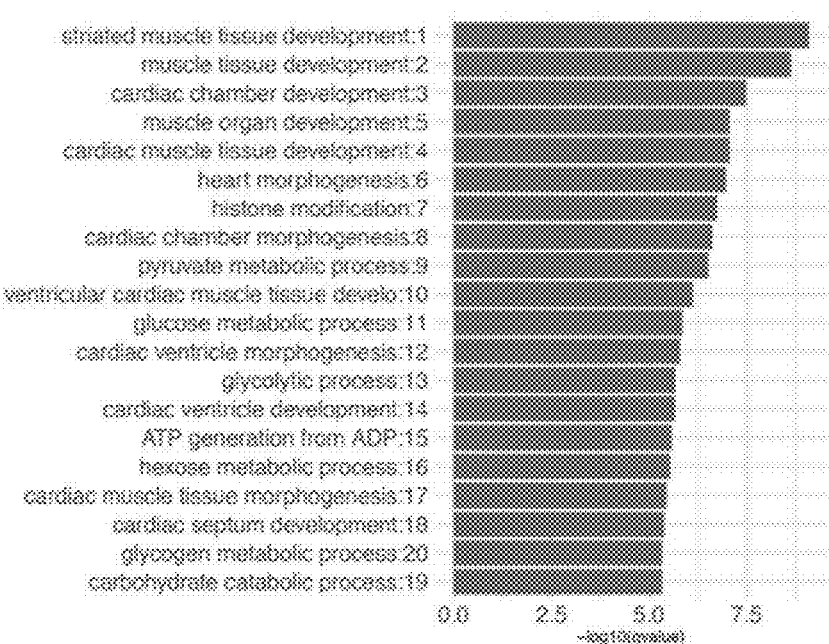
Figure 22:
Figure 22:
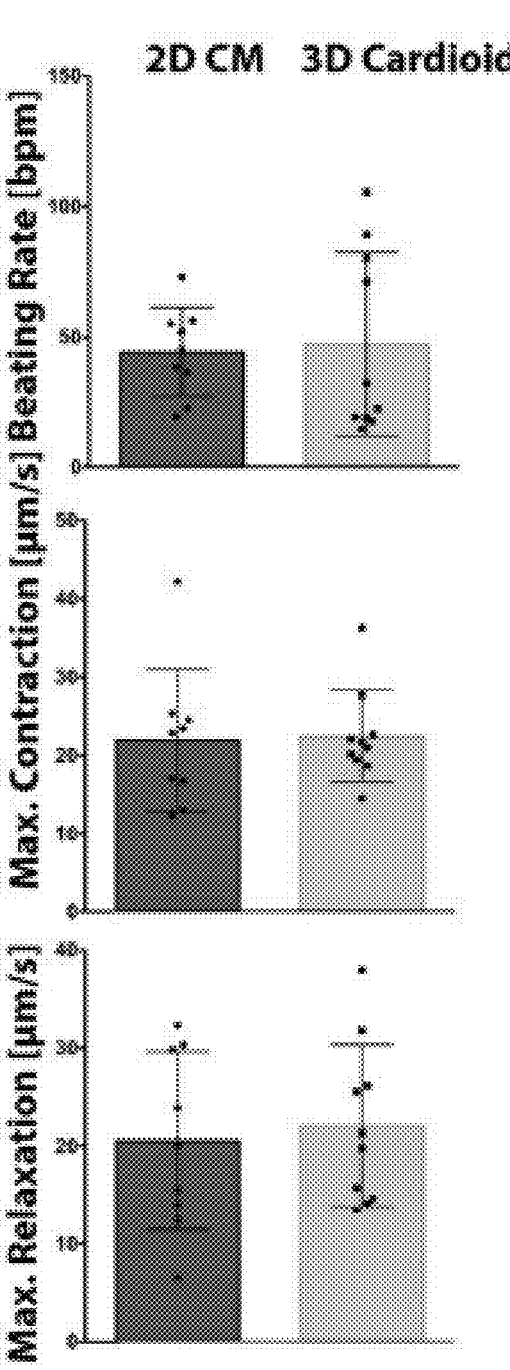

We next sought to characterize cardioids at the molecular level. An RNA-seq time-course analysis of cardioids revealed an expression signature most similar to the first heart field (FHF) lineage of cardiac mesoderm (HAND1$^+$, TBX5$^+$, NKX2-5$^+$, TBX1$^-$) (FIG. 14E), which in vivo gives rise to the heart tube—the primary precursor of the left ventricular chamber and to a smaller extent the atria. During cardioid specification and maturation, structural and ion channel gene expression, as well as β-adrenergic receptors 1 and 2 expression, increased (FIG. 22A). When we compared expression profiles of cardioids relative to CMs differenti-ated in 2D, we noted that genes encoding ion channels (e.g. the HERG channel KCNH2), structural proteins (TNNI1, TTN, MYH6), cardiac transcription factors (TBX5, MEF2C) and sarcoplasmic reticulum proteins (RYR2, ATP2A2) showed higher expression levels in 3D cavity-forming structures, suggesting improved functionality (FIG. 22B). GO-term analysis showed that cardioids exhibited gene expression patterns of heart morphogenesis and devel-opment, which were significantly upregulated over 2D CMs (FIG. 22C) and aggregated 3D CM microtissues (FIG. 22D). In both models, beating started between day 5 and 7 of differentiation, continued at a similar rate and frequency (Ca$^{2+}$ transients, beating frequency) (FIG. 22E, 22F), and cardioids could be maintained in culture for at least three months. Overall, we successfully generated functional hPSC-derived cardioids that reproducibly self-assembled and maintained their molecular CM identity.

We further aimed to explore the CM subtype potential of cardioids. The initial RNA-seq analysis of cardioids indi-cated a mixed ventricular (IRX4$^+$, MYL2$^+$) and atrial (NR2F2$^+$, KCNJ3$^+$) profile (FIG. 22A, 22B) consistent with its FHF origin. Considering mesoderm induction and low RA signaling dosage as critical for posterior heart tube and left ventricular chamber specification, we optimized WNT and ACTIVIN dosage during mesoderm induction, and reduced RA dosage during the cardiac mesoderm stage. These optimizations resulted in increased expression of ventricular-specific markers (IRX3, IRX4, HEY2, MYL2) and near absence of atrial-specific marker expression (NR2F2, HEY1) as seen by RTqPCR, immunocytochemis-try and single cell RNA-seq (scRNA-seq) analysis of CMs (FIGS. 14F, G, H). Consistent with these data, action poten-tial measurements using a FluoVolt dye assay indicated a primarily ventricular-like profile (FIG. 22G). In conclusion, cardioids can be directed towards an early left ventricular chamber-like identity.

Figure 15:
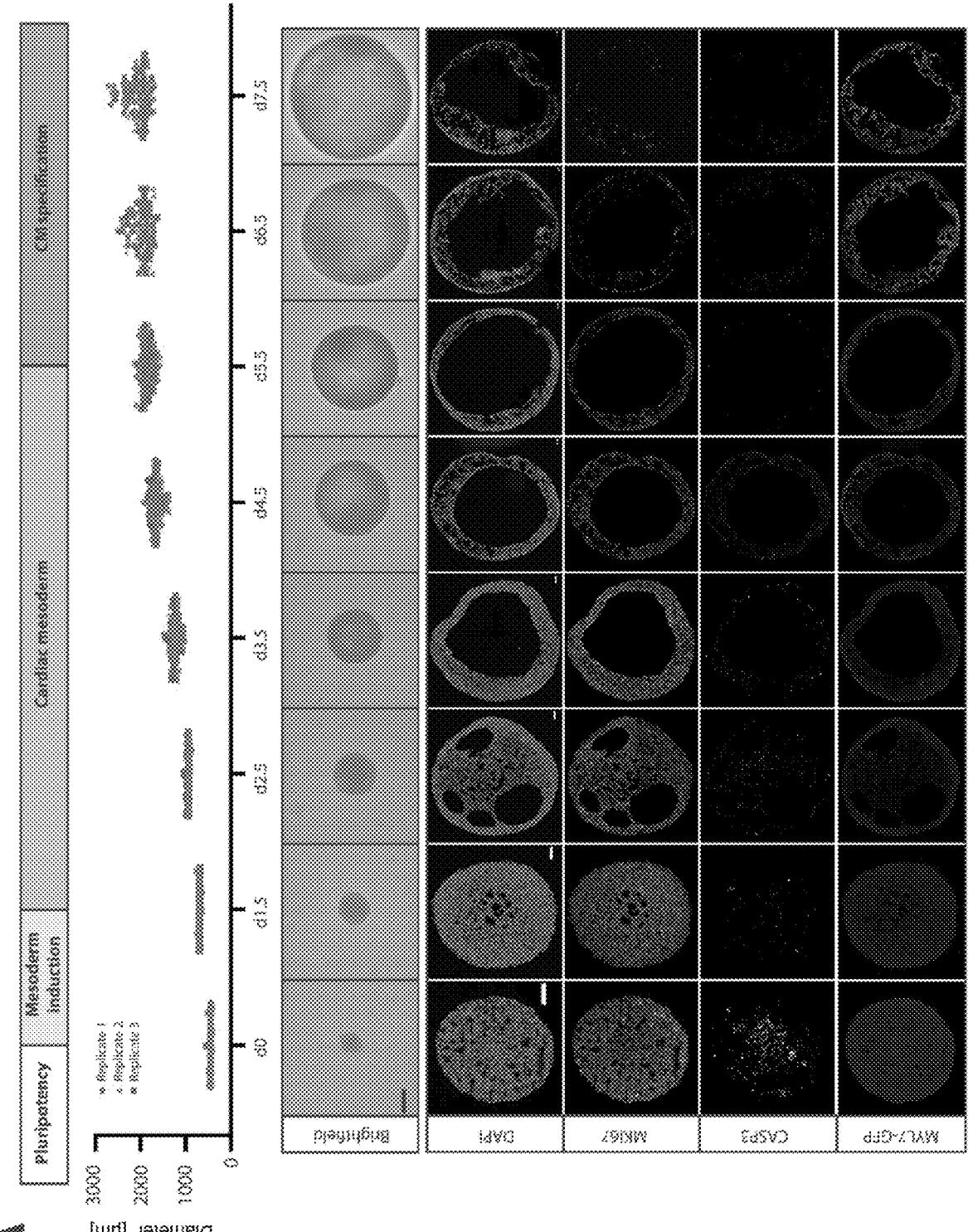
FIG. 15. Cardiac Mesoderm Self-organizes Forming a Cavity in vitro and ex vivo. (A) Time-course of cardioid formation. Top: Quantification of size-change in the course of differentiation. Bottom: Whole mount brightfield images and immunostaining of cryosections showing the size increase and cavity formation over time. Cavities can first be seen at d2.5 and are not formed by apoptosis (Casp3 negative) or regional proliferation (KI67+) differences. Scalebars: 500 μm (brightfield images), 50 μm (sections). (B) Cardiac mesoderm explants from chick embryos in human cardiac mesoderm conditions form chamber-like CM structures with cavities. Scalebar: 200 μm. (C) Detailed images of organoids (ranging from the periphery to the center) between d1.5 and d2.5 showing formation of loose and dense mesodermal compartments at the onset of the cardiac mesoderm stage by differential expression of F-actin (Phalloidin), membrane-bound beta-catenin (PY-654-beta-catenin) and N-cadherin. (D) Representative image and quantification of number of nuclei in a 65 μm² square in loose (central) versus dense (peripheral) layer of cardiac mesoderm (N=3, n=14). Used cell lines in this figure: WTC.
Figure 15:
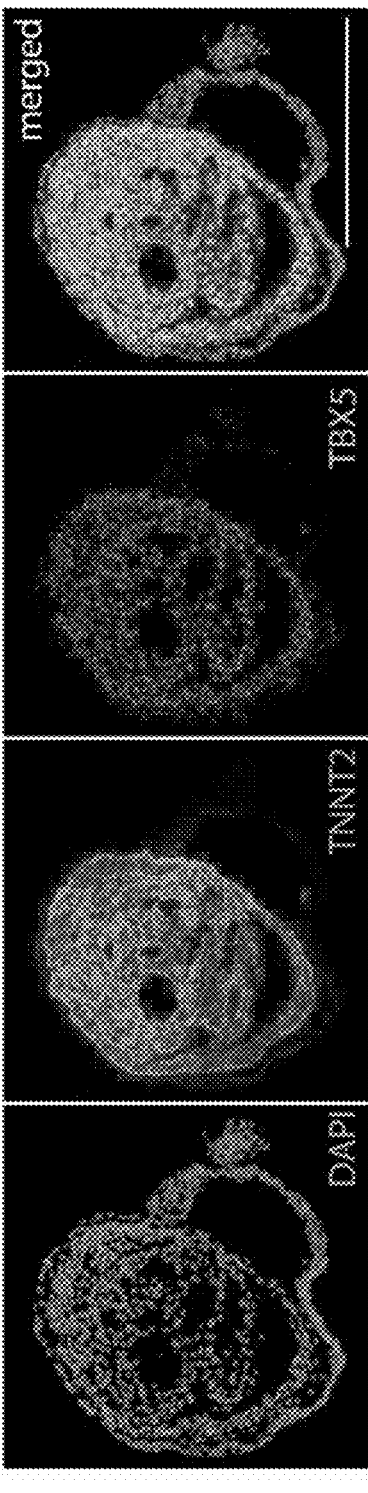
Figure 15:
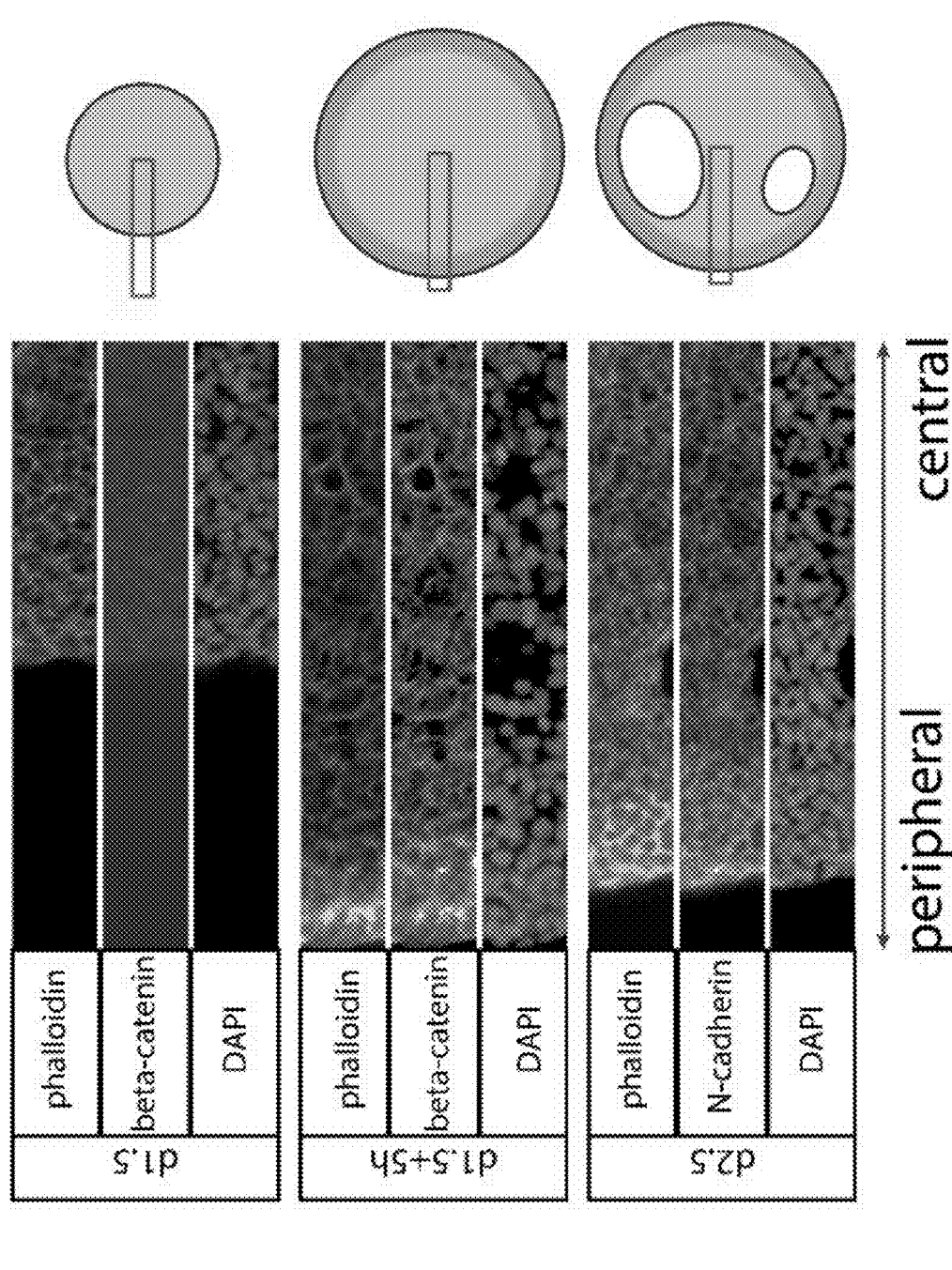
Figure 15:
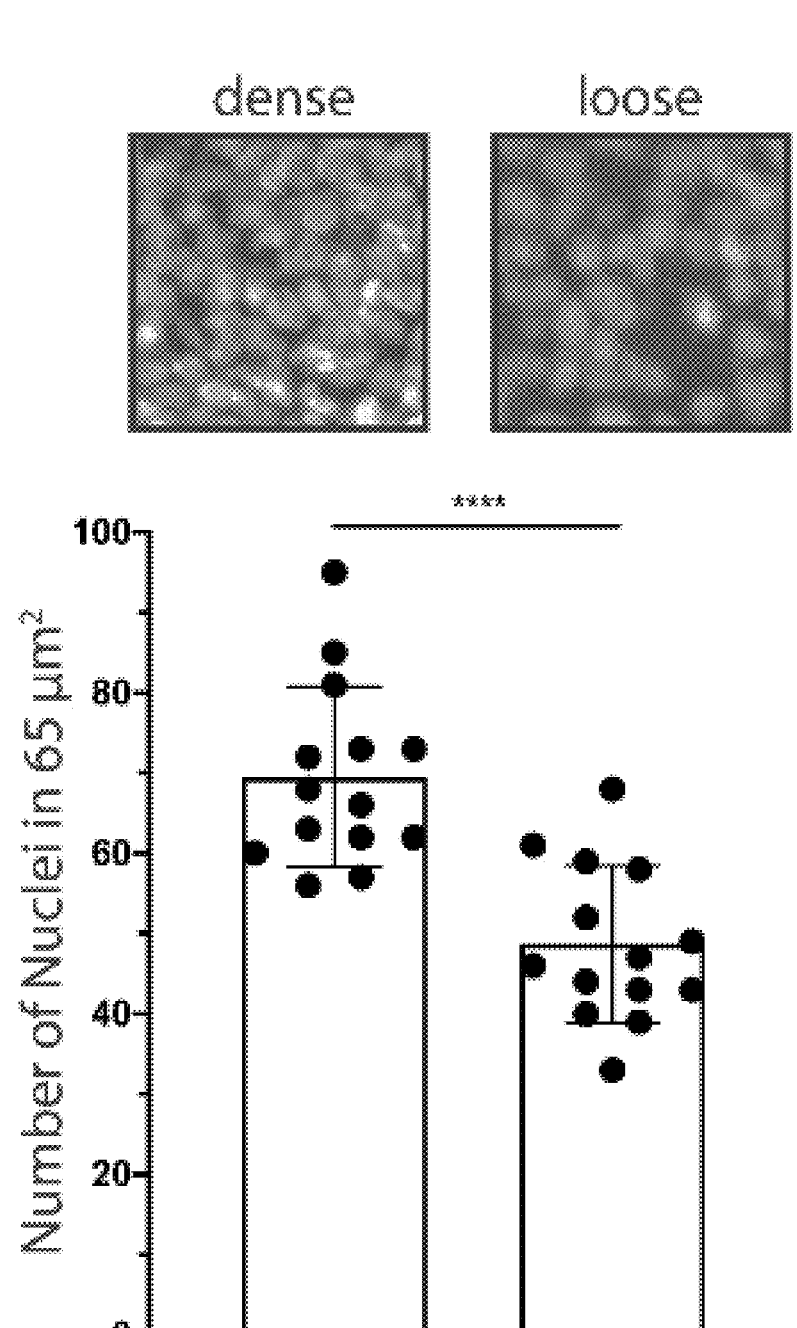

Example 9: Cardiac Mesoderm Self-Organizes to Form a Cavity In Vitro and Ex Vivo We next employed this system to ask whether the cavity within cardioids is formed by an intrinsic morphogenesis. By analyzing the developmental time-course capturing cav-ity formation, we found that cavities were initiated and expanded robustly during the cardiac mesoderm (HAND1+) stage preceding expression of key cardiac structural mark-ers, such as MYL7 (FIG. 14E; FIG. 15A). Cardioids expanded rapidly and reproducibly due to proliferation and formation of multiple cavities. Most smaller cavities even-tually coalesced into one major cavity. Cavity expansion was neither driven by apoptosis nor regional proliferation dif-ferences, as evidenced by cleaved CASP3 and MKI67 staining (FIG. 15A). Importantly, SOX17$^+$/EOMES$^+$ endoderm was absent during differentiation, indicating that car-diac mesoderm cavities were not generated as a result of endoderm instruction (FIG. 23A). This is consistent with findings in vivo, as bilateral hearts can still form when foregut endoderm morphogenesis is disrupted. Lumen for-mation also occurred when VEGF-driven endothelial cell (EC) differentiation was inhibited using the potent VEGFR inhibitor Sunitinib (FIG. 23B) suggesting an endothelium-independent mechanism. We concluded that cardiac meso-derm has an intrinsic capacity for self-assembly into a CM-made chamber-like structure.

In vivo, cardiac mesoderm does not require foregut endo-derm for basic morphogenesis of the heart in the mouse (Li et al., 2004, Science 305, 1619-1622) and in the chick (DeHaan and DeHaan, 1959, Developmental Biology 1, 586-602). We therefore asked whether ex vivo dissected mesoderm from developing chick embryos can also form chamber-like structures in conditions we developed for human cardiac self-organization. Strikingly, in the absence of SOX2$^+$ foregut, chick mesodermal explants developed into beating chamber-like structures in vitro similar to human cardiac mesoderm, demonstrating robust conserva-tion of in vitro cardiogenic self-morphogenesis under per-missive conditions (FIG. 15B, FIG. 23C, 23D).

Besides self-morphogenesis during specification, intrinsic self-patterning of a homogeneous starting cell population is a key hallmark of self-organization. To this end, we per-formed a closer analysis of cardiac mesoderm to determine when the first self-patterning event occurs. While mesoderm at the induction stage appeared homogeneous, we observed a higher peripheral signal of F-actin and membrane bound beta-catenin at the onset of the cardiac mesoderm stage. Subsequent cavitation coincided with increased mesoderm density at the periphery, reflected by accumulation of F-ac-tin, N-cadherin and higher nuclear density (FIG. 15C, 15D). It is likely that this denser cardiac mesoderm layer acts as a permeability barrier, as the cavity structures were imperme-able to low-molecular-weight (4 kDa) dextran. In contrast, the central part of the developing structures, where cavities first appeared, had a looser appearance with decreased N-cadherin and beta-catenin signal (FIG. 15C). These obser-vations are consistent with the in vivo pattern of N-cadherin and beta-catenin in the denser dorsal region of cardiac mesoderm and the less compact region facing endocardial tubes and foregut endoderm (Linask, 2003, Birth Defects Research Part C: Embryo Today: Reviews 69, 14-24). This far, we concluded that human cardioids feature the key hallmarks of self-organization, ongoing specification, intrin-sic self-patterning into mesoderm layers and self-morpho-genesis to shape a cavity.

Example 10: WNT and BMP Control Cardioid Self-Organization

We next used cardioids to dissect how signaling controls intrinsic morphogenesis and patterning during cardioid specification. To quantify phenotypes with high statistical power, we combined the high-throughput cardioid platform with a custom-made semi-automated imaging/analysis FIJI-pipeline. Using this setup, we examined which signals control cardioid self-organization and at what stage of mesodermal specification they act. We first systematically tested the effects of key mesoderm and cardiac mesoderm signaling dosages (e. g. WNT, BMP) on cardiac cavity self-morphogenesis. Surprisingly, we found that higher dos-ages of WNT signaling during mesoderm induction drove cavity expansion during the later cardiac mesoderm stage (FIG. 16A, 16B), which has not been reported before. An intermediate WNT dosage promoted both cavity morphogenesis and CM specification. The optimal WNT activation range was consistent for each hPSC line but differed across lines, consistent with numerous studies showing line-specific signaling responses. Importantly, the highest WNT dosage promoted cavity formation without CM specification (FIG. 16A), highlighting a striking difference in signaling control of cell-fate specification versus morphogenesis.

Figure 16:
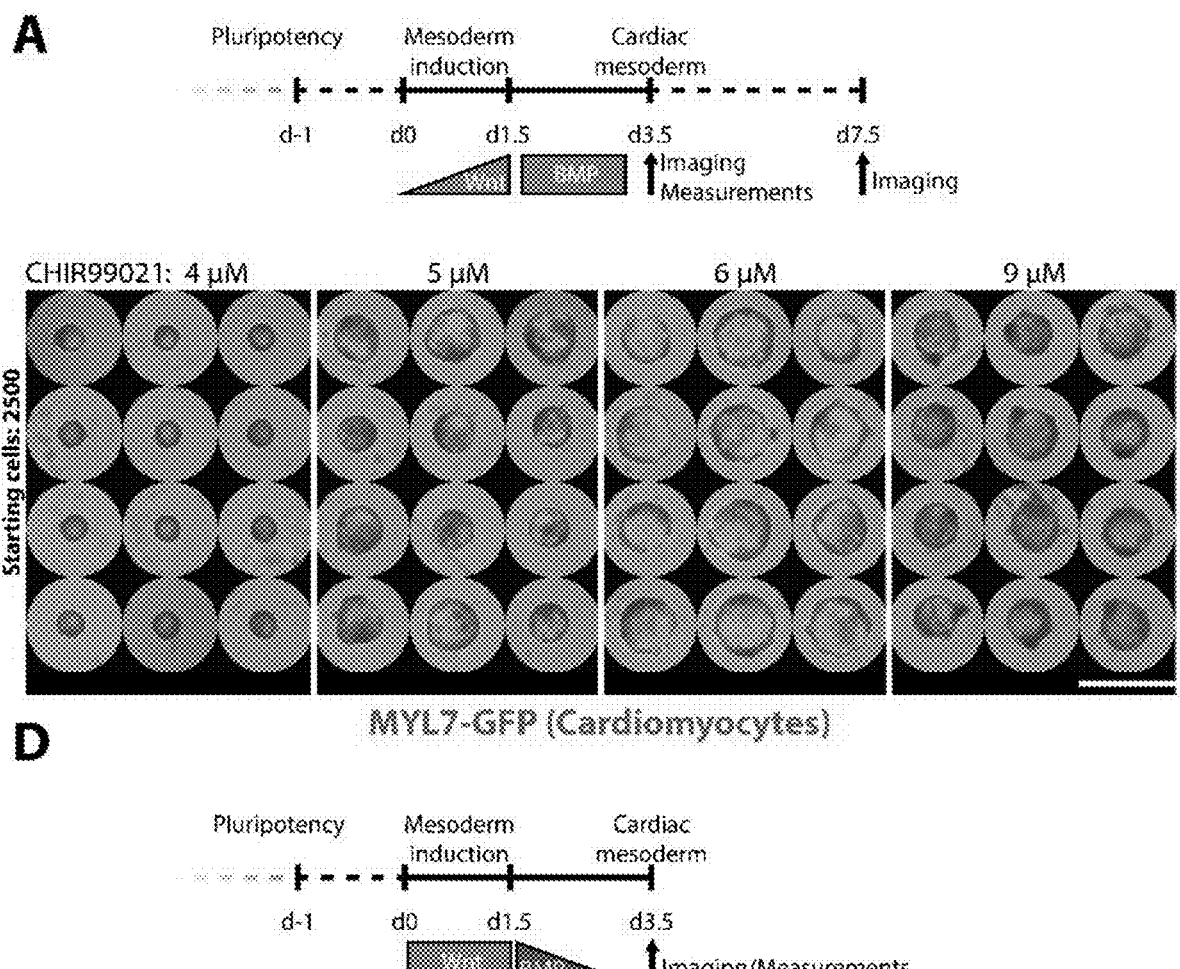
FIG. 16. WNT and BMP Control Cardioid Self-Organization and Specification. (A) Range of CHIR99021 concentrations during mesoderm induction shows dramatic effects on cardioid diameter (day 3.5) and CM specification (day 7.5). Protocol starting with 2500 hPSCs. Scalebar: 2500 μm. (B) Quantification of cardioid diameters at day 3.5 during cardiac mesoderm specification. (C) BMP target genes (HAND1, IRX3, BMP4, BMP2, BMPR2) are upregulated in cavity-forming conditions (8 μM CHIR99201), while EC genes (PECAM1, CDH5, VEGFA) are upregulated when 4 μM CHIR99021 is used. (D) BMP-inhibition with either Noggin (100 ng/ml) or LDN193189 (0.2 μM) reduces cardioid diameter. Protocol starting with 7500 hPSCs. Scalebar: 1958 μm. (E) Quantification of cardioid diameters at day 3.5 with or without BMP-inhibition. (F) Cell counting of cells/ organoid reveals that the reduced diameter is not a function of fewer cells. (G) Noggin and LDN193189 treatments interfere with cavity expansion. Scalebars: 200 μm. (H) Wnt activation during the cardiac mesoderm stage inhibits CM-differentiation but not cavity expansion. Scalebar: 200 μm. All bar graphs show: Mean+/−SD. Used cell lines in this figure: H9, WTC.
Figure 16:
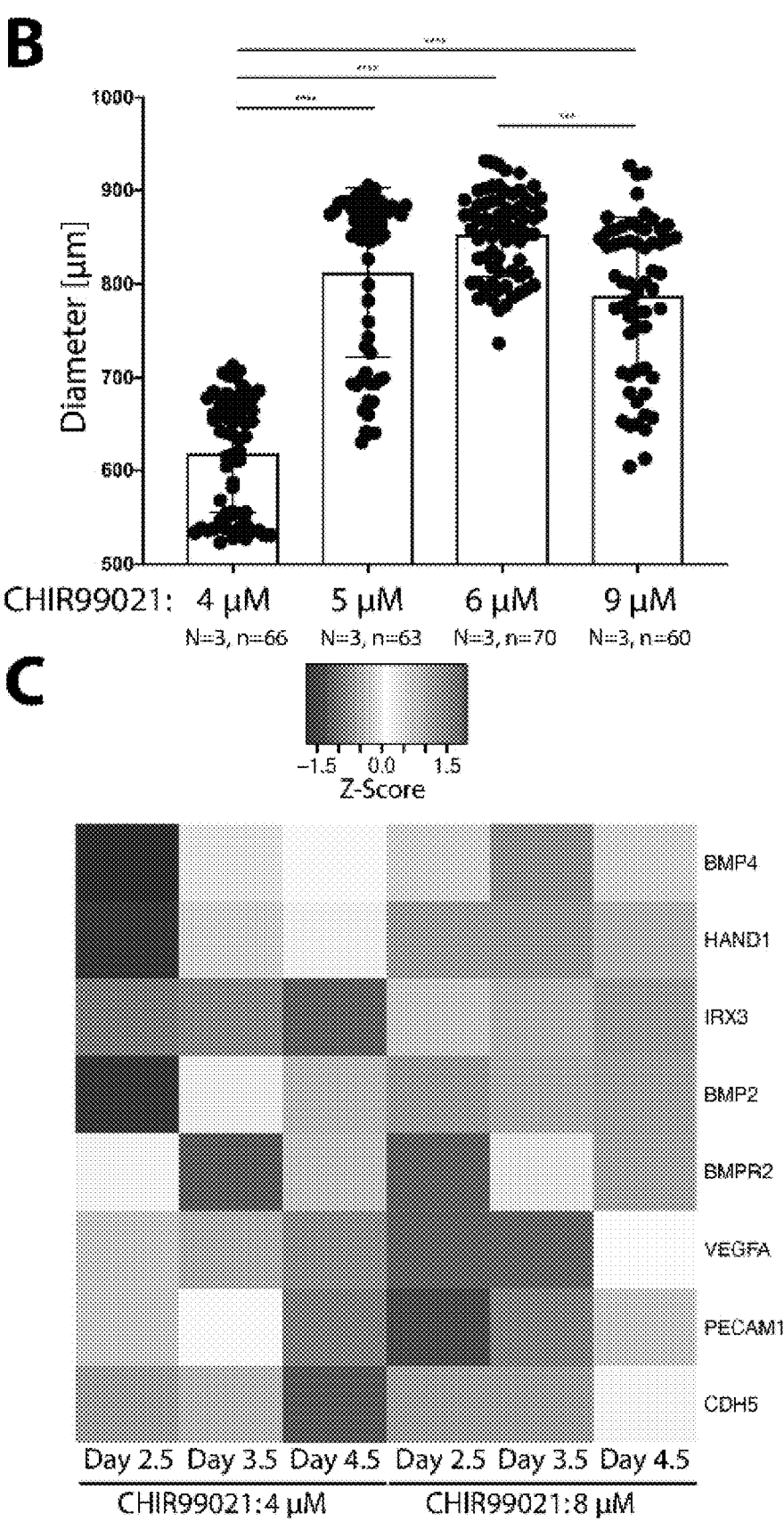
Figure 16:
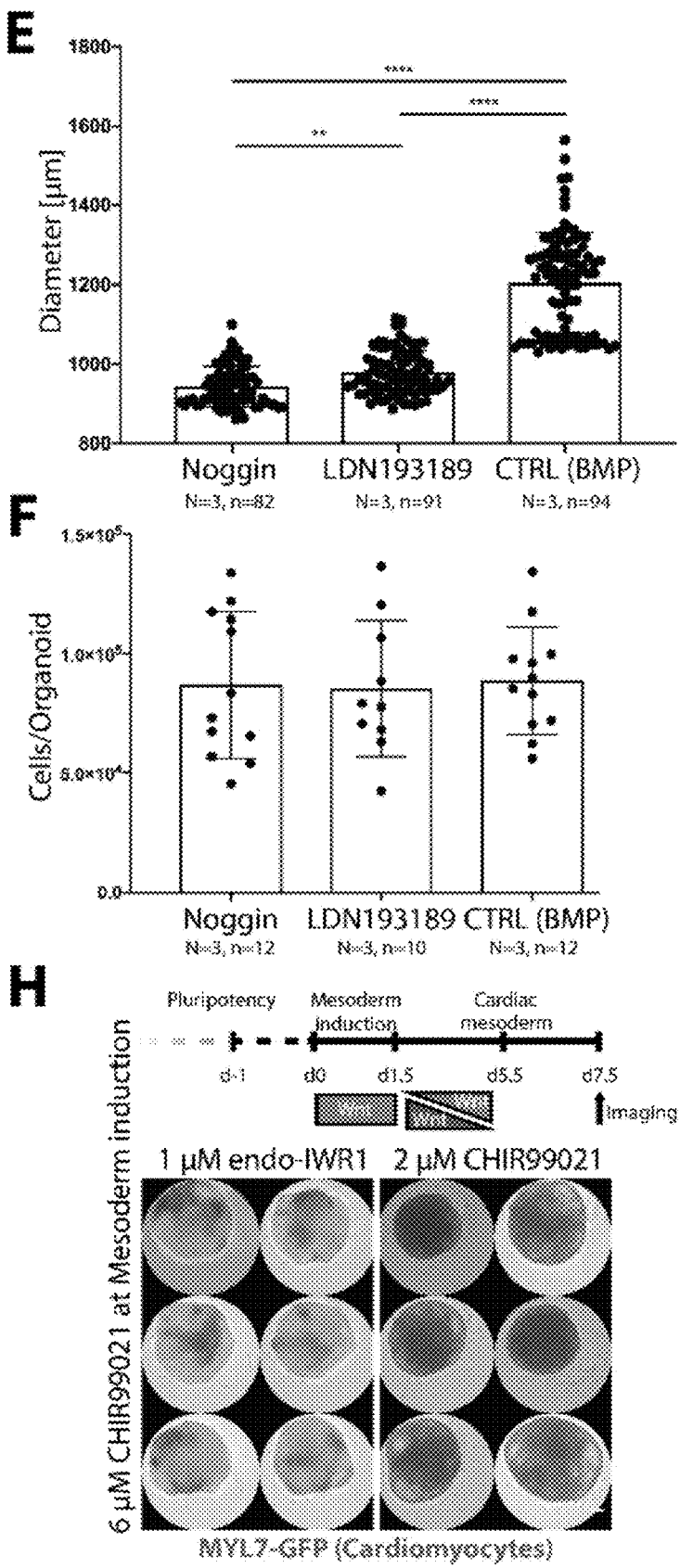
Figure 16:
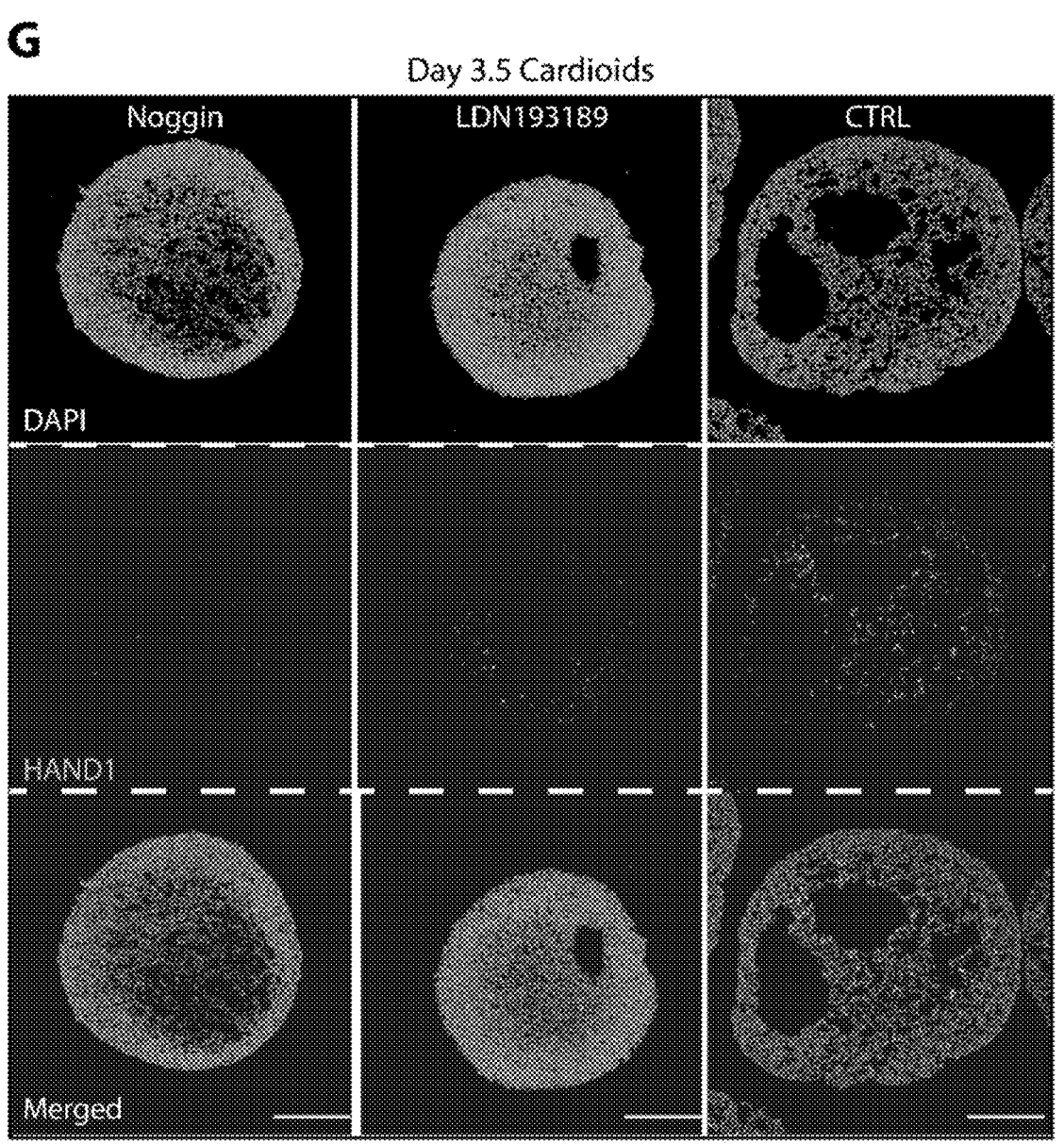

To identify downstream mediators of WNT that control cardiac cavity morphogenesis, we performed RNA-seq analysis and compared gene expression profiles of mesoderm induced by higher (large cavity) and lower (small cavity) WNT signaling dosages. Among differentially expressed genes at the later cardiac mesoderm stage, we identified known cardiac mediators of BMP signaling (BMP4, BMP2, BMPR2) and some of its mesodermal targets (HAND1, IRX3) (FIG. 16C). BMP drives cardiac specification at multiple stages, and we asked whether BMPs can instruct patterning and morphogenesis to form a cardiac cavity. To answer this question, we blocked BMP signaling using either the natural inhibitor Noggin or the compound LDN193189 during the initial two days of the cardiac mesoderm stage. BMP inhibition resulted in impaired cavity morphogenesis, denser cardiac mesoderm and decreased cardioid size while cell number per cardioid remained stable (FIG. 16D, 16E, 16F, 16G). In contrast, WNT inhibition at the cardiac mesoderm stage was not necessary for cavity formation (FIG. 16H). These findings emphasize that control of specification versus morphogenesis can be fundamentally different processes, and that a mesodermal WNT-BMP signaling axis controls self-patterning and self-morphogenesis—both key self-organizing processes.

Example 11: HAND1 Acts in Cardioid Self-Organization

Mutations in signaling and downstream transcription factors affect heart tube and chamber development and cause severe human cardiac malformations. For instance, in Hypoplastic Left Heart Syndrome, the most severe congenital defect in humans, disrupted levels of the BMP-regulated genes NKX2-5 and HAND1 are associated with a severely reduced cardiac cavity within the left ventricular chamber. The earliest phenotype in mutant Nkx2-5 and Hand1 mice manifests as defects in heart tube and early left ventricular chamber morphogenesis respectively, but the disease etiology and the underlying morphogenetic mechanism in humans are less clear. Here, we generated knock-out (KO) hPSC lines for either HAND1 or NKX2-5 to assess whether these genes were required to achieve intrinsic self-organization in the absence of non-cardiac tissues. In NKX2-5 KO lines we did not detect any cavity formation defects at the cardiac mesoderm stage and they eventually formed TNNT2$^+$ cardioids (FIG. 24A, 24B, 24C). HAND1 expression in NKX2-5 KO cardiac mesoderm remained unaffected and this is in line with the delayed onset of NKX2-5 relative to HAND1 expression in cardioids (FIG. 24C, FIG. 14E) as well as in human and mouse FHF cardiac mesoderm. However, HAND1 expression appeared reduced at the CM stage in NKX2-5 KO cardioids (FIG. 24C), which is in agreement with findings in mouse and human CMs where NKX2-5 is acting upstream of HAND1.

Figure 17:
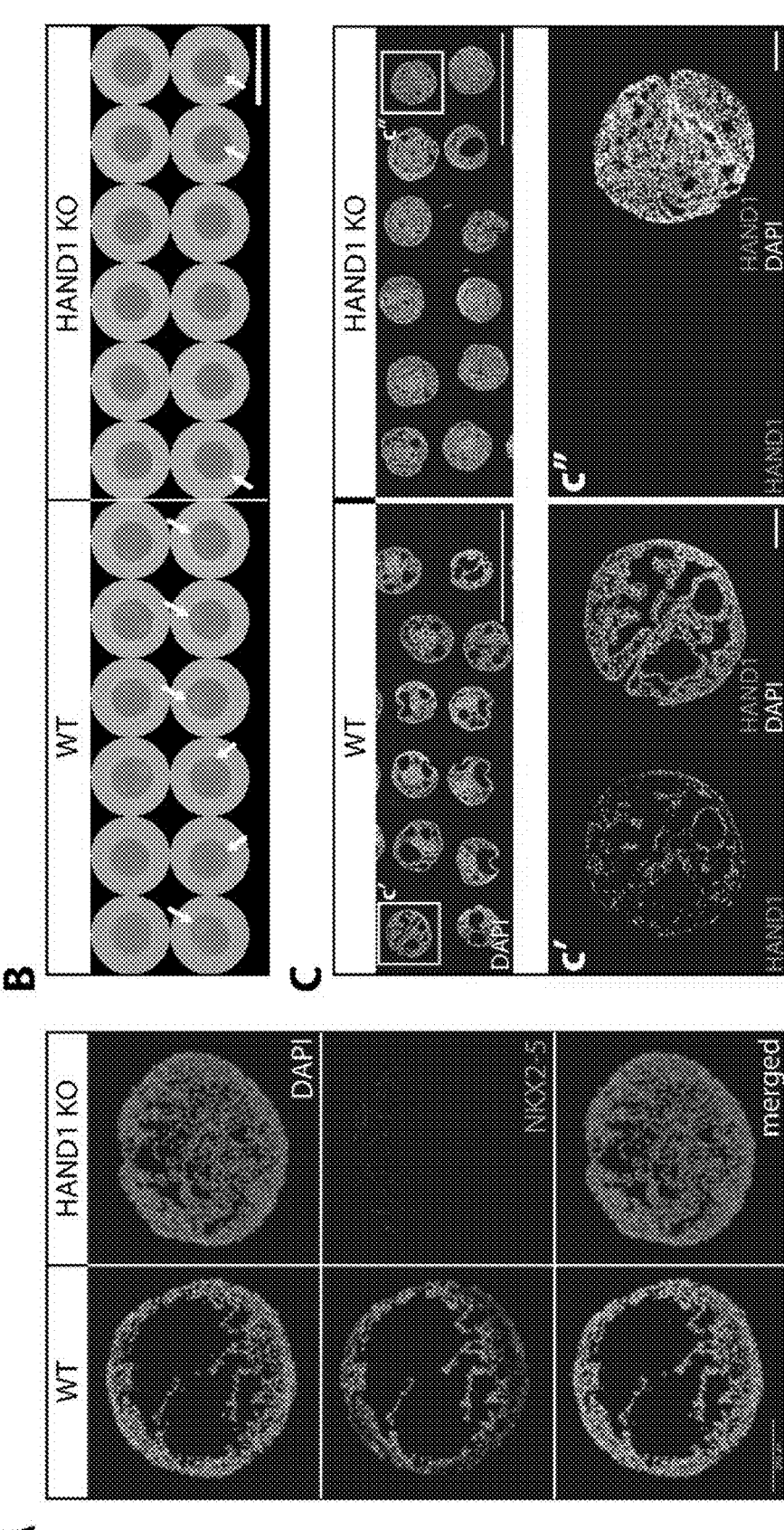
FIG. 17. HAND1 is Required for Cardiac Mesoderm (d3.5) Self-organization (A) HAND1 KO cardioid showing downregulation of NKX2-5. Scalebar: 200 μm. (B) WT cardioids show increased number of cavities (arrows) and diameter compared to HAND1 KO cardioids. Scalebar: 2000 μm. (C) HAND1 KO cardioids show smaller and decreased number of cavities. Scalebars: 2000 μm. (c') and (c''), Detail of C and HAND1 KO confirmation by HAND1 staining. Scalebars: 200 μm. (D) Quantification of cardioid cavity expansion as a function of diameter in HAND1 KO and WT cardioids. (E) Percentage of cardioid area covered by cavities in WT and KO cardioids. (F) Timeline of organoid formation until day 3.5 (cardiac mesoderm stage), the point of analysis. Increased WNT signaling (CHIR99021) during mesoderm induction rescues cavity defect in HAND1 KO organoids (arrows). Scalebar: 2500 μm. (G) Quantification of cardioid diameter shows that increased WNT activation rescues the HAND1 KO cavity defect. All bar graphs show: Mean+/−SD. All data in this figure originated from cardioids at d3.5. Used cell lines in this figures HAND1 KO (H9), NKX2-5 KO (H9).
Figure 17:
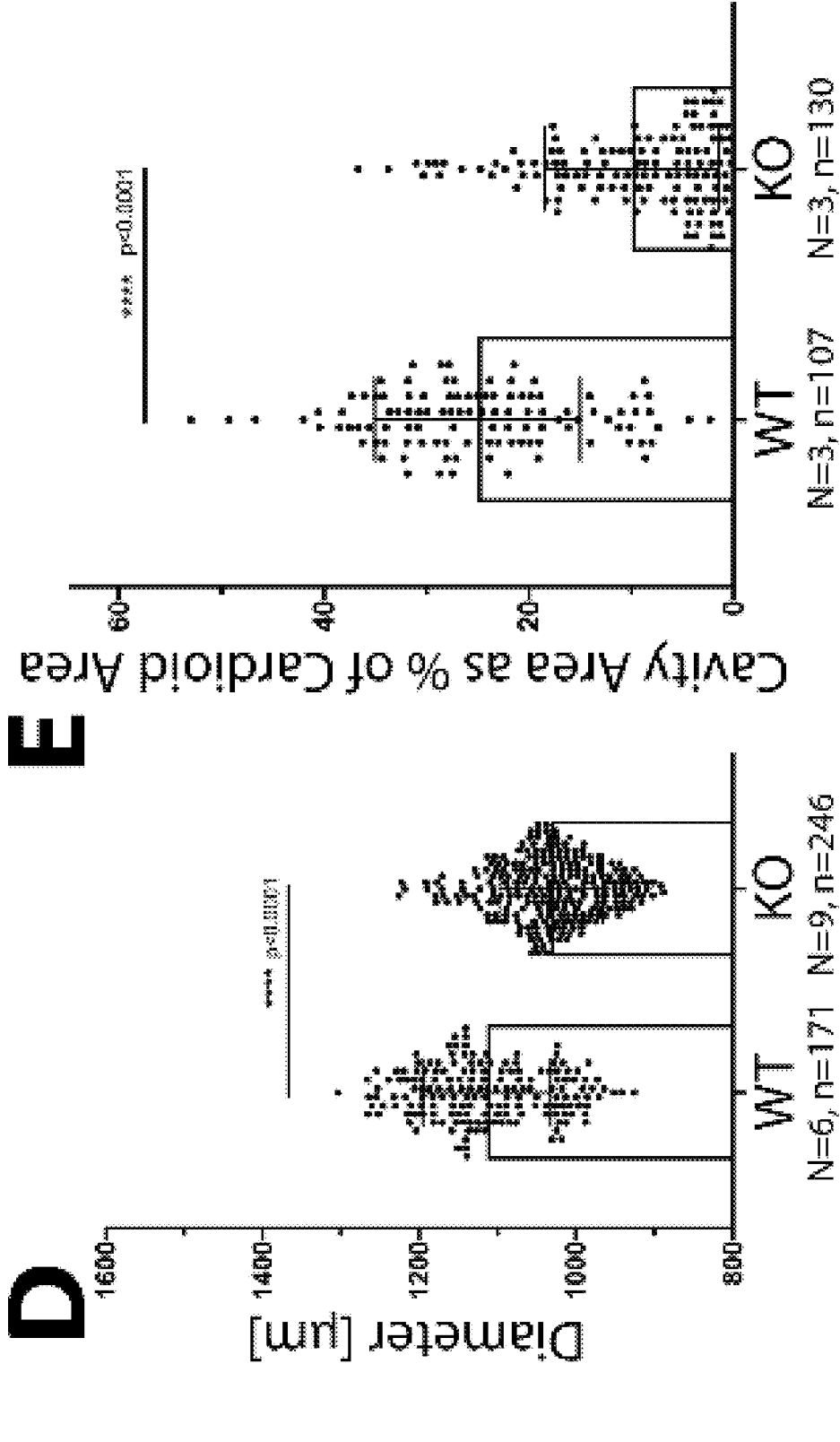
Figure 17:
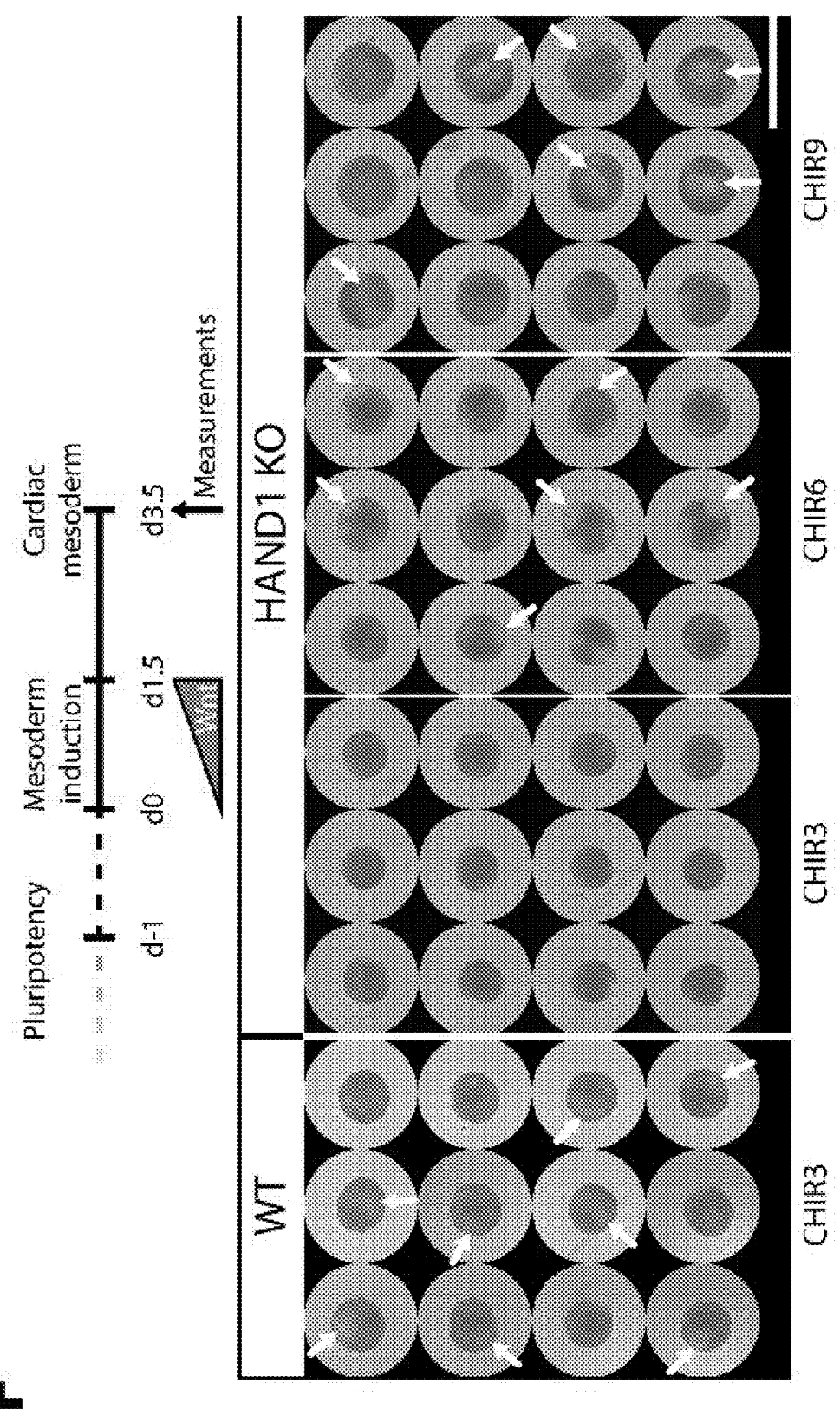
Figure 17:
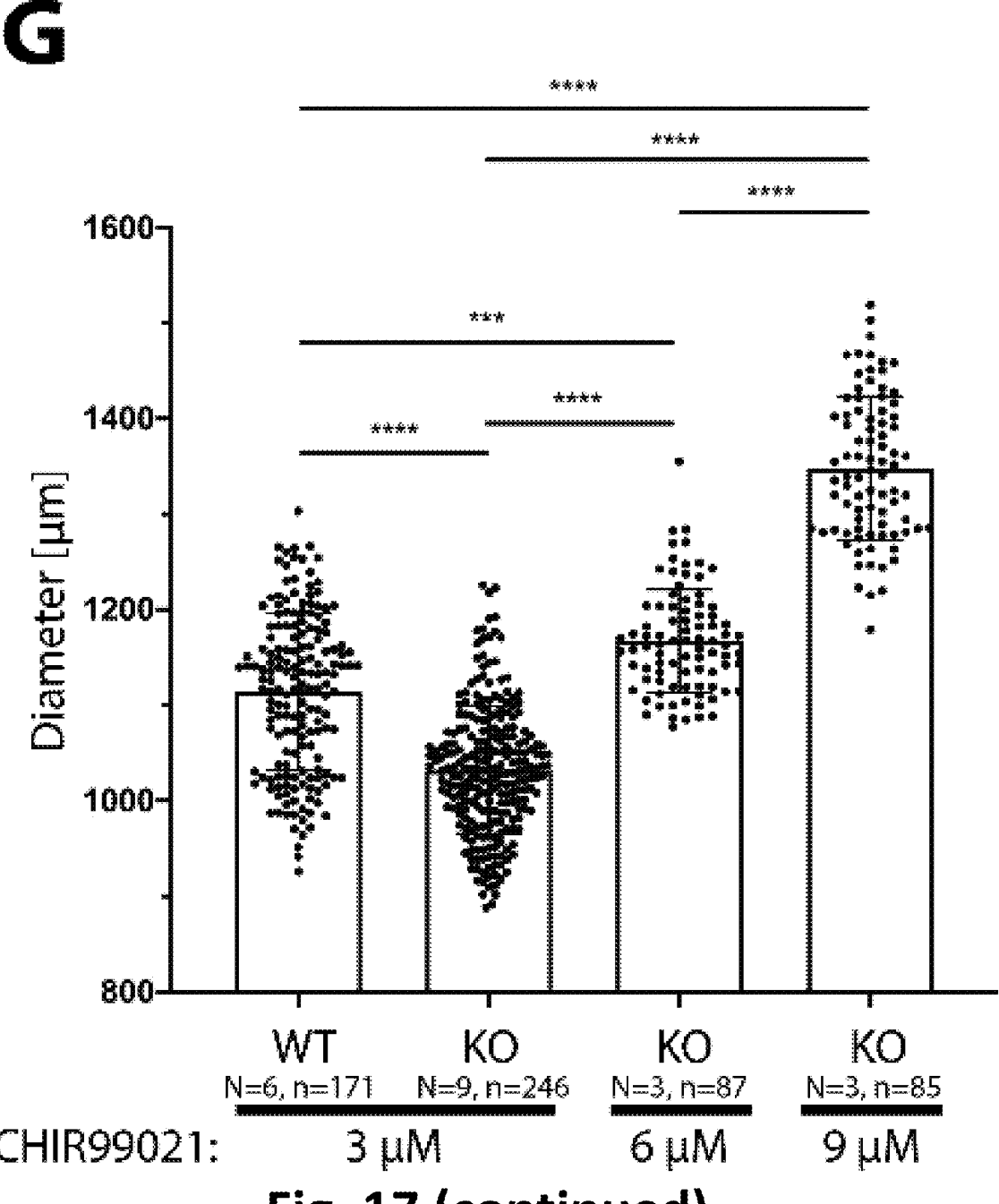

In HAND1 KOs, on the other hand, we observed reduced NKX2-5 protein levels in cardiac mesoderm but not in CMs (FIG. 17A, FIG. 17D, 24E). These results highlight the importance of stage-specific analysis as, our data suggest that HAND1 functions upstream of NKX2-5 in cardiac mesoderm while NKX2-5 is upstream of HAND1 in later stage CMs. Consistent with this hypothesis, and distinct from NKX2-5 null cardioids, HAND1 KO cardioids showed a clear defect in cardiac cavity self-organization and size at the cardiac mesoderm stage. This phenotype manifested as cardioids of smaller size (N=9, n=246) forming smaller cavities (N=3, n=130) (FIG. 17B-17E, FIG. 24G). These defects were not caused by a difference in cell number per cardioid, as both KO and WT showed similar cell counts (FIG. 24F). Importantly, despite these defects in patterning and morphogenesis of cardiac mesoderm, later CM specification (TNNT2$^+$) was still functional in HAND1 KO cardioids (FIG. 24E). These observations further underscore the crucial distinction between control of cell specification vs. tissue patterning and organ morphogenesis that can be dissected in the context of a cardiac malformation in cardioids.

We next asked whether the HAND1 KO phenotype could be rescued by exogenous signaling factors. Increased dosage of WNT signaling during mesoderm induction rescued the HAND1 KO phenotype, confirming the involvement of WNT in cavity morphogenesis (FIG. 17F, 17G). Consistently, HAND1, a human-specific FHF and early ventricular chamber marker, was upregulated in high WNT conditions that also promoted cavity expansion (FIG. 16C). Moreover, HAND1 protein levels were diminished upon BMP inhibition, confirming that a WNT-BMP-HAND1 axis drives cardioid cavity self-organization (FIG. 16G). Taken together, these data show that self-organization and genetic cardiac defects can be quantitatively modeled in our high-throughput cardioid platform.

Figure 18:
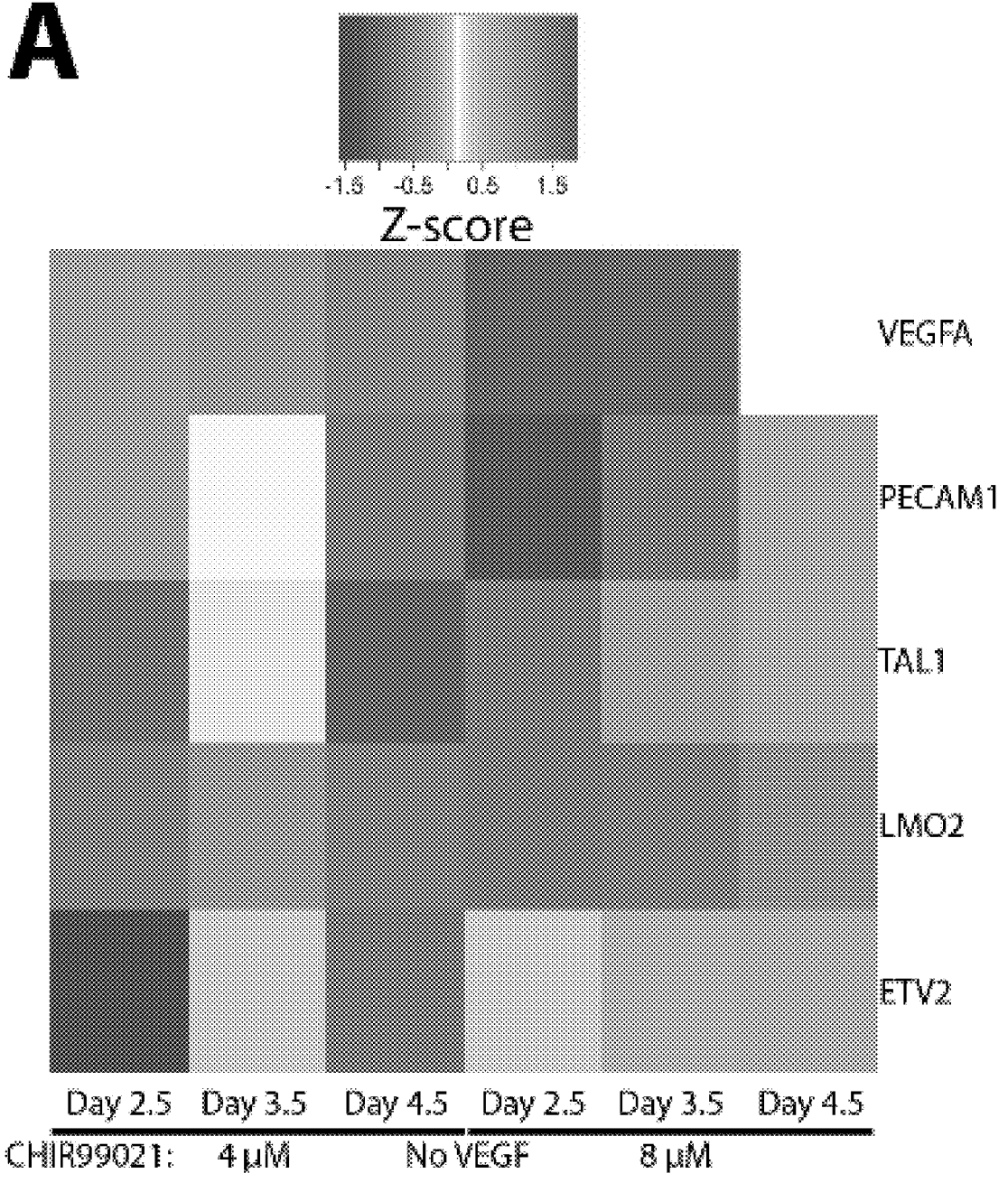
FIG. 18. WNT, ACTIVIN and VEGF Coordinate Endothelial and Myocardial Self-Organization. (A) Low WNT dosage (CHIR99021, 4 μM) during mesoderm induction results in higher expression of EC-specifying genes (VEGFA, TAL1, LMO2, ETV2, PECAM1) compared to high WNT (CHIR99021, 8 μM). (A') Timeline of differentiations performed with no VEGF addition and low or higher WNT and Activin dosages. (B) Percentage of VEGF expressing CMs (single-cell sequenced) is increased in optimized, ventricular-like CMs (low WNT (CHIR: 4 μM)/ Low Activin (4 ng/ml), N=2, n=1717) compared to the intermediate WNT (CHIR: 6 μM)/high Activin (50 ng/ml) condition (N=2, n=5097). (C) Example images of emergence of partial EC-lining in "No Activin" condition. Scalebars: 200 μm. (D) Quantification of the different EC formation and lining occurrences. N=4, n=29. (E) Example images for Categories 1 and 2. Scalebars: 200 μm. (F) Timeline of differentiations performed with added VEGF and intermediate WNT (CHIR: 6 μM)/High Activin (50 ng/ml) dosages as well as WNT inhibition. (F') Quantification of FACS data showing a robust ratio of CMs and ECs in cardioids. Mean+/−SD. (F'') Cardioids show separation of CM and EC layers as well as emergence of a layer of fibroblast-like cells (COL1A1+). Scalebars: 200 μm. (G) Timeline of differentiations performed with added VEGF and intermediate WNT (CHIR: 6 μM)/High Activin (50 ng/ml) dosages as well as lack of WNT inhibition. (G') Cryo-section of cardioids containing only ECs and fibroblast-like cells without CMs when WNT is not inhibited during the cardiac mesoderm stage and VEGF is supplemented. Used cell lines in this figure: WTC.
Figure 18:
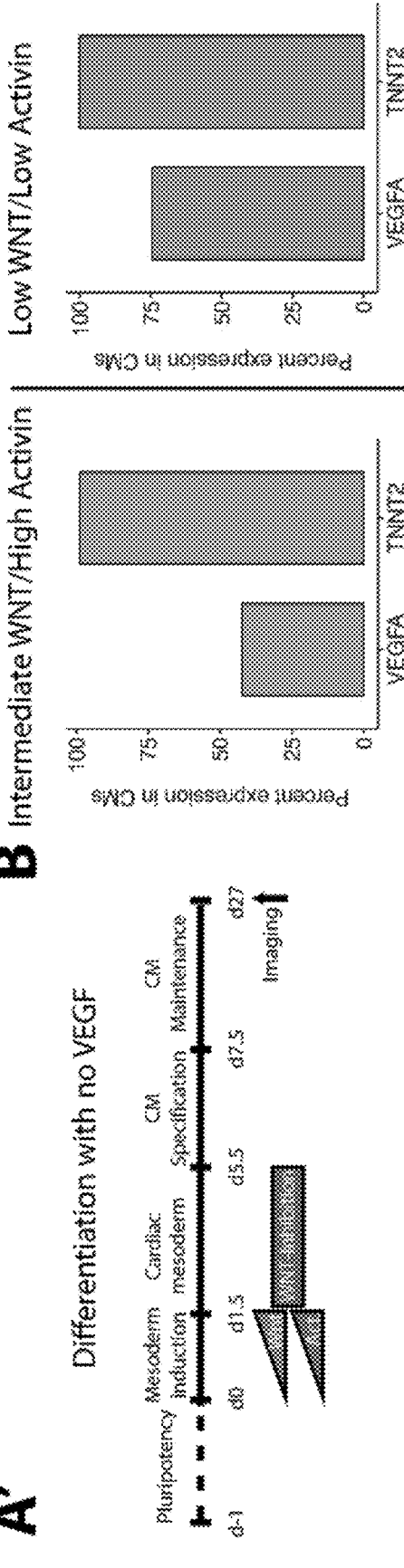
Figure 18:
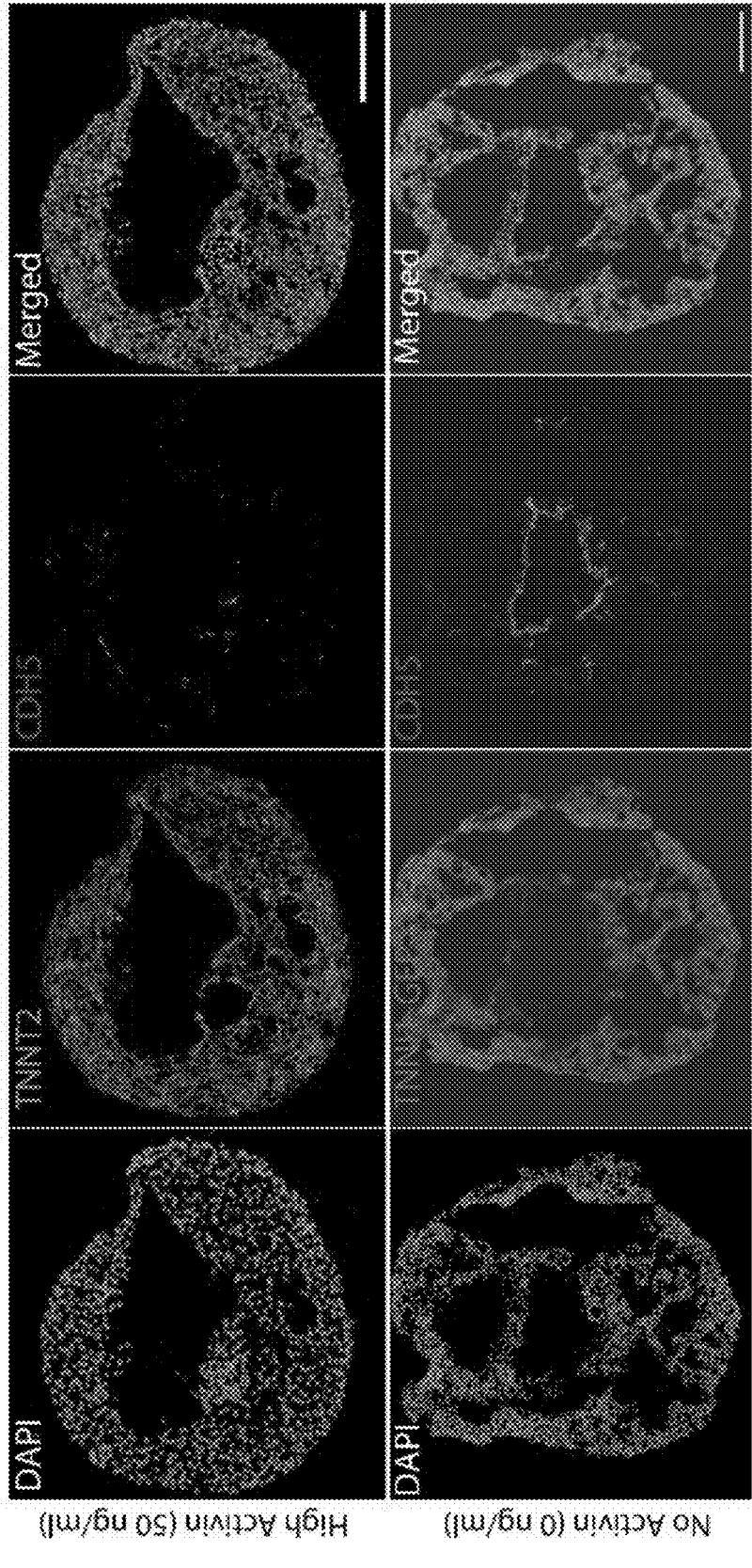
Figure 18:
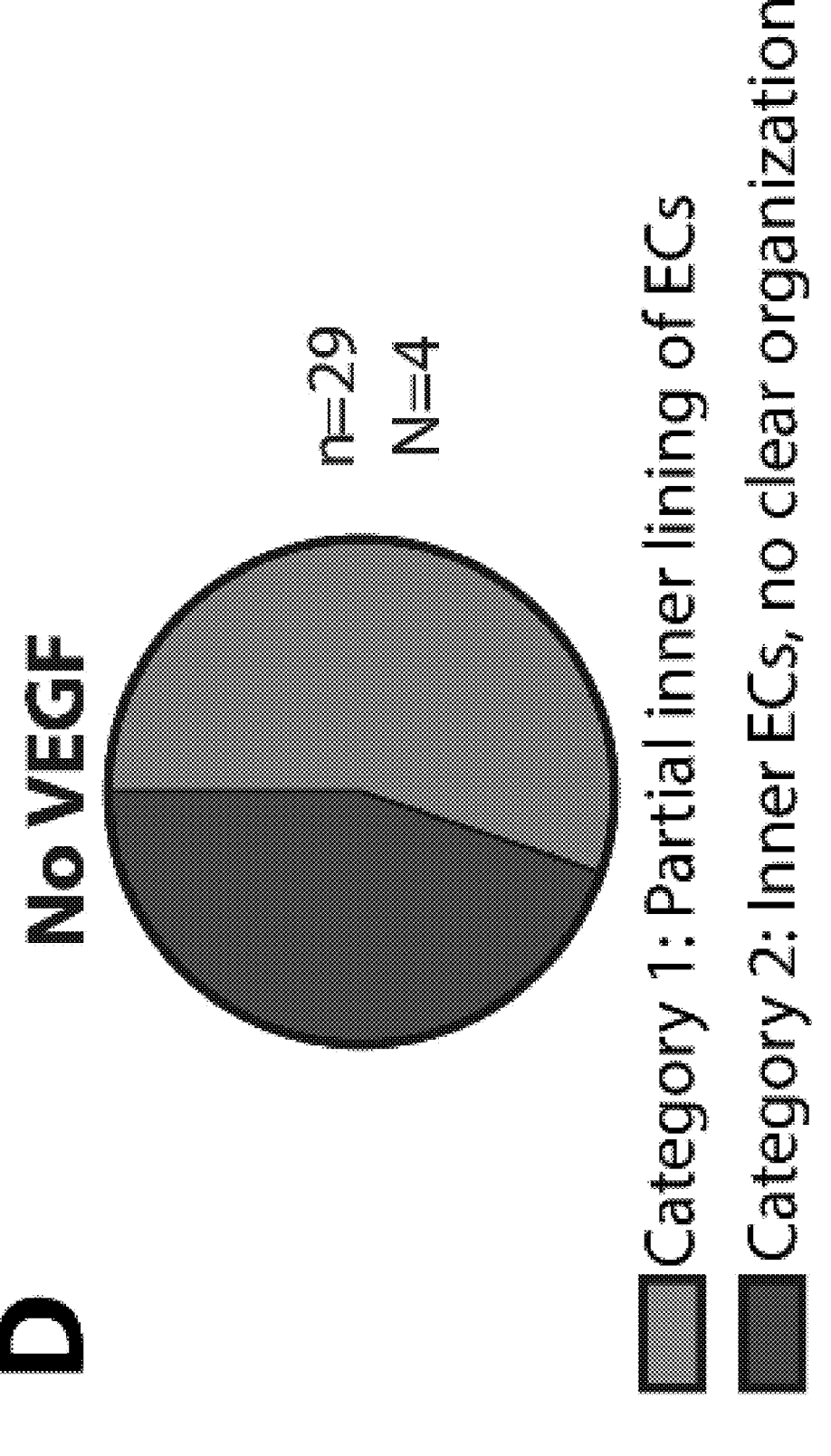
Figure 18:
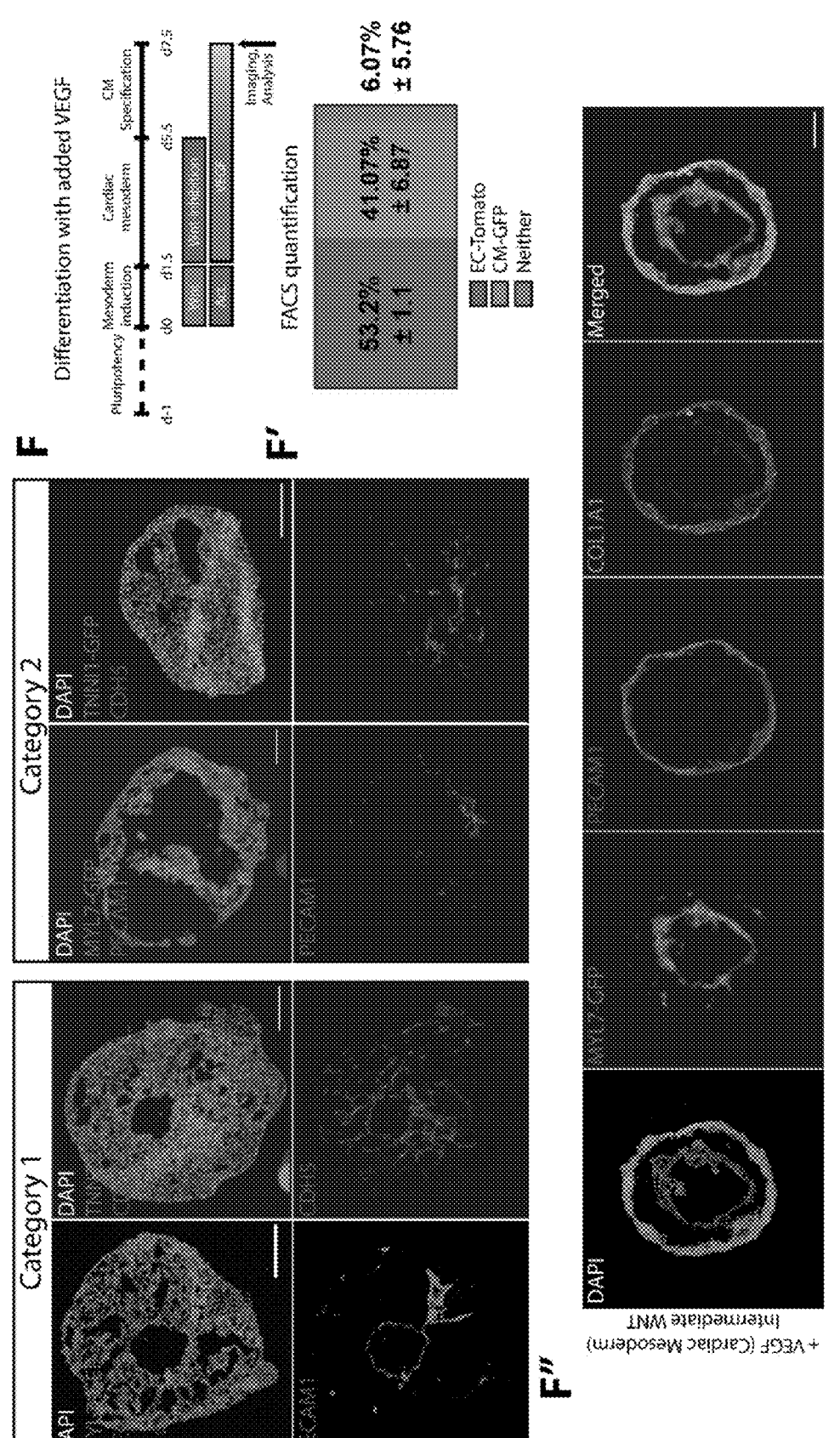
Figure 18:
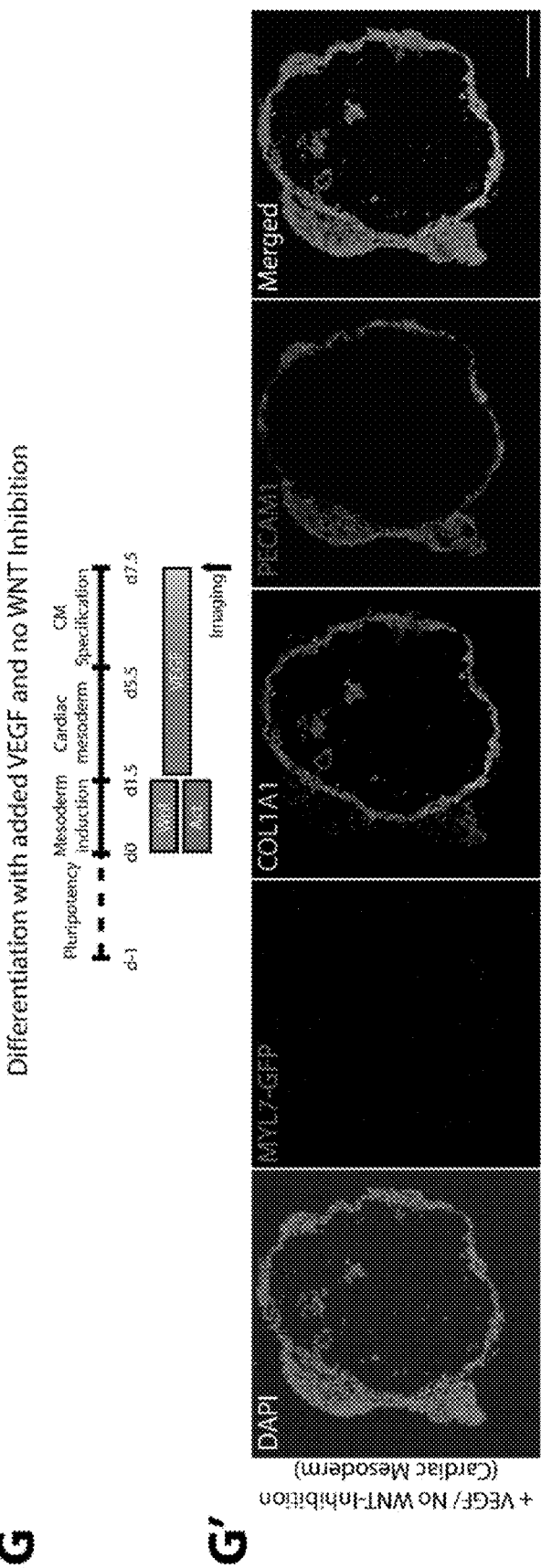

Example 12: WNT, ACTIVIN and VEGF Coordinate Endothelial and Myocardial Self-Organization We next explored whether cardioids can be used to dissect signaling pathways directing patterning and separation of the myocardium and endocardium to form an inner lining, a hallmark feature of the heart chamber. To probe these relationships, we compared the RNA-seq time-course of cardioids, which were generated using high vs. low WNT activation dosage during mesoderm induction. We found that lower WNT activation resulted in upregulation of VEGF-A, and other EC specifying factors (ETV2, TAL1, LMO2, PECAM1) during the cardiac mesoderm stage (FIGS. 18A, 18A'). At the same time, single cell RNA-seq analysis of ventricular-like cardioids induced with low WNT/low ACTIVIN conditions revealed a higher proportion of CMs expressing VEGF-A in comparison to cardioids induced with intermediate WNT/high ACTIVIN (FIG. 18B). We therefore hypothesized that low WNT and ACTIVIN signaling dosages coordinate CM and EC co-specification by inducing VEGF-A in cardiac mesoderm and in CMs to stimulate EC differentiation. Indeed, we discovered that lower levels of WNT signaling in combination with low ACTIVIN signaling dosages during mesoderm induction promoted later ECs self-organization within cardioids (FIGS. 18C, 18D). Those ECs often (55.2%, N=4, n=29) formed a partial inner lining of the cardioid cavity (FIGS. 18C, 18D, 18E, 25A, 25A') but not on the outside of cardioids, resembling the in vivo tissue architecture. In contrast, in higher WNT and ACTIVIN dosage conditions, we did not observe EC self-organization in the absence of exogenous VEGF (FIG. 18C). In conclusion, optimal WNT and ACTIVIN signaling dosages during mesoderm induction control later EC self-organization resulting in a partial lining of the cardioid cavity.

We next interrogated the effects of exogenous VEGF on CM and EC co-specification in cardioids (FIG. 18F). When we included VEGF-A after the CM specification stage, we occasionally observed formation of an EC layer lining the cardioid cavity, but also some EC specification on the surface of cardioids (FIG. 25B, 25C, 25D). To further elucidate whether we can control the early self-organization of CM and EC layers in cardiac mesoderm, we included VEGF-A at this stage. As CMs and ECs co-differentiated from cardiac mesoderm into cavity-containing structures in the presence of VEGF-A, they separated into CM and EC layers (FIG. 18F, 18F', 18F"). Here, using an optimal (intermediate) WNT activation during mesoderm induction always resulted in an EC layer surrounding the CM layer (FIG. 18F", FIG. 26A, 26C, 26D). Moreover, a third layer of COL1A1$^+$ cells emerged next to the EC layer (FIG. 18F"). In contrast to cardioids, aggregates of ECs and CMs initially differentiated in 2D formed intermingled networks, but they did not pattern into layers (FIG. 26B). This suggested that VEGF stimulates the early separation of the two layers, which is an important aspect seen in embryonic cardiac mesoderm and at the heart tube stage. However, exogenous VEGF was not sufficient to control the correct outer vs. inner orientation of the EC lining. Thus, the dosage of WNT/ACTIVIN and timing of VEGF signaling coordinate specification, cavity morphogenesis and in vivo-like patterning of CM and EC lineages.

To further dissect the WNT and VEGF signaling control of lineage specification and morphogenesis in cardioids, we asked whether an EC cell layer can be formed without CM co-differentiation. In the absence of WNT inhibition and in the presence of VEGF during the cardiac mesoderm stage, we discovered that cardioid-like structures that contained primarily ECs and COL1A1$^+$ cells, without CMs, could be reproducibly formed (FIG. 18G, G', FIG. 26F). This observation again underscores how signaling control of morphogenesis could be separated from signaling control of cell specification in cardioids. Collectively, these data show that as cardioids self-organize to give rise to the first two heart lineages, they can be used to dissect aspects and stages of myocardial and endocardial co-development.

Example 13: Endocardial and Fibroblast-Like Cells in Cardioids

Figure 19:
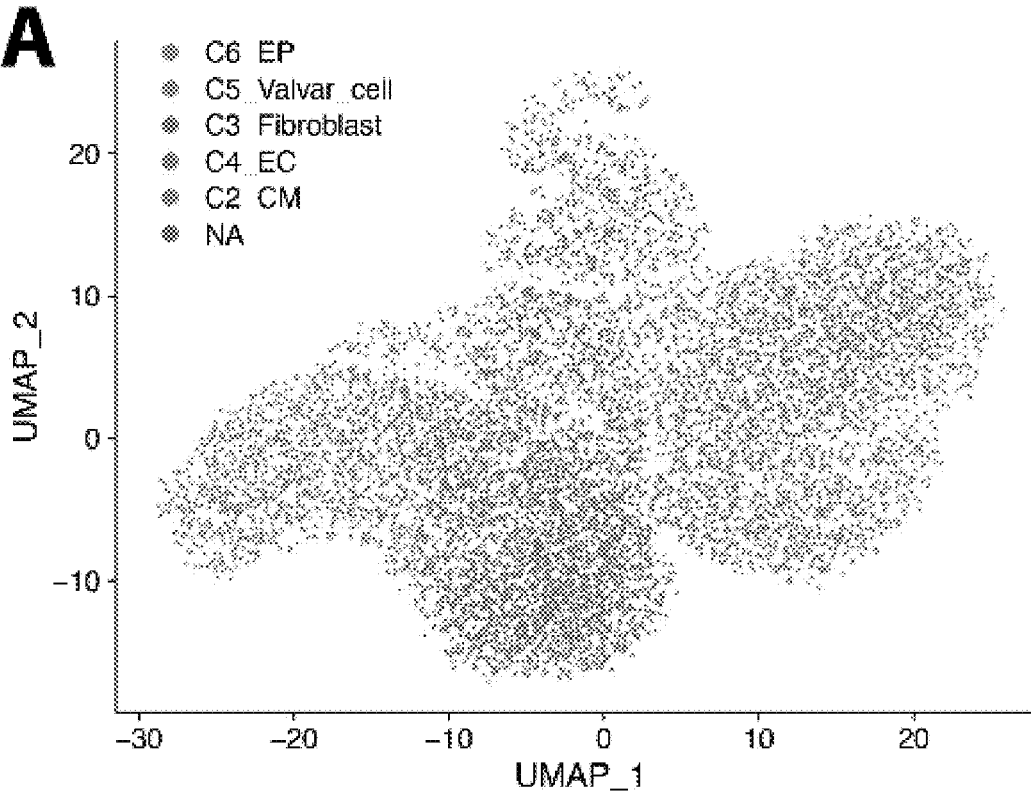
FIG. 19. Cellular Identities of Cardioid Cells upon VEGF Treatment. (A) Classification of cells of VEGF-supplemented cardioids based on markers determined by (Cui et al., 2019) (human fetal hearts). CM: cardiomyocytes, EC: cardiac endothelial cells, EP: epicardial cells. Selected markers for cardiac endothelial cells (PECAM1, CDH5, NPR3), cardiomyocytes (TNNT2, MYL7) and fibroblast-like cells (COL1A1, COL3A1) are shown. (B, B', B'') Cardiac endothelial cells in cardioids express mechanosensing genes (e.g. KLF2, SOX18). Scalebar: 200 μm. (C) PCA of: 2D-derived ECs (Anterior, Patsch et al., Human Cardiac Microvascular (HCMEC), Human Umbilical Vein (HU-VEC)), hPSC and 3D-derived ECs from Cardioids (day 7.5, intermediate WNT dosage) and Vascular Organoids ((Wimmer et al., 2019) Day >18)). Anterior ECs: H9 line, Patsch et al., Vascular Organoid ECs as indicated by (Wimmer et al., 2019). (D) Differential expression of mechanosensing and maturation genes, cardiac transcription factors, EC transcription factors, endocardial-like and general EC genes in FACS-sorted ECs. Used cell lines in this figure (unless otherwise stated): WTC.
Figure 19:
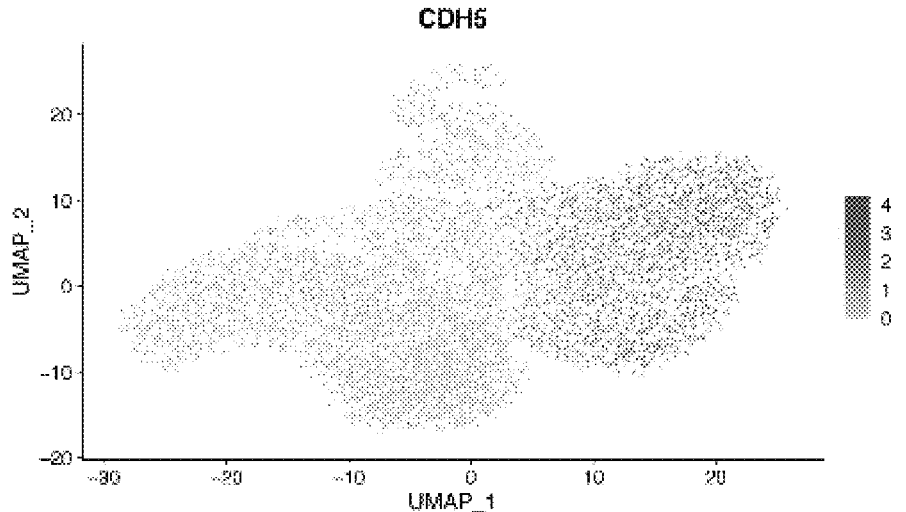
Figure 19:
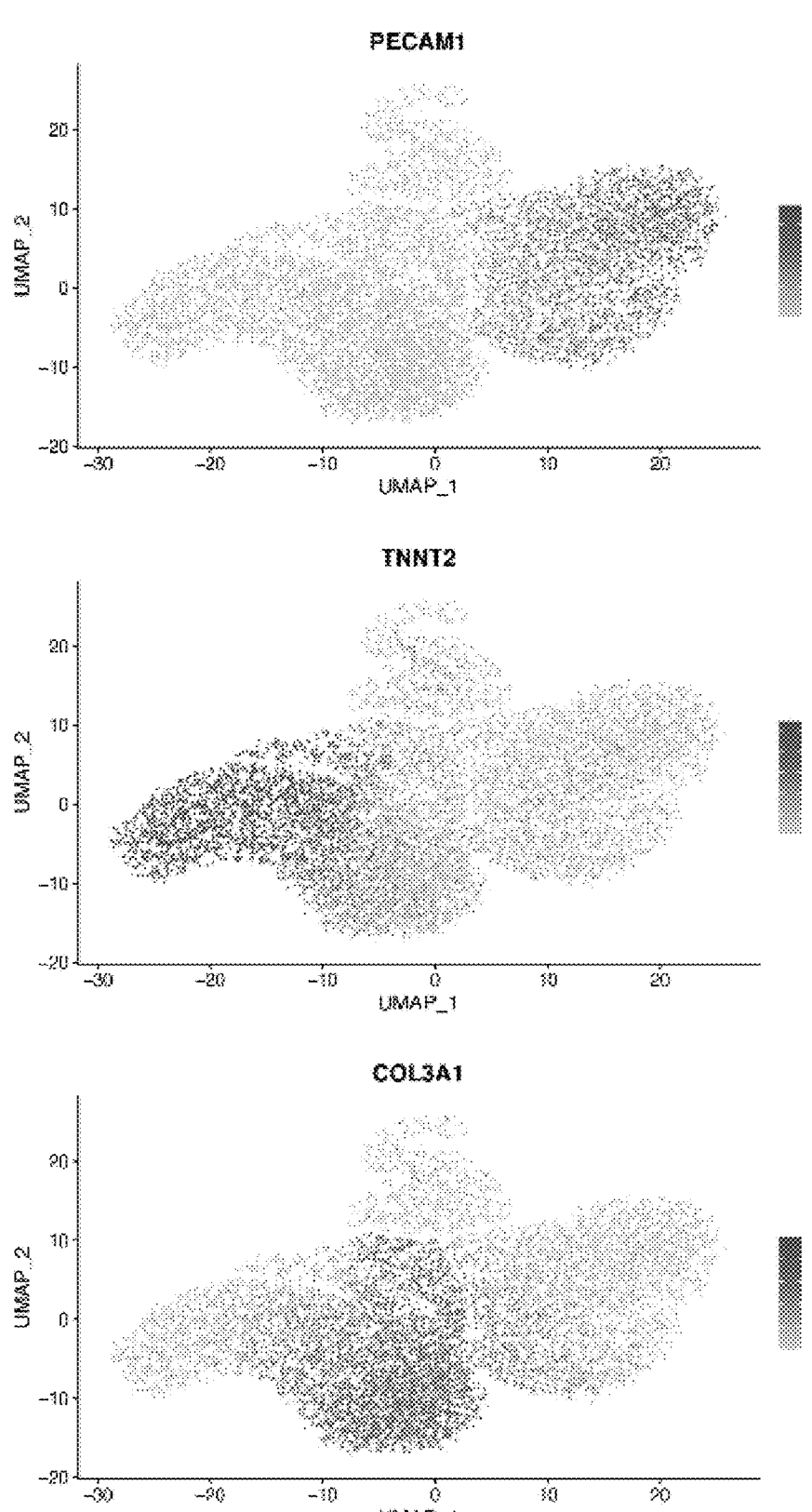
Figure 19:
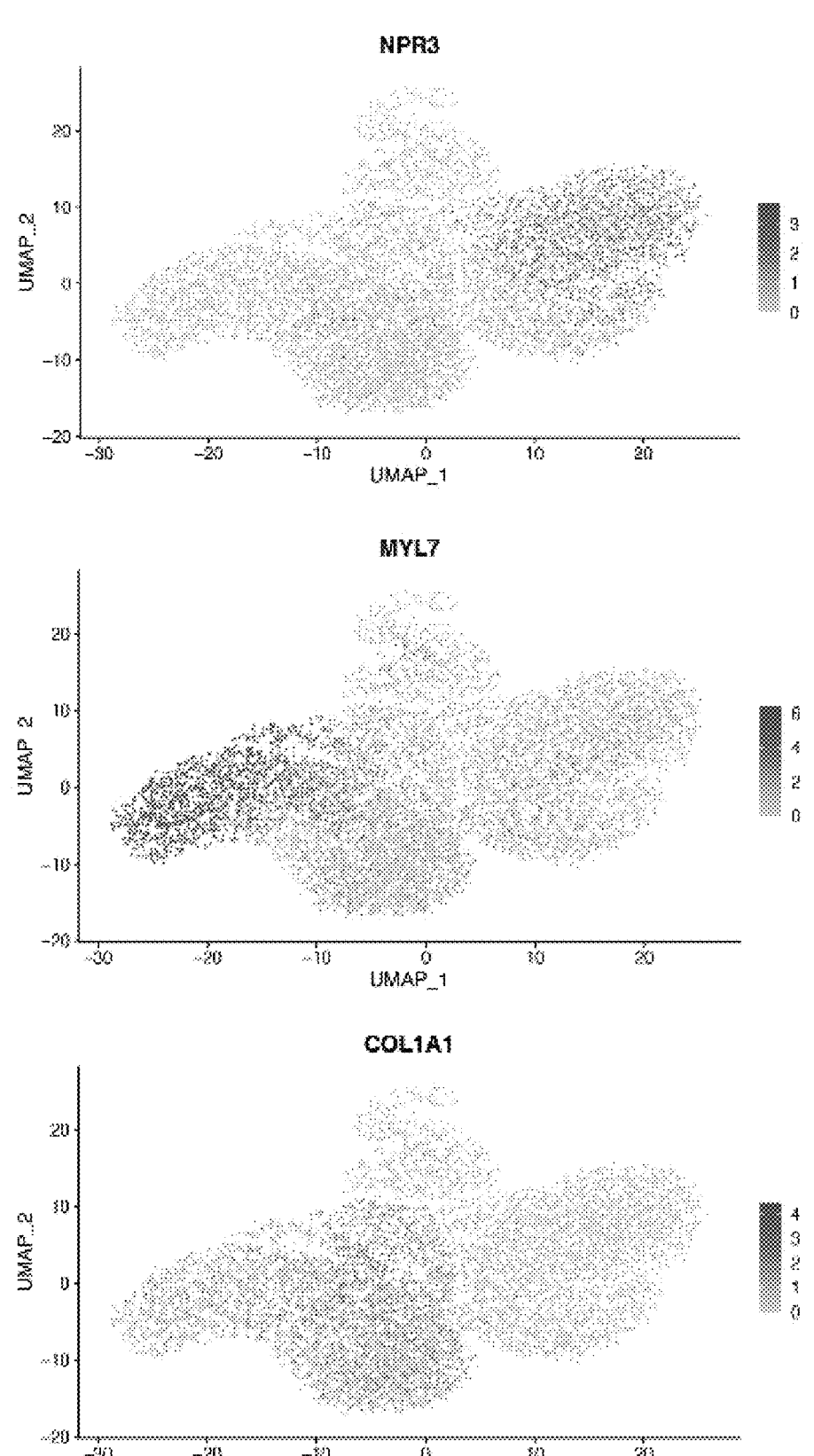
Figure 19:
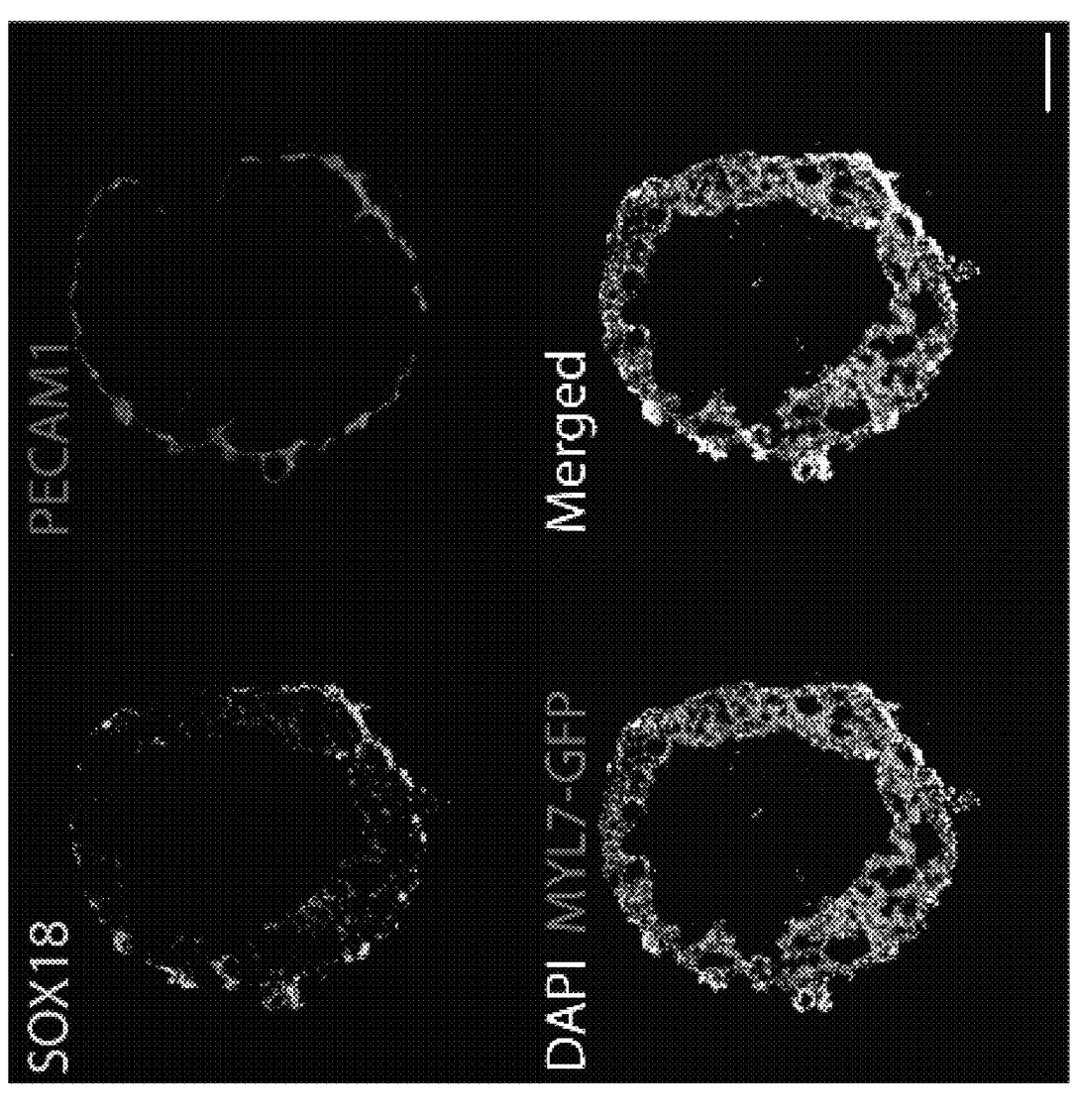
Figure 19:
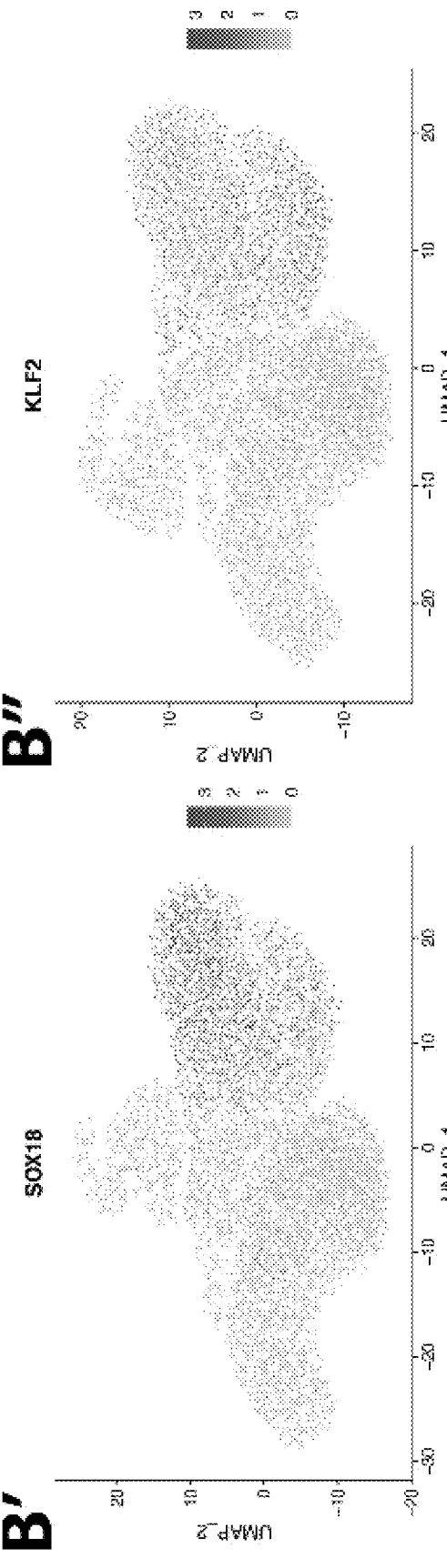
Figure 19:
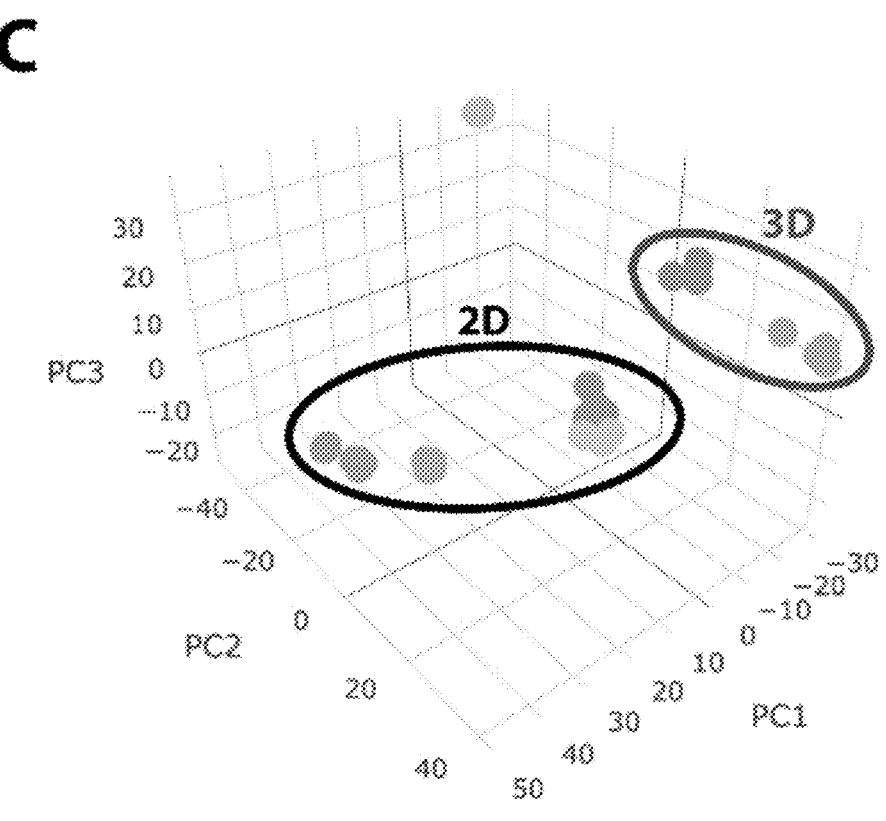
Figure 19:
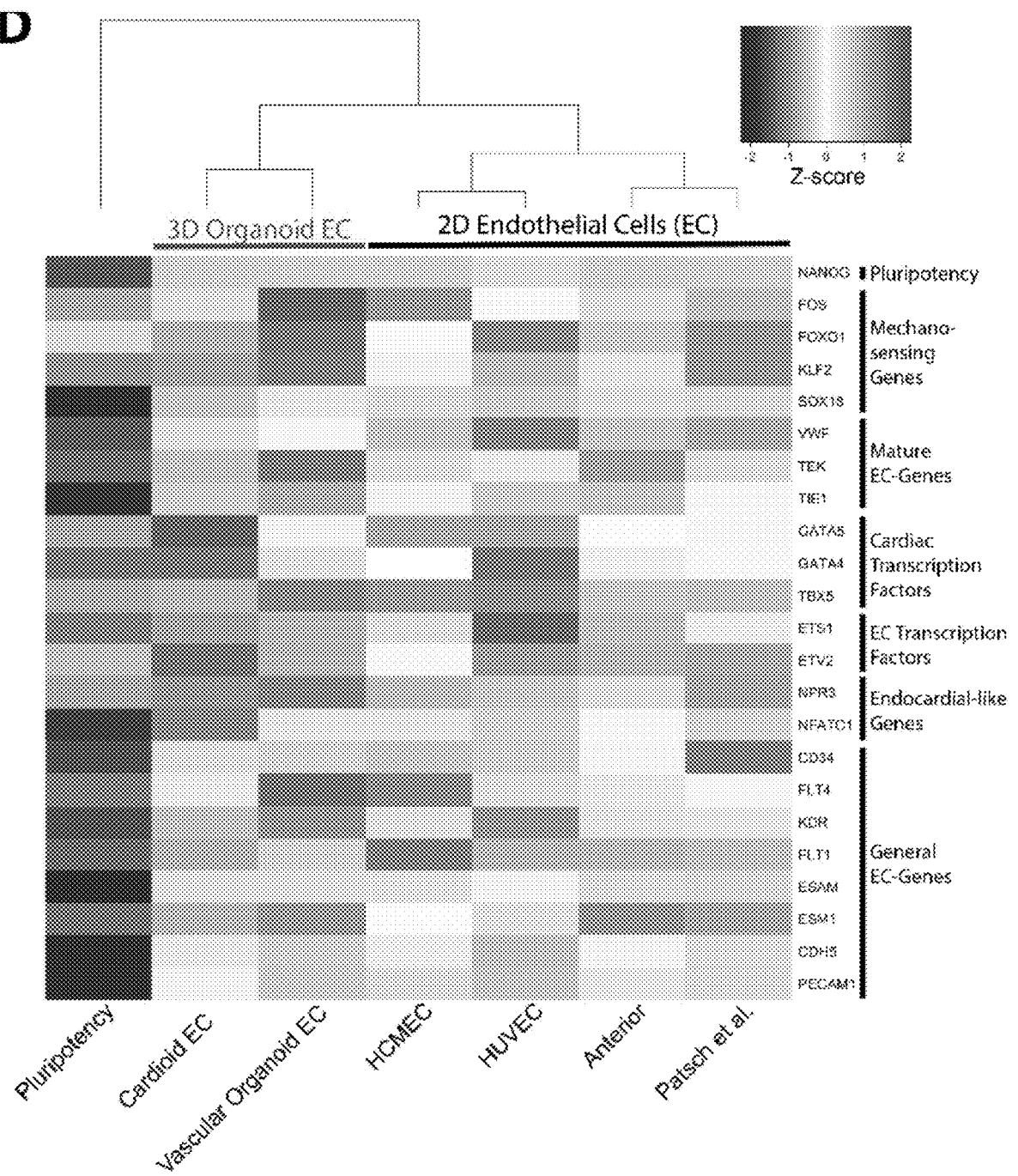

All self-organizing organoids share related tissue-like specification, patterning and morphogenesis processes, but are distinguished by their organ-specific cell types. Hence, we next investigated cellular heterogeneity within cardioids. When we used intermediate WNT activation and VEGF, we found that the ratio of CMs to ECs was stable at 41% (MYL71 to 53% (CDH51 (FIG. 18F'), which facilitated quantitative analysis using this model. This observation was further corroborated by the deconvolution of bulk RNA-seq data (Wang et al., 2019, Nature Communications 10, 1-9) and a cardiac cell-type-specific single-cell expression reference (Cui et al., 2019, CellReports 26, 1934-1950.e5) for the developing human heart (FIG. 27A). Smart-seq2 of sorted cells (FIG. 26E) and scRNA-seq analysis used to categorize cells based on the in vivo human heart data (Cui et al., 2019) further confirmed key CM and EC marker profiles and GO-terms (FIG. 19A, FIG. 27D, 27E), while the remaining cells (MYL7–/CDH51 expressed genes (e.g. SOX9, MSX1/2, COL1A1, COL3A1) related to putative EC-derived fibroblast-like cells (FIG. 19A, 26E, 27F). Finally, bulk proteomic analysis of cardioids confirmed their CM and EC proteome expression signatures (FIG. 27B).

All vascularized tissues and organs contain specific EC subtypes, and accordingly, the endocardium has an identity-specific EC gene expression signature. To determine EC identity in cardioids, we performed a Smart-seq2 analysis on sorted CDH5$^+$ cardioid ECs and compared them to ECs generated using a well-established 2D differentiation protocol (Patsch et al., 2015, Nature Cell Biology 17, 994-1003), our 2D differentiation protocol using similar media conditions as in 3D, ECs from vascular organoids (Wimmer et al., 2019, Nature 29, 40), human umbilical vein endothelial cells (HCVECs), and human cardiac microvascular endothelial cells (HCMECs) (FIG. 19C, 19D). We found that cardioid-derived ECs were most similar to ECs from vascular organoids despite their age difference (Day 7.5 vs. Day >18). Importantly, ECs from cardioids showed increased transcript levels for cardiac transcription factors, such as GATA4/5, and genes associated with an endocardial-like identity (NFATC1, NPR3) (FIG. 19D). Importantly, NFATC1 was also found in the proteomics data (FIG. 27B) and NPR3 in the scRNA-seq data (FIG. 19A). Their anterior HOX gene expression profile matched that of HCMECs from the adult human heart and that of ECs derived from cardiac mesoderm in 2D (Anterior ECs), but not that of the other analyzed more posterior EC subtypes (FIG. 27C). Thus, the signature of ECs derived from cardioids is consistent with an endocardial-like identity.

The ability of endothelium to sense fluid flow, pressure and mechanical stretch is an instrumental requirement for its developmental and physiological roles, especially in the heart. As expected for a bona fide model of cardiac development, a Smart-seq2 analysis of sorted ECs from cardioids revealed an upregulation of mechanosensitive genes (SOX18, KLF2, FOXO1, FOS) compared to ECs in 2D (FIG. 19B, 19B', 19B", 19D), similar to the more matured 3D vascular organoid ECs. These observations were confirmed in the scRNA-seq dataset and with staining for SOX18. Markers of EC maturation (VWF, TEK, TIE1) were also upregulated in cardioid ECs compared to 2D EC differentiations (FIG. 19D). Overall, these results indicate that self-organization of CMs and ECs in 3D triggers essential aspects of endocardial identity and endothelial physiology.

Example 14: Tri-Lineage Cardioid Platform as a Developmental Injury Model

Figure 20:
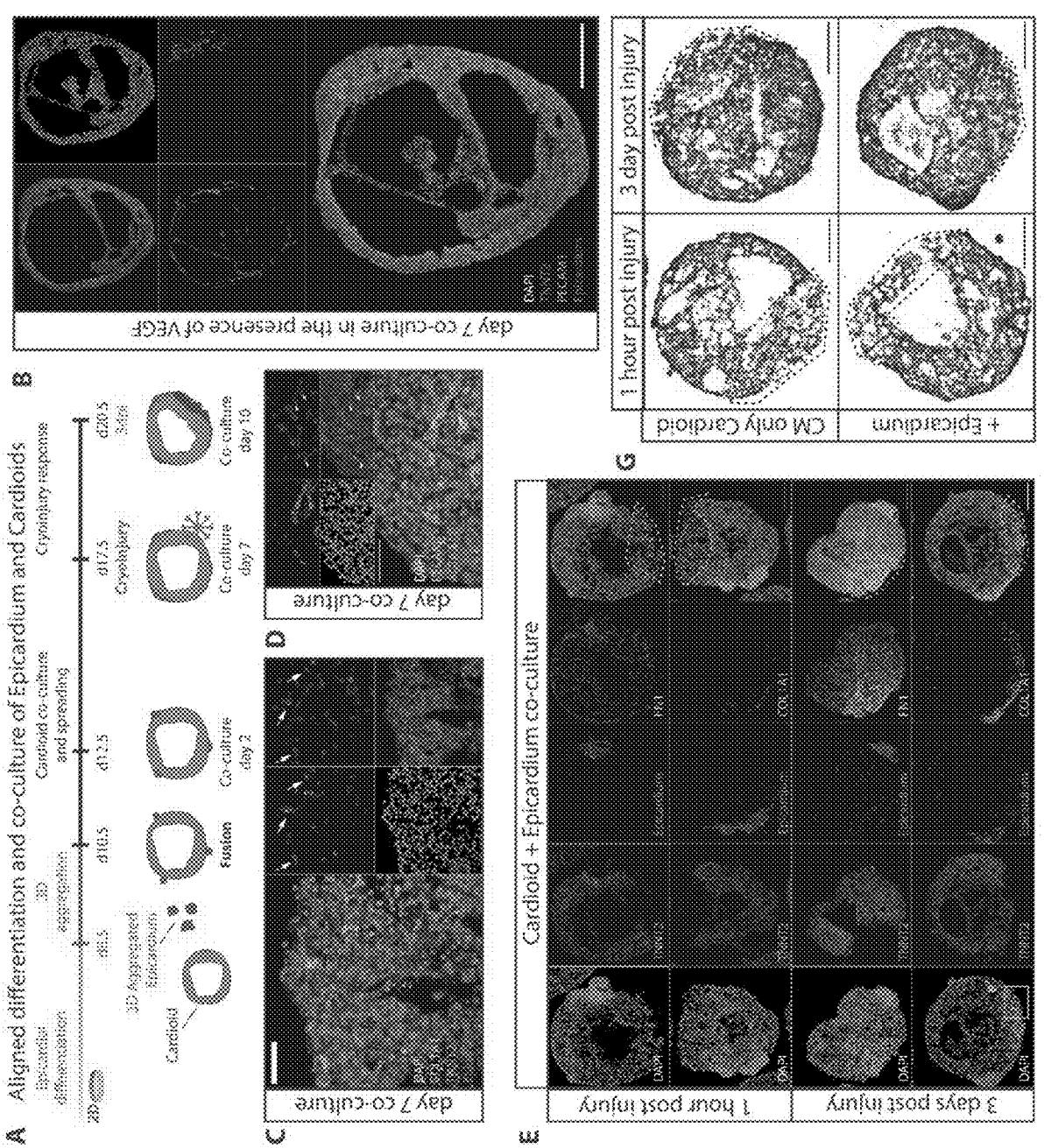
FIG. 20. Epicardium Interacts with Cardioids and the Epicardial- or Endocardial-derived Fibroblasts React to Cryoinjury. (A) Schematic of epicardial co-culture and cryo-injury. (B) Confocal images of fluorescently labeled epicardial derivatives after 7 days of co-culture with cardioids (TNNT2+) encompassing EC (PECAM1+) inner lining in the presence of 100 ng/ml VEGF-A. Scalebar: 200 μm. (C-D) Confocal images of COL1A1+ (C) and ACTA2+ (D) epicardial derivatives after 7 days of co-culture with cardioids containing ECs (PECAM1+). Scalebars: 50 μm. (E-F) Confocal images of cryoinjury response (1 hour and 3 days after injury) staining fibronectin (FN1) and COL1A1+ cells in cardioids in the presence (E) or absence (F) of epicardium. Scalebar: 200 μm (E, F) and 50 μm (e'-detail of E). (G) Masson's trichrome staining (Blue: Connective tissue, Red: Muscle) of cryo-injured cardioids in the presence or absence of epicardium 1 hour and 3 days post injury. Scalebar: 200 μm. (H) Confocal images of CM+EC+Fibroblast co-differentiated cardioids 3 days post injury marking FN1 and COL1A1+ cells. Scalebar: 200 μm. (I) Quantification of COL1A1+ cells in the injured (purple) vs. healthy (blue) area of co-differentiated CM+EC+Fibroblast cardioids 3 days post injury. Number of COL1A1+ cells was normalized to injured area/total area. Dashed lines mark the injury area in figures. Used cell lines in epicardial figures: H9, experiments also repeated with WTC lines. Used cell lines for CM/EC/Fibroblast co-differentiations: WTC.
Figure 20:
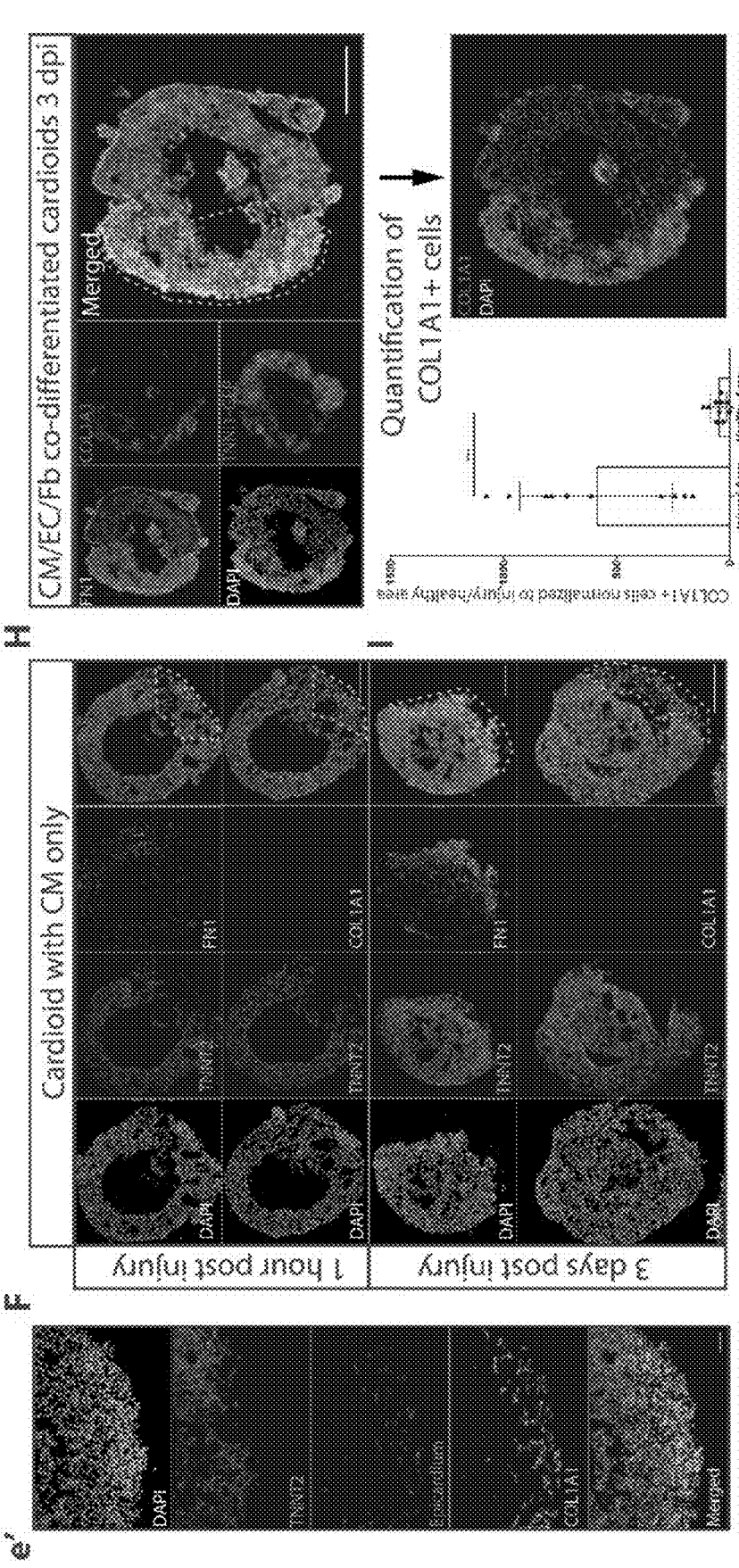

After endocardial lining formation, the epicardium envelopes early myocardial chambers, thereby adding the third major cardiac lineage to the heart. The epicardium originates from a small cellular clump called the pro-epicardial organ and goes on to cover the outer surface of the heart. After engulfment, signals from the CM layer (TGF-b, PDGF-b, FGFs) drive epicardial cell differentiation into smooth muscle cells (SMCs) and cardiac fibroblasts (CFs)—both relevant for further development, maturation and regeneration of the heart upon injury. To mimic this self-organization process in cardioids, we developed an epicardial differentiation protocol compatible with cardioids and based on the signaling sequence known to specify the pro-epicardial organ in vertebrates and hPSCs (FIG. 20A, 28A, 28B, 28C). We then co-cultured cardioids with epicardial aggregates in media without exogenous TGF-b, FGF and PDGF to test whether endogenous expression of these signaling factors by cardioids (FIG. 28D) is sufficient to stimulate epicardial/ cardioid interactions. Within 2-7 days, we observed spreading of epicardial cells on top of cardioids (FIG. 28E, 28F, 28G). After 7 days and without additional growth factors, epicardial cells interacted with the CM layer, migrated into it, and underwent differentiation (FIG. 20B, 20C, 20D, 28H, 28I). The migrating cells downregulated epicardial WT1 and upregulated the SMC and CF markers ACTA2 (FIG. 20D, 28I) and COL1A1 (FIG. 20C, 28H), as occurs in vivo. Strikingly, some of the migrating epicardium-derived cells started to interact with cardioid ECs (FIG. 20B, 20D). We concluded that co-culture in the absence of external signals triggers intrinsic spreading of epicardium on cardioids, its inward migration, differentiation and interactions with CMs and ECs.

A postulated advantage of self-organizing developmental organoid models are their pathophysiological-like responses. However, current cardiac in vitro models do not recapitulate important aspects of either myocardial regeneration seen in fetal, early postnatal and adult in vivo injury models, or fibrosis seen in disease models and patients. For instance, in prior tissues, after cryoinjury of bioengineered heart organoids, there is only limited proliferation but no initial extracellular matrix (ECM) accumulation typical for the early stages of both regeneration and fibrosis. Given that cardioids contain all three major cardiac lineages, solely relying on developmental mechanisms and not requiring external ECM scaffolds, we reasoned that cardioids would likely produce a more physiological response upon cryoinjury. To test the potential of the cardioid platform as a developmental injury model, we performed cryoinjuries in mono- (containing CM only) and tri-lineage (containing CMs (FIG. 20G, 20F), either ECs (FIG. 20H, 20I, 28J, 28K, 28L) or epicardium (FIG. 20E, 20G), and associated fibroblast-like cells) cardioids (FIGS. 29-34). The injury sites were characterized by intense, compacted DAPI signals, severe necrosis detected by TUNEL staining (FIG. 28J), limited apoptosis and no clear CM proliferative response (FIG. 28K). In time course experiments, we observed trichromium staining at the injury site, indicating localized ECM accumulation (FIG. 20G). Mono-lineage cardioids showed lower fibronectin accumulation and absence of COL1A1+ expressing fibroblast-like cells at the injury site (FIG. 20G, 20F). In contrast, in trilineage cardioids, we observed significant tropism of COL1A1+ fibroblasts toward the injury site and strong fibronectin accumulation (FIG. 20E, 20G). This rapid recruitment of either EC or epicardial associated fibroblast-like cells (FIG. 20E, 20H, 20I) is consistent with in vivo observations during injury responses. We could therefore dissect cell type-specific processes upon cardiac injury and conclude that cardioids are capable of mimicking an important early aspect of regenerative and fibrotic responses.

CONCLUSIONS

In conclusion, we have established a high-throughput human cardioid platform with capacity for intrinsic self-organization into patterned layers and 3D structures reminiscent of the early human left ventricular heart chamber. We also show that this resource can be used to model mechanisms underlying development of the three major cardiac lineages, including cavity formation, and injury response.

Although organoids mimic organotypic self-organisation in vitro, their variability and complexity can still hinder precise modelling of morphogenetic defects. We tackled the variability challenge by leaving out exogenous ECM and by using a high-throughput approach to reach optimal conditions from an optimised range of parameters. By controlling the incorporation of the three main cardiac lineages into the organoid platform and by its high reproducibility, we can dissect when and where genetic mutations cause a defect with high statistical power. There are other key cardiac sub-lineages that could be incorporated into this system including the second heart field lineage and the conduction system. By using this platform, we showed that cardiac mesoderm in vitro is sufficient to form a cavity in the absence of endothelium and endoderm via a WNT-BMP-driven mechanism. Overall, our approach of controlled in vitro reconstitution of cardiogenesis has a wide potential to explore developmental mechanisms and cardiac defects, as well as for the generation of more mature and complex human cardiac models suitable for drug discovery and regenerative medicine. The variability and complexity of self-organizing organoid systems still hinders quantitative modelling of morphogenetic defects. In cardioids, we address this challenge by omitting exogenous ECM and using a high-throughput approach to reach optimal signaling conditions. We further increased reproducibility by tightly controlling self-organization via signaling and the stepwise incorporation of the three main cardiac lineages into cardioids. This approach allows dissecting, with high statistical power, when and where the functions of specific factors are required. The simplicity of the system that can contain either one, two, or three cardiac lineages, without interference of non-cardiac tissues, makes it possible to reduce self-organization and its underlying molecular and cell biological mechanisms to its bare essentials. Complexity in cardioids can therefore be tailored to the biological question asked. This is an important advantage for an organoid model as complex biological systems often employ redundant mechanisms that are otherwise challenging to tease apart.

Cardioids, as all other self-organizing organoid systems, recapitulate some aspects of development but also differ from embryogenesis in others. Self-organization encompasses only a subset of intrinsic developmental mechanisms, which are sufficient to recapitulate aspects of the in vivo-like architecture. Consequently, using cardioids, we showed that cardiac mesoderm alone, instructed by signaling, is sufficient to form a chamber-like cavity in vitro. We propose that this cavity could be analogous to the cavity of the heart tube and early left ventricular heart chamber. In vivo, the first cavity arises from foregut endoderm-assisted migration and fusion of bilateral cardiac mesoderm and endocardial tubes into a single heart tube. However, bilateral heart tubes and chambers can form in the absence of either endocardium or foregut endoderm constriction, but the mechanism was still unknown. This indicates the inherent capability of cardiac mesoderm to intrinsically form cavities and chambers in vivo, which is in agreement with the self-organization we observed in cardioids and chick embryo explants in vitro. Lateral plate mesoderm, a subtype comprising cardiac mesoderm, has a similar potential to form a cavity—the pericardial body cavity. Thus, cavitation is likely a more general characteristic of mesoderm that could be called upon in embryos with a foregut defect. Finally, the HAND1 KO cavity phenotype in cardioids is consistent with the hypoplastic left ventricular chamber phenotype in Hand1 KO mice, and with the Hypoplastic Left Heart Syndrome chamber cavity phenotype in humans, demonstrating the modelling potential of cardioids.

We used the cardioid platform to demonstrate that WNT and BMP drive chamber-like self-organization. These pathways are known to regulate cardiac specification in vivo and in vitro, but whether and at what stage they control cardiac patterning and morphogenesis was unclear. The surprising finding that early mesodermal WNT controls later cardiac self-organization is consistent with early cardiac lineage diversification during mesoderm induction in vivo. Patterning and morphogenesis occur in parallel with specification, but they are not necessarily linked. In agreement with this notion, cavities can self-organize in the absence of cardiac specification and in HAND1 KO cardioids there is a defect in self-organization but not in CM specification. Conversely, inhibition of WNT signaling at the cardiac mesoderm stage is essential for CM specification but does not regulate cardioid self-organization. Cardioids are therefore a powerful system to intrinsically dissect regulation of specification and morphogenesis. At the same time, cardioids are simple enough to determine sufficiency of a factor for one of these processes and are thus complementary to more complex systems.

We found that WNT, ACTIVIN and VEGF control CM and EC self-organization in cardioids. In vivo, cardiac ECs first form endocardial tubes, later become separated from the outer CM tube by an ECM-filled (cardiac jelly) interspace, and finally form the inner lining of the heart chambers. How signaling coordinates these patterns and morphogenetic processes with specification was unclear. In cardioids, the patterning and morphogenesis of CM and EC lineages is controlled by the dosage of WNT and ACTIVIN at the earliest stage of mesodermal differentiation, and by VEGF that directs both specification and patterning of the EC layer in cardiac mesoderm. Interestingly, the same range of lower WNT and ACTIVIN signaling dosages stimulated ventricular specification and EC lining formation suggesting a potential coordination between these processes. When ECs and CMs are aggregated in microtissues, they do not form separate layers and lining. Generation of a separate EC layer/lining is crucial for activation of mechanosensing in the context of a chamber in vivo. Cardiac chamber mechanobiology is required for physiological EC and CM crosstalk, driving the next stages of heart development like trabeculation, myocardial compaction and interaction with epicardium. Cardioids are therefore a promising system to study the underlying mechanisms of CM and EC patterning and crosstalk in the context of a beating chamber.

During development, the (pro-)epicardium makes contact with the early heart chambers, engulfs them, and concomitantly differentiates and migrates into the myocardium. By co-culturing cardioids with epicardium, we observed epicardial spreading, migration and differentiation reminiscent of these processes in vivo. Epicardial and CM co-cultures have been studied before using microtissues, but not in the context of a cardiac chamber-like model. This aspect is important because the crosstalk between derivatives of the epicardial, EC and CM lineages is dependent on the mechanobiology of the heart chamber. We therefore propose that self-organization of the three cardiac lineages in chamber-like cardioids will be important to reignite the developmental and regenerative crosstalk that drives growth, maturation and pathophysiological responses of the heart as in vivo. The striking difference in response upon cryoinjury between bioengineered organoids and self-organizing cardioids, supports the argument that developmental mechanisms impact later pathophysiology.

The invention claimed is:

1. A method of generating a heart organoid comprising the steps of a1) providing pluripotent stem cells; and b1) inducing mesoderm differentiation in the presence of a WNT activator and/or GSK3-beta inhibitor, and further in the presence of a PI3 kinase inhibitor, in a 3D culture in a low attachment culture, wherein the cells bind to each other instead of a culturing vessel to form aggregates of the cells, thereby producing an aggregate of mesoderm cells; or a2) providing pluripotent stem cells in a 2D culture; and b2) inducing mesoderm differentiation in a 3D culture in a low attachment culture with at least 100 pluripotent cells from step a2), in the presence of CHIR99021, wherein CHIR99021 and/or an optional PI3 kinase inhibitor are in an amount sufficient to differentiate the pluripotent stem cells to exit pluripotency in an amount at least 90% of the pluripotent stem cells within 40 hours of starting induction, wherein CHIR99021 is in a concentration of at least 9 μM, wherein the pluripotent stem cells are further treated with fibroblast growth factor and/or albumin, thereby producing an aggregate of mesoderm cells; and c) differentiating the mesoderm cells of step b1) or b2) into cardiac cells in a 3D culture in a low attachment culture, wherein the cells aggregate with each other instead of binding to a culturing vessel to form aggregates of the cells, in the presence of cardiac differentiation factors and in the absence of a WNT activator and/or in the presence of a WNT antagonist, for at least 3 days, for cardiac mesoderm formation and formation of an inner cavity.

2. The method of claim 1, wherein the WNT activator in step b1) is a WNT ligand, WNT-3a, or CHIR99021.

3. The method of claim 1, wherein the pluripotent stem cells are induced pluripotent stem cells or cells from a cell line and/or wherein the provided pluripotent stem cells of step a) have been passaged.

4. The method of claim 1, wherein mesoderm differentiation is induced in a medium comprising activin A and/or bone morphogenetic protein.

5. The method of claim 1, further comprising d) further differentiating the aggregate with cardiac mesoderm into a tissue with a cardiomyocyte layer with cardiac differentiation factors for a further one day or more.

6. The method of claim 1 for screening or testing a candidate compound on its effects on heart development or functionality, comprising: generating the heart organoid while treating the cells with the candidate compound and comparing development or functionality of the heart organoid with development of a heart organoid that was not treated with the candidate compound.

7. The method of claim 1, comprising observing the effects of suppressed or overexpressed genes during heart development comprising: generating a heart organoid according to claim 1, wherein the cells have a suppressed candidate gene or overexpress a candidate gene and comparing development of the heart organoid with development of a heart organoid that was not generated with a suppressed or overexpressed gene.

8. The method of claim 2, wherein the WNT activator is in an amount sufficient to differentiate the pluripotent stem cells to exit pluripotency in an amount at least 90% of the pluripotent stem cells within 40 hours of starting induction, and wherein CHIR99021 is the WNT activator, wherein CHIR99021 is in a concentration of at least 6 μM.

9. The method of claim 8, wherein CHIR99021 is in a concentration of at least 12 μM.

10. The method of claim 2, wherein the PI3 kinase inhibitor is present and CHIR99021 is the WNT activator, wherein CHIR99021 is in a concentration of at least 0.5 μM.

11. The method of claim 10, wherein CHIR99021 is in a concentration of 0.5 μM to 12 μM.

12. The method of claim 3, wherein the provided pluripotent stem cells of step a) have been passaged in a medium comprising albumin and/or a fibroblast growth factor.

13. The method of claim 12, wherein the medium further comprises BMP and/or insulin.

14. The method of claim 1, wherein the provided pluripotent stem cells of step a) have been grown in a medium comprising at least 1.5% (w/v), albumin and/or at least 100 ng/ml fibroblast growth factor.

15. The method of claim 14, wherein the medium further comprises BMP and/or insulin.

16. The method of claim 4, wherein the medium further comprises fibroblast growth factor.

17. The method of claim 10, wherein mesoderm differentiation is induced in a medium comprising at least 1 ng/ml bone morphogenetic protein.

18. The method of claim 17, wherein the bone morphogenetic protein is BMP4.

19. The method of claim 7, wherein the at least 3 days are 3-7 days.

20. The method of claim 1, wherein fibroblast growth factor is FGF2.

21. A method of generating a heart organoid comprising the steps of:

a) providing pluripotent stem cells;

b) inducing mesoderm differentiation in the presence of a WNT activator and/or GSK3-beta inhibitor, and further in the presence of a PI3 kinase inhibitor, in a 3D culture in a low attachment culture, wherein the cells bind to each other instead of a culturing vessel to form aggregates of the cells, thereby producing an aggregate of mesoderm cells; and c) differentiating the mesoderm cells of step b) into cardiac cells in a 3D culture in a low attachment culture, wherein the cells aggregate with each other instead of binding to a culturing vessel to form aggregates of the cells, in the presence of cardiac differentiation factors and in the absence of a WNT activator and/or in the presence of a WNT antagonist, for at least 3 days, for cardiac mesoderm formation and formation of an inner cavity.

22. A method of generating a heart organoid comprising the steps of:

a) providing pluripotent stem cells in a 2D culture; and b) inducing mesoderm differentiation in a 3D culture in a low attachment culture, wherein a culture comprises at least 100 pluripotent cells from step a), in the presence of CHIR99021, wherein CHIR99021 and/or an optional PI3 kinase inhibitor are in an amount sufficient to differentiate the pluripotent stem cells to exit pluripotency in an amount at least 90% of the pluripotent stem cells within 40 hours of starting induction, wherein CHIR99021 is in a concentration of at least 9 μM, wherein the pluripotent stem cells are further treated with fibroblast growth factor and/or albumin, thereby producing an aggregate of mesoderm cells; and c) differentiating the mesoderm cells of step b) into cardiac cells in a 3D culture in a low attachment culture, wherein the cells aggregate with each other instead of binding to a culturing vessel to form aggregates of the cells, in the presence of cardiac differentiation factors and in the absence of a WNT activator and/or in the presence of a WNT antagonist, for at least 3 days, for cardiac mesoderm formation and formation of an inner cavity.

* * * * *